US012691078B2

(12) United States Patent
Moaseri

(10) Patent No.: US 12,691,078 B2
(45) **Date of Patent: \*Jul. 28, 2026**

(54) STABLE COMPOSITIONS OF FUNCTIONAL INGREDIENTS AND METHODS OF MAKING THE SAME

(71) Applicant: Nulixir Inc., Austin, TX (US)

(72) Inventor: Ehsan Moaseri, Austin, TX (US)

(73) Assignee: Nulixir Inc., Austin, TX (US)

( * ) Notice: Subject to any disclaimer, the term of this patent is extended or adjusted under 35 U.S.C. 154(b) by 259 days.

This patent is subject to a terminal disclaimer.

(21) Appl. No.: 17/945,010

(22) Filed: Sep. 14, 2022

(65) Prior Publication Data

US 2023/0111238 A1     Apr. 13, 2023

Related U.S. Application Data

(60) Provisional application No. 63/356,389, filed on Jun. 28, 2022, provisional application No. 63/321,596, filed on Mar. 18, 2022, provisional application No. 63/244,105, filed on Sep. 14, 2021.

(51) Int. Cl.
| | |
|---|---|
| *A61K 9/51* | (2006.01) |
| *A61K 31/00* | (2006.01) |
| *A61K 31/13* | (2006.01) |
| *A61K 31/137* | (2006.01) |
| *A61K 31/165* | (2006.01) |
| *A61K 31/343* | (2006.01) |
| *A61K 31/4025* | (2006.01) |
| *A61K 31/4458* | (2006.01) |
| *A61K 31/465* | (2006.01) |
| *A61K 31/522* | (2006.01) |
| *A61K 31/60* | (2006.01) |
| *A61K 36/07* | (2006.01) |
| *A61K 36/16* | (2006.01) |
| *A61K 36/23* | (2006.01) |
| *A61K 36/258* | (2006.01) |
| *A61K 36/28* | (2006.01) |
| *A61K 36/37* | (2006.01) |
| *A61K 36/481* | (2006.01) |
| *A61K 36/53* | (2006.01) |
| *A61K 36/54* | (2006.01) |
| *A61K 36/67* | (2006.01) |
| *A61K 36/88* | (2006.01) |
| *A61K 36/9068* | (2006.01) |

(52) U.S. Cl.
CPC ................ *A61K 9/51* (2013.01); *A61K 31/13* (2013.01); *A61K 31/137* (2013.01); *A61K 31/165* (2013.01); *A61K 31/343* (2013.01); *A61K 31/4025* (2013.01); *A61K 31/4458* (2013.01); *A61K 31/465* (2013.01); *A61K 31/522* (2013.01); *A61K 31/60* (2013.01); *A61K 31/658* (2023.05); *A61K 36/07* (2013.01); *A61K 36/16* (2013.01); *A61K 36/23* (2013.01); *A61K 36/258* (2013.01); *A61K 36/28* (2013.01); *A61K 36/37* (2013.01); *A61K 36/481* (2013.01); *A61K 36/53* (2013.01); *A61K 36/54* (2013.01); *A61K 36/67* (2013.01); *A61K 36/88* (2013.01); *A61K 36/9068* (2013.01)

(58) Field of Classification Search
CPC .......... A61K 9/51; A61K 31/05; A61K 31/13; A61K 31/137; A61K 31/165; A61K 31/343; A61K 31/352; A61K 31/4025; A61K 31/4458; A61K 31/465; A61K 31/522; A61K 31/60; A61K 36/07; A61K 36/16; A61K 36/23; A61K 36/258; A61K 36/28; A61K 36/37; A61K 36/481; A61K 36/53; A61K 36/54; A61K 36/67; A61K 36/88; A61K 36/9068; A61K 36/00; A61K 45/06; A23L 33/10; A23L 33/105
See application file for complete search history.

(56) References Cited

U.S. PATENT DOCUMENTS

| | | | |
|---|---|---|---|
| 5,296,224 | A | 3/1994 | Schwabe |
| 5,332,595 | A | 7/1994 | Gaonkar |
| 6,720,007 | B2 | 4/2004 | Walt et al. |
| 10,028,919 | B2 | 7/2018 | Kaufman |
| (Continued) | | | |

FOREIGN PATENT DOCUMENTS

| | | |
|---|---|---|
| EP | 2201937 A1 | 6/2010 |
| WO | 2010013224 A2 | 2/2010 |
| (Continued) | | |

OTHER PUBLICATIONS

Kesarwani K, Gupta R, Mukerjee A. Bioavailability enhancers of herbal origin: an overview. Asian Pac J Trop Biomed. Apr. 2013;3(4):253-66. doi: 10.1016/S2221-1691(13)60060-X. PMID: 23620848; PMCID: PMC3634921. (Year: 2013).*
Kesarwani_Bioavailability_Enhancers (Year: 2013).*
M. Logozzi, et al., "The Potentiality of Plant-Derived Nanovesicles in Human Health—A Comparison with Human Exosomes and Artificial Nanoparticles," International Journal of Molecular Sciences, Apr. 28, 2022, https://www.ncbi.nlm.nih.gov/pmc/articles/PMC9101147/, 17 pages.

(Continued)

*Primary Examiner* — Michael B. Pallay
(74) *Attorney, Agent, or Firm* — Pillsbury Winthrop Shaw Pittman, LLP

(57) ABSTRACT

Provided is a composition, including: an aqueous suspension, comprising: a first plurality of active ingredients, and one or more nanoparticles, wherein: the one or more nanoparticles encapsulate a second plurality of active ingredients; the second plurality of active ingredients are insoluble in the aqueous suspension; the one or more nanoparticles solubilize the second plurality of active ingredients in the aqueous suspension; and the one or more nanoparticles have a Z-average diameter between 50 to 950 nanometers.

20 Claims, 9 Drawing Sheets

(56) References Cited

U.S. PATENT DOCUMENTS

| | | | |
|---|---|---|---|
| 10,738,268 B2 | 8/2020 | Leo | |
| 10,851,077 B2 | 12/2020 | Durkacz et al. | |
| 10,945,953 B1 | 3/2021 | Moaseri | |
| 11,497,760 B2 | 11/2022 | Saar et al. | |
| 11,497,809 B2 | 11/2022 | Wu et al. | |
| 11,964,049 B2 * | 4/2024 | Moaseri | A61K 36/53 |
| 2002/0086438 A1 | 7/2002 | Elsohly et al. | |
| 2005/0208134 A1 | 9/2005 | Magdassi et al. | |
| 2006/0188534 A1 | 8/2006 | Muller | |
| 2009/0186093 A1 | 7/2009 | Liu et al. | |
| 2010/0068290 A1 | 3/2010 | Ziegler et al. | |
| 2010/0193349 A1 | 8/2010 | Braam | |
| 2010/0255087 A1 | 10/2010 | Coulter | |
| 2011/0021592 A1 | 1/2011 | Magdassi et al. | |
| 2011/0091636 A1 | 4/2011 | Elleman et al. | |
| 2011/0111020 A1 | 5/2011 | Yan et al. | |
| 2011/0182998 A1 | 7/2011 | Reb et al. | |
| 2011/0189298 A1 | 8/2011 | Vos et al. | |
| 2013/0316006 A1 | 11/2013 | Popov et al. | |
| 2014/0037744 A1 | 2/2014 | Buisson et al. | |
| 2014/0154191 A1 | 6/2014 | Doucet | |
| 2015/0104545 A1 | 4/2015 | Dardelle et al. | |
| 2015/0150822 A1 | 6/2015 | Perumal et al. | |
| 2015/0158004 A1 | 6/2015 | Meiners et al. | |
| 2015/0190348 A1 | 7/2015 | Haksar et al. | |
| 2015/0209298 A1 | 7/2015 | Haksar et al. | |
| 2016/0008237 A1 | 1/2016 | Goldstein et al. | |
| 2017/0079921 A1 | 3/2017 | Krishnamurthy et al. | |
| 2017/0157049 A1 | 6/2017 | Dandl et al. | |
| 2017/0281558 A1 | 10/2017 | Castan et al. | |
| 2017/0368022 A1 | 12/2017 | Sorbo et al. | |
| 2018/0296493 A1 | 10/2018 | Kaufman | |
| 2019/0105261 A1 | 4/2019 | Waugh et al. | |
| 2019/0201350 A1 | 7/2019 | White et al. | |
| 2019/0254302 A1 | 8/2019 | Abbaspourrad et al. | |
| 2019/0358169 A1 | 11/2019 | Bishop et al. | |
| 2020/0037638 A1 * | 2/2020 | Faraci | A61K 9/1075 |
| 2020/0079751 A1 | 3/2020 | Durkacz et al. | |
| 2021/0023155 A1 | 1/2021 | Opperman | |
| 2021/0069083 A1 | 3/2021 | Meyer et al. | |
| 2021/0169816 A1 | 6/2021 | Moaseri | |
| 2021/0177754 A1 | 6/2021 | Keller et al. | |
| 2022/0241305 A1 | 8/2022 | Erickson et al. | |
| 2023/0079480 A1 | 3/2023 | Moaseri | |
| 2023/0081296 A1 | 3/2023 | Moaseri | |
| 2023/0082651 A1 | 3/2023 | Moaseri et al. | |
| 2023/0110485 A1 | 4/2023 | Moaseri et al. | |
| 2023/0111190 A1 | 4/2023 | Moaseri et al. | |
| 2023/0111238 A1 | 4/2023 | Moaseri | |
| 2023/0111756 A1 | 4/2023 | Moaseri et al. | |
| 2023/0149829 A1 | 5/2023 | Moaseri | |
| 2023/0157963 A1 | 5/2023 | Moaseri et al. | |
| 2023/0157964 A1 | 5/2023 | Kvitnitsky et al. | |
| 2023/0157973 A1 | 5/2023 | Moaseri et al. | |

FOREIGN PATENT DOCUMENTS

| | | | | |
|---|---|---|---|---|
| WO | 2018/152334 A1 | 8/2018 | | |
| WO | 2018183115 A1 | 10/2018 | | |
| WO | 2019071213 A1 | 4/2019 | | |
| WO | 2019204630 A1 | 10/2019 | | |
| WO | 2020037403 A1 | 2/2020 | | |
| WO | 2020/044116 A1 | 3/2020 | | |
| WO | WO-2020104970 A2 * | 7/2020 | ........... | A23L 33/105 |
| WO | 2020186212 A1 | 9/2020 | | |
| WO | 2022157726 A1 | 7/2022 | | |
| WO | 2022201066 A1 | 9/2022 | | |

OTHER PUBLICATIONS

M. Logozzi, "Nanovesicles from Organic Agriculture—Derived Fruits and Vegetables: Characterization and Functional Antioxidant Content," International Journal of Molecular Sciences, vol. 22, Issue 15, Jul. 29, 2021, https://www.proquest.com/openview/be7c83a60ff36647ad849b10cfa7ef08/1?pq-origsite=gscholar&cbl=2032341, 18 pages.

Extended Search Report for related European Patent Application 20862499.9 received Aug. 4, 2023, 15 pages.

Muschiolik, Gerald, et al., "Double Emulsions Relevant to Food Systems: Preparation, Stability, and Applications: Double emulsions in food," Comprehensive Reviews in Food Science and Food Safety, Institute of food technologists, vol. 16, No. 3, Chicago, IL, May 1, 2017, pp. 532-555, 24 pages.

International Preliminary Report on Patentability for related International Patent Application PCT/US2022/043549 issued on Mar. 28, 2024, 5 pages.

Final Office Action for related U.S. Appl. No. 17/945,038 issued May 22, 2024, 17 pages.

International Search Report and Written Opinion for related International Patent Application PCT/US2022/043549 issued on Jan. 16, 2023, 8 pages.

Peshkovsky, Alexey. "CAN CBD or THC Be Made Water-Soluble?" Can CBD or THC Be Made Water-Soluble?, Jul. 3, 2016, blog. sonomechanics.com/blog/water-soluble-cbd (Year: 2016).

Santamaria-Echart et al. "New Trends in Natural Emulsifiers and Emulsion Technology for the Food Industry" Natural Food Additives, Sep. 1, 2021, https://www.intechopen.com/chapters/78387 (Year: 2021).

Molaveisi, Mohammad, et al. "Controlled Release and Improved Stability of Vitamin D3 Within Nanoliposomes Stabilized by Palmitic Acid." Journal of food safety 41.5 (2021 ): n. pag. Web (Year: 2021).

Non-Final Office Action issued in related U.S. Appl. No. 17/945,038, dated Aug. 11, 2023.

Non-Final Office Action for related U.S. Appl. No. 17/945,037 issued on Jul. 30, 2024, 98 pages.

Dionisio, Marita, et al. "Locust bean gum: Exploring its potential for biopharmaceutical applications," Journal of Pharmacy and Bioallied Sciences, 31 pages [online], 2012, [retrieved on Oct. 30, 2024]. Retrieved from the Internet: <URL: https://pmc.ncbi.nlm.nih.gov/articles/PMC3425165/> <DOI: 10.4103/0975-7406.99013>.

Pateiro, Mirian, et al. "Nanoencapsulation of Promising Bioactive Compounds to Improve Their Absorption, Stability, Functionality and the Appearance of the Final Food Products," molecules, 26 pages [online], 2021 [retrieved on Oct. 30, 2024]. Retrieved from the Internet: <URL: https://www.mdpi.com/1420-3049/26/6/1547> <DOI: 10.3390/molecules26061547>.

Biswas, Sayan, et al. "Optimized piperine-phospholipid complex with enhanced bioavailability and hepatoprotective activity," Pharmaceutical Development and Technology, 6 pages [online], 2021, [retrieved on Oct. 30, 2024]. Retrieved from the Internet: <URL: https://www.tandfonline.com/doi/full/10.1080/10837450.2020.1835956> <DOI: 10.1080/10837450.2020.1835956>.

"Ashwagandha and Rhodiola—Combination," 8 pages [online], 2015 [retrieved on Oct. 30, 2024]. Retrieved from the Internet: <URL: https://88herbs.com/ashwagandha-rhodiola-combination/>.

Napierala, Marta, et al. "Nicotine and caffeine: influence on dopaminergic transmission," abstract, 1 page [online], 2016 [retrieved on Oct. 30, 2024]. Retrieved from the Internet: <URL: https://pubmed.ncbi.nlm.nih.gov/29689686/>.

Non-Final Office Action for related U.S. Appl. No. 17/945,035, issued on Jan. 7, 2025, 40 pages.

Sungpud, C., et al., Ultrasonic-assisted virgin coconut oil based extraction for maximizing polyphenol recovery and bioactivities of mangosteen peels, 2020, J Food Sci Technol., 57( 11 ):4032-4043, 12 pages. <https://doi.org/10.1007 /s 13197-020-04436-z> (Year: 2020).

Wu, J., et al., Ultrasound-assisted extraction of ginseng saponins from ginseng roots and cultured ginseng cells, 2001, Ultrasonics Sonochemistry, 8:347-352, 6 pages. <https://doi.org/10.1016/S1350-4177(01)00066-9> (Year: 2001).

Da Silva, S. B., et al., Chitosan-based nanoparticles for rosmarinic acid oculardelivery-In vitro tests, 2016, Int J Bio Macromolecules, 84:112-120, 9 pages. <dx.doi.org/10.1016/j.ijbiomac.2015.11.070> (Year: 2016).

(56) References Cited

OTHER PUBLICATIONS

Jafarinejad, S., 7—Solid-Waste Management in the Petroleum Industry, 2017, Petroleum Waste Treatment and Pollution Control, pp. 269-345, 7 pages. <https://doi.org/10.1016/B978-0-12-809243-9.00007-9> (Year: 2017).

Majors, R.E., Salting-out liquid-liquid extraction (SALLE), 2009, Chromatography Online, 13 pages. Accessed Dec. 11, 2024. < https://www.chromatographyonline.com/view/salting-out-liquid-liquid-extraction-salle> (Year: 2009).

Singh, T., et al., Application of Nanotechnology in Food Science: Perception and Overview, 2017, Frontiers Microbial., 8:1501, 7 pages. <https://doi.org/10.3389/fmicb.2017.01501> (Year: 2017).

Non-Final Office Action for related U.S. Appl. No. 17/945,038, issued on Feb. 12, 2025, 40 pages.

Nushtaeva, "Natural food-grade solid particles for emulsion stabilization", Colloids and Surfaces A: Physicochem. Eng. Aspects, 2016, 504, 449-457. (Year: 2016).

Non-Final Office Action for related U.S. Appl. No. 17/945,011, issued on Feb. 12, 2025, 79 pages.

Luque de Castro, M.D. and Garcia-Ayuso, L.E .. Soxhlet extraction of solid materials: an outdated technique with a promising innovative future. Analytica Chimica Acta, 369, p. 1-10. (Year: 1998).

Elgie, K.. What is a Rotary Evaporator ?. httos://Awww.asynt.com/blog/what-is-a-rotary-evaporator/, posted Feb. 14, 2022 (Year: 2022).

Chemat, F., Rombaout, N., Sicaire, A-G., Meullemiestre, A., Fabiano-Tixier, A-S., and Abert-Vian, M.. Ultrasound assisted extraction of food and natural products. Mechanisms, techniques, combinations, protocols and applications. A review. Ultrasonics Sonochemistry, 34, p. 540-560. (Year: 2017).

Majekodunmi, S.O.. Review of extraction of medicinal plants for pharmaceutical research. Merit Research Journal of Medicine and Medicinal Sciences, 3, p. 521-527. (Year: 2015).

Prausnitz, P. H.. Fritted Glass Filter Disks. Industrial and Engineering Chemistry, 16, p. 370. (Year: 1924).

Chinapongtitiwat, V., Jongaroontaprangsee, S., Chiewchan, N., Devahastin, S.. Important flavonoids and limonin in selected Thai citrus residues. Journal of Functional Foods, 5, p. 1151-1158. (Year: 2013).

Smith, M.C., Crist, R.M., Clogston, J.D., and McNeil, S.E.. Zeta potential: a case study of cationic, anionic, and neutral liposomes. Anal Bioanal Chem, 409, p. 5779-5787. (Year: 2017).

Final Office Action for related U.S. Appl. No. 17/945,037, issued on Mar. 19, 2025, 27 pages.

"Stomach Acid Test." Mount Sinai Health System, https://web.archive.org/web/20170203235855/https://www.mountsinai.org/health-library/tests/stomach-acid-test. Retrieved Jan. 10, 2024. (Year: 2017).

Melro, Elodie et al. "Chitosan Films in Food Applications. Tuning Film Properties by Changing Acidic Dissolution Conditions." Polymers vol. 13,1 1. Dec. 22, 2020, doi:10.3390/polym13010001 (Year: 2020).

Non-Final Office Action issued for corresponding U.S. Appl. No. 17/944,985, dated Jan. 19, 2024.

Final Office Action issued for corresponding U.S. Appl. No. 17/944,985, dated Oct. 28, 2024.

Pall, Introduction to Tangential Flow Filtration for Laboratory and Process Development Applications, Published 2003 (Year: 2003).

Non-Final Office Action issued for corresponding U.S. Appl. No. 17/945,036, dated Sep. 25, 2024.

Final Office Action for related U.S. Appl. No. 17/945,036, issued on Jun. 12, 2025, 31 pages.

Non-Final Office Action for related U.S. Patent Application 17/944,985, issued on Jun. 17, 2025, 17 pages.

Non-Final Office Action for related U.S. Appl. No. 17/945,012, issued on Jul. 1, 2025, 140 pages.

Final Office Action for related U.S. Appl. No. 17/945,035, issued on Jul. 28, 2025, 36 pages.

Final Rejection issued for Related U.S. Appl. No. 17/945,011, dated Sep. 23, 2025; 33 pages.

Non-Final Office Action Issued in Related U.S. Appl. No. 17/945,037, dated Oct. 1, 2025; 14 pages.

Final Rejection Issued in Related U.S. Appl. No. 17/945,038, dated Nov. 13, 2025; 26 pages.

Non-Final Office Action Issued in Related U.S. Appl. No. 17/945,036, dated Feb. 5, 2026; 13 pages.

Non-Final Office Action Issued in Related U.S. Appl. No. 17/945,001, dated Jan. 26, 2026, 21 pages.

Szukalska, et al. (Nicotine and Caffeine: Influence on Dopaminergic Transmission, 2016). Year: 2016.

Ovadia, et al. (Journal of Pharmaceutical Sciences, 1965, vol. 54, pp. 1013-1016) Year: 1965.

Stearic Acid SDS obtained from ThermoFisher (Jun. 2, 2014), pp. 1-8 (Year: 2014).

Krave Beauty, "Should I Refrigerate My Skincare?", 2019, pp. 1-3 (Year: 2019).

https://88herbs.com/ashwagandha-rhodiola-combination/ (Year: 2015).

Final Office Action Issued in U.S. Appl. No. 17/945,012, dated Mar. 19, 2026, 25 pages.

Non-Final Office Action Issued in U.S. Appl. No. 17/945,011, dated Apr. 21, 2026, 26 pages.

Non-Final Office Action Issued in U.S. Appl. No. 17/945,038, dated May 6, 2026, 33 pages.

Final Office Action Issued in U.S. Appl. No. 17/945,037, dated May 13, 2026, 14 pages.

Final Office Action Issued in U.S. Appl. No. 18/168,394, dated May 18, 2026, 126 pages.

Kesarwani, "Bioavailability Enhancers of Herbal Origin: An Overview," Asian Pacific Journal of Tropical Biomedicine, 3 (4): pp. 253-266, 2013.

Dionisio, et al. "Locust Bean Gum: Exploring Its Potential for Biopharmaceutical Applications," J. Pharm Bioallied Sci, 2012.

Biswas, et al., "Optimized Piperine-Phospholipid Complex with Enhanced Bioavailability and Hepatoprotective Activity," Pharmaceutical Development and Technology, 2021.

Pateiro, et al., Nanoencapsulation of Promising Bioactive Compounds to Improve Their Absorption, Stability, Functionality, and the Apperance of the Final Food Products; Molecules, 2021.

Abbaspoor, Sogand, Ali Ashrafi, and Mehdi Salehi, "Synthesis and Characterization of Ethyl Cellulose Micro/ Nanocapsules Using Solvent Evaporation Method," Colloid and Polymer Science 296.9 (2018): 1509-1514.

Tepsongkroh, Benjarat, et al., "Influence of Polyglycerol Polyricinoleate and Biopolymers on Physical Properties and Encapsulation Efficiency of Water-In-Oil-In-Water Emulsions Containing Mango Seed Kernel Extract," Journal of Dispersion Science and Technology 36.8 (2015): 1126-1133.

Vergallo, Cristian, "Nutraceutical Vegetable Oil Nanoformulations for Prevention and Management of Diseases," Nanomaterials 10.6 (2020): 1232.

Fundueanu, Gheorghe, et al., "Preparation and Characterization of Ca-alginate Microspheres by a New Emulsification Method," International Journal of Pharmaceutics 170.1 (1998): 11-21.

Zidan, Ahmed, Osama AA Ahmed, and Bader M. Ajaeid, "Nicotinamide Polymeric Nanoemulsified Systems: A Quality-By-Design Case Study for a Sustained Antimicrobial Activity," International Journal of Nanomedicine (2016): 1501-1516.

Mu, Li and Shi-Shen Feng, "Vitamin E-TPGS Used as Emulsifier in the Solvent Evaporation/Extraction Technique for Fabrication of Polymeric Nanospheres for Controlled Release Paclitaxel (TaxolA)," Journal of Controlled Release 80.1-3 (2002): 129-144.

* cited by examiner

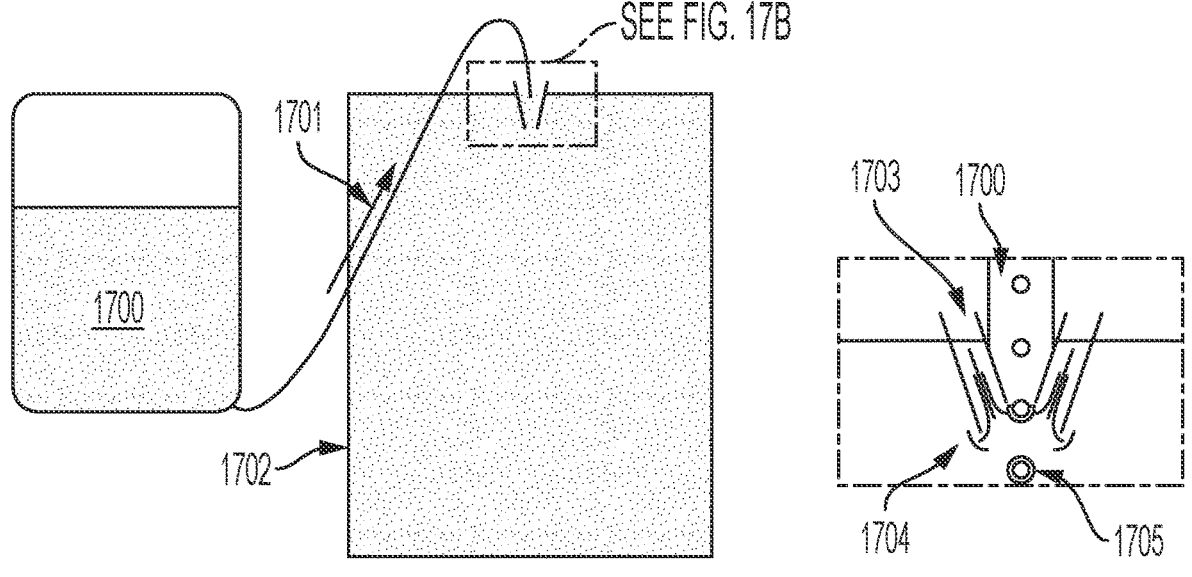
FIG. 17A                    FIG. 17B

STABLE COMPOSITIONS OF FUNCTIONAL INGREDIENTS AND METHODS OF MAKING THE SAME

CROSS-REFERENCE TO RELATED APPLICATIONS

The present application claims the benefit of the three following provisional patent applications: U.S. Provisional Patent Application 63/244,105, titled ALIMENTARY-RELATED PARTICLES, PRODUCTION METHODS, AND PRODUCTION APPARATUS, filed 14 Sep. 2021; U.S. Provisional Patent Application 63/356,389, titled STABLE COMPOSITIONS OF FUNCTIONAL INGREDIENTS AND METHODS OF MAKING THE SAME, filed 28 Jun. 2022; and U.S. Provisional Patent Application 63/321,596, titled ALIMENTARY-RELATED PARTICLES, PRODUCTION METHODS, AND PRODUCTION APPARATUS, filed 18 Mar. 2022. The entire content of each aforementioned patent filing is hereby incorporated by reference.

BACKGROUND

1. Field

The present disclosure relates generally alimentary products containing nutrients or other payloads, methods of making the same, and devices for making the same.

2. Description of the Related Art

Encapsulation of one substance in another may take a variety of forms. Often, encapsulation involves entrapping or otherwise enveloping a liquid, solid, or gas (referred to as the core material, internal phase, first phase, or payload, interchangeably) in an enclosing material commonly referred to as the carrier, particle, shell, wall, capsule, or membrane interchangeably, as a delivery platform to transport nutrients to the body. Historically, certain types of encapsulations, and particularly those with limited or no mouthfeel imparted by capsules, were regarded as commercially infeasible in the food and beverage industry for many use cases due to cost, shelf stability, limited delivery, and various other challenges.

SUMMARY

Aspects include a composition, including: an aqueous suspension, comprising: a first plurality of active ingredients, and one or more nanoparticles, wherein: the one or more nanoparticles encapsulate a second plurality of active ingredients; the second plurality of active ingredients are insoluble in the aqueous suspension; the one or more nanoparticles solubilize the second plurality of active ingredients in the aqueous suspension; and the one or more nanoparticles have a Z-average diameter between 50 to 950 nanometers.

Aspects include a method of making and using the above-described composition.

BRIEF DESCRIPTION OF THE DRAWINGS

Aspects of the present techniques will be better understood when the present application is read in view of the following figures in which like numbers indicate similar or identical elements:

FIG. 17A is a schematic diagram that illustrates an example of a production process of a particle aggregate, in accordance with some embodiments.

FIG. 17B is an enlarged view of a portion of FIG. 17A.

Figure 1:
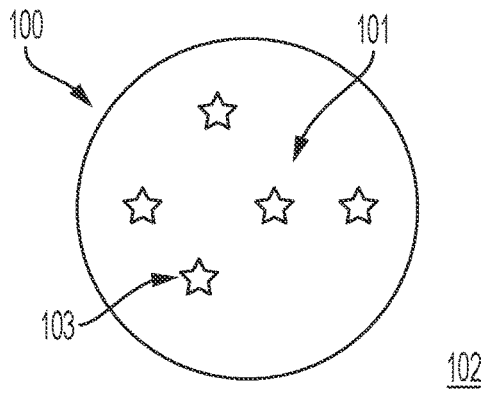
FIG. 1 is a schematic diagram that illustrates an example of a single-phase particle, in accordance with some embodiments.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the fields of food, beverage, supplements, nutraceuticals, and related industries. Indeed, the inventors wish to emphasize the difficulty of recognizing those problems that are nascent and will become much more apparent in the future should trends in industry continue as the inventors expect. Further, because multiple problems are addressed, some of the present embodiments are problem-specific, and not all embodiments address every problem with traditional systems described herein or provide every benefit described herein. That said, improvements that solve various permutations of these problems are described below.

This patent filing extends on the techniques described in U.S. patent application Ser. No. 17/020,729, titled WATER SOLUBLE COMPOSITIONS AND METHODS OF MAKING THE SAME, filed 14 Sep. 2020, and the techniques described herein may be implemented in the products described therein, with the equipment described therein, using the processes described therein, as modified below. The entire content of U.S. patent application Ser. No. 17/020,729 is hereby incorporated by reference for all purposes.

1. Introduction

Some forms of encapsulation are used in pharmaceuticals for various purposes. For example, particles with controlled-release mechanisms are used to provide a steady delivery of drugs to the body. Other examples include using smart particles, containing cancer drugs. These techniques, however, are generally not suitable for use in the food and beverage industry due to the high cost of manufacturing, expensive materials required for encapsulation, differences in host environments in which the encapsulated materials are deployed, and differences in the materials being encapsulated.

To the extent encapsulation technology is used in food and beverage industry, generally, the particles are either too large (e.g., may be felt in the mouth of the user, often with particles so large as to induce unpleasant sensory experience) or are only capable of encapsulating a limited number of ingredients, in certain host materials, in limited ranges of concentration. An example is microencapsulation of fish oils to fortify bread. Such encapsulation often mitigates or eliminates the fishy aroma and taste of such oils, with an added benefit of less susceptibility to oxidation and less development of rancidity. However, techniques to manufacture such particles are generally capable of encapsulating only water-insoluble cargoes. Another example is cannabidiol (CBD)-infused beverages wherein an emulsion of CBD particles is stabilized in water via various types of surfactants. Emulsification techniques, used to manufacture CBD-infused beverages, generally may produce stable emulsions with particles only in the size range of tens of nanometers. Bigger particles often may not be stabilized with this technique because the stabilizer agent used in these techniques are small molecule surfactants that cannot stabilize particles in the size range of hundreds of microns. This is believed to limit the amount of cargo that may be encapsulated and added into a beverage. In addition, many of these techniques are also limited to encapsulation of water-insoluble cargoes. Finally, some approaches used in pharmaceuticals may not use encapsulants that are generally regarded as safe (GRAS) by the Food and Drug Administration. (None of which is to suggest that embodiments also suffering from these issues are disclaimed or that the preceding, or any other, discussion of tradeoffs herein constitutes a disclaimer.)

Thus, many existing approaches to encapsulate ingredients are too expensive, have short shelf-life, or produce particles that are too large to remain un-noticed by the consumer. A need exists for a technique for manufacturing small particles (e.g., such that mouthfeel is unaffected), capable of encapsulating a variety of water-insoluble and water-miscible ingredients, which may be dispersed in a variety of mediums, is cost-compatible with margins in the food and beverage industry, and produces a smaller or no change in the mouthfeel and quality of the host material, which is not to suggest that embodiments are limited to approaches that address all of these needs or that any other description herein is limiting.

2. Example Particles

1. Example Attributes of Products

Different types of particles are described herein. Properties of various embodiments of such particles follow. Discussion of a particle having a property should not be attributed to all embodiments of particles, which is not to suggest that any other description is limiting.

In some embodiments, particles containing (e.g., encapsulating) a variety of ingredients may be produced. In some embodiments, particles may be produced as a product themselves. In some embodiments, particles containing a variety of ingredients may be incorporated into a product, like a host beverage, food product, skin-care product, nutraceutical product, beauty product, or the like. In some embodiments, particles containing a variety of ingredients may be produced and utilized as ingredient within a product (produced together concurrently or sequentially). In some embodiments, a collection of particles may include different kinds of particles with different properties, as discussed below.

In some embodiments, the particles are expected to mask the flavor of the encapsulated ingredients, control the release kinetics of the encapsulated ingredients after consumption, control the delivery location (e.g., organ) of the encapsulated ingredients, stabilize the encapsulated ingredients in the host material, prolong the shelf life of the encapsulated ingredients, expedite the absorption kinetics (e.g., onset time) after consumption, or enhance the bioavailability of the encapsulated ingredients.

In some embodiments, the particles are expected to mask the flavor (e.g., partial masking or full masking) of the encapsulated ingredients (or some of the ingredients), in some cases making the taste of those ingredients almost unnoticeable for the consumer according to measures discussed below. For example, some embodiments are expected to mask the bitter taste of kanna (*Sceletium tortuosum*) in a beverage (e.g., water, juice, soda, or other mixers) by encapsulating the kanna extract in the particles, dispersed in a host beverage, by maintaining a barrier between the kanna extract (e.g., molecules such as mesembrine) and the consumer's taste buds, until the particles rupture or dissolve in the digestive tract to release their encapsulants. In some embodiments, only some of the kanna may be encapsulated to partially mitigate the taste. In some embodiments, the taste of kanna is expected to be reduced for a given concentration of kanna in a beverage. For instance, when tested by a panel of adult subjects given a blind taste test, it is expected that more than half will report a lower-concentration of kanna in a beverage subject to the present treatment relative to a control beverage with substantially the same concentration of kanna (e.g., within 5%)—a test protocol that applies to other assertions of change in taste where unless another protocol is specified.

In some embodiments, particles may delay release of encapsulated ingredients into a continuous media where the particles are dispersed, like a host beverage or carrier liquid. In some embodiments, delayed release of encapsulated ingredients from particles may be used to mask the flavor of the encapsulated components (e.g., active ingredients). In some embodiments, delayed release of encapsulated ingredients from particles may be used to slow down the digestion and absorption of the encapsulated ingredients inside the body.

In some embodiments, particles (e.g., exterior surfaces thereof, like shells) may be composed of pH triggered materials as ingredients, whereby the particles release the encapsulated ingredients (e.g., interior to such shells) in media with specific pH ranges. In some embodiments, particles may be tuned to release the encapsulated ingredients in acidic environment of the stomach or the intestine. In some embodiments, the particles are made of enzyme-digestible materials, whereby the particles release the encapsulated ingredients in presence of enzymes. In some cases, such enzymes are available enzymes in the digestive tract. In some embodiments, the particles are made of materials that dissolve in presence of digestive juices from the pancreas, liver, and intestine, thereby releasing the encapsulated ingredients. In some embodiments, particles may be composed of ingredients expected to keep certain active ingredients encapsulated in the particles and to keep particles stable while dispersed in continuous media with acidic pH (e.g., pH 1, 2, 3, or 4), while those same ingredients from which the particles are composed may dissolve in the same or other continuous media with higher pH (e.g., 5, 6, 7, 8, 9, or 10), thereby releasing the encapsulated ingredients into the continuous media and degrading the particles in which they were previously encapsulated.

In some embodiments, particles may be composed of ingredients expected to protect an encapsulated ingredient from structural damage before or after consumption. For example, probiotics may be damaged and deactivated in acidic environment of the digestive tract before reaching the small intestine. By encapsulating probiotics, embodiments of particles described below expected deliver probiotics without any (or with reduced) damage before reaching the small intestine by preventing or impeding a direct interaction between the probiotics and the digestive tract until the particle reaches the small intestine and starts releasing the encapsulated probiotics. In some embodiments, particles may be made of (full particle or only some of the layers of the particle) a polymer which degrades in the presence of bacterial enzymes with a pH-independent polymer. Such polymers may control the release of the encapsulants in a pre-determined site of the digestive tract (e.g., in the distal large intestine, beginning at the cecum, and continuing through the ascending, transverse, and descending colon, and ending in the sigmoid colon.)

In some embodiments, particles may keep an immiscible component dispersed in a host solution. For example, cannabidiol (CBD) oil, a lipophilic ingredient, is immiscible in a variety of water-based beverages, like water, sodas, beer, wine, liquor, fruit juice, seltzer, smoothies, kombucha, and the like. By encapsulating CBD oil, a stable dispersion of CBD oil droplets, encapsulated inside a polymeric shell, in a water-based beverage is expected to be obtainable (e.g., with less than half of the CBD oil separating out at a 1% concentration by mass over one week at room temperature). In some embodiments, particles have a hydrophilic exterior that may increase the immiscible component concentration within a host solution (continuous medium, external to particles) such that the dispersed particles act to indirectly make the immiscible component soluble (e.g., component is regarded as soluble if more than a 0.1% concentration by mass is stable at room temperature, unless another criterion for solubility is specified by industry standards for a particular host beverage at issue, in which case the industry practice governs) and dispersible in water-based solutions.

In some embodiments, particles are expected to prolong the shelf life of encapsulants (relative to un-encapsulated version of encapsulated ingredients) by protecting the encapsulants from direct interaction with the surrounding medium. For example, particles may hinder exposure of the encapsulants to moisture or oxygen and prolong the shelf life.

In some embodiments, particle dispersions are expected to increase the bioavailability of the encapsulated active ingredients. For example, bioavailability of cannabidiol (CBD) oil is increased by encapsulating the CBD oil in water soluble small particles (e.g., 50 nm, 100 nm, or 200 nm). In some embodiments, a bioavailability of an ingredient may be increased by encapsulating the ingredient in a particle that has bioavailability enhancer compounds.

In some embodiments, particles may be added to, formed within, or contain, various host food or beverage products or other alimentary products. In some embodiments, these particles may be added to, formed within, or contain various drugs and other pharmaceutical products. As an example, some active ingredients may have limited shelf life before consumption such as nicotinamide riboside which is known to degrade in aqueous solutions. In some embodiments, nicotinamide riboside may be encapsulated in the particles to prevent any direct interaction between nicotinamide riboside and the surrounding aqueous medium before consumption to extend the shelf life of an aqueous-based product containing Nicotinamide Riboside, an exemplar hydrophilic active ingredient. After consumption, particles may be dissolved in the digestive tract, releasing the nicotinamide riboside for absorption.

A particle is referred to as globular if the length-width ratio (meaning the ratio of the length (largest dimension) of the particle divided by the width (smallest dimension) which is fixed at an angle of 90° in relation to the length) is less than about 10. The length-width ratio of a globular particle may be less than about 5, 2, 1.8, 1.5, 1.2, or 1.1. Some embodiments have globular particles.

In some embodiments, a particle may be a capsule having a boundary wall (e.g., shell) that defines (and separates) an interior and exterior of the respective capsule. In some embodiments, the boundary shell may have multiple layers.

In some embodiments, a particle may be made of droplets. In some embodiments, a particle may be formed of a droplet with a stabilizing layer covering the droplet at the interface between the droplet and surrounding medium. In some embodiments, a particle may be covered by a stabilizing layer such as a polymeric shell. In some embodiments, a particle may be covered by a stabilizing layer formed by interface stabilizing agents, such as a surfactant, coated on the droplet. In some embodiments, the stabilizing layer may be made of an impermeable material. For example, a droplet of aqueous solution may be covered by a layer of oil acting as the boundary wall. In some embodiments, the stabilizing layer may be formed of a plurality of above-mentioned embodiments.

In some embodiments, a particle may contain some active ingredients, referred to as the encapsulants, and some non-active ingredients, referred to as fillers.

In some embodiments, particles may have a boundary wall that defines (and separates) an interior and exterior of the respective particle. The interior may contain an "encapsulant," which is the material inside the particle's boundary, as distinct from the boundary wall itself.

In some embodiments, particles may possess a boundary wall that defines (and separates) an interior and exterior of the respective particle is made of encapsulant. In some embodiments, particles may have a boundary wall that defines (and separates) an interior and exterior of the respective particle is partially made of encapsulant. For example, droplets of *Bacopa monnieri* (*bacopa*) extracts may be formed in an aqueous solution and the droplet may be stabilized by stabilizing agents. In this example, the boundary may include (or consist of) a stabilizing agent and some compounds of the *bacopa* extract.

In some embodiments, particles may have a boundary wall that defines (and separates) an interior and exterior of the respective particle made of, at least in part, a polymeric shell. In some embodiments, particles may contain a concentration gradient of the encapsulants in the boundary wall. In some embodiments, particles may contain a concentration of the encapsulants that decreases across the boundary wall with higher concentration in regions of the boundary wall closer to the interior and lower concentrations in the regions of the boundary wall closer to the exterior of the particle. In some embodiments, particles may contain a concentration of the encapsulants that increases across the boundary wall exterior to the interior of the particle (to the center of the particle or up to the surface of a sphere of smaller radius, concentric with the particles under consideration)

In some embodiments, particles may not have a defined boundary wall and the encapsulants might be distributed (e.g., evenly) throughout the particle. A particle may be made of inactive ingredients or filler that serves to retain the shape of the particle while maintaining the encapsulants inside the particle. Inactive ingredients are not limited to those ingredients that are inert. Rather, the term distinguishes these ingredients from the active ingredient causing the effect the particle is configured to deliver. In some embodiments, particles may exhibit no chemical or electrical (e.g., ion sharing) reactions between the fillers and the encapsulants. In some embodiments, particles may exhibit chemical or electrical (e.g., ion sharing) interactions between the fillers and the encapsulants (agar as the filler and zinc cations as encapsulants). In some embodiments, particles may be held together (stabilized) and the encapsulants are retained within the particles by the structural framework provided by the fillers.

In some embodiments, a product (or formulation, formula, particle dispersion) may be a phase mixture or a structure of molecules designed and synthesized (or otherwise formed) within a phase or phase mixture, to be administered to an organism or intended to serve a function influencing an organism or other product (in part or in whole) by design. In some embodiments, a product may be created, design or used to achieve intended effects that cannot be obtained from its components (e.g., ingredients) when the components are used in isolation, individually, or singly. In some embodiments, a product may be created, designed, or used to achieve a higher degree of effectiveness for achieving desired properties of composite ingredients after application, formation, administration, storage, exposure to stimuli (e.g., air and light), or combinations thereof 2. Example Phases 2.1. Examples of Attributes of Phases In some embodiments, a phase may be a product such as a product composed of a single ingredient functioning as a phase. In some embodiments, a phase mixture may, similarly, be a product.

In some embodiments, a phase may be a region of space throughout which all physical properties of a material are essentially uniform including categorization of phases into equilibrium phases (stable), quasi-equilibrium phases (meta-stable), nonequilibrium phases (dynamic and irreversible), and time-periodic phases (dynamic and reversible). In some embodiments, a phase may be a nonequilibrium phase or time-periodic phase when specified as such or during processes specified and their exclusion is not intended to preclude their existence but to simplify description of the structures and processes and emphasize the importance of the other categories considered, equilibrium phases and quasi-equilibrium phases (metastable phases). In some embodiments, all phases are assumed to be equilibrium phases or quasi-equilibrium phases unless stated otherwise.

In some embodiments, a phase may be an equilibrium phase (and spatially uniform phase) such that it exists in a particular state of matter including solid, liquid, gas, or plasma. In some embodiments, a phase may be a quasi-equilibrium phase and is treated as an equilibrium phase and behaves like an equilibrium phase over the time interval between preparation of the phase and use of the phase for intended purpose (e.g., administration of a product purchased commercially). In some embodiments, a phase may be composed of heterogeneously distributed pair-wise states of matter (solid, liquid, gas, plasma) and is considered a nonequilibrium phase such as a phase undergoing a change in state of matter in transition between two equilibrium or quasi-equilibrium states of matter.

In some embodiments, a phase may be continuous (connected) within a product volume such that a path may be drawn within the product volume (or, if product volume is separated into disjoint containers, a path may be drawn within the confines of each container holding the product) between every two possible choices of sub-volumes within a phase while not crossing interfaces between phases or through a different intermediate phase. In some embodiments, a phase may be contained within a volume that may itself be a sub-volume of the phase without any loss of generality for the case of homogeneous equilibrium and quasi-equilibrium phases considered.

In some embodiments, a phase may be a continuous phase composed of media that is considered continuously connected such that the entirety of the product containing the phase and if distributed amongst disjoint macroscopic containers, within each container across which a continuous phase is partitioned.

In some embodiments, a phase may be dispersed (disconnected, disjoint) within a product volume such that a path cannot be drawn in the product volume (or, if product volume is separated into disjoint containers, within every container holding the product) between every two possible choices of sub-volumes of the phase without crossing interfaces between phases or crossing into different phases.

In some embodiments, a phase may be dispersed (not-connected, disjoint) and referred to as a dispersed phase. In some embodiments, phases are assumed homogeneously distributed in time-averaged (average of molecular disorder) spatial sub-volumes of the phase up to spatial translations and rotations, and thus homogeneous, unless stated otherwise.

In some embodiments, a phase may be isotropic such that there are no changes in structure under spatial operations of translation, reflection, or rotation within the phase. In some embodiments, a phase may not be isotropic and is called anisotropic.

2.2. Examples of Phase Composition

In some embodiments, a phase may include ingredients and portions of ingredients that function as a phase medium or multiple phase media, such as olive oil or coconut milk, respectively. In some embodiments, a phase medium may be a solvent, gas, liquid, solid, semi-solid, plasma, cosolvent, and combinations thereof.

In some embodiments, a phase may include ingredients and portions of ingredients that function as a phase stabilizer incorporated to change mechanical and chemical properties of phase and phase-phase interfaces, such as phase matrices, phase surfactants, phase emulsifiers, and phase processing aids.

In some embodiments, a phase solute may be an ingredient or any substance that is soluble and forms a homogeneous solution with the phase media and phase media stabilizers within a phase such that the ingredient or substance may be dissolved (solubilized). In some embodiments, a phase solute may be a phase stabilizer as well. In some embodiments, a phase solute may be an interface stabilizer. In some embodiments, a phase solute may be a processing aid.

In some embodiments, a phase solvent may be a phase medium. In some embodiments, a phase solvent may be a phase medium and any dissolved ingredient or substances in a phase.

In some embodiments, a phase or component of a phase may be a processing aid such as ethanol or an interface stabilizing agent.

In some embodiments, a phase may exist as different states of matter as a function of temperature, pressure, and concentration of phase stabilizers and phase solutes, relative to concentration of phase media.

In some embodiments, a phase may be a pure phase composed of a single molecular species. In some embodiments, a phase may be entirely composed of a pure phase medium. In some embodiments, a phase medium may be a pure phase medium composed of a single molecular species. In some embodiments, a phase solute may be a pure phase solute composed of a single molecular species. In some embodiments, a phase stabilizer may be a pure phase stabilizer composed of a single molecular species. In some embodiments, an interface stabilizer may be a pure interface stabilizer composed of a single molecular species. In some embodiments, processing agent may be a pure processing agent composed of a single molecular species. In some embodiments, a pure material may be any material where the material has less than 5% by mass impurities, unless stated otherwise.

In some embodiments, a phase and components thereof may be a composed of two or more molecular, macromolecular, or material species, including other phases.

In some embodiments, a phase mixture may be a single phase. In some embodiments, a phase mixture may be composed of multiple phases regardless of their mutual miscibility and dynamics upon mixing.

2.3. States of Some Embodiments and Components Thereof
2.3.1. Gases, Subcritical Fluids, Supercritical Fluids, Plasmas & Vacuums In some embodiments, a phase or phase mixture may possess a state of matter categorized as fluid where the phase continuously deforms or flows under an applied shear stress or other external force such as a liquid or gas. In some embodiments, a phase or phase mixture may be a compressible fluid such that the phase or phase mixture experiences a volume reduction or change in density upon the application of pressure or at supersonic velocities such as carbon dioxide. In some embodiments, a phase or phase mixture may be an incompressible fluid such that the phase or phase mixture experiences negligible variations in volume and density with changes in pressure or flow velocity such as water or oil. In some embodiments, an incompressible fluid may be treated as a compressible fluid when the variations in volume and density with changes in pressure or flow velocity impact the formation and structure of the fluid.

In some embodiments, a phase or phase mixture may possess a state of matter of gas such as carbon dioxide ($CO_2$), oxygen, air, argon, nitrogen, neon, hydrogen, helium. In some embodiments, a phase or phase mixture may possess a state of matter categorized as gas where the phase is a compressible fluid.

In some embodiments, a phase or phase mixture may be a gas (e.g., air, $CO_2$, nitrogen, forming gas) may be added or removed (e.g., vacuum), serving as either an ingredient or processing aid for the process of formulation synthesis.

In some embodiments, a phase or phase mixture may be a supercritical fluid (e.g., supercritical $CO_2$) may be an ingredient or processing aid. An example is addition of a supercritical $CO_2$ extract of *Piper methysticum* dried plant matter as an ingredient in a product to incorporate a broad spectrum of contained phytochemicals such as kavalactones and kavaflavones.

In some embodiments, a phase or phase mixture may be a subcritical fluid (e.g., subcritical $CO_2$) may be an ingredient or processing aid. An example is addition of a subcritical $CO_2$ extract of Lion's Mane fruiting bodies as an ingredient in a product to incorporate maximal amounts of temperature sensitive erinacines and hericenones.

In some embodiments, a phase or phase mixture may be in a plasma state of matter and called a plasma when the phase is an ionized substance with high electrical conductivity possessing gaseous behavior.

2.3.2. Liquids

In some embodiments, a phase or phase mixture may possess a state of matter categorized as liquid where the phase is an incompressible or nearly incompressible fluid that conforms to the shape of the vessel containing the component and the component retains a near constant volume with variations in external pressure, far from any transitions between states of matter called phase transitions. In some embodiments, a phase or phase mixture may possess a state of matter categorized as a liquid where the phase is an incompressible fluid.

In some embodiments, a phase or phase mixture may be a liquid, such as ethanol, may be added, removed or a combination thereof, and acts as an ingredient, part of the process of formulation synthesis, or both. In some embodiments, a processing aid or ingredient may be a liquid.

In some embodiments, a phase or phase mixture may be a fluid with a known compressibility and be a gas or liquid state of matter.

In some embodiments, a phase or phase mixture may be a fluid with a known Reynolds number (ratio of inertial forces to viscous forces) and be a gas or liquid state of matter.

In some embodiments, a phase or phase mixture may be a fluid with a known viscosity and be a gas or liquid state of matter.

In some embodiments, a phase or phase mixture may be a fluid with a known turbulence and be a gas or liquid state of matter.

In some embodiments, a phase or phase mixture may be a fluid with a known boundary layer and be a gas or liquid state of matter.

In some embodiments, a phase or phase mixture may be a supercooled liquid or supercooled gas such that the liquid or gas phase is below the temperature required to freeze or deposit, respectively, but exists in a metastable (quasi-equilibrium) state that is stabilized kinetically.

2.3.3. Solids & Semisolids

In some embodiments, a phase or phase mixture may possess a state of matter called a solid. In some embodiments, an ingredient may be a solid in a solid state of matter. A solid (solid state of matter) is a state of matter that does not flow to take the shape of contains nor expand to fill a contained volume like liquids and gases, respectively.

In some embodiments, a phase or phase mixture may be a solid, semi-solid, crystalline solid, polycrystalline solid, glass, gel, network, or amorphous solid serves as an ingredient or participant in the formulation synthesis, or both.

In some embodiments, a phase or phase mixture may be in a state of matter called a gel. In some embodiments, a phase may be in a state of matter called a polymer gel where the network component of the gel is a polymer.

In some embodiments, a phase or phase mixture may be in a state of matter with properties intermediate to properties characteristic of liquid and solid states of matter such that a single property or multiple properties characteristic of both liquid and solid states of matter are possess simultaneously or during particle and product formation such as liquid crystals and gels.

In some embodiments, a phase or phase mixture may be in a solid state of matter and may not also be in a liquid or gas state of matter. In some embodiments, a phase may be in a liquid state of matter and may not also be in a solid or gas state of matter. In some embodiments, a phase may be in a gas state of matter and may not also be in a solid or liquid state of matter.

In some embodiments, a phase or phase mixture may be in a solid or liquid-solid intermediate state of matter that is called a liquid phase when exhibiting characteristic physio-chemical properties associated with liquid states of matter for either clearly illustrating an aspect of or process associated with the embodiment or based on possessing more physiochemical properties, and magnitudes thereof, shared with properties of liquids than with properties of solids.

In some embodiments, a phase or phase mixture may be in a glass state of matter or may be a glass such that the phase is non-crystalline, amorphous and possesses a glass transition.

In some embodiments, a phase or phase mixture may be in a crystalline solid state of matter or may be a crystalline solid such that the composite atoms, molecules, or ions are organized in a spatially repetitive order.

In some embodiments, a phase or phase mixture may be in a polycrystalline solid state of matter or may be a polycrystalline solid such that the composite atoms, molecules, or ions are organized in a spatially repetitive order in sets of sub-volumes throughout the phase while disordered between the sub-volumes. In other words, a phase may be a polycrystalline solid if it is composed of crystalline regions between which there is rotational disorder and there may exist a distribution in total volume of each crystalline region.

In some embodiments, a phase or phase mixture may be a plastic crystalline solid state of matter or may be a plastic crystalline solid or plastic crystal such that the phase possesses long-range positional order in its organization but amongst the positions that are crystalline, the constituent species have rotational freedom and disorder, such as some organic crystals.

In some embodiments, a phase or phase mixture may be a quasi-crystalline solid state of matter or may be a quasi-crystalline solid or quasi-crystal such that the phase possesses long-range order but with no spatial repetition characteristic of crystals.

In some embodiments, a phase or phase mixture may be in an amorphous solid state of matter or may be an amorphous solid such that the composite atoms, molecules, or ions have no long-range positional order to their spatially organization.

In some embodiments, a phase or phase mixture may be in a solid or liquid-solid intermediate state of matter that is disordered (limited spatial repetition in structure or lack of repetition in spatial structure). In some embodiments, a phase or phase mixture may be in a solid or liquid-solid intermediate state of matter that is partially ordered or ordered.

In some embodiments, a phase or phase mixture may be a semi-solid or quasi-solid such that the phase holds its shape like a solid but possesses properties of a liquid such as conforming in shape and flowing in response to applied pressure.

In some embodiments, a phase or phase mixture may be partially ordered or ordered such that the phases and chemical structures of the phase within a volume demonstrate repetitive spatial structure by translation and rotation. In some embodiments, a partially ordered or ordered sub-volume of a phase may be the entire phase volume. In some embodiments, a partially ordered or ordered sub-volume of a phase may be a volume with at least one spatial dimension extent greater than three lengths of the smallest dimension of highest molecular mass molecule (or macromolecule) contained with structural repetition of atoms throughout. In some embodiments, a partially ordered or ordered sub-volume of a product may contain repetitive distributions of phases and interfaces between phases.

In some embodiments, a partially ordered or ordered sub-volume of a phase or phase mixture may have regions with ordered atomic structure while other regions are disordered in their atomic positions.

In some embodiments, a phase or phase mixture may be in a solid or liquid-solid intermediate state of matter that is a disordered, partially ordered, or ordered gelatin.

In some embodiments, a phase or phase mixture may be in a solid or liquid-solid intermediate state of matter that is a disordered, partially ordered, or ordered gel. In some embodiments, a phase or phase mixture may be a gel such that it is a nonfluid colloid or polymer network spanning the volume of the phase with fluid filling the whole phase volume as a component of the phase. In some embodiments, a gel may contain particulate (or particle) disordered structures such as metal oxide and silicate gels or fibrillar protein gels. In some embodiments, a gel may contain lamellar structures including mesophases such as phospholipids and clays. In some embodiments, a gel may contain a polymer network formed through glassy junction points such as block copolymers. In some embodiments, a gel may contain a polymer network formed through the physical aggregation of polymer chains via hydrogen boning, crystallization, superstructure formation (like, helix or beta-sheet formation), complexation, covalent or ionic crosslinking, and combinations thereof. In some embodiments, a gel may contain a covalent polymer network such as crosslinked polymer chains or via nonlinear polymerization. In some embodiments, a gel may be a hydrogel where the fluid portion of the phase is liquid water. In some embodiments, a gel may be an organogel where the fluid portion of the phase is an organic liquid such as ethanol or terpenes. In some embodiments, a gel may be a xerogel where the fluid portion of the phase has been removed after forming the gel phase network. In some embodiments, a gel may be an aerogel where the fluid portion of the phase is a gas such as air or carbon dioxide.

In some embodiments, a phase or phase mixture may be in a solid or liquid-solid intermediate state of matter that is a disordered, partially ordered, or ordered lipid structure, such as a lipid bilayer, a vesicle, a micelle, a lipid nanorod, or other documented structures of lipids.

In some embodiments, a phase or phase mixture may be may be in a solid or liquid-solid intermediate state of matter that is a disordered, partially ordered, or ordered liquid crystalline phase. In some embodiments, the liquid crystalline phase is referred to as a nematic phase when less ordered and behaves more similarly to a liquid phase. In some embodiments, the liquid crystalline phase is referred to as a smectic phase when the constituent molecules are rod-shaped in the abstract (one-dimensional in spatial extent), possess more long-range orientational order along the long axis of the rod-shaped molecules, demonstrate more short-range positional order, and behaves more similarly to a solid phase. In some embodiments, the liquid crystalline phase is referred to as a columnar phase when the constituent molecules are disk-shaped in the abstract (two-dimensional in spatial extent), possess more long-range orientational order along the long axis of the rod-shaped molecules, demonstrate more short-range positional order, and behaves more similarly to a solid phase.

3. Examples of Phase Properties & Attributes

In some embodiments, a phase or phase mixture may have physical properties that are intensive, called intensive properties, and do not depend on the size, total volume, or total mass of the phase the property describes.

In some embodiments, a phase or phase mixture may possess properties that are homogeneously distributed throughout the volume. In some embodiments, properties of phases and phases are assumed to be homogeneously distributed unless stated otherwise. In some embodiments, a property describing a phase may be heterogeneously or non-uniformly distributed and is indicated as such.

In some embodiments, a phase or phase mixture may possess an intensive property, including examples such as temperature (t, positive real valued), refractive index (n, complex valued), density (rho, positive real valued), specific gravity, chemical potential, vapor pressure, color, concentration, magnetic permeability, melting point, freezing point, gelling temperature, glass transition temperature, specific electrical conductivity, specific heat capacity, specific internal energy, surface tension, thermal conductivity, speed of sound, viscosity, hardness (eta, positive real valued), or combinations thereof. However, the use of intensive properties to describe phases over molecular length scales or below one micron in length may be avoided for intensive properties that are either collective in nature (cease to be appropriate sub-micron) or are macroscopic by definition.

In some embodiments, a phase or phase mixture may have physical properties that are extensive, called extensive properties.

In some embodiments, a phase or phase mixture may have properties that are intensive for sub-volumes greater than or equal to 100 microns in all spatial dimensions and an extensive property for sub-volumes with at least one spatial dimension less than 100 microns.

In some embodiments, a phase or phase mixture may have extensive properties that are additive in magnitude and sign between sub-volumes (subsets) of the phases imbued with the property. In some embodiments, a phase or phase mixture may have extensive properties for describing a product volume or product ingredient volumes including examples such as mass (m, positive real valued), volume (V, positive real valued), particle number (N, positive integer valued), enthalpy, Gibbs free energy, Helmholtz free energy, and entropy (S, positive real valued), and combinations thereof.

In some embodiments, products, phases, phase mixtures, particles, particle dispersions, processes, and products experience or occur at ambient temperatures (20-25° C.) and may be described as experiencing or occurring at room temperature (RT).

Unless stated otherwise, processes, formulations, and products are presumed to occur or reside in open containers in contact with air and are subject to environmental temperature and pressure conditions defined by and commonly referenced Normal Temperature and Pressure (NTP) with <20% variation in temperature and pressure in the NTP definition, and other standard environmental conditions referenced or defined in the absence of or in addition to other specified errors, which is not to suggest that such constraints should be read into the claims or than any other described feature should be read into the claims. Normal Temperature and Pressure (NTP) is defined as 20° C. and ~101.3 kPa (1 atm). Standard Temperature and Pressure (STP) or Standard Atmospheric Temperature and Pressure (SATP) are also referenced when specifying certain material properties and processes. STP is defined as 0° C. and 100 kPa (1 bar). SATP is defined as 25° C. and 100 kPa (1 bar). Unless stated otherwise, Relative Humidity (RH) of 60%+/−20% is assumed.

In some embodiments, particles and products reside in closed containers in contact with air and nearly equivalent pressure and temperature conditions.

In some embodiments, a phase or phase mixture in a solid state of matter may undergo melting to a liquid state of matter or sublimation to a gas state of matter. In some embodiments, a phase or phase mixture in the liquid state of matter may undergo freezing to the solid state of matter or vaporization to the gas state of matter. In some embodiments, a phase or phase mixture in the gas state of matter may undergo deposition to the solid state of matter or condensation to the liquid state of matter. In some embodiments, a phase or phase mixture in the gas state of matter may undergo ionization a plasma state of matter. In some embodiments, a phase or phase mixture in the plasma state of matter may undergo recombination to the gas state of matter.

In some embodiments, product storage and production may require increases or decreases in temperature such that production costs of the particles and products are increased or decreased and viscosity, density and surface tension of the phases present in the processing and final form of the product are as desired. In some cases, the process may be tuned to accommodate other temperatures.

In some embodiments, an ingredient may possess a critical micellar concentration (CMC) such that the ingredient, usually an interface stabilizing agent, surfactant, or emulsifier, exists at a concentration where the ingredient exists only in micelles formats when it is the only solute in the solution containing the ingredient and such that any more ingredient added forms micellar structures.

4. Examples of Mixed Phases

In some embodiments, a phase or mixed phase may be an ingredient during synthesis, formed in the process of synthesis, or during the synthesis process but not functioning as an ingredient.

In some embodiments, a phase may be a solution or solvent. In some embodiments, a phase may be a solution where solvents are gases and solutes are gases, such as a homogeneous, miscible gas mixture. In some embodiments, a phase may be a solution where solvents are liquids and solutes are gases, such as a gas phase homogeneously dissolved in a liquid phase. In some embodiments, a phase may be a solution where solvents are solids and solutes are gases, such as a gas phase homogeneously dissolved in a solid phase. In some embodiments, a phase may be a solution where solvents are liquids and solutes are liquids, liquid/liquid (liquid in liquid) such as any liquid homogeneously dissolved in another liquid. Liquid/solid (liquid in solid) such as homogeneous, metallic amalgams. Solid/liquid (solid in liquid) such as a solid phase homogeneously dissolved in liquid phase. Solid/solid (solid in solid) such as homogeneous metal alloys or solid dopants homogeneously dissolve in a solid phase (e.g., a plasticizer dissolved in a plastic)

Miscible is used here and throughout to mean the property of a substance in relation to another substance of being able to be mixed into a single phase over the range of concentrations used in a formulation at the range of temperatures and pressures a formulation would experience during manufacturing, storage, and consumption.

Immiscible is used here and throughout to mean the property of a substance in relation to another substance of not being able to be mixed into a single phase over the range of concentrations used in a formulation at the range of temperatures and pressures a formulation would experience during manufacturing, storage, and consumption.

Two substances are considered immiscible with respect to each other (neither substance is miscible in the other substance) when the two substances exist in a phase or mixed phase in a mass ratio with respect to one another such that the two substances do not form a homogeneous phase with each other but instead separate into two distinct phases distinguished by either an interface formed between the distinct phases, across which there is a change in refractive index or, in the case of two distinct phases possessing the same refractive index across one or more intervals of photon energy, there is an interface across which there is a change in the composition defining the spatial separation of two phases between mutually immiscible substances.

5. Examples of Phase Interfaces

In some embodiments, an interface may be a sub-volume between two distinct, homogeneous phases such that the sub-volume has physical properties and composition that are combinations of physical properties and composition describing each distinct homogeneous phase independently or are not described by the composition or physical properties of one or both phases in contact throughout the sub-volume which the physical properties are not described by either phase forming the boundary.

In some embodiments, an interface may be called a surface when the interface is between a product, phase mixture, or phase and their respective surroundings (e.g., air).

In some embodiments, an interface may be called a surface when the interface is the outer most interface of a particle (e.g., closest interface to external continuous phase defining a particle).

In some embodiments, an interface may be formed by any two distinct phases in contact (e.g., no third phase in volume between the two distinct phases) with a phase mixture demonstrates different qualities depending on the state of matter of each distinct phase.

In some embodiments, a product, in part or whole, may be composed of ingredients (in part or whole) that are components of phases and phase mixtures, two of which are in a liquid state of matter, forming interfaces between two distinct liquid phases called liquid-liquid interfaces.

In some embodiments, a product, in part or whole, may be composed of ingredients (in part or whole) that are components of phases and phase mixtures, two of which are in a gas state of matter, forming interfaces between two distinct gases called gas-gas interfaces.

In some embodiments, a product, in part or whole, may be composed of ingredients (in part or whole) that are components of phases and phase mixtures, two of which are in a solid state of matter, forming interfaces between two distinct solids (may only differ by rotation) called solid-solid interfaces, such as grain boundary interfaces between crystals in a polycrystalline solid.

In some embodiments, a product, in part or whole, may be composed of ingredients (in part or whole) that are components of phases and phase mixtures, one of which is in a gas state of matter while the other is in a liquid state of matter, forming interfaces between a gas phase and a liquid phase called liquid-gas (gas-liquid) interfaces, such as water-air interfaces and $CO_2$-oil interfaces.

In some embodiments, a product, in part or whole, may be composed of ingredients (in part or whole) that are components of phases and phase mixtures, one of which is in a gas state of matter while the other is in a solid state of matter, forming interfaces between a gas phase and a solid phase called solid-gas (gas-solid) interfaces, such as interfaces between solid particles and air.

In some embodiments, a product, in part or whole, may be composed of ingredients (in part or whole) that are components of phases and phase mixtures, one of which is in a liquid state of matter while the other is in a solid state of matter, forming interfaces between a liquid phase and a solid phase called solid-liquid (liquid-solid) interfaces, such as interfaces between solid particles (solid dispersed phase) and a liquid continuous phase.

In some embodiments, phases or phase mixtures may be in a state of matter to solid and liquid states of matter and called semi-solids or soft matter. In some embodiments, a state of matter possessing properties of both solids and liquids may be described as a solid or called a solid. In some embodiments, a state of matter possessing properties of both solids and liquids may be described as a liquid or called a liquid.

In some embodiments, particles or phase mixtures may induce the formation of interfacial states that are absent from the bulk volume of the phases forming the interface. In some embodiments, interfacial states are intrinsic (usual to one phase forming the interface) to the formation of an interface such as the case of surface reconstruction deviating from bulk structure at the interface. In some embodiments, interfacial states are extrinsic and depend not only on the presence of an interface but typically arise from disorder such as interfaces with point defects or translationally periodic defects, or physisorption and chemisorption of adsorbates.

In some embodiments, solid phase-solid phase interfaces are formed and are amorphous solid phase—amorphous solid phase interfaces, amorphous solid phase—crystalline solid phase interfaces, crystalline solid phase—crystalline solid phase interfaces, combinations thereof and intermediates between the classes when categorization based on order of phases forming the interface is not clearly defined. An example of a crystalline-crystalline solid interface with a lattice mismatch (translational, rotational, or arising from an interfacial reconstruction in interfaces between either two instances of the same phase or different phases.

6. Examples of Phase Interface Properties & Attributes

Examples of properties of phase-phase interfaces are surface tension, contact angle (solid-liquid), roughness, hydrophilicity, hydrophobicity, surface charge, surface energy, and surface states (quantum mechanical and classical states present only at interfaces), to name a few.

7. Examples of Molecules, Phases, Mixed Phases, & Interfaces: Processes & Forces In some embodiments, a phase, mixed phase, collection of particles, particle dispersion, product, or combination thereof, may experience a perturbation, force, or weakly or strongly coupled process (dynamics) to influence the dynamics of boundaries, internal structure (whether molecular or organizational) or state of matter.

Intramolecular interactions are forces within a single molecule between atoms, nuclei, electrons, nucleons, other particles accepted under the standard model of fundamental forces and particles including chemicals bonds (e.g., ionic bonds, covalent bonds, hydrogen bonds, halogen bonds) and Pauli repulsion (exchange mediated repulsion, Pauli exclusion repulsion), and electrostatic interactions that don't explicitly involve electron or nuclear exchange interactions.

Intermolecular interactions are forces between two distinct molecules of the same molecular identity or between molecules with different composition or structure. The class of interactions between molecules includes those within a single molecule, with the understanding that once a covalent bond is formed between two distinct (identical or different structurally) molecules the molecules in question become a single molecule rigorously, though referring to them as distinct molecules in the context of chemical change (e.g., formation of covalent bond) is benefiting in the context of some embodiments. In addition to the aforementioned intramolecular and intermolecular interactions, electrostatic interactions such as ground-state dipole-dipole, ground-state multipole-multipole, charge-charge attraction and repulsion, and electrodynamic interactions (e.g., van der Waals and London dispersion forces, excited-state dipole-dipole, excited-state dipole-charge, excited-state multipole-multipole) are of more importance when considering chemical reaction dynamics, self-assembly, relative diffusion and related multimolecular translational and rotational dynamics.

For fluids, $2^{nd}$ law of thermodynamics necessitates non-negative viscosity (if zero, as in the case of a Bose-Einstein condensate, the substance is deemed a superfluid or ideal fluid. Trouton's ratio is ratio of extensional viscosity to shear viscosity. Extensional viscosity or elongational viscosity is the viscosity coefficient or tensor describing phase response to applied extensional stress. Shear viscosity is the viscosity coefficient or tensor describing phase response to applied shear stress. The Trouton ratio of a Newtonian fluid is 3. Viscosity of general fluid is the measure of fluid resistance to deformation at a given rate (generally varies with rate of deformation). Viscosity of Newtonian fluid is the measure of fluid resistance to deformation at a given rate (approximately invariant to rate of deformation).

A phase may undergo or be coaxed into a deformation either directly and instantaneously upon the start of perturbative coaxing, indirectly and subsequently from the initiation of some action or event, or preemptively by design or otherwise. Deformation is the continuum mechanics transformation of a body from a reference configuration of said body (be it a phase, molecule, mixed phase or general combination thereof) to a current configuration. Alternatively, deformation is considered a transformation of an electronic density (probability) arising from a reference configuration of said body. A configuration is a set containing the positions of all particles of the body in an instance, over a time interval, or over the totality of the event in question (under observation). Generally, a deformation may occur and is subsequently perceived as some perturbation from a snap-shot in time of form (or dynamics) instigated by (initiated by, responding to), state change in tandem with (congruently with, in synchronicity with, simultaneous to, relative to) or in premeditation of a force or general event, transient, occupied in time (possesses some residence with respect to the time interval under consideration), or applied about the time interval referenced for the deformation. A deformation may occur because of a force applied by an act (instantaneously applied action) or a state (an action applied over an interval) of tension, compression, impact (generally less than a third of characteristic time interval of other processes considered), vibration, slosh dynamics, momentum, oscillation, inertial force, massless force, massive force, and combinations thereof.

In some embodiments, a liquid phase, or liquid phase medium, behaves as a Newtonian fluid. In some embodiments, a liquid phase, or liquid phase medium, behaves as a non-Newtonian fluid. In some embodiments, a fluid phase (liquid phase) is a non-Newtonian fluid and demonstrates a shear-stain dependent viscosity with viscosity either increasing with the rate of shear strain (shear-thickening liquid phase) or decreasing with the rate of shear strain (shear-thinning liquids). In some embodiments, a fluid phase (or more specifically, in most cases a liquid phase) is a non-Newtonian fluid and demonstrates a time dependent viscosity with viscosity either increasing with time when shaken, agitated or otherwise perturbed (rheopective fluid phase or more specifically rheopective liquid phase) or decreasing with time when shaken, agitated or otherwise perturbed (thixotropic fluid phase or more specifically thixotropic liquid phase).

In some embodiments, a fluid phase is a non-Newtonian fluid, called a Bingham plastic fluid phase, behaving as a solid phase at low shear stresses (or other stresses) while flowing as a viscous fluid at high shear stresses. In some embodiments, a fluid phase is a non-Newtonian fluid, called a magnetorheological fluid phase, with viscosity of the phase dependent on external magnetic field magnitude and direction of field lines with respect to the internal coordinates of the phase.

In some embodiments, a phase mixture may be the combination of two or more phases, as defined above, that may exist separate from one another as distinct and uniquely identifiable phases in isolation before mixing whether the phase media of each phase from which the phase mixture is composed are miscible or immiscible in combination or piecewise.

In some embodiments, phase mixture may be called a multiphasic system in some embodiments. In some embodiments, a multiphasic system may be called a biphasic mixture when the phase mixture includes two phases, a triphasic mixture when the phase mixture includes three phases, a tetraphasic mixture when the phase mixture includes three phases, and a polyphasic mixture when the phase mixture includes four or more phases.

8. Examples of Particles & their Dispersions

In some embodiments, a product may be composed of phases and interfaces between phases in contact (phase-phase interfaces; interfaces formed at the boundary between phases). In some embodiments, a product is a particle dispersion.

In some embodiments, a particle dispersion may be a single phase, a collection of phases or phase mixtures. In some embodiments, a particle dispersion may be in a single container or in multiple containers. In some embodiments, a particle dispersion may be in a single format or in multiple formats.

In some embodiments, a phase, phase mixture, particle dispersion, collection of particles, product or combinations thereof may be in contact with volumes of vacuum or volumes wherein the pressure is less than 1 atm or 1 bar.

In some embodiments, a particle dispersion, or parts thereof, may contain a particle dispersion. In some embodiments, a particle dispersion may be the mixture of two or more particle dispersions.

In some embodiments, a particle dispersion may be an ingredient in a product. In some embodiments, a particle dispersion may be formed in the process of product synthesis. In some embodiments, a particle dispersion may not be an ingredient but may be necessary for or aid the process of product synthesis.

In some embodiments, a particle dispersion may be a colloidal dispersion (colloidal particle dispersion).

In some embodiments, a colloidal particle dispersion may be a dispersed gas phase (gaseous dispersed phase) in a continuous liquid phase (gas in liquid; gas/liquid; gas particles dispersed in a liquid) such as a liquid foam (e.g., whipped cream).

In some embodiments, a colloidal particle dispersion may be a dispersed gas phase (gaseous dispersed phase) in a continuous liquid phase (gas in liquid; gas/liquid; gas particles dispersed in a liquid) such as a liquid foam (e.g., whipped cream). An example of a colloidal dispersion of a gas phase in a solid phase (gas/solid) is a solid foam (e.g., aerogel, Styrofoam, pumice).

In some embodiments, a colloidal particle dispersion may be a dispersed gas phase (gaseous dispersed phase) in a continuous liquid phase (gas in liquid; gas/liquid; gas particles dispersed in a liquid) such as a liquid foam (e.g., whipped cream). An example of a colloidal dispersion of a liquid phase in a gas phase (liquid/gas) is a liquid aerosol (e.g., fog, mist, vapor, hair sprays).

In some embodiments, a colloidal particle dispersion may be a dispersed gas phase (gaseous dispersed phase) in a continuous liquid phase (gas in liquid; gas/liquid; gas particles dispersed in a liquid) such as a liquid foam (e.g., whipped cream). An example of a colloidal dispersion of a liquid phase in another liquid phase (liquid/liquid) is an emulsion (e.g., milk, mayonnaise, hand cream).

In some embodiments, a colloidal particle dispersion may be a dispersed gas phase (gaseous dispersed phase) in a continuous liquid phase (gas in liquid; gas/liquid; gas particles dispersed in a liquid) such as a liquid foam (e.g., whipped cream). An example of a colloidal dispersion of a liquid phase in a solid phase (liquid/solid) is a gel (e.g., agar, gelatin, silica gel, opal).

In some embodiments, a colloidal particle dispersion may be a dispersed gas phase (gaseous dispersed phase) in a continuous liquid phase (gas in liquid; gas/liquid; gas particles dispersed in a liquid) such as a liquid foam (e.g., whipped cream).

An example of a colloidal dispersion of a solid phase in a gas phase (solid/gas) is a solid aerosol (e.g., smoke, ice cloud, solid air particulates). An example of a colloidal dispersion of a solid phase in a liquid phase (solid/liquid) is a liquid sol (e.g., pigmented ink, blood). An example of a colloidal dispersion of a solid phase in another solid phase (solid/solid) is a solid sol (e.g., cranberry glass).

In some embodiments, particles may be structured and formed with the use of individual particle, interparticle, or particle dispersion qualities, quantities, properties, and dynamics, including their combinations.

In some embodiments, particles may have a distribution of sizes, with a high-side characteristic size value, referred to as a maximum size. In some embodiments, the maximum size of the particles may be three standard deviations larger than the mean size-ranges. In some embodiments, the particle size (diameter) of each particle within a particle dispersion may have a Gaussian distribution. In some embodiments, the particle size (diameter) of each particle within a particle dispersion may not have a Gaussian distribution indicative of heterogeneity amongst a particular subset of particles measured or multiple Gaussian distributions are required to fit the data satisfactorily indicative of multiple subsets of particles with different mean diameters in each subset of particles.

In some embodiments, the particle size (diameter) of each particle within a particle dispersion may be measured directly as in the case of a single particle or collection of particles deposited on a substrate like lacey carbon with sufficient transparency to electrons to detect variation in the attenuation of an electron beam in transmission geometry for transmission electron microscopy (TEM). In some embodiments, the size and form of the particles in solution is taken to be that measured in TEM. Another example of direct size measurement of a particle or collection thereof may include the detection of the particle or collection deposited along with the solution in which they were dispersed in a thin film with atomic force microscopy. In some embodiments, the size measurements of the ensemble of particles may be inferred via models appropriate for measurement of choice and sufficient at fully or partially describing data collected in the measurement of choice to within a threshold error (e.g., $\pm 1$ nm, $\pm 5$ nm, $\pm 10$ nm, $\pm 50$ nm, or $\pm 100$ nm). In some embodiments, the particle sizes within a sample are expected to consist of two or more distinct size distributions (size intersections of the size distributions, whether continuous or discrete in nature or model, is zero) of the same composition molecular composition and molecular organization in space yet with different characteristic mean sizes. Distributions of this type, whether Gaussian in character or otherwise (e.g., skewed-Gaussian, Lorentzian and Voigt distributions, along with all other probability distributions listed and combinations thereof), will henceforth be referred to as multimodal distributions. In some cases, multimodal distributions may contain particles of the same molecular composition and organization and the distributions have a non-zero overlap in particle sizes.

In some embodiments, physical, physiochemical or process parameters may describe particle form and behavior in a distribution across a collection of particles such as size, stabilizer numbers, active ingredient content, and particle density.

In some embodiments, particles may undergo processes and transformations that may be sufficiently described by individual particle properties and dynamics to design and control the of formation, form, properties, and dynamics of an entire particle dispersion, a single particle, or subset of particles. In some embodiments, interparticle interactions and dynamics may be neglected in the design of a particle dispersion or the description of a particle dispersion's structure and dynamics.

In some embodiments, particles may undergo processes and transformations that may not be sufficiently described by individual particle properties and dynamics are not sufficient (insufficient) for the design and control of formation, form, properties, and dynamics of an entire particle dispersion, a single particle, or subset of particles. In some embodiments, processes, and transformations sufficient for the description of pairwise particle properties and dynamics (properties and dynamics necessary to describe pairs of particles in a particle collection, such as interparticle interactions) are sufficient and necessary for the description of formation, form, properties, and dynamics of an entire particle dispersion, a single particle, or subset of particles. In some embodiments, processes and transformations sufficient for the description of more than pairwise (three-body, four-body, all particles) particle properties and dynamics (properties and dynamics necessary to describe sets of particles in a particle collection greater than two particles) are necessary for the description of formation, form, properties, and dynamics of an entire particle dispersion, a single particle, or subset of particles. In some embodiments necessitating the description of particle dispersion structure and dynamics that involve more than individual particle structure and dynamics, the particle dispersion is sufficiently described such that necessary information (e.g., stability, viscosity) is obtained by considering pairwise particle structure and dynamics. In some embodiments necessitating the description of particle dispersion structure and dynamics that involve more than individual particle structure and dynamics, the particle dispersion is sufficiently described such that necessary information (e.g., stability, viscosity) is obtained by considering the structure and dynamics of three or more particles relative to each other as well as collectively. In some embodiments, interparticle interactions and dynamics may be neglected in the design of a particle dispersion or the description of a particle dispersion's structure and dynamics.

In some embodiments, aggregation may be present during any stage in the life cycle of a formulation or is a target against or towards which formulation design and synthesis occurs. Aggregation is the process of a collection of particles that remain within either stagnant together or move together as a group.

In some embodiments, particle dispersions may experience flocculation during any stage in the life cycle of a formulation or is a target against or towards which formulation design and synthesis occurs. Flocculation is the process of particle aggregate formation by the aggregation and bonding (covalent or otherwise) between particles. Flocculation often leads to the formation of insoluble aggregates of particles that sediment out of solution.

In some embodiments, particle dispersions may experience coalescence during any stage in the life cycle of a formulation or is a target against or towards which formulation design and synthesis occurs. Flocculation is the process of particle aggregate formation by the aggregation and bonding (covalent or otherwise) between particles. Coalescence is the process by which two or more particles first aggregate and then merge into a single particle or aggregate less than or equal to the volume of the two or more particles merging.

In some embodiments, particle dispersions may experience creaming during any stage in the life cycle of a formulation or is a target against or towards which formulation design and synthesis occurs. Creaming is the migration of particles upwards under the influence of gravity with the process of buoyancy when appreciable differences in density are present between the particles and surrounding continuous phase.

In some embodiments, particle dispersions may experience sedimentation during any stage in the life cycle of a formulation or is a target against or towards which formulation design and synthesis occurs. Sedimentation is the deposition of particles in suspension out of suspension, settling particles out of the containing continuous phase of a particle dispersion or product.

In some embodiments, particle dispersions may experience Ostwald ripening during any stage in the life cycle of a product including the production process, sometimes advantageous and used to control a process and sometimes avoided to maintain particle stability and desired size distributions (usually in the case of very monodisperse distributions of particle diameter, where the energetically favorable state of the particle dispersion may have a broad distribution of particle sizes or multimodal distributions of particle diameter). Ostwald ripening is the diffusion of molecular components of particles between particles, through the continuous phase, leading to changes in particle size distribution.

In some embodiments, a molecule, particle, particle dispersion, ingredient, product or combinations thereof may experience Brownian motion with no net velocity over timescales with the same order of magnitude as a second. In some embodiments, a particle or particle dispersion may experience no net macroscopic force and thus may not experience a net acceleration such that the particles remain homogeneously dispersed. In some embodiments, ingredients, particles and products may be subjected to gravitational and centripetal forces such they become heterogeneously dispersed, aggregate, or settle out of a state of dispersion (sediment).

In some embodiments, particle dispersions may experience a net velocity in the direction of gravitational force (gravitation). In some embodiments, particle dispersions may experience a net acceleration in the direction of gravitational force (gravitation).

In some embodiments, particle dispersion formation and ensuing dynamics may be sufficiently understood, controlled, and described by the formation and ensuing dynamics of individual particles within the particle dispersion such as local and single particle processes including examples such as sedimentation (by gravitation, centrifugation, electromagnetic forces) of type 1 where particles settle individually with constant settling velocity and no flocculation occurs.

In some embodiments, particle dispersion formation and ensuing dynamics may not be sufficiently understood, controlled, and described by the formation and ensuing dynamics of individual particles but may instead necessitate understanding, control, and description of formation and ensuing dynamics of a particle pairs, groupings of particles containing more than two particles, or even the entirety of a particle dispersion such as multiparticle, interparticle, global or collective processes including examples such as sedimentation of type 2 where particles settle collectively and may flocculate. In type 2 sedimentation, particle sizes and settling velocities may change during settling, flocculation, and aggregation, including increases in the probability of other interparticle processes occurring such as Ostwald ripening. In some embodiments, particle dispersion formation and ensuing dynamics may experience another form of sedimentation that may be called zone sedimentation (type 3 sedimentation) where zones of high particle concentration form as a result of processing conditions or interparticle attractive interactions leading to net diffusion together followed by flocculation and rapid sedimentation such that flocculation occurs nonuniformly and usually flocculation and sedimentation are initiated by the presence of defects in contact with the phase mixture or with the presence of a seed for either process. In some embodiments, differentiating between these cases and developing a mechanistic and causal understanding for individual and collective particle processes occurring in all or some cases may be critical for the stability, processing, and efficacy upon administration of particle containing products.

In some embodiments, particle dispersions may undergo aggregation, creaming, sedimentation, Ostwald ripening, flocculation, coalescence, and other processes. In some embodiments, particle dispersions or individual particles within the interior of larger surrounding particles, beads, or aggregates may undergo aggregation, creaming, sedimentation, Ostwald ripening, flocculation, coalescence, and other processes amongst the encapsulated particle dispersion or individual particle in the larger particle, bead, or aggregate interior. In some embodiments, particle dispersions or individual particles within the interior of larger surrounding particles, beads, or aggregates may undergo aggregation, creaming, sedimentation, Ostwald ripening, flocculation, coalescence, and other processes with the continuous phase in which the larger particle, bead, or aggregate is dispersed. In some embodiments, particle dispersions or individual particles within the interior of larger surrounding particles, beads, or aggregates may undergo aggregation, creaming, sedimentation, Ostwald ripening, flocculation, coalescence, and other more exterior phases and phase interfaces, usually with associated phase media miscible with the encapsulated particle dispersed phase media.

In some embodiments, particles may form a solution (or sol) in the surrounding medium to which they are solvated or dispersed.

In some embodiments, particles may form a colloidal dispersion in the surrounding medium to in which they are formed, modified, solvated, or dispersed. In the case of a colloidal dispersion, the particles may be composed of combinations of phases composed of phase media that are immiscible or miscible with the surrounding phase media and less than 100 microns in diameter along the axis of largest diameter (width) for general particle structure. Particles forming colloidal dispersions with greatest diameter (width) less than 1000 nm (1 micron) may be referred to as nanoparticles. Particles forming colloidal dispersions with greatest diameter (width) less than 100 microns may be referred to as microparticles. In some embodiments, the colloidal dispersion may be referred to as a particle dispersion, particle suspension, colloidal suspension, or similar phrases.

In some embodiments, particles may form a particle suspension in the surrounding medium to in which they are formed, modified, solvated, or dispersed. In the case of a colloidal dispersion, the particles may be composed of combinations of phases composed of phase media that are immiscible or miscible with the surrounding phase media and greater than 100 microns in diameter along the axis of largest diameter (width) for general particle structure. In some embodiments, particles forming a particle suspension may be call macroparticles (otherwise, miniparticles or mesoparticles).

In some embodiments, a particle dispersion may be a phase mixture (ingredient mixture) wherein a subset of the phases from which the phase mixture is composed are dispersed phases that may form particles while one or many phases within the phase mixture are called continuous phases that are continuously connected, and may be a phase mixture themselves, within a spatial volume whose boundary is the container, vessel, or general boundary between a formulation or substance and the surrounding environment after formation and prior to administration regardless of the number of containers. In other words, the distinction between a dispersed phase and a continuous phase is that within a particular volume containing a formulation or part of a larger formulation volume (or disjoint volumes) existing as a phase mixture, dispersed phases necessarily have phase interfaces and a continuous phase (or continuous phases) separating portions of a dispersed phase from other portions within the same container.

In some embodiments, a particle dispersion may be called a solution and considered a special case of a particle dispersion where the particles are macromolecules, molecules, isolated ingredients or sets of ingredients dissolved, dispersed, or suspended as solutes in a solvent (in this scenario, acting as both the continuous and dispersed phase), and whose particle interfaces are defined so as to distinguish the spatial extent and distribution of the dispersed phase (particles) from the continuous phase at any point in time by the atomic density, including nuclear and electronic density, distributed (whether density is dynamically or statically distributed) about the ingredients (molecular and macromolecular constituents) of a particle that are in closest proximity to, and experience the largest atomic density overlap with, molecular components of the bulk continuous phase as defined.

In some embodiments, the phase, phases, or phase mixtures may be contained within an individual particle, a particle dispersion, a subset of a particle dispersion (regardless of metrics used during categorization, distinguishing properties amongst particles, or structure of categorization used to classify, partition, identify, sort, discuss, and choose individual particles or subsets of particles in a particle dispersion) and may subsequently be referenced as distinct, different, similar, indistinguishable, or combinations thereof. For example, two subsets of particles within a particle dispersion may be distinct based on the metric of particle radius if a subset of the particles has a radius less than or equal to 500 nm, while another subset of particles has a radius greater than 500 nm.

In some embodiments, particles may be porous throughout the entirety of the particles, in particular phases within the particle, or at particular interfaces within the particle or at the particle interface with the continuous media containing the particles, impacted by particle properties such as interfacial area (width of interface), particle phase and interface structure, density of particle phases and interfaces, particle stability in part or full, and combinations thereof in order to control particle behavior such as release mechanism and rates of ingredients in particles. In some embodiments, particle phases or interfaces may be porous due to increased interface area and phase or interface permeability to increase reactivity of the particle with other ingredients or the environment of an organism targeted for administration of a product containing particles. In some embodiments, porosity is defined as the ratio of particle pore, or void, volume to total particle volume (or sub-volume when considering a particular phase or interface in the particle).

9. Examples of Single-Phase Particles

FIG. 1. Illustrates an example single-phase particle 100 containing components of a dispersed phase 101 dispersed in a continuous phase 102. In some embodiments, the components of a dispersed phase 101 may include phase media. In some embodiments, the components of a dispersed phase 101 may include phase stabilizers. In some embodiments, the components of a dispersed phase 101 may include surface stabilizers. In some embodiments, the components of a dispersed phase 101 may include encapsulated active ingredients 103. In some embodiments, the components of a dispersed phase 101 may include a combination phase media, phase stabilizers, surface stabilizers, and encapsulated active ingredients 103. In some embodiments, the components of the continuous phase 102 may include a phase media. In some embodiments, the components of the continuous phase 102 may include phase stabilizers. In some embodiments, the components of the continuous phase 102 may include surface stabilizers. In some embodiments, the components of a continuous phase 102 may include a combination phase media, phase stabilizers, surface stabilizers.

In some embodiments, a dispersed phase may be a single Phase dispersed throughout a Continuous Phase (e.g., hydrophilic, hydrophilic phase) or Phase Mixture and is referred to as Single-phase Particles. In some embodiments, a particle dispersion may be composed of a mixture of compositionally distinct particle dispersions called a mixed particle dispersion, or simply as a particle dispersion when appropriate or sufficient for statement referencing a mixed particle dispersion. In some embodiments, a particle dispersion of single-phase particles may be composed of two or more distinct single-phase particle varieties (e.g., single-phase particle varieties differentiated by intraparticle), include single continuous phase containing two distinct sets of single-phase particles.

9.1. Examples of Miscible Single-Phase Particles

Figure 2:
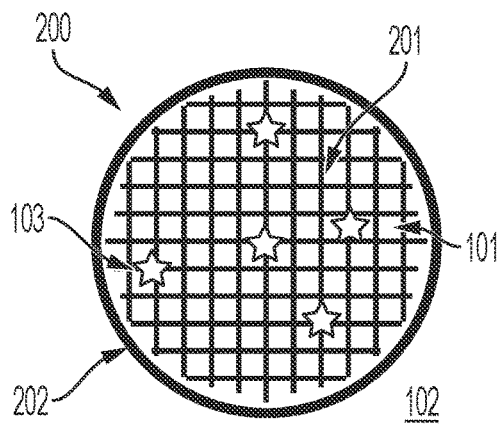
FIG. 2 is a schematic diagram that illustrates an example of miscible single-phase particle, in accordance with some embodiments.

FIG. 2 illustrates example miscible single-phase particles 200, which in some embodiments of miscible single-phase particles, may be considered a class of single-phase particles 100. In some embodiments of miscible single-phase particles, the formulation includes (e.g., consists of) a continuous phase 102 containing a dispersed phase 101 composed of single-phase particles which may be primarily (e.g., <50%) composed of components miscible with the continuous phase. In some embodiments of miscible single-phase particles, the dispersed phase contains an encapsulated active ingredient 103. In some embodiments of miscible single-phase particles, all components of the dispersed phase are miscible or fully soluble at their given concentrations in the continuous phase.

In some embodiments of miscible single-phase particles, the stability of the particle and continued encapsulation of the dispersed phase's components is achieved by the presence of phase stabilizing agents that limit the diffusion of some or all components of dispersed phases into the continuous phase. In some embodiments of miscible single-phase particles, this barrier is present throughout the phase and is referred to as a matrix 201. In some embodiments of miscible single-phase particles, this barrier is present at or near the interface between the dispersed and continuous phase and is known as a shell 202. In some embodiments of miscible single-phase particles both a matrix 201 and shell 202 may be present.

In some embodiments of miscible single-phase particles, the phase stabilizing agent may prevent diffusion of encapsulated components, such as active ingredients 103, from the dispersed phase to the continuous phase by creating a physical barrier with which the encapsulated components are unable to diffuse through. In some embodiments of miscible single-phase particles, the physical barrier is formed by inducing a change in the state of matter of the entire dispersed phase to one that greatly limits the diffusion of all components of the phase to form a barrier matrix 201, such as the temperature induced gelling or crystallization seen when some dispersed phases containing gums or 12-HSA are cooled. In some embodiments of miscible single-phase particles, the phase stabilizing agent may form a physical barrier by selectively undergoing a change of the state of matter at or near the interface between the dispersed and continuous phase and effectively forming a barrier shell 202 around the dispersed phase which limits diffusion between the phases, such as the case of Na alginate in the dispersed phase being cured by calcium ions in the continuous phase at the interface between the two phases.

In some embodiments of miscible single-phase particles chemical interactions between the phase stabilizing agents in a matrix 201 present in the dispersed phase and the components of the dispersed phase, particularly the active ingredients 103, maintain stability of the particle. In some embodiments of miscible single-phase particles, these chemical interactions may be covalent bonds. In some embodiments of miscible single-phase particles, these chemical interactions may be covalent bonds which are reversable. In some embodiments of miscible single-phase particles, these chemical interactions may be covalent bonds which are selectively reversable under given conditions, for example bonds which may be broken by enzymes in the body or the acidic environment of the gut. In some embodiments of miscible single-phase particles, the chemical interactions present may be ionic bonds for example, encapsulation of zinc in a dispersed phase containing alginate, where the zinc forms ionic bonds with the alginate, crosslinking it and preventing the zinc from diffusing out of the particle.

In some embodiments of miscible single-phase particles physical interactions between the phase stabilizing agents in the matrix 201 present in the dispersed phase and the components of the dispersed are expected to maintain the stability of the particle. In some embodiments of miscible single-phase particles, these physical interactions may be hydrogen bonding interactions. For example, encapsulated components, such as active ingredients 103, containing carbonyl, hydroxyl, carboxylic acid, amine, amide, or other polar functional groups may form hydrogen bonds with polysaccharide phase stabilizing agents like agar or alginic acid which may slow or prevent diffusion out of the dispersed phase.

In some embodiments of miscible single-phase particles, hydrophilic miscible single-phase particles known as W/W formulations may be formed by addition of a dispersed hydrophilic phase containing a phase stabilizing agent to a hydrophilic continuous phase. In some embodiments of miscible single-phase particles, a W/W formulation is prepared by curing an aqueous sodium alginate solution containing a hydrophilic active ingredient with a calcium source and dispersing this solution in a hydrophilic medium using ultrasonication. For example, caffeine may be encapsulated in a hydrophilic sodium alginate particle dispersed in water. This is accomplished by preparing a solution of 100 mg of caffeine dissolved in 5 mL of a 0.3% by weight (w/w) solution of sodium alginate in pH 5 water. The positively charged caffeine may selectively form chemical interactions with the negatively charged carboxyl moieties of the sodium alginate. 4 mL of a 3.35 mg/ml calcium chloride solution is then added over 30 minutes to crosslink the sodium alginate, forming particles consisting of localized gel networks. This solution is then sonicated to disperse the gel nanoparticles, which is expected to yield a dispersal of hydrophilic particles suspended in a hydrophilic medium (W/W formulation).

In some embodiments of miscible single-phase particles, hydrophobic miscible single-phase particles known as O/O formulations may be formed by addition of a dispersed hydrophobic phase containing a phase stabilizing agent to a hydrophobic continuous phase. In some embodiments of miscible single-phase particles, a O/O formulation is prepared by dispersing active ingredient containing hydrophobic oleogel particles in a hydrophobic medium using ultrasonication. For example, 600 mg of caffeine may be dispersed in a solution of 74.6% weight to volume ethyl cellulose dissolved in MCT oil at 130° C. (above the melting point of the mixture). This solution is added dropwise to 20 mL of LCT oil held at a constant temperature of 25° C. which is being exposed to ultrasonic waves. The MCT may be dispersed into particles and quickly cools, leading to the MCT phase undergoing a change in the state of matter to a gel, entrapping the contents of the MCT phase, yielding a dispersal of hydrophobic particles suspended in a hydrophobic medium (O/O formulation).

In some embodiments of miscible single-phase particles, formulations may contain a mixture of miscible single-phase particles prepared together or separately and mixed. For example, two sodium alginate solutions, one containing caffeine and one containing Dynamine™, may be prepared and cured separately, then dispersed in the solution, forming a mixture of dispersed hydrophilic particles suspended in a hydrophilic medium (mixed W/W formulation). In another example, cured sodium alginate particles containing caffeine and cured agar particles containing Dynamine™ may be prepared separately, then dispersed in the same solution, forming a mixture of dispersed hydrophilic particles in a hydrophilic medium (mixed W/W formulation).

9.2. Examples of Immiscible Single-Phase Particles

Figures 3A, 3B:
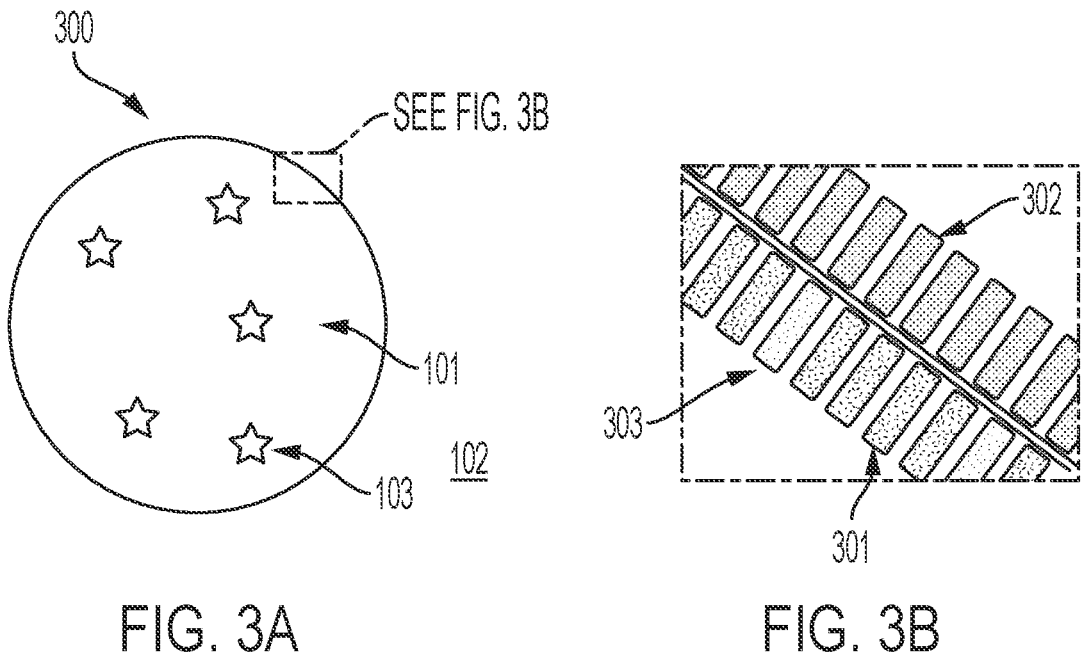
FIG. 3A is a schematic diagram that illustrates an example of an immiscible single-phase particle, in accordance with some embodiments.
FIG. 3B is an enlarged view of a portion of FIG. 3A.

In some embodiments of immiscible single-phase particles, a formulation consists of immiscible single-phase particles 300 illustrated in FIG. 3. Immiscible single-phase particles consist of a single dispersed phase 101, which is immiscible in the continuous phase 102 it is dispersed in. In some embodiments of immiscible single-phase particles, the dispersed phase contains some combination of a phase media, phase stabilizers, surface stabilizers, encapsulated active ingredients 103, and phase solutes. In some embodiments of immiscible single-phase particles, these formulations contain particles of one phase that are stably dispersed in the other phase by surface and phase stabilizing agents. In some embodiments of immiscible single-phase particles, only one surface stabilizing agent 301, is added to only one phase. In some embodiments of immiscible single-phase particles, only one surface stabilizing agent 301 may be added to one phase and only one other surface stabilizing agent 302 may be added to another phase. In some embodiments of immiscible single-phase particles, a mixture of any number of surface stabilizing agents may be added to either phase; for example, a system that contains two surface stabilizing agents in the dispersed phase (301 and 303) and one surface stabilizing agent in the continuous phase 302. In some embodiments of immiscible single-phase particles, no interface stabilizer may be present.

In some embodiments of immiscible single-phase particles, components of the inner phase remain encapsulated due solely to their low solubility in the continuous phase. In some embodiments of immiscible single-phase particles, the choice of continuous phase, including media, stabilizers, and solutes, may be chosen such that components in the dispersed phase have sufficiently low solubilities to not disrupt the desired properties of the formulation (e.g., taste, extended release, targeted release). In some embodiments of immiscible single-phase particles, choice of a continuous phase is critical, such as when amphiphilic molecules are included in the dispersed phase. In an example of a continuous phase being chosen due to low solubility of encapsulants in it, LCT is chosen over MCT as a continuous hydrophobic medium when caffeine is being encapsulated in a hydrophilic dispersed phase due to the lower solubility of caffeine in LCT than MCT in the temperature range encountered during production (25-100° C.). In some embodiments of immiscible single-phase particles, components of the inner phase remain encapsulated because of the presence of phase stabilizing agents in the inner phase, outer phases, or combination of the same or difference phase stabilizing agents in the inner phase and outer phase. In some embodiments of immiscible single-phase particles, the phase stabilizing agents may prevent diffusion of the encapsulated components through chemical interactions with the encapsulated components, physical interactions with the encapsulated components, or through the formation of a physical barrier.

In some embodiments of immiscible single-phase particles, particles may be formed by diffusion and self-assembly of ingredients contributing in part or full to the final composition of the particles. In some embodiments of immiscible single-phase particles, self-assembly may occur spontaneously and is controlled by specific environmental conditions of the ingredients in the continuous phase, dispersed phase, or both. In some embodiments of immiscible single-phase particles, self-assembly may form ordered nanostructures, supramolecular structures (ordered aggregates), and secondary structures of molecules and macromolecules as a function of the physiochemical properties and composition of participating phases. In some embodiments of immiscible single-phase particles, particles may be formed by self-assembly between individual subunits (e.g., molecules, macromolecules, identical intermolecular structures, multiple distinct intermolecular structures) driven by thermodynamically favorable combinations of intramolecular atomic (electronic and nuclear) rearrangements and conformations, intermolecular atomic configurations, covalent and ionic bonds between subunits, and noncovalent interactions through electrostatics (e.g., hydrogen bonding, π-π stacking) and electrodynamics. While these interactions alone are quite weak, when combined they can form strong, self-supporting architectures whose structure may be changed simply with the addition of an ingredient before, during, or after the formation of the self-assembled structure, whether the particle is the self-assembled structure, or the self-assembled structure is a component of the particle.

In some embodiments of immiscible single-phase particles, particles may be formed by self-assembly under thermodynamically favorable conditions (e.g., increase in entropy or decrease in enthalpy).

In some embodiments of immiscible single-phase particles, particles may be formed by self-assembly under thermodynamically unfavorable conditions (e.g., decrease in entropy or increase in enthalpy) or into structures that may not be the thermodynamic global or local minimum (e.g., forming structures that are not the lowest energy structure out of all possible structures or forming structures that are not the lowest energy structure out of a subset of structures with only changes in nuclear and electronic configurations along a few degrees of freedom).

In some embodiments of immiscible single-phase particles, particles may be formed by self-assembly into structures constrained by kinetic considerations (e.g., insufficient diffusion to self-assemble or degrade self-assembled structures, self-assembled subunits are sterically hindered from degrading or changing their atomic configurations internally) including favoring formation of structures with kinetics possessing faster characteristic timescales over those with relatively slow characteristic timescales and stabilizing desired configurations (lowering free energy) during self-assembly relative to local or global free energy minima or destabilizing states occupied in transition from desired configurations to local or global free energy minimum (increasing transition energy) to maintain a particular higher energy structure under temperature conditions insufficient in energy to reorganize into a transition state structure and subsequently occupy an undesired atomic configuration with lower free energy, whether locally or globally.

In some embodiments of immiscible single-phase particles, particles may form by relative intermolecular diffusion and interaction to self-assemble by a complex interplay of thermodynamic and kinetic constraints on the dynamics and structure of self-assembled structure in whole or in part.

In some embodiments of immiscible single-phase particles, particles may form by self-assembly under thermodynamic control, aggregation proceeds towards energetic minima and the consequent structures formed may be highly ordered—crystals, nanotubes, and nanowires.

In some embodiments of immiscible single-phase particles, particles may form by self-assembly under kinetic drivers and constraints as dictated by participating phase properties and surrounding environment properties, such as pH, temperature, enzymatic activity, and combinations thereof. In some embodiments of immiscible single-phase particles, particles may form by self-assembly under thermodynamically driven conditions followed by kinetically driven or constrained dynamics to form higher-energy, metastable structures, such as nanofibers, micelles and nanovesicles, and nanospheres.

In some embodiments of immiscible single-phase particles, particles may form while exposed to external stimuli (e.g., ultrasound, cavitation, heat, shearing) to access thermodynamically unfavorable self-assembled structures that may attain thermodynamically favored structures (local minima), such as transitions from nanofibers to three-dimensional gels.

In some embodiments of immiscible single-phase particles, immiscible single-phase particles are formed through self-assembly. In some embodiments of immiscible single-phase particles, a dispersed phase containing a surface stabilizing agent is added to a continuous phase and allowed to spontaneously form particles which diffuse from the interface of the two phases into solution. In some embodiments of immiscible single-phase particles, an emulsion phase inversion technique is used where a continuous phase is added to a dispersed phase containing a surface stabilizing agent until enough continuous phase has been added to disperse the dispersed phase. In some embodiments of immiscible single-phase particles, the ratios of dispersed phase, continuous phase, and surface stabilizers and temperature strictly dictate the range in which a self-assembled particle dispersion is stable.

In some embodiments of immiscible single-phase particles, immiscible single-phase particles are created using mechanical energy to mix the two phases. In some embodiments of immiscible single-phase particles, the mechanical energy is introduced through shear mixing, using a conventional mixing device such as a magnetic stir bar, impeller, or blender. In some embodiments of immiscible single-phase particles, the mechanical energy is introduced through a high-shear mixer, such as a rotor-stater homogenizer. In some embodiments of immiscible single-phase particles, the mechanical energy is introduced through collisions, such as a high-pressure homogenizer. In some embodiments of immiscible single-phase particles the mechanical energy is introduced through high intensity acoustical waves, such as ultrasonication.

In some embodiments of immiscible single-phase particles, particles of a hydrophilic phase are dispersed in a hydrophobic continuous phase in what is known as a W/O formulation. In some embodiments of immiscible single-phase particles, a W/O formulation may be prepared by dissolving a hydrophilic active ingredient or ingredients in a hydrophilic medium such as water, then dispersing the hydrophilic phase in a hydrophobic phase, composed of a hydrophobic medium using mechanical energy. In some embodiments of immiscible single-phase particles, the hydrophilic phase may additionally contain phase or surface stabilizers. In some embodiments of immiscible single-phase particles, the hydrophobic phase may additionally contain phase or surface stabilizers. For example, 1 g of glutathione may be dissolved in 15 mL of water at 90° C. (the hydrophilic phase) and subsequently dispersed into a solution of 3 mL of Palsgaard PGPR dissolved in 40 mL of MCT heated to 70° C. (the hydrophobic phase) using magnetic stirring and ultrasonication to yield a stable dispersion of hydrophilic particles in a hydrophobic phase (W/O formulation).

In some embodiments of immiscible single-phase particles, particles of a hydrophobic phase are dispersed in a hydrophilic continuous phase in what is known as a O/W formulation. In some embodiments of immiscible single-phase particles, a O/W formulation may be prepared by dissolving a hydrophobic active ingredient or ingredients in a hydrophobic medium such as MCT, then dispersing the hydrophobic phase in a hydrophilic phase, composed of a hydrophilic medium, using mechanical energy. In some embodiments of immiscible single-phase particles, the hydrophilic phase may additionally contain phase or surface stabilizers. In some embodiments of immiscible single-phase particles, the hydrophobic phase may additionally contain phase or surface stabilizers. For example, 240 mg of CBD and 12 g of lecithin may be dissolved in 20 mL of LCT at 90° C. to form a hydrophobic phase which is subsequently dispersed in in the hydrophilic phase composed of 10 mL of Q-Naturale 300 dissolved in 60 mL of water using magnetic stirring and ultrasonication to yield a stable dispersion of hydrophobic particles in a hydrophilic phase (O/W formulation).

In some embodiments of immiscible single-phase particles, components may be added to a formulation before or during processing and subsequently removed before processing is complete and are known as processing aids. In some embodiments of immiscible single-phase particles, processing aids may be added to alter the chemical or physical properties of a phase or phases in order to make possible or ease processing. In some embodiments of immiscible single-phase particles, processing aids may be added to increase or decrease the solubility of certain components in a phase or phases. In some embodiments of immiscible single-phase particles, processing aids may be added to increase or decrease the viscosity of a phase. In some embodiments of immiscible single-phase particles, processing aids may be removed through evaporative processes, for example, removing ethanol from a hydrophobic phase by either heating the phase or putting the phase under vacuum and distilling away the ethanol. In some embodiments of immiscible single-phase particles, processing aids may be removed via diffusion, for example diffusion of sodium chloride or glycerol through a semi-permeable membrane such as dialysis tubing. In some embodiments of immiscible single-phase particles, processing aids may be removed through filtration methods, for example tangential flow filtration (TFF).

In some embodiments of immiscible single-phase particles, undesirable components present in the formulation, such as impurities, by products, sediment, or particles that do not meet the desired properties may be removed before processing is completed. In some embodiments of immiscible single-phase particles, undesirable components may be removed via filtration, for example, by passing the formulation through a conventional membrane filter or through a TFF system. In some embodiments of immiscible single-phase particles, undesirable components may be removed from via diffusion, for example, through a semi permeable membrane such as dialysis tubing. In some embodiments of immiscible single-phase particles, insoluble undesirable components may be removed via surface filtration or decanting if the insoluble components are aggregate on the top or bottom of the formulation after some amount of time. In some embodiments of immiscible single-phase particles, undesirable components may be removed via centrifugation.

In some embodiments of immiscible single-phase particles, an active ingredient may be added to a formulation in the form of an extract. In some embodiments of immiscible single-phase particles, extracted ingredients may be added as a solution in the solvent in which they were extracted into. In some embodiments of immiscible single-phase particles, the extract solvent may serve as the phase media for the phase of a particle system in which the extracted active is encapsulated. For example, performing and extraction of an active ingredient in MCT, then using said extract as both the active ingredient and phase media for the dispersed phase in an O/W particle system. In some embodiments of immiscible single-phase particles, the extract solvent may be the same as the phase media in which the phase it is added to consists of. For example, performing an extraction of an active ingredient in MCT, then using said extract in a O/W formulation which utilizes additional MCT as a carrier oil. In some embodiments of immiscible single-phase particles, the extract solvent may be miscible or soluble to the point that it fully forms a homogenous solution with the phase it is added to. For example, performing an extraction of an active ingredient in MCT, then using said extract in a O/W formulation which utilizes LCT as a carrier oil. In some embodiments of immiscible single-phase particles, the extract solvent may be used as a processing aid and removed during manufacturing of the particle system. For example, performing and extraction of an active ingredient in ethanol, then using said extract in an O/W formulation that utilizes MCT as a carrier oil, but removing the ethanol before production is completed.

10. Examples of Double-Phase Particles

Figure 4:
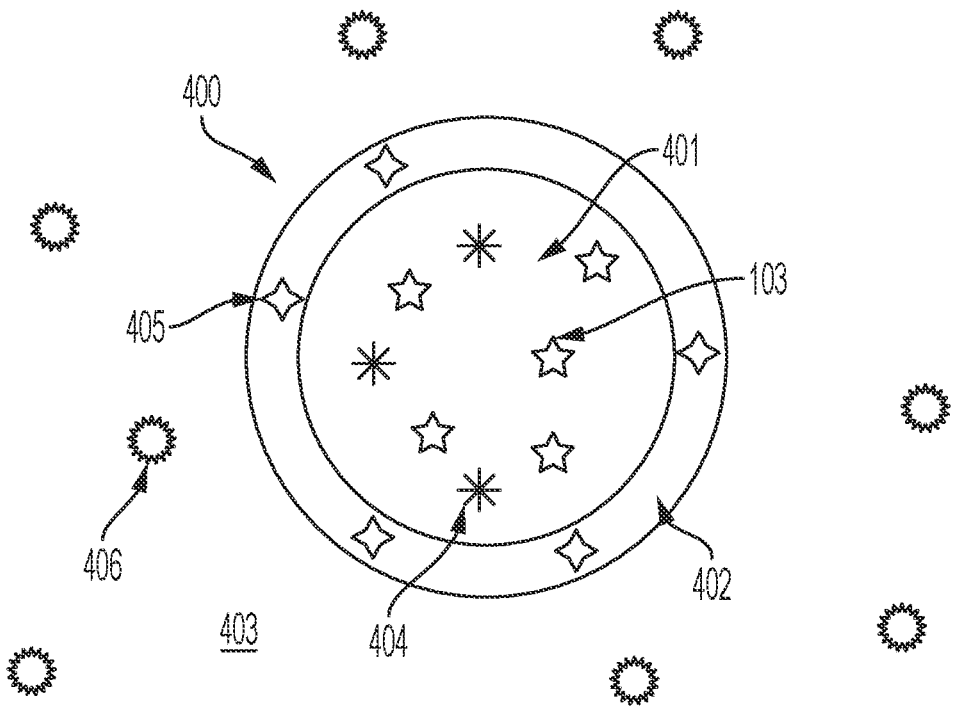
FIG. 4 is a schematic diagram that illustrates an example of a double-phase particle, in accordance with some embodiments.
Figure 5:
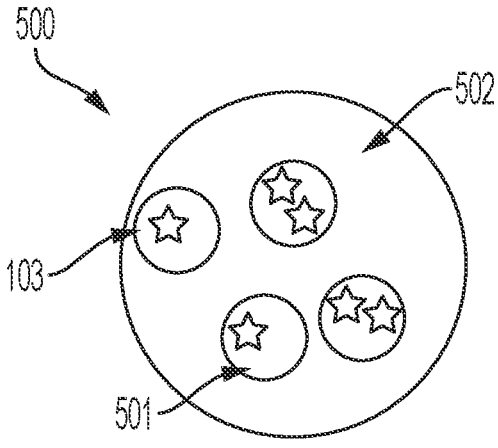
FIG. 5 is a schematic diagram that illustrates an example of a double-phase particle with multiple dispersed particles, in accordance with some embodiments.

FIG. 4 illustrates a double-phase particle 400 containing a dispersed inner phase 401 which is dispersed in a dispersed secondary phase 402 which is itself dispersed in a continuous phase 403. In some embodiments of double-phase particles, the components of an inner dispersed phase 401 may include phase media. In some embodiments of double-phase particles, the components of an inner dispersed phase 401 may include phase stabilizers. In some embodiments of double-phase particles, the components of an inner dispersed phase 401 may include surface stabilizers. In some embodiments of double-phase particles, the components of an inner dispersed phase 401 may include encapsulated active ingredients 103. In some embodiments of double-phase particles, the components of an inner dispersed phase may be a single active ingredient or any number of active ingredients, for example two active ingredients 103 and 404 encapsulated in the inner phase of the double-phase particle 400. In some embodiments of double-phase particles, the components of an inner dispersed phase 401 may include a combination phase media, phase stabilizers, surface stabilizers, and encapsulated active ingredients. In some embodiments of double-phase particles, the components of a dispersed secondary phase 402 may include a phase media. In some embodiments of double-phase particles, the components of a dispersed secondary phase 402 may include phase stabilizers. In some embodiments of double-phase particles, the components of a dispersed secondary phase 402 may include surface stabilizers. In some embodiments of double-phase particles, the components of a dispersed secondary phase 402 may include encapsulated active ingredients 405. In some embodiments of double-phase particles, the active ingredients in one phase may be the same or different than active ingredients in another phase; for example, the active ingredient in the secondary phase 405 of a double phase particle 400 may be the same as one of the active ingredients in the inner phase 103 or 404 or may be different. In some embodiments of double-phase particles, the components of a dispersed secondary phase 402 may include a combination phase media, phase stabilizers, surface stabilizers, and encapsulated active ingredients. In some embodiments of double-phase particles, the components of the continuous phase 403 may include a phase media. In some embodiments of double-phase particles, the components of the continuous phase 403 may include phase stabilizers. In some embodiments of double-phase particles, the components of the continuous phase 403 may include surface stabilizers. In some embodiments of double-phase particles, the components of the continuous phase 403 may include unencapsulated active ingredients 406. In some embodiments of double-phase particles, the unencapsulated ingredient or ingredients in 406 may be the same or different than the encapsulated active ingredients 103, 404, or 405. In some embodiments of double-phase particles, the components of a continuous phase 403 may include a combination phase media, phase stabilizers, surface stabilizers, and unencapsulated active ingredients.

In some embodiments of double-phase particles, the dispersed secondary phase 402 of each double phase particle 400 may contain a single particle of the inner dispersed phase 401, as is seen in FIG. 4. In some embodiments of double-phase particles, the dispersed secondary phase 502 of each double phase particle 500 may contain multiple particles of the inner dispersed phase 501, as is seen in FIG.

5. In some embodiments of double-phase particles, the dispersed particles 501 may contain active ingredients 103. In some embodiments of double-phase particles, a formulation containing double phase particles may contain a mixture of double phase particles containing a single particle 400 and multiple particles 500 of the inner dispersed phase in the secondary phase.

In some embodiments of double-phase particles, a dispersed phase mixture may be composed of a distinct inner dispersed phase dispersed in a distinct secondary phase which is itself dispersed in a distinct continuous and is referred to as double-phase particles.

10.1. Examples of Immiscible Double-Phase Particles

In some embodiments of immiscible double-phase particles, a formulation may consist of immiscible double-phase particles. Immiscible double-phase particles contain an inner phase 401 stably dispersed in a secondary phase 402 it is immiscible in which is itself dispersed in a final outer phase 403 which is immiscible with the secondary phase 402. In some embodiments of immiscible double-phase particles, immiscible double-phase particles are created by the dispersal of a single-phase particle system into another phase, such that the continuous phase of the single-phase particle system becomes a dispersed phase in the immiscible continuous outer phase of the double-phase particle system. In some embodiments of immiscible double-phase particles, an immiscible double-phase particle system is formed by dispersing a miscible single-phase particle system in an immiscible outer continuous phase.

In some embodiments of immiscible double-phase particles, a formulation may consist of immiscible double-phase particles. Immiscible double-phase particles contain an inner phase stably dispersed in a secondary phase it is immiscible in which is itself dispersed in a final outer phase which is immiscible with the secondary phase. In some embodiments of immiscible double-phase particles, immiscible double-phase particles are created by the dispersal of a single-phase particle system into another phase, such that the continuous phase of the single-phase particle system becomes a dispersed phase in the immiscible continuous outer phase of the double-phase particle system. In some embodiments of immiscible double-phase particles, an immiscible double-phase particle system is formed by dispersing a miscible single-phase particle system in an immiscible outer continuous phase.

In some embodiments of immiscible double-phase particles, a W/W formulation is dispersed into a hydrophobic phase, forming a W/W/O formulation. For example, 5 mL of a dispersion of caffeine containing sodium alginate particles in water (the dispersed phase) may be dispersed in a solution of 3 mL of PGPR dissolved in 40 mL of MCT (the hydrophobic phase) heated to 70° C. using a rotor-stator homogenizer to yield a hydrophilic dispersed phase which consists of a W/W particle system dispersed in a hydrophobic continuous phase (W/W/O formulation).

In some embodiments of immiscible double-phase particles, a O/O formulation is dispersed in a hydrophilic phase, forming a O/O/W formulation. For example, 12 g of lecithin may be dissolved in 20 mL of a dispersion of caffeine containing oleogel particles in LCT at 50° C. (the dispersed phase) and then dispersed in a solution of 10 mL of Q-Naturale 300 dissolved in 60 mL of water using a rotor-stator homogenizer to yield a hydrophobic dispersed phase which consists of a O/O particle system dispersed in a hydrophilic continuous phase (O/O/W formulation).

In some embodiments of immiscible double-phase particles, an immiscible double-phase particle system is formed by dispersing an immiscible single-phase particle system in an immiscible outer continuous phase. In some embodiments of immiscible double-phase particles, a W/O formulation is dispersed in a hydrophilic phase, forming a W/O/W formulation. For example, 1.45 g of glutathione and 200 mg of locust bean gum may be dissolved in 6 mL of DI water to form a hydrophilic inner phase. The hydrophilic inner phase may be dispersed in a solution of 1.5 g of ethyl cellulose, 1.2 g of PGPR, and 1.05 g of lecithin dissolved in 17 mL of MCT (hydrophobic secondary phase) at 90° C. using ultrasonication to form a W/O particle system. The W/O particle system is dispersed in the outer hydrophilic phase, which consists of 1 mL of tween 80 in 65 mL of water at 85° C., using ultrasonication to yield a hydrophilic inner phase encapsulating glutathione dispersed in a hydrophobic secondary phase which is itself dispersed in a hydrophilic continuous phase (W/O/W formulation).

In some embodiments of immiscible double-phase particles, a O/W formulation is dispersed in a hydrophobic phase, forming a O/W/O formulation. For example, a O/W formulation containing a dispersed hydrophobic phase of CBD and Caprol MPGO in MCT and a continuous hydrophilic phase of vitamin E TPGS in water maybe be dispersed in an outer continuous phase of MCT and PGPR using a rotor-stator homogenizer to yield an inner hydrophobic phase encapsulating an active ingredient dispersed in a secondary hydrophilic phase which is itself dispersed in a hydrophobic outer phase (O/W/O formulation).

For a double-phase particle system to be successfully formed, care must be taken to maintain the encapsulation of the inner phase. In some embodiments of immiscible double-phase particles, a lower input of mechanical energy must be used during dispersal of the single-phase particle into the double-phase system to prevent disruption of the original single-phase particles. In some embodiments of immiscible double-phase particles, lower intensity sonication or less sonication may be used in the second dispersal step than the first to prevent disruption of the inner single-phase particles. In some embodiments of immiscible double-phase particles, lower energy methods may be used to disperse the single-phase particle system into the outer phase, for example, using conventional shear mixing or a rotor-stator homogenizer to form a double-phase particle system from a single-phase particle system formed using ultrasonication. In some embodiments of immiscible double-phase particles, a combination of methods may be used to reduce the overall energy of the second dispersal step.

Figure 6:
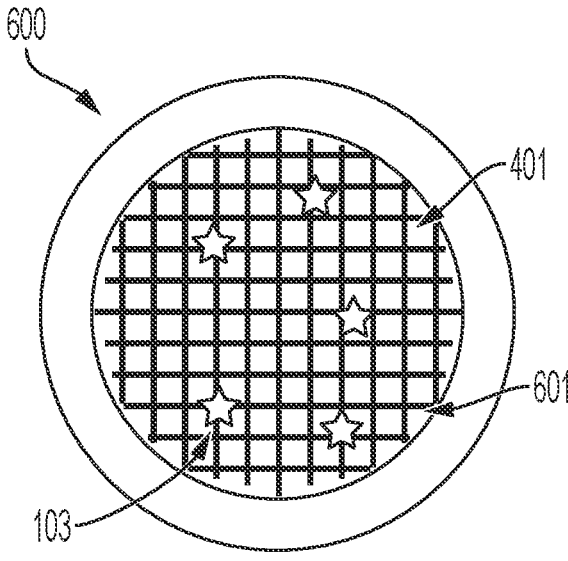
FIG. 6 is a schematic diagram that illustrates an example of a double-phase particle with a phase stabilizer in the inner phase, in accordance with some embodiments.

In some embodiments of immiscible double-phase particles, phase stabilizing agents may be added to the inner or secondary phase of a double phase particle system to increase its mechanical and chemical stability to prevent disruption during dispersal of the single-phase particles into a double-phase system and increase overall stability and shelf life. In some embodiments of immiscible double-phase particles, a phase stabilizing agent 601 is added to the inner phase to stabilize the double-phase system, as illustrated in FIG. 6, which depicts a double-phase particle 600 whose inner phase 401 is stabilized by a phase stabilizing agent 601. In some embodiments of immiscible double-phase particles a phase stabilizing agent 601 is added to the inner phase 401 to help prevent the diffusion of encapsulated ingredients 103 into the secondary or outer phase.

Figures 7, 8:
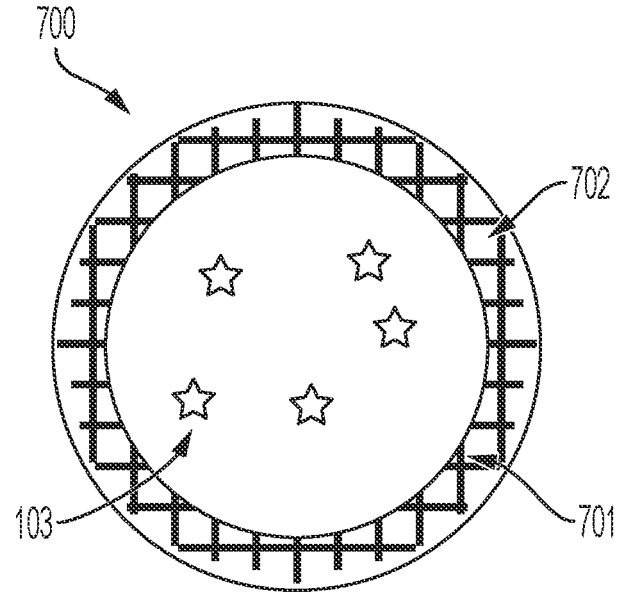
FIG. 7 is a schematic diagram that illustrates an example of a double-phase particle with a phase stabilizer in the secondary phase, in accordance with some embodiments.
FIG. 8 is a schematic diagram that illustrates an example of a multi-phase particle, in accordance with some embodiments.

In some embodiments of immiscible double-phase particles, a phase stabilizing agent 701 is added to the secondary phase to stabilize the double-phase system, as illustrated in FIG. 7, which depicts a double-phase particle 700 whose secondary phase 402 is stabilized by a phase stabilizing agent 701. In some embodiments of immiscible double-phase particles, a phase stabilizing agent 701 is added to the second phase 402 to prevent diffusion of encapsulated ingredients 103 from the inner or secondary phase to the outer phase. In some embodiments of immiscible double-phase particles, a phase stabilizing agent is added to both the inner and secondary phase to either stabilize the particle, prevent diffusion of active ingredients into the continuous phase, or both.

In some embodiments of immiscible double-phase particles, an active ingredient is added only to the inner phase of a double phase particle system. For example, collagen and gelatin may be dissolved in water (hydrophilic inner phase) which is dispersed in a solution oil and PGPR (hydrophobic secondary phase) using ultrasonication to form a W/O particle dispersion. The W/O particle dispersion may subsequently be dispersed in a solution of vitamin E TPGS in water (hydrophilic continuous phase) using a rotor-stator homogenizer and lower intensity ultrasonication to yield a W/O/W formulation with active ingredients located only in the inner phase.

In some embodiments of immiscible double-phase particles, active ingredients are added to both the inner and secondary phase of a double-phase particle system. For example, agar and zinc acetate (inner hydrophilic phase) may be dissolved in water and subsequently dispersed in a secondary hydrophobic phase consisting of ethyl cellulose, PGPR, lecithin, and vitamin $D_3$ dissolved in MCT using ultrasonication to form a W/O particle system. The W/O particle system is subsequently dispersed in an outer hydrophilic phase consisting of tween-80 and water using an ultrasonicator to yield a W/O/W formulation with active ingredients encapsulated in both the inner and secondary phase.

In some embodiments of immiscible double-phase particles, a double-phase particle system may contain a mixture of dispersed inner phase particles containing unique ingredients dispersed in a single secondary dispersed phase; for example, a W/O/W particle system which contains two distinct hydrophilic inner dispersed phases, one containing caffeine and sodium alginate and the other containing GHS and agar, both dispersed in a hydrophobic secondary dispersed phase.

10.2. Examples of Miscible Double-Phase Particles

In some embodiments of miscible double-phase particles, a formulation may consist of miscible double phase particles. Miscible double-phase particles contain an inner phase 401 stably dispersed in a secondary phase 402 it is miscible in, which is itself dispersed in a final outer continuous phase 403 for which the secondary phase is miscible in. In some embodiments of miscible double-phase particles, miscible double-phase particles are formed by dispersing miscible single-phase particles in a continuous phase in which they are miscible.

In some embodiments of miscible double-phase particles, a formulation may consist of miscible double phase particles. Miscible double-phase particles contain an inner phase stable dispersed in a secondary phase it is miscible in, which is itself dispersed in a final outer phase for which the secondary phase is miscible in. In some embodiments of miscible double-phase particles, miscible double-phase particles are formed by dispersing miscible single-phase particles in a continuous phase in which they are miscible.

In some embodiments of miscible double-phase particles, the stability of the particles and continued encapsulation of the both the inner and secondary dispersed phase's components is achieved by the presence of phase stabilizing agents which limit the diffusion of some or all components of dispersed phases into the continuous phase. In some embodiments of miscible double-phase particles, the phase stabilizing agents may prevent diffusion of the encapsulated components through chemical interactions with the encapsulated components, physical interactions with the encapsulated components, or through the formation of a physical barrier. In some embodiments of miscible double-phase particles, encapsulated components of the dispersed phases remain encapsulated due to low solubility in other phases.

In some embodiments of miscible double-phase particles, active ingredients may be encapsulated only in the inner phase of a miscible double-phase particle system. In some embodiments of miscible double-phase particles, active ingredients may be only placed in the inner phase of a miscible double-phase system so that their release kinetics may be delayed until the secondary phase is broken down. In some embodiments of miscible double-phase particles, active ingredients may be only placed in the inner phase of a miscible double-phase system so that their diffusion into the continuous phase is slowed. In some embodiments of miscible double-phase particles, active ingredients may be encapsulated in both the inner and secondary phase of miscible double-phase particle systems. In some embodiments of miscible double-phase particles, the same active ingredient is encapsulated in both the inner and secondary phase to provide a different release kinetic profile than a miscible single-phase particle system. In some embodiments of miscible double-phase particles, a larger concentration of active ingredient may be encapsulated in the secondary phase than the inner phase, leading to a release profile with larger concentration of active being released toward the beginning of the profile. In some embodiments of miscible double-phase particles, a larger concentration of active ingredient may be encapsulated in the inner phase than the secondary phase, leading to a release profile with larger concentration of active being released toward the end of the profile. In some embodiments of miscible double-phase particles, different active ingredients may be added to the inner and secondary phase so that the release profile of the active encapsulated in the secondary phase is shifted to earlier times after use of the particle system than the active encapsulated in the inner phase.

In some embodiments of miscible double-phase particles, a W/W formulation is dispersed in a hydrophilic phase, forming a W/W/W formulation. For example, a W/W particle system consisting of an inner phase of crosslinked sodium alginate and caffeine in water and an outer phase of water and excess calcium chloride may be dispersed in a solution of sodium alginate with the aid of ultrasonication. As the calcium chloride in the secondary phase comes in contact with the sodium alginate in the outer phase, crosslinking occurs, and a physical barrier is created at the interface of the secondary and continuous phase.

In some embodiments of miscible double-phase particles, a O/O formulation is dispersed in a hydrophobic phase, forming a O/O/O formulation. For example, a O/O particle system consisting of an inner phase of solidified ethyl cellulose and vitamin D3 in MCT and secondary phase of LCT and a crystalizing agent heated above the phases melting point can be dispersed in a hydrophobic continuous phase that is held at a substantially lower temperature than the melting point of the secondary phase using ultrasonication. Upon dropping below the melting point of the secondary phase, the secondary phase solidifies, forming a O/O/O formulation.

11. Examples of Multi-Phase Particles

FIG. 8 illustrates an example of a three-phase particle 800 consisting of an inner dispersed phase 801 dispersed in a secondary phase 802, which is itself dispersed in a tertiary phase 803. The tertiary phase 803 is dispersed in a continuous phase 804. A three-phase particle system is the simplest example of a multi-phase particle. Multi-phase particles consist of an inner phase dispersed in any number of subsequent phases (indexed as secondary, tertiary, etc. as their distance from the innermost phase increases) dispersed in a final continuous phase. In some embodiments of miscible double-phase particles, a multi-phase particle may contain active ingredients 103 in one or multiple phases.

In some embodiments of miscible double-phase particles, a dispersed phase mixture may be composed of more than two distinct phases dispersed throughout a continuous phase or continuous phase mixture and is referred to as multi-phase particles.

11.1. Examples of Immiscible Multi-Phase Particles

In some embodiments of immiscible multi-phase particles, a formulation consists of immiscible multi-phase particles. Immiscible multi-phase particles consist of an inner phase dispersed in any number of subsequent phases (indexed as secondary, tertiary, etc. as their distance from the innermost phase increases) dispersed in a final outer continuous phase. In some embodiments of immiscible multi-phase particles, multi-phase particles with n phases are formed by dispersing multi-phase particles with n−1 phases in an outer continuous phase; in an example of a multi-phase particle being formed this way, a W/O/W emulsion formed as previously described may be itself dispersed in a hydrophobic phase using shear mixing to form a W/O/W/O particle system. In some embodiments of immiscible multi-phase particles, multi-phase particles may be formed using solely emulsification techniques. In some embodiments of immiscible multi-phase particles, multi-phase particles may be formed using a combination of emulsification techniques and conventional coating equipment such as a conventional coating pan, an airless spray technique, a fluidized bed, a spray dryer, or the like.

Immiscible multi-phase particles can be formed using any combination of phases so long as the phases remain stable and distinct under the environmental conditions present after their formation.

In some embodiments of immiscible multi-phase particles, an active ingredient is added only to the inner phase of the multiple-phase particle system. In some embodiments of immiscible multi-phase particles, additional layers are added to the system to alter the release kinetics of the active ingredient, for example extended release or targeted release.

In some embodiments of immiscible multi-phase particles, active ingredients may be added to multiple phases of the multiple particle system. In some embodiments of immiscible multi-phase particles, the same active ingredients may be added to multiple phases to alter the release kinetics and provide an extended release. In some embodiments of immiscible multi-phase particles, different active ingredient or mixtures thereof are added to different layers such that different active ingredients are released and metabolized at different times after digestion.

11.2. Examples of Miscible Multi-Phase Particles

In some embodiments of miscible multi-phase particles, multi-phase particles may include particles containing one or more interfaces internal to the particle between distinct miscible phases such as a W/W/W/W particle containing two interfaces between pairs of three distinct yet miscible hydrophilic phases, an example being a particle composed of an inner water phase in a gelled state with the gel formed by carob bean gum with a second water phase in a gelled state with the gel formed by calcium alginate, further coated in a third water phase in a gelled state with the gel formed by xanthan gum, dispersed in a liquid water continuous phase.

12. Examples of Particle Aggregates

Figure 9:
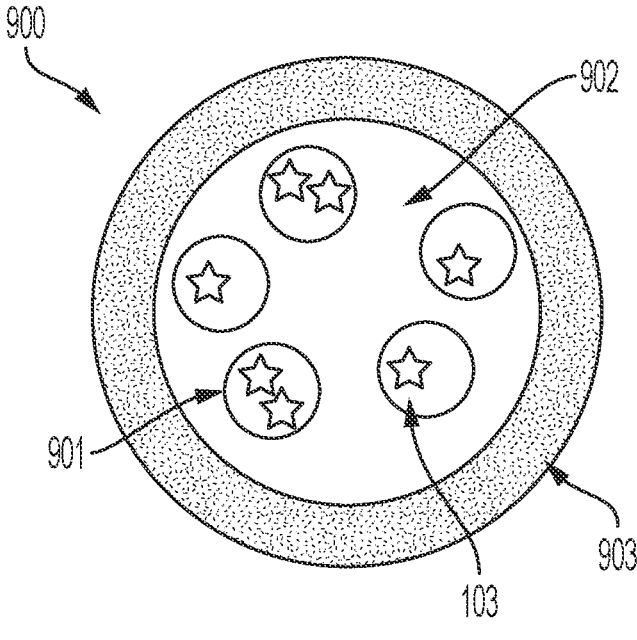
FIG. 9 is a schematic diagram that illustrates an example of a particle aggregate, in accordance with some embodiments.
Figure 10:
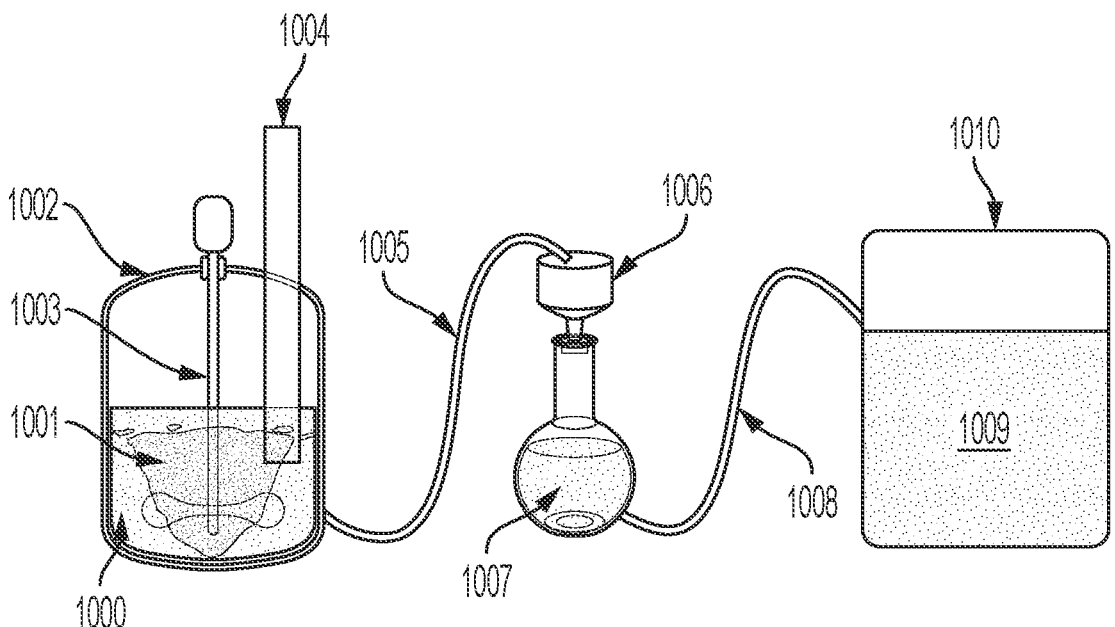
FIG. 10 is a schematic diagram that illustrates an example of a production process for preparing an extract of plant matter, in accordance with some embodiments.

In some embodiments of particle aggregates, a formulation may consist of particle aggregates 900, which consist of a plurality of a previously discussed particles 901 containing active ingredients 103 dispersed in a solidified or semi-solidified continuous phase 902, as displayed in FIG. 9.

In some embodiments of particle aggregates, the particles 901 dispersed in the aggregate may be single-phase, double-phase, or multi-phase particles. In some embodiments of particle aggregates, the particles dispersed in the aggregate may be a mixture of different particles. In some embodiments of particle aggregates, the average size of the dispersed particles may be less than 1000 (or 50, 100, 200, 500, 750, 2000, 10000, 50000) nm.

In some embodiments of particle aggregates, particle aggregates may be formed by having a phase stabilizing agent added to the continuous phase of a particle system, either during or after production, in concentrations such that the continuous phase, and therefore the entire particle system, is a solid or gel at certain temperatures higher than the phase's freezing point (e.g., R.T., 30° C., 40° C., 50° C., 70° C., 85° C., 97° C.) without the phase stabilizing agent.

In some embodiments of particle aggregates, the continuous phase can be solidified or gelled through a reversable process such as freezing. In some embodiments of particle aggregates, the continuous phase can be solidified or gelled through a thermodynamically irreversible process, such as the formation of crosslinking covalent bonds between components in the continuous phase.

In some embodiments of particle aggregates, the continuous phase can be solidified or gelled through chemical means. In some embodiments of particle aggregates, chemically induced solidification or gelation may be reversable, such as the crosslinking of sodium alginate with divalent cations. In some embodiments of particle aggregates, chemically induced solidification or gelation may be irreversible, such as the crosslinking of polysaccharides such as starch with one or multiple di- or poly-carboxylic acids such as citric acid to form a crosslinked gel that is GRAS. In some embodiments of particle aggregates, chemically induced solidification or gelation may be irreversibly induced to create a biocompatible gel such as the crosslinking of polysaccharides using free radical initiators such a persulfate salts. In some embodiments of particle aggregates, the continuous phase can be solidified or gelled through physical means. In some embodiments of particle aggregates, physically induced solidification or gelation may be reversable. In some embodiments of particle aggregates, reversible physically induced solidification or gelation may be triggered by temperature, such as the solidification or gelation of a phase as it is cooled below its freezing or glass transition point.

In some embodiments of particle aggregates, solidification or gelation of the continuous phase may occur at the desired temperature without the addition of phase stabilizing agents; for example, if a phase media which is solid or gelled at the desired temperature is used (e.g., waxes, ghee, shortening or other saturated fats). In some embodiments of particle aggregates, solidification or gelation of the continuous phase may be induce though the addition of GRAS small molecule phase stabilizing agents such as waxes or mono or di glycerides which may crystalize in a phase below a certain temperature and induce gelation. In some embodiments of particle aggregates, solidification or gelation of the continuous phase may be induce though the addition of biocompatible small molecule phase stabilizing agents such as 12-HSA which may crystalize in a phase below a certain temperature and induce gelation. In some embodiments of particle aggregates, solidification or gelation of the continuous phase may be induced through addition of polymers (e.g., polysaccharides, proteins, polyolefins, polyglycols) which may form gel networks below a certain temperature. In some embodiments of particle aggregates, solidification or gelation of the continuous phase may be induced through addition of GRAS polymers such as proteins (e.g., whey, casein), polysaccharides (e.g., starches, gums, chitosan), modified polysaccharides (e.g., methylcellulose, ethyl cellulose, hydroxypropyl methylcellulose), or combinations thereof, which may form gel networks below a certain temperature. In some embodiments of particle aggregates, solidification or gelation of the continuous phase may be induced through addition of GRAS polymers such as proteins (e.g., whey) and polysaccharides (e.g., starches, gums, chitosan) which may form cross linked gel networks when additional chemical or physical stimuli are added to the formulation.

In some embodiments of particle aggregates, solidification of the continuous phase, and thus formation of particle aggregates, may be induced after the continuous phase has been converted into individual droplets, for example when a particle system is cooled below its freezing point after being expelled into small droplets from the nozzle of a spray cooler system. For example, a W/O system containing a dispersed phase of water and collagen dispersed in a continuous phase consisting of PGPR, rice bran wax, and MCT heated to 80° C. can be sprayed out of the nozzle of a spray chiller into a room-temperature steam of air to induce solidification of the particle system at approximately 60° C., forming particles of aggregate. In some embodiments of particle aggregates, formation of an aggregate is followed by a processing step in which the continuous phase is broken up into smaller pieces or particles. In some embodiments of particle aggregates, the aggregates are broken into smaller particles with mechanical grinding. In some embodiments of particle aggregates, the nanovesicle aggregates are ground until an average particles size of 500 μm (or 5000, 2500, 1000, 750, 500, 250, 100, or 50 μm) is achieved.

In some embodiments of particle aggregates, an aggregate system may be further coated in any number of distinct phases 903. In some embodiments of particle aggregates, the particle aggregates may be coated in additional layers using conventional coating technologies such as a conventional coating pan, an airless spray technique, a fluidized bed, a spray dryer, or the like. In some embodiments of particle aggregates, the coating layers may consist of a phase media and phase stabilizing agent that is soluble in that phase media, such as shellac, proteins, polysaccharides, or small molecules which induce crystallization. In some embodiments of particle aggregates, the phase media is removed after coating to form a solid coating. In some embodiments of particle aggregates, the coating is solidified or gelled through a temperature induced phase change such as freezing or glass transition.

In some embodiments of particle aggregates, additional components known as pore formers may be added to any solidified or gelled phase. In some embodiments of particle aggregates, pore formers are components that crystalize in a given phase under manufacturing and storage conditions, but dissolve faster than the solidified or gelled phase. In some embodiments of particle aggregates, the dissolution of pore formers from a phase creates distinct pores in the phase that may allow diffusion of material into or through the phase at rates higher than the rates of diffusion through the solidified or gelled regions of the phase. In some embodiments of particle aggregates, pore formers are chosen such that they are substantially more soluble than the solid or gelled components in the medium in which the formation of the pores is desired; for example, simple sugars such a glucose could be used as pore formers in a crosslinked protein coating when the formation of pores is desired upon exposure of a particle system to water. In some embodiments of particle aggregates, when pores formation is desired after consumption by a human, pore formers may be any GRAS macromolecule or small molecule that is readily soluble under biological conditions, such as sugars (e.g., glucose, fructose, mannitol, galactose, sorbitol, or dextran), polysaccharides (e.g. sodium alginate, or hydroxypropyl cellulose) or salts (e.g. sodium chloride, sodium bromide, or potassium citrate).

In some embodiments of particle aggregates, the formation of an aggregate form a particle system may provide different and desired properties to the particle system. In some embodiments of particle aggregates, formation of an aggregate may increase stability of the particle system. In some embodiments of particle aggregates, formation of an aggregate may increase stability of the individual dispersed particles, preventing them from kinetically degrading through methods such a coalescence.

In some embodiments of particle aggregates, an increase in stability may lead to an increased shelf life; for example, a particle system that is stable for 12 months as a liquid may have a shelf life of 24 or 36 months when it is solidified into an aggregate. In some embodiments of particle aggregates, formation of an aggregate may further prevent active ingredients from diffusing out of the dispersed phase or decomposing. In some embodiments of particle aggregates, formation of an aggregate may change release kinetics. In some embodiments of particle aggregates, formation of an aggregate may cause the active to be release more slowly while the continuous phase is dissolved, leading to an extended-release kinetic profile for the active. In some embodiments of particle aggregates, formation of an aggregate may cause the active to release only under certain chemical or physical conditions, leading to a targeted release; for example, a coating which is composed of crosslinked polysaccharide gel which insoluble at the acidic pH of the stomach but swells and allows diffusion of its encapsulated contents in a neutral pH, such as those found in the intestines.

13. Examples of Particle Properties

In some embodiments, the surface charge of nanoparticles and their tendency to coagulate may be determined directly as a predictive measure of stability in solution. Zeta potential quantifies the difference in potential between the bulk solution (continuous phase containing particle dispersion) in which particle are dispersed and the layer of that bulk solution in contact with the particle surface. This evaluation of superficial charge is a useful metric in understanding the chemistry and behavior of colloids in solution, particularly at the submicron scale. Zeta potentials approximately 30 mV or larger in either the positive or negative direction establish a stable particle dispersion, as charges of high magnitudes repel each other in solution; on the other hand, values below that threshold tend to aggregate and flocculate. A Zetasizer Nano instrument (e.g., dynamic light scattering instrument or photon correlation spectrometer) determines zeta potential by applying an electric field to a diluted particle suspension and measures its velocity through laser doppler electrophoresis; combining that value with intrinsic properties of the dispersion medium—viscosity and dielectric constant—allows for a final calculation.

3. Example Materials

In some embodiments, materials, phases, processing agents, or ingredients (and their combinations) may be incorporated as a component before, during, or after processing (and, in some cases, subsequently removed before, during, or after processing) of particles and products in order to serve a particular role in designing control of dynamics, structure, formation, state, kinetics, assembly, function, stability, bioactivity, reaction to external stimuli (e.g., heat transfer, light, sound, pH, enzymes) and combinations or extensions thereof.

In some embodiments, materials, phases, processing agents, or ingredients may be grouped and referenced by the intended function they serve in the processing or final form of particles and products into which they are incorporated or aid in their formation in the case of processing agents.

In some embodiments, materials, phases, processing agents, and ingredients may be grouped and referenced by their intended function in the processing, production, synthesis, or subsequent applications to a target organism to illicit a biochemical and physiological response (e.g., bioactivity).

In some embodiments, materials, phases, processing agents, and ingredients may be grouped and referenced by their intended function for processing, production, synthesis, stabilization, achieving desired forms, or manufacture (including combinations thereof) of particles and products (regardless of any additional function and bioactivities that may arise as a result of their inclusion during particle and product production and final forms).

In some embodiments, a product may be composed of particles, particle dispersions, and combinations thereof. In some embodiments, a partial product may include particles, particle dispersions, or combinations thereof, such that the product in its entirety or parts of the product may include particles, particle dispersion, and combinations thereof. In some embodiments, a product may not contain particles.

1. Examples of Active Ingredients

In some embodiments, ingredients may be referenced and categorized as active ingredients, either based on the intended function of the ingredient or on effects achieved by including the ingredients in question.

In some embodiments, active ingredients may be a component of a product such that the resulting or intended function may be to initiate (illicit, induce, affect) biological responses upon product administration to an organism (regardless of whether the product was designed for a particular organism or class of organisms including intended routes of administration or groups of administration routes specified).

In some embodiments, an active ingredient may induce or intensify intended biological and physiological responses when administered in isolation or together with other ingredients. In some embodiments, an active ingredient may induce or intensify intended biological and physiological responses only when administered with groups of other ingredients (sometimes just one other ingredient) or when administered as a component of a product with all other ingredients from which the product is composed and may additionally depend on the production process and subsequent forms within the product.

In some embodiments, ingredients may be classified as small molecules ("small molecule ingredients"). In some embodiments, active ingredients may be classified as small molecules ("small active molecule ingredients") such as PQQ, caffeine, and amino acids. Small molecules are defined as those with a molar mass below 1000 g/mol (or average molar mass below 1000 g/mol, or molecular mass below one thousand Daltons for systems of identical molecules in composition, or average molecular mass below 1000 Daltons for systems of molecules of variable identity in composite) or possessing an average molecular mass below 1000 g/mol.

In some embodiments, ingredients may be classified as macromolecules ("large molecules"). In some embodiments, active ingredients may be classified as macromolecules ("large molecules") such as collagen and pea proteins. Macromolecules are defined as those with a molar mass larger than or equal 1000 g/mol (or average molar mass larger than or equal 1000 g/mol, or molecular mass larger than or equal 1000 Daltons for systems of identical molecules in composition, or average molecular mass larger than or equal 1000 Daltons for systems of molecules of variable identity in composite) or possessing an average molecular mass larger than or equal 1000 g/mol. In some embodiments, ingredients (active ingredients or inactive ingredients) may be classified or referred to as molecules such that their components are composed of small molecules, macromolecules, and mixtures thereof without preference unless specified otherwise.

In some embodiments, active ingredients and their constituent molecules (or other indivisible components) may possess a center of inversion that does not yield the same molecule under the spatial operations of translation and rotation, such that the constituent molecules and other indivisible components have chirality (are chiral) and may be present as an enantiomerically pure form (only one mirror image of component present), a racemic mixture of enantiomers (both mirror images of component present), or chosen such that the racemic mixture of enantiomers has a higher population of a specific enantiomer, regardless of relative bioactivity or in some cases to leverage the difference in bioactivity or differences related to processing such as enantiomer and chirality dependent chemistries. In some embodiments, ingredients, in particular active ingredients, with composition including chiral molecules or other components may be chosen and designed such that upon incorporation into particles and products the desired functions and forms may be varied and improved. An example demonstrating the use of ingredients with chiral components is a case of amino acids (or amino acid derivatives) chosen as active ingredients in a formulation where one enantiomer of the amino acids may exhibit a desired biological activity as much as an order of magnitude more than the opposite enantiomer, in which case the active ingredient is chosen to be enantiomerically pure for such amino acids with the higher activity and decreased material and any related side effects. Another example with a chiral amino acid is when both enantiomers of an amino acid have bioactivities on the same order of magnitude and either act on different varieties of receptors or compete in a way that provides unique bioactivity (e.g., D-phenylalanine and L-phenylalanine), in this example the relative amount of each enantiomer may be varied to achieve a desired bioactivity or chemical reaction kinetics during or after production of products in which they are ingredients. The situation of using racemic (equal molarity) or skewed-racemic (unequal molarity) may be further leveraged if the active ingredient or molecular components therein may interconvert between enantiomers in a controlled or uncontrolled fashion that allows for complex kinetics when coupled to controlled or targeted active ingredient release strategies in vivo.

In some embodiments, active ingredients may be amino acids, the monomers that comprise peptides and proteins, as well as their chemically modified forms and synthetic amino acid varieties. In some embodiments, amino acids referenced without specifying a particular enantiomer, racemic mixture, or other mixtures of enantiomers may be used as particular enantiomers or mixtures of enantiomers, unless specified otherwise. In some embodiments, active ingredients may be amino acids with hydrophobic, aliphatic side chains including alanine, isoleucine, leucine, methionine, and valine. In some embodiments, active ingredients may be amino acids with hydrophobic, aromatic side chains including phenylalanine, tryptophan, and tyrosine. In some embodiments, active ingredients may be amino acids with hydrophilic, polar neutral side chains including asparagine, cysteine, glutamine, serine, and threonine. In some embodiments, active ingredients may be amino acids with hydrophilic, electrically charged, acidic side chains including aspartic acid and glutamic acid. In some embodiments, active ingredients may be amino acids with hydrophilic, electrically charged, basic side chains including arginine, histidine, and lysine. In some embodiments, active ingredients may be amino acids that are classified as unique amino acids including glycine and proline.

In some embodiments, amino acids may be categorized and chosen individually or in groups from the categories of very hydrophobic, hydrophobic, neutral, and hydrophilic as a function of pH. In some embodiments, phases may possess a pH less than 5 or pH greater than 5 and contains amino acids, and similarly structured molecules (signs shown in parentheses correspond to sign of logP)

In some embodiments, active ingredients may be amino acids in a phase at pH less than 5 and categorized as very hydrophobic amino acids such as leucine, isoleucine, phenylalanine, tryptophan, valine, and methionine. In some embodiments, amino acids in a phase at pH less than 5 may be categorized as hydrophobic amino acids such as cysteine, tyrosine, and alanine. In some embodiments, amino acids in a phase at pH less than 5 may be categorized as neutral amino acids such as threonine, glutamic acid, glycine, serine, glutamine, and aspartic acid. In some embodiments, amino acids in a phase at pH less than 5 may be categorized as hydrophilic amino acids such as arginine, lysine, asparagine, histidine, and proline.

In some embodiments, active ingredients may be amino acids in a phase at pH greater than 5 categorized as very hydrophobic amino acids such as phenylalanine, isoleucine, tryptophan, leucine, valine, and methionine. In some embodiments, active ingredients may be amino acids in a phase at pH greater than 5 categorized as hydrophobic amino acids such as tyrosine, cysteine, and alanine. In some embodiments, active ingredients may be amino acids in a phase at pH greater than 5, categorized as neutral amino acids (or amphiphilic amino acids) such as threonine, histidine, glycine, serine, and glutamine. In some embodiments, active ingredients may be amino acids in a phase at pH greater than 5 and categorized as hydrophilic amino acids such as arginine, lysine, asparagine, glutamic acid, proline, and aspartic acid.

In some embodiments, active ingredients may be amino acids categorized and chosen from categories (individually or as mixtures) such as essential, conditionally essential, or non-essential human (Homo sapiens) amino acids. In some embodiments, active ingredients may be essential amino acids such as histidine, isoleucine, leucine, lysine, methionine, phenylalanine, threonine, tryptophan, and valine. In some embodiments, active ingredients may be conditionally essential amino acids such as arginine, cysteine, glutamine, glycine, proline, and tyrosine. In some embodiments, amino acids in a phase may be non-essential amino acids include alanine, aspartic acid, asparagine, glutamic acid, serine, selenocysteine, and pyrrolysine, and combinations thereof.

In some embodiments, active ingredients may be ligands or cofactors (coenzymes) administered with an enzyme, macromolecule, protein, or functional structure that exists in vivo and interacts with the cofactor of interest. In some embodiments, active ingredients may be ligands or cofactors (coenzymes) administered without any additional interacting moieties during administration such as enzymes or other interacting molecular or macromolecular structures, covalent or otherwise.

In some embodiments, active ingredients may be a ligand or coenzyme (cofactor) classified as inorganic and may subsequently function to mediate or initiate bioactivity with a microscopic mechanism (e.g., interaction with a macromolecule such as a protein, enzyme, macromolecular superstructure, self-assembled or covalent in nature, or otherwise) or interaction in mind or a macroscopic interaction in mind (e.g., physiological response) whether the mechanism is known in part or whole. Examples of inorganic ligands and cofactors, whether fully solvated by an aqueous or polar medium of a phase, partially solvated, or coordinated by small molecules or macromolecules therein, includes calcium ions (e.g., $Ca^{2+}$), copper ions (e.g., cupric ions, cytochrome oxidase), iron ions (e.g., ferrous, ferric, hydrogenase, nitrogenase, cytochrome, heme, catalase), magnesium ions (e.g., glucose 6-phosphatase, hexokinase, DNA polymerase), manganese ions (e.g., arginase), molybdenum ions (e.g., nitrate reductase, xanthine oxidase, nitrogenase), potassium ions (e.g., $K^+$, nickel ions (e.g., urease), zinc ions (e.g., $Zn^{2+}$), and combinations thereof.

In some embodiments, active ingredients may be inorganic anions (including all charge states, associated neutrally charged counterparts, oxides, complexes) solvated by a phase medium or bound by covalent, ionic, or halogen bonds to other ingredients solvated within a phase medium, may function active ingredient such as chloride ions (e.g., $Cl^-$), selenium ion (e.g., $Se^{2-}$), sulfur ions (e.g., $S^{2-}$), silicon ions, silicate ions, and combinations thereof.

In some embodiments, active ingredients may be neutral or charged inorganic clusters or solids, such nanocrystalline solids, amorphous solids, or as extended solids, examples include $Fe_2S_2$, $Si_2O_6$, silicon dioxide nanocrystals, and amorphous titania nanoparticles.

In some embodiments, active ingredients may be inorganic anions, cations, neutral clusters, complexes, particles, nanocrystals, and combinations thereof. In some embodiments, an active ingredient may be a particular element or a mineral containing a particular element such as boron, calcium, chloride, chromium, copper, iron, magnesium, manganese, molybdenum, potassium, selenium, silicon, sodium, zinc. In some embodiments, an active ingredient may be a mineral or mixture of minerals, either solvated or dispersed in contained phases.

In some embodiments, active ingredients may be ligands or coenzymes (cofactors) classified as organic may function as an active ingredient to mediate or initiate bioactivity with a microscopic mechanism (e.g., interaction with a macromolecule such as a protein, enzyme, macromolecular superstructure, self-assembled or covalent in nature, or otherwise)

or interaction in mind or a macroscopic interaction in mind (e.g., physiological response) whether the mechanism is unknown, known in part, or known in whole. Examples of organic ligands and cofactors are coenzyme F420, flavin adenine dinucleotide, flavin mononucleotide, ascorbic acid, menaquinone, tetrahydrofolic acid, coenzyme A, biotin, cobalamins, methylcobalamin, pyridoxal phosphate, NAD⁺, NADP⁺, thiamine pyrophosphate, 5-HTP (5-hydroxytrypto-phan), acetyl L-carnitine, alanine, arginine, glutamic acid, glutamine, glutathione, glycine, L-theanine, lysine, phenyl-alanine, tyrosine, phosphatidylserine, and combination or close molecular structures thereof.

In some embodiments, active ingredients may be organic salts, inorganic salts, or elemental ions (e.g., metal cations or halogen anions), metal containing molecular species, or molecules containing elements other than hydrogen, carbon, oxygen, and nitrogen to provide particular elements, their ions (in various oxidation states, where desired), or inor-ganic molecular species to impart or influence bioactivity directly (or indirectly). In some embodiments, active ingre-dients may affect bioactivity by influencing the bioactivity of other active ingredients administered simultaneously while inhabiting the same particles or other portions of product administered. In some embodiments, active ingre-dients may affect bioactivity when administered to indirectly influence the bioactivity and ensuing response of the organ-ism via interactions molecular targets intrinsic to the organ-ism or with additional active ingredients of other products or particles that are administered prior (in rapid succession or days or weeks after) to administration of the second product. In some embodiments, active ingredients may circumvent or alter metabolism of molecules and macromolecules intrinsic to organism targeted for administration or other ingredients, including metabolism to metabolites that have additional bioactivity, or combinations thereof (in some cases, referred to as bioenhancers).

In some embodiments, active ingredients may be vitamins or their components that are essential micronutrients for an organism targeted for administration. In some embodiments, active ingredients may be vitamins or vitamin components for humans (Homo sapiens), including species with similar vitamin requirements for a particular application.

In some embodiments, active ingredients may be one or multiple vitamins such as vitamin A, vitamin B, vitamin C, vitamin D, vitamin E, vitamin K and combinations thereof, commonly referred to as multivitamins. In some embodi-ments, vitamins may be further distinguished as hydropho-bic vitamins or hydrophilic vitamins or be grouped depend-ing on their physiochemical properties (e.g., logP) including by chemical functional groups. In some embodiments, active ingredients may be a vitamin, such as vitamin A, vitamin B, vitamin C, vitamin D, vitamin E, or vitamin K, such that the vitamin is one variety of molecule or multiple molecules and molecular mixtures (including those present in ingredients generally) that satisfy the criteria for alleviating symptoms or possessing bioactivity potential characteristic of the vita-min class specified. In some embodiments, active ingredi-ents may be hydrophobic vitamins such as vitamin A, vitamin D, vitamin E, and vitamin K. In some embodiments, active ingredients may be hydrophilic vitamins utilized as active ingredients include vitamin A, vitamin D, vitamin E, and vitamin K.

In some embodiments, active ingredients may not be classified as commonly accepted vitamins in precise struc-ture and composition but may be similar in molecular structure to ingredients commonly accepted as vitamins. In some embodiments, active ingredients may be classified as vitamins by molecular structure, mixtures of molecules considered together, nuclear composition in the case of molecular rearrangements, and combinations thereof. In some embodiments, active ingredients may be classified as vitamins by their bioactivity and physiological response functions with similar, enhanced, or categorically related bioactivity and physiological responses fulfilling the needs of the vitamin or vitamins in question when administered to an organism displaying vitamin deficiency symptoms or related responses. In some embodiments, a vitamin may be one or more vitamers (molecules, macromolecules, and their mixtures that alleviate vitamin deficiency symptoms asso-ciated with a class of vitamins).

In some embodiments, active ingredients may be vitamin A or associated vitamers. In some embodiments, an active ingredient may be vitamin B such as vitamin B1 (thiamine), vitamin B12 (cobalamin), vitamin B2 (riboflavin), vitamin B3 (niacin), vitamin B5 (pantothenic acid), vitamin B6 (pyridoxine), vitamin B7 (biotin), vitamin B9 (folate), vita-min B complex, and mixtures thereof, including their vita-mers. In some embodiments, an active ingredient may be vitamin C or associated vitamers. In some embodiments, an active ingredient may be vitamin D such as vitamin D2, and vitamin D3 or associated vitamers. In some embodiments, an active ingredient may be vitamin D analogues with modified side chains or other difference in chemical struc-ture aimed at reducing common vitamin D side effects such as alfacalcidol, calcipotriol, doxercalciferol, falecalcitriol, paricalcitol, and tacalcitol, or associated vitamers. In some embodiments, an active ingredient may be vitamin E and associated vitamers. In some embodiments, an active ingre-dient may be vitamin K and associated vitamers.

In some embodiments, active ingredients may be mol-ecules classified as nootropics function as active ingredients such as 5-HTP, acetyl-L-carnitine, alpha GPC, ascorbic acid, asparagine, aspartic acid, berberine, biotin, boron, caffeine, creatine, curcumin, cysteine, GABA, choline bitartrate, citi-coline, DHA, EPA, folic acid, huperzine A, leucine, luteolin, magnesium, melatonin, methylcobalamin, methylliberine, N-acetyl cysteine, pantothenic acid, phenylalanine, phos-phatidylcholine, phosphatidylserine, piracetam, pterostil-bene, pyrroloquinoline quinone (PQQ), racetam, sibutramine, taurine, theacrine, theanine, thiamine, tyrosine, zinc, and combinations thereof.

In some embodiments, active ingredients may be dietary supplements for a target organism.

1.1. Examples of Hydrophobic Active Ingredients (Small Molecule)

In some embodiments having small-molecule hydropho-bic active ingredients, active ingredients may have a positive logP with magnitude strictly greater than to zero (logP>0). In some embodiments having small-molecule hydrophobic active ingredients, active ingredients may have positive logP and be referred to as hydrophobic active ingredients. In some embodiments having small-molecule hydrophobic active ingredients, active ingredients may be hydrophobic active ingredients referred to as lipophilic active ingredients interchangeably. In some embodiments having small-mol-ecule hydrophobic active ingredients, active ingredients may have a positive logP with magnitude less or equal to 1 and strictly greater than zero (1≥logP>0) and be referred to as hydrophobic (lipophilic) active ingredients, amphiphilic active ingredients, or simultaneously, hydrophobic (lipo-philic) active ingredients and amphiphilic active ingredients. In some embodiments having small-molecule hydropho-bic active ingredients, active ingredients may be cannabi-noids. In some embodiments having small-molecule hydrophobic active ingredients, active ingredients may be cannabinoids derived or extracted from various sources including exemplars, hemp (e.g., whole plant, stalk, stem, seed) and *Cannabis* (e.g., whole plant, flower, leaf, stalk, stem, seed). Examples of cannabinoids include cannabigerol-type (CBG), cannabigerolic acid (CBGA), cannabigerolic acid monomethylether (CBGAM), cannabigerol monomethyl ether (CBGM), cannabichromene-type (CBC), cannabichromanon (CBCN), cannabichromenic acid (CBCA), cannabichromevarin-type (CB CV), cannabichromevarinic acid (CBCVA), cannabidiol-type (CBD), tetrahydrocannabinol-type (THC), iso-tetrahydrocannabinol-type (iso-THC), cannabinol-type (CBN), cannabinolic acid (CBNA), cannabinol methylether (CBNM), cannabinol-$C_4$ (CBN-$C_4$), cannabinol-$C_2$ (CBN-$C_2$), cannabiorcol (CBN-$C_1$), cannabinodiol (CBND), cannabielsoin-type (CBE), cannabielsoic acid A (CBEA-A), cannabielsoic acid B (CBEA-B), cannabicyclol-type (CBL), cannabicyclolic acid (CBLA), cannabicyclovarin (CBLV), cannabicitran-type (CRM), cannabitriol (CBT), cannabitriolvarin (CBTV), ethoxy-cannabitiolvarin (CBTVE), cannabivarin-type (CBV), cannabinodivarin (CBVD), tetrahydrocannabivarin-type (THCV), cannabidivarin-type (CBDV), cannabigerovarin-type (CBGV), cannabigerovarinic acid (CBGVA), cannabifuran (CBF), dehydrocannabifuran (DCBF), cannabiripsol (CBR), and combinations thereof.

In some embodiments having small-molecule hydrophobic active ingredients, active ingredients may be referenced as tetrahydrocannabinol (THC) and may be composed of one or more isomers such as delta-6a,7-tetrahydrocannabinol, delta-7-tetrahydrocannabinol, delta-8-tetrahydrocannabinol, delta-9,11-tetrahydrocannabinol, delta-9-tetrahydrocannabinol, delta-10-tetrahydrocannabinol, and delta-6a, 10a-tetrahydrocannabinol, and combinations thereof. In some embodiments having small-molecule hydrophobic active ingredients, active ingredients may be referred as delta-9-tetrahydrocannabinol (D9-THC) and may be composed of one or more stereoisomers including (6aR,10aR)-delta-9-tetrahydrocannabinol, (6aS,10aR)-delta tetrahydrocannabinol, (6aS,10aS)-delta-9-tetrahydrocannabinol, (6aR, 10aS)-delta tetrahydrocannabinol, and combinations thereof. In some embodiments having small-molecule hydrophobic active ingredients, active ingredients may be one or many stereoisomers of other THC isomers, structural or otherwise.

In some embodiments having small-molecule hydrophobic active ingredients, an active ingredient may be an isolate of a cannabinoid or set of cannabinoids. In some embodiments having small-molecule hydrophobic active ingredients, an active ingredient may be a broad-spectrum distillate, in part or in whole, such as a THC-free broad-spectrum distillate. In some embodiments having small-molecule hydrophobic active ingredients, an active ingredient may be an extract, distillate, powder, tincture, or isolate with terpene content removed or augmented with other terpenes to achieve a desired pharmacological response upon administration or to achieve sensory experiences, especially in the case of oral administration.

In some embodiments having small-molecule hydrophobic active ingredients, hydrophobic active ingredients may be vitamins such as vitamin D (e.g., vitamin D2, vitamin D3).

In some embodiments having small-molecule hydrophobic active ingredients, hydrophobic active ingredients may be a component of (or entire) medium of a hydrophobic phase in a formulation may additionally function as a hydrophobic active ingredient of the same phase. ingredients that are commonly utilized as both a hydrophobic medium and a hydrophobic active ingredient of a hydrophobic phase In some embodiments having small-molecule hydrophobic active ingredients, chemicals derived from plants, commonly referred to as phytochemicals including herein, may be utilized as hydrophobic active ingredients. Most phytochemicals can be grouped into four major biosynthetic classes differentiated by molecular composition and structure.

In some embodiments having small-molecule hydrophobic active ingredients, a hydrophobic active ingredient may be a purified phytochemical extracted from plant matter of a single species or variety, and mixtures of plant matter from two or more different species, such as acacetin, antirrhinin, apigenin, berberine, capsaicin, chrysanthemin, chyrsin, ubiquinone-10 (coenzyme Q10, CoQ10), curcumin, crocetin, cyanidin, cyanin, delphinidin, diosmetin, fisetin, forskolin, galangin, gingerol, gossypetin, helenalin, hesperidin, ideain, kaempferol, luteolin, malvidin, moronic acid, myricetin, myrtillin, naringenin, nasunin, oroxylin a, pyrroloquinoline quinone, quercetin, resveratrol, rosmarinic acid, rutin, silybin, tangeritin, tulipanin, ursolic acid, violdelphin, and combinations thereof.

In some embodiments having small-molecule hydrophobic active ingredients, active ingredients may be ubiquinones, taken to mean ubiquinone-10 or coenzyme Q10 unless specified. In some embodiments having small-molecule hydrophobic active ingredients, active ingredients may be ubiquinones classified as hydrophobic, hydrophilic, or amphiphilic including chemically modified varieties and those with surrounding medium of ingredient or any impurities thereof changing the relative solubility of ingredient in reference phases from which logP is defined (e.g., water and n-octanol, unless stated otherwise). In some embodiments having small-molecule hydrophobic active ingredients, a hydrophobic active ingredient may be a purified form or mixture of any number of ubiquinones or coenzymes that are distinct from coenzyme Q10, regardless of the inclusion of coenzyme Q10 as an ingredient. In some embodiments having small-molecule hydrophobic active ingredients, hydrophobic active ingredients may be mixtures of ubiquinones and coenzymes, including their chemically modified varieties.

In some embodiments having small-molecule hydrophobic active ingredients, active ingredients may be plant phytochemicals. In some embodiments having small-molecule hydrophobic active ingredients, plant phytochemicals that are hydrophobic in nature whether by the direct addition of plant matter to a formulation, addition of extractions of plant matter, purified to varying degrees, or synthetically manufactured from plants may function as an active ingredient such as berberine, berberine chloride, berberine hydrochloride, berberine sulfate, dehydrated berberine chloride, berberine chloride monohydrate, berberine chloride dihydrate, berberine chloride trihydrate, berberine chloride monohydrate berberine chloride tetrahydrate, and their combinations including associated ion exchanged salts and combinations with other salts.

In some embodiments having small-molecule hydrophobic active ingredients, ingredients (active or inactive) may be phytochemicals. In some embodiments having small-molecule hydrophobic active ingredients, ingredients (active or inactive) may be synthetic or chemically modified phytochemicals. In some embodiments having small-molecule hydrophobic active ingredients, ingredients (active or inactive) may be alkaloids and nitrogen containing molecules. In some embodiments having small-molecule hydrophobic active ingredients, ingredients (active or inactive) may be phenylpropanoid phytochemicals. In some embodiments having small-molecule hydrophobic active ingredients, ingredients (active or inactive) may be polyketides phytochemicals. In some embodiments having small-molecule hydrophobic active ingredients, ingredients (active or inactive) may be terpenoid phytochemicals.

In some embodiments having small-molecule hydrophobic active ingredients, active ingredients may be hydrophobic quaternary ammonium salts containing molecules or their biosynthetic precursors including berberine derivatives, berberine metabolites, protoberberine molecules, benzylisoquinoline alkaloids, reticuline, tertiary amine alkaloids, and combinations thereof. In some embodiments having small-molecule hydrophobic active ingredients, an active ingredient may include californidine, alloocryptopine, eschscholtzine, and Papaveraceae alkaloids.

In some embodiments having small-molecule hydrophobic active ingredients, active ingredients may be hydrophobic phytochemicals and containing medium, including plant matter (e.g., whole plant, dried whole plant, dried roots, dried rhizomes,) or an extraction of plant matter, in whole or in part, harvested from plant species such as the *Berberis* species, *Berberis vulgaris* (barberry), *Berberis aristata* (tree turmeric), *Mahonia aquifolium* (Oregon grape), *Hydrastis canadensis* (goldenseal), *Xanthorhiza simplicissima* (yellowroot), *Phellodendron amurense* (Amur cork tree), *Coptis chinensis* (Chinese goldthread), *Tinospora cordifolia, Argemone mexicana* (prickly poppy), *Eschscholzia californica* (Californian poppy), and combinations thereof.

In some embodiments having small-molecule hydrophobic active ingredients, active ingredients may be plant phytochemicals that are hydrophobic in nature whether by the direct addition of plant matter to a formulation, addition of extractions of plant matter, purified to varying degrees, or synthetically manufactured from plants may function as an active ingredient such as phytochemicals contained in extracts of plants by hydrophobic phases and any processing thereof before and after their addition as an ingredient.

In some embodiments having small-molecule hydrophobic active ingredients, ingredients (active or inactive) may be terpenes and terpenoids including synthetic terpenes and those derived from other plant matter sources, such as 1,8-cineole, 2,2'-diketospirilloxanthin, 3'-hydroxyechinenone, abietic acid, actinioerythrin, alloxanthin, amyrin, andrastin A, andrastin B, andrastin C, andrastin D, andropholide, anethole, β-apo-2'carotenal, apo-2-lycopenal, apo-6'-lycopenal, aromadendrene, astacein, astacene, astaxanthin, astragaloside I, astragaloside II, astragaloside III, astragaloside IV, astragaloside V, astragaloside VI, astragaloside VII, astramembranoside A, astramembranoside B, azadirachtin, azafrinaldehyde, azukisaponin, bacopaside I, bacopaside II, bacopaside III, bacopaside IV, bacopaside V, bacopaside VI, bacopaside VII, bacopaside VIII, bacopaside IX, bacopaside X, bacopaside XI, bacopaside XII, bacopaside N1, bacopaside N2, bacosaponin A, bacosaponin B, bacosaponin C, bacosaponin D, bacosaponin E, bacosaponin F, bacosaponin G, bacosaponin H, bacoside A3, bacosine, barbatusin, barbatusol, benzyl benzoate, α-bergamotol, α-bergamotene, α-bergamotenol, betulin, betulinic acid, bisabolene, bisabolol, bixin, borneol, cadinene, cafestol, campesterol, camphene, camphor, canthaxanthin, capsanthin, capsorubin, carane, carene, α-carotene, β-carotene, γ-carotene, δ-carotene, ε-carotene, ζ-carotene, α-carotenone, β-carotenone, carvacrol, carvone, caryophyllene, α-cedrene, β-cedrene, chavicol, chloraeudolide, chlorajapolide A, chlorajapolide B, chlorajapolide C, chlorajapolide D, chlorajapolide E, chlorajaponol, chlorajaposide, cinerone, citral, citronellal, citronellol, citranaxanthin, citroxanthin, coleon A, coleon B, coleon C, coleon D, coleon E, coleon F, copaene, crocetin, crocetinsemialdehyde, crocin, crustaxanthin, cryptocapsin, cryptomonaxanthin, β-cryptoxanthin, cubenole, cucurbitacin, α-curcumene, cymene, cylocanthoside E, cynthiaxanthin, decaprenoxanthin, delta-3-carene, diadinoxanthin, echinenone, elemene, elemol, eleutheroside A, eleutheroside B, eleutheroside C, eleutheroside D, eleutheroside E, eschscholtzxanthin, eschscholtzxanthone, eucalyptol, eudesmol, farnesene, farnesol, fenchol, flexixanthin, foliachrome, forskolin, fucoxanthin, gazaniaxanthin, geosmin, geraniol, geranyl, germanicol, guaiene, guaiol, hexahydrolycopene, himachalene, hinokitiol, hopane, hopkinsiaxanthin, humulene, humulone, hydroxyspheroidenone, isofucoxanthin, isohumulone, jujobogenin, labdane, lanostane, ledene, limonene, limonin, linalool, longifolene, loroxanthin, lupane, lupeol, lutein, luteoxanthin, lycopene, lycopersene, lycoxanthin, malabaricane, manoalide, menthol, moronic acid, mutatoxanthin, myrcene, myrtanol, neochrome, nerol, nerolidol, neurosporene, nomilin, nomilinic acid, nonaprenoxanthin, norpatchoulenol, octanol, ocimene, okenone, oleanane, oleanolic acid, oscillaxanthin, paracentrone, patchoulene, patchoulol, pectenolone, pectenoxanthin, peridinin, α-phellandrene, β-phellandrene, phleixanthophyll, phoeniconone, phoenicopterone, phoenicoxanthin, physalien, phytoene, phytofluene, phytol, picocrocin, α-pinene, β-pinene, piperitone, plectrin, plectrinon A, plectrinon B, pulegone, pyrrhoxanthininol, retinol, rhodopin, rhodopinal, rhodopinol, rhodovibrin, rhodoxanthin rose oxide, rubixanthone, sabinene, safranal, santalol, santene, saproxanthin, sarcandralactone A, sarcandralactone B, sarcandrolide A, sarcandrolide B, sarcandrolide C, sarcandrolide D, sarcandrolide E, selinene, semi-α-carotenone, semi-β-carotenone, β-sesquiphellandrene, sintaxanthin, siphonaxanthin, siphonein, β-sitosterol, γ-sitosterol, spathulenol, spheroidene, stigmasterol, tangeraxanthin, terpinene, terpineol, terpinolene, thujene, thujone, thymol, torularhodin, torularhodinaldehyde, torulene, triphasiaxanthin, trollichrome, ursolic acid, valencene, vaucheriaxanthin, verbenol, verbenone, vetivazulene, warmingone, withaferin A, withaferin B, withanolide A, withanolide B, withanolide C, withanolide D, withanolide E, withanolide F, withanolide G, withanoside I, withanoside II, withanoside III, withanoside IV, withanoside V, withanoside VI, withanoside VII, α-zeacarotene, zeaxanthin, zeaxanthin furanoxide, zingiberene, and combinations thereof.

In some embodiments having small-molecule hydrophobic active ingredients, active ingredients may be synthetically derived, naturally derived or naturally extracted constituents (e.g., molecules and proteins) of plant matter harvested from *Sceletium* species including any combinations thereof. Examples of such species from which constituents may be extracted or modelled are *Sceletium albanense, Sceletium anatomicum, Sceletium archeri, Sceletium boreale, Sceletium compactum, Sceletium concavum, Sceletium crassicaule, Sceletium dejagerae, Sceletium emarcidum, Sceletium exalatum, Sceletium expansum, Sceletium framesii, Sceletium gracile, Sceletium joubertii, Sceletium namaquense, Sceletium ovatum, Sceletium regium, Sceletium rigidum, Sceletium, strictum, Sceletium subvelutinum, Sceletium tortuosum, Sceletium tugwelliae, Sceletium varians,* and regional varieties including combinations thereof.

In some embodiments having small-molecule hydrophobic active ingredients, active ingredients may be synthetically derived, naturally derived or naturally extracted constituents (e.g., molecules and proteins) of plant matter harvested from *Astragalus* species including combinations thereof. Examples of such species from which constituents may be extracted or modelled are *Astragalus amblolepis, Astragalus angustifolia, Astragalus armatus, Astragalus aspen, Astragalus aureus, Astragalus baibutensis, Astragalus bicuspis, Astragalus bombycinus, Astragalus campylosema, Astragalus caprinus, Astragalus caspicus, Astragalus caucasicus, Astragalus chivensis, Astragalus cicer, Astragalus corniculatus, Astragalus cruciatus, Astragalus dissectus, Astragalus eremophilus, Astragalus erinaceus, Astragalus ernestii, Astragalus flavescens, Astragalus galegiformis, Astragalus halicacabus, Astragalus hareftae, Astragalus hamosus, Astragalus icmadolphilus, Astragalus illyricus, Astragalus kahiricus, Astragalus lehmannianus, Astragalus macropus, Astragalus membranaceus, Astragalus microephalus, Astragalus mongholicus, Astragalus mucidus, Astragalus oldenbergii, Astragalus oleifolius, Astragalus orbiculatus, Astragalus peregrinus, Astragalus propinquus, Astragalus schottianus, Astragalus sieversianus, Astragalus stereocalyx, Astragalus taschkendicus, Astragalus tauricolus, Astragalus tomentosus, Astragalus unifoliolatus, Astragalus verrucosus, Astragalus wiedemannianus*, and regional varieties including combinations thereof.

In some embodiments having small-molecule hydrophobic active ingredients, active ingredients may be synthetically derived, naturally derived or naturally extracted constituents (e.g., molecules and proteins) of plant matter harvested from *Salvia* species including combinations thereof. Examples of such species from which constituents may be extracted or derived are *Salvia alba, Salvia anatolica, Salvia apiana, Salvia arizonica, Salvia azurea, Salvia buchananii, Salvia cacaliifolia, Salvia candelabrum, Salvia chinensis, Salvia columbariae, Salvia cynica, Salvia divinorum, Salvia elegans, Salvia forreri, Salvia fruticosa, Salvia fulgens, Salvia grandifolia, Salvia guaranitica, Salvia harleyana, Salvia hispanica, Salvia indica Salvia involucrata, Salvia juriscii, Salvia leucantha, Salvia microphylla, Salvia miltiorrhiza, Salvia nemorosa, Salvia officinalis, Salvia palaestina, Salvia patens, Salvia pratensis, Salvia reptans, Salvia roemeriana, Salvia rosmarinus, Salvia sclarea, Salvia spathacea, Salvia splendens, Salvia uliginosa, Salvia vasta, Salvia viridis, Salvia viscosa, Salvia yunnanensis*, and regional varieties including combinations thereof.

1.2. Examples of Hydrophilic Active Ingredients (Small Molecule)

In some embodiments having small-molecule hydrophilic active ingredients, active ingredients may have a negative logP with magnitude strictly less than zero (logP<0). In some embodiments having small-molecule hydrophilic active ingredients, active molecules may have a negative logP and be referred to as hydrophilic active ingredient. In some embodiments having small-molecule hydrophilic active ingredients, active ingredients may have a negative logP with magnitude less or equal to 1 and less than zero ($-1 \leq logP < 0$) and be referred to as hydrophilic active ingredients, amphiphilic active ingredients, or, simultaneously, hydrophilic active ingredients and amphiphilic active ingredients.

In some embodiments having small-molecule hydrophilic active ingredients, an active ingredient has a negative logP (or average negative logP in the case of active ingredients containing multiple molecular species) with magnitude greater than or equal to unity (logP=<−1). Herein, active ingredients with positive logP as described here are referred to as hydrophilic active ingredients. Ingredients generally, particularly hydrophilic active ingredients for the purposes of immediately following descriptions, may possess pH dependent logP values arising from changes in molecular structure including protonation, deprotonation, internal rearrangements, charge state transitions (accepting or donating an electron to a molecule or surrounding medium), chemistries with other ingredients in the containing hydrophilic phase or neighboring phase interfaces with the hydrophilic phase solubilizing the active ingredient, and combinations thereof. For molecules (ingredients) described herein, the logP and subsequent categorization of the ingredient as hydrophobic, hydrophilic, or amphiphilic is assumed to be the categorization at pH=7, unless stated otherwise.

In some embodiments having small-molecule hydrophilic active ingredients, active ingredients may contain hydrogen bond acceptors, hydrogen bond donors, or combinations thereof and may be hydrophilic active ingredients used in combination with other hydrophilic ingredients to change the solubility, bioactivity, or structure of some or all hydrophilic phases and components thereof.

In some embodiments having small-molecule hydrophilic active ingredients, active ingredients may be sulfonic acids and other sulfur containing organic molecules and macromolecules classified as hydrophilic active ingredients such as taurine.

In some embodiments having small-molecule hydrophilic active ingredients, active ingredients may be minerals classified as hydrophilic active ingredients such as selenium, sulfur, silicate, and zinc containing salts.

In some embodiments having small-molecule hydrophilic active ingredients, active ingredients may be amino acids classified as hydrophilic active ingredients such as L-alanine, L-theanine (logP~=−3), L-phenylalanine (logP~=−1.38), L-tyrosine (logP~=−1.87), Mg L-threonate (logP~=−2.1), GABA (gamma-aminobutyric acid) (logP~=−3), 5-HTP (logP~=−2) and combinations thereof, including their diastereomers, enantiomers, and racemic mixtures.

In some embodiments having small-molecule hydrophilic active ingredients, active ingredients may be hydrophilic active ingredients such as purified phytochemical extracted from plant matter of a single species or variety, and mixtures of plant matter from two or more distinct species, such as ascorbic acid, catechin, crocetin, epicatechin gallate, epigallocatechin gallate, gallocatechin, glutathione, hibiscitin, sodium copper chlorophyllin, vanillic acid, vanillin, and combinations thereof.

In some embodiments having small-molecule hydrophilic active ingredients, ingredients may be added to the hydrophilic phase such as pH buffers to maintain a particular pH range or added acidic and basic molecules to adjust to a particular pH during particle formation, particle stabilization, storage, in vivo or a combination thereof. In some embodiments having small-molecule hydrophilic active ingredients, ingredients may be pH buffers such that constituents, piecewise or collectively, may be considered an active ingredient in scenarios where pH adjustment of a particular or multiple hydrophilic phases present in a product determines the magnitude or character of the bioactivity of all active ingredients in the hydrophilic phases in question, regardless of whether the pH adjustment arising from the addition of pH buffers, acids, or bases directly influences bioactivity of the particles upon after administration or whether the added pH buffers, acids, or bases indirectly effect the magnitude and character of all active ingredient bioactivity via chemistries between active ingredients, chemistries of individual active ingredients (including internal molecular rearrangements), or changes in active ingredient protonation or charge states. In some embodiments having small-molecule hydrophilic active ingredients, ingredients may be pH buffers, bases, and acids may be incorporated into hydrophilic phases and considered an inactive ingredient (e.g., hydrophobic stabilizing agent or interface stabilizing agent) in formulations where bioactivity is not tuned but instead the pH adjustment arising from pH buffer, acid, and base additions are to initiate changes in particle formation, stability, structure, and combinations thereof.

In some embodiments having small-molecule hydrophilic active ingredients, ingredients (active or inactive) may be pH buffers including acid, bases, ionic salts, and their combinations. In some embodiments having small-molecule hydrophilic active ingredients, ingredients (active or inactive) may be phosphoric acid and its salts or citric acid and its salts (e.g., sodium or potassium salts of phosphoric and citric acid).

In some embodiments having small-molecule hydrophilic active ingredients, ingredients (active or inactive) may be pH buffers formed by adding an acid alone to the target hydrophilic phase, whether dispersed or continuous. The acid, together with the other solutes (e.g., metal, inorganic, or organic cations), media, and general ingredients in the hydrophilic phase, may form the pH buffer. In some embodiments having small-molecule hydrophilic active ingredients, ingredients (active or inactive) may be pH buffers formed by directly adding an acid and a particular or various salts into hydrophilic phase, again for both the cases of continuous and dispersed hydrophilic phases.

In some embodiments having small-molecule hydrophilic active ingredients, active ingredients may be phenolic compounds or flavonoids. In some embodiments having small-molecule hydrophilic active ingredients, inactive ingredients may be phenolic compounds functioning with intended effect not to provide bioactivity upon product administration to organism. In some embodiments having small-molecule hydrophilic active ingredients, active ingredients and inactive ingredients may be phenolic compounds, synthetic flavonoids, and those derived from plant matter and fungal matter such as 2-gingerol, 4-gingerol, 6-gingerol, 8-gingerol, 10-gingerol, 12-gingerol, 6-shogaol, 10-shogaol, 6-paradol, 3-hydroxyflavone, 6-dehydrogingerdione, 6-hydroxyflavone, 6-hydroxyluteolin, 8-prenylnaringenin, abyssinones, acacetin, acerosin, acutissimin A, acutissimin B, alnetin, amurensin, apiforol, apigenin, apiole, arbutin, aromadedrin, artocarpetin, astragalin, azaleatin, azalein, baicalein, bidesmethoxycurcumin, biochanin A, blumeatin, butein, butin, caffeic acid, camelliatannin A, camelliatannin B, camelliatannin C, camelliatannin D, camelliatannin E, camelliatannin F, camelliatannin G, camelliatannin H, carnosol, catechin, catechin gallate, capsaicin, cerrosillin, chalconaringenin, chrysin, chrysoeriol, ciliatoside A, ciliatoside B, cinnamic acid, cirsiliol, cirsimaritin, cirsilineol, chlorogenic acid, corymbosin, coumarin, cyanidin, curcumin, daidzein, dehydrosilybin, delphinidin, deoxysilycistin, deoxysilydianin, desmethoxycurcumin, dillapiole, diosmetin, echiodinin, ellagic acid, engeletin, epiafzelechin, epicatechin, epicatechin gallate, eipcutissimin A, epigallocatechin, epigallocatechin gallate, eriodictyol, esculatin, eupatilin, eupatorin, farobin A, farobin B, ferulic acid, fisetin, fisetinidol, flavokavain A, flavokavain B, flavokavain C, formononetin, galangin, gallic acid, gallocatechin, gallocatechin gallate, gardenin D, genistein, genkwanin, geraldone, gericudranin A, gericudranin B, gericudranin C, gericudranin D, gericudranin E, gingerenone A, gingerenone B, gingerenone C, ginkgetin, glabratephrin, glaziovianin A, glycitein, gossypetin, guibourtinidol, herbacetin, hesperidin, hesperitin, hibiscetin, hibiscitrin, hispidulin, homoeriodictyol, hydnocarpin, hydnowightin, hydroxytyrosol, hymenoxin, hyperoside, hypolaetin, icariin, isoglabratephrin, isoquercetin, isorhamnetin, isosakuranetin, isoscutellarein, isoxanthohumol, jaceosidin, justicidin A, justicidin B, justicidin C, kaempferide, kaempferitrin, kaempferol, lanceolatin A, leucocyanidin, leucodelphinidin, leucofisetinidin, leucomalvidin, leucopelargonidin, leucopeonidin, leucorobinetinidin, liquiritigenin, luteoforol, luteolin, macluraxanthone, malvidin, matairesinol, melacacidin, mesquitol, mikanin, mongolicain A, mongolicain B, morin, myricetin, naringin, naringenin, natsudaidain, negletein, neosilyhermin, nepetin, nevadensin, nicotiflorin, nobiletin, nodifloretin, norartocarpetin, norwogonin, okanin, oleocanthal, oleuropein, onopordin, oroxylin, pachypodol, palstatin, pectolinaringenin, pedalitin, pelargonidin, peonidin, petunidin, phloretin, phloridzin, piceatannol, pilloin, pinocembrin, pinoresinol, pinosylvin, piperine, podophyllotoxin, poncirin, pratensein, primetin, primuletin, procumbenoside A, procumbenoside B, pterostilbene, quercetin, resveratrol, rhamnazin, rhamnetin, rhodiolin, rhodioniside, robinetin, robinetinidol, robinin, rosarin, rosavin, rosin, rosiridin, rutin, sakuranetin, sakuranin, salcolin A, salcolin B, salicylic acid, salidroside, scaposin, schisandrin A, schisandrin B, schisandrin C, scopoletin, scutellaprostin A, scutellaprostin B, scutellaprostin C, scutellaprostin D, scutellaprostin E, scutellaprostin F, scutellarein, secoisolariciresinol, serpyllin, silandrin, silibinin, sinensetin, silyamandin, silybin, silybinome, silychristin, silydianin, silyhermin, sinapinic acid, sorbifolin, spiraeoside, steganacin, sterubin, sudachitin, syringic acid, taiwanhomoflavone A, taiwanhomoflavone B, taiwanhomoflavone C, tamarixetin, tangeritin, tannic acid, taxifolin, tectochrysin, tephroapollin F, teracacidin, theaflavin, theaflavin-3-gallate, theaflavin-3'-gallate, theaflavin-3, 3'-digallate, tithonine, tricetin, tricin, troxerutin, tyrosol, vanillin, and vanillic acid, velutin, vitexycarpin, wightin, wogonin, xanthomicrol, xanthorhamnin, zapotin, zapotinin, zingerone, and combinations thereof.

1.3. Examples of Amphiphilic Active Ingredients (Small Molecule)

In some embodiments having small-molecule amphiphilic active ingredients, active ingredients may positive or negative logP with magnitude less than or equal to zero ($1 \geq logP \geq -1$). In some embodiments having small-molecule amphiphilic active ingredients, active ingredients may have positive or negative logP with magnitude less than or equal to 1 ($1 \geq logP \geq -1$) and referred to as amphiphilic active ingredients. In some embodiments having small-molecule amphiphilic active ingredients, active ingredients may have positive or negative logP with magnitude less than or equal to 1.5 ($1.5 \geq logP \geq -1.5$) and referred to as amphiphilic active ingredients under the consideration of experimental uncertainties associated with experimental measurement of logP.

In some embodiments having small-molecule amphiphilic active ingredients, active ingredients may be amphiphilic active ingredients with positive logP. In some embodiments having small-molecule amphiphilic active ingredients, amphiphilic active ingredients may have a logP of zero and may be referred to as hydrophobic or hydrophilic active ingredients, referenced as such depending on the hydrophilicity or hydrophobicity of the containing phases or phase mixtures. In some embodiments having small-molecule amphiphilic active ingredients, active ingredients may be amphiphilic active ingredients possessing a negative logP such that the active ingredient may be classified as hydrophilic active ingredients instead of or in addition to classification as amphiphilic active ingredients. In some embodiments having small-molecule amphiphilic active ingredients, active ingredients may be amphiphilic active ingredients possessing a positive logP such that the active ingredient may be classified as hydrophobic active ingredients instead of or in addition to classification as amphiphilic active ingredients. Amphiphilic active ingredients are given their own classification as they demonstrate solubilities within an order of magnitude when dissolved in the two reference solvents (e.g., n-octanol and water) used to define logP and have their own processing considerations and challenges when incorporated in a product or encapsulated within particles.

In some embodiments having small-molecule amphiphilic active ingredients, active ingredients may be amphiphilic active ingredients such as PQQ (logP~=0.4).

In some embodiments having small-molecule amphiphilic active ingredients, active ingredients may be adenosine and xanthine derivatives. In some embodiments having small-molecule amphiphilic active ingredients, active ingredients may be methylated-xanthine derivatives such as caffeine (logP=−0.07), methylliberine (Dynamine™) (logP~=−0.083), theacrine (logP~=−1.06), theobromine (logP~=−0.78), and theophylline, including mixtures thereof. In some embodiments having small-molecule amphiphilic active ingredients, active ingredients may be adenosine, xanthine, and, particularly, methylated xanthine derivatives classified as amphiphilic active ingredients such as caffeine and methylliberine (Dynamine™). In some embodiments having small-molecule amphiphilic active ingredients, active ingredients may be adenosine, xanthine, and, particularly, methylated xanthine derivatives classified as hydrophobic active ingredients or hydrophilic active ingredients (e.g., theacrine and theobromine), regardless of whether the derivatives under consideration carry additional classification as amphiphilic active ingredients. In some embodiments having small-molecule amphiphilic active ingredients, active ingredients may be mixtures of adenosine and xanthine derivatives combined in various ratios, including associated metabolites, to illicit bioactivity that manifests effects, alters effects, tunes effect timescales of any or all active ingredient bioactivity, alters metabolism, or changes character or dynamics may be active ingredients. In some embodiments having small-molecule amphiphilic active ingredients, active ingredients may be mixtures of adenosine and xanthine derivatives to induce an entourage effect in bioactivity upon administration.

In some embodiments having small-molecule amphiphilic active ingredients, active ingredients may be botanical or fungal matter extracts. In some embodiments having small-molecule amphiphilic active ingredients, active ingredients may be botanical and fungal matter extracts produced with purified, processed, or otherwise unaltered apart from any drying processes after plant and fungus matter is harvested.

In some embodiments having small-molecule amphiphilic active ingredients, active ingredients may be botanical extracts that may be incorporated for their adenosine and xanthine derivative content or other sets of phytochemicals considered separately from or in consideration of adenosine and xanthine derivative content desired as components in the botanical extracts including examples such as *Camellia gymnogyna, Camellia ptilophylla* (cocoa tea), *Theobroma cacao* (cocoa tree), *Ilex guayusa* (guayusa), *Camellia assamica, Camellia kucha, Camellia puanensis, Camellia sinensis* (tea), *Coffee arabica, Coffee caniphora, Coffee liberica, Coffee dewevrei* (coffee beans), *Paullinia cupana* (guarana), *Cola acuminata, Cola nitida* (kola nut), *Ilex vomitoria* (yaupon holly), *Ilex paraguariensis* (yerba mate), and combinations thereof 1.4. Examples of Large Molecule (Macromolecule) Active Ingredients In some embodiments having macromolecule active ingredients, active ingredients may be macromolecules (e.g., protein, peptide, polymer, macrocycles, oligomers), defined as molecules and molecular mixtures with molar mass or average molar mass of active ingredient greater than 1000 g/mol (1000 Daltons for average molecular mass).

In some embodiments having macromolecule active ingredients, active ingredients may be members or entire classes of proteins, purified or in mixtures, such as plant protein, animal protein, or milk protein, including members in each class when specified as pure isolate or a component in a mixture of other members of the class of proteins specified or other ingredients.

1.4.1. Examples of Hydrophilic Macromolecular Active Ingredients

In some embodiments having hydrophilic macromolecule active ingredients, active ingredients may be hydrophobic macromolecules, with molar mass equal to or greater than 1000 g/mol (average molecular mass for the case of mixtures of different molecular and macromolecular active ingredient components) with average negative logP of active ingredient strictly less than zero and referred to as hydrophobic macromolecular active ingredients, or more generally as hydrophobic active ingredients, macromolecular active ingredients and macromolecular ingredients.

In some embodiments having hydrophilic macromolecule active ingredients, active ingredients may be hydrophilic proteins and peptides such as plant proteins, whey proteins, casein, caseinate proteins, associated salts, and combinations thereof.

In some embodiments having hydrophilic macromolecule active ingredients, active ingredients may be human or other mammalian collagen proteins of which there are at least 28 identified types in humans (e.g., type I, type II, type III, . . . , type XXVII). Of all the types of collagens identified, collagen type I is the most common, accounting for over 90% of the collagen content in the average human body. The rest are broadly categorized as either fibrillar or non-fibrillar, fibrillar including type I, II, III, V, and XI, while the remaining types are members of the non-fibrillar collagen category. Collagen proteins span all classes of hydrophilic macromolecular, hydrophobic macromolecular, and amphiphilic macromolecular active ingredients. In some embodiments having hydrophilic macromolecule active ingredients, active ingredients may be collagen types found in humans or other species, including synthetic or chemically modified varieties, added as a component in an ingredient, a single purified collagen, or as mixtures thereof 1.4.2. Examples of Hydrophobic Macromolecular Active Ingredients In some embodiments having hydrophobic macromolecule active ingredients, ingredients may be hydrophobic macromolecules, with molar mass equal to or greater than 1000 g/mol (average molecular mass for the case of mixtures of different molecular species) and positive logP greater than or equal to unity in magnitude, may function as an active ingredient and are referred to as hydrophobic macromolecular active ingredients, or generally as hydrophobic active ingredients, macromolecular active ingredients, or, broadly, active ingredients.

In some embodiments having hydrophobic macromolecule active ingredients, ingredients within a formulation that are most often classified strictly as hydrophobic phase media and hydrophobic inactive ingredients may be used as hydrophobic active ingredients in formulations and particle dispersions where either the hydrophobic phase medium in question (e.g., olive oil) itself has bioactivity desirable for the intended effect after application to the target organism or excipients (e.g., impurities, phenols, sterols, flavins).

In some embodiments having hydrophobic macromolecule active ingredients, active ingredients may be macromolecules, including mono-, di-, and tri-glyceride species, as well as proteins contained within, may function as a hydrophobic macromolecular active ingredient. In some embodiments having hydrophobic macromolecule active ingredients, triglycerides and other hydrophobic solvents derived from or extracted directly from common species used for seed oils including *Prunus amygdalus* (almond), *Brassica* species (canola), *Zea mays* L. (corn), *Gossypium* species (cottonseed), *Linum usitatissimum* L (flax), *Vitis vinifera* (grape seed), *Cannabis sativa* L. (hemp), *Abelmoschus esculentus* (okra), *Olea europaea* (olive), *Arachis hypogaca* L. (peanut), *Carthamus tinctorius* L. (safflower), *Sesamum indicum* (sesame), *Glycine max* (soybean), and *Helianthus annuus* (sunflower), *Jugla regia* (walnut). Additionally, examples of associated proteins that may function as macromolecular active ingredients include cruciferin, zein, 11S protein, 12S protein, arachin, carmin, alpha-globulin, glycinin, and helianthin, all of which may be used independently or in combination whether pure or as unprocessed oils.

1.4.3. Examples of Amphiphilic Macromolecular Active Ingredients

In some embodiments having amphiphilic macromolecule active ingredients, ingredients may be amphiphilic macromolecules, with molar mass equal to or greater than 1000 g/mol (average molecular mass for the case of mixtures of different molecular species) and positive or negative logP less than unity in magnitude, may function as an active ingredient and are referred to as amphiphilic macromolecular active ingredients, or generally as amphiphilic active ingredients, macromolecular active ingredients, or, broadly, active ingredients. In some instances, amphiphilic macromolecular active ingredients may be referred to as hydrophobic macromolecular active ingredients or hydrophilic macromolecular active ingredients when the macromolecule or mixture of macromolecules possess a logP with positive or negative sign, respectively. In some embodiments having amphiphilic macromolecule active ingredients, reference to the sign of logP has more significance than the magnitude for an application or formulation and as such the categorization may be changed for simplicity or to illustrate a particular aspect of the embodiment or in comparison to other embodiments.

1.5. Examples of Plant Matter, Fungal Matter, & Extracts as Active Ingredients

In some embodiments having plant/fungal/extract active ingredients, active ingredients may be plants, plant matter, and extractions of plant matter, and associated phytochemicals, purified or otherwise, such that plant matter may be selected from at least one plant species such as the plants are selected from at least one of *Abelmoschus* spp., *Abies* spp., *Abroma augusta*, *Acacia* spp., *Acalypha indica*, *Acanthus mollis*, *Acer* spp., *Achillea* spp., *Achyranthes bidentata*, *Acmella oleracea*, *Acorus calamus*, *Actaea* spp., *Actinidia* spp., *Adansonia digitata*, *Adiantum* spp., *Adoxa moschatellina*, *Aegopodium podagraria*, *Aesculus* spp., *Aframomum* spp., *Agathosma* spp., *Agave* spp., *Agrimonia* spp., *Ajuga* spp., *Alaria esculenta*, *Albizia* spp., *Alcea rosea*, *Alchemilla vulgaris*, *Aletris farinosa*, *Alisma* spp., *Alliaria petiolata*, *Allium* spp., *Alnus* spp., *Aloe* spp., *Aloysia citriodora*, *Alpinia* spp., *Althaea officinalis*, *Amaranthus* spp., *Ammi*

*visnaga*, *Amomum villosum*, *Amorphophallus konjac*, *Amyris balsamifera*, *Anacardium occidentale*, *Ananas comosus*, *Andrographis paniculata*, *Anemarrhena asphodeloides*, *Angelica* spp., *Angostura trifoliata*, *Aniba rosaeodora*, *Annona* spp., *Anogeissus latifolia*, *Anredera baselloides*, *Antennaria dioica*, *Anthem is* spp., *Anthriscus* spp., *Anthyllis vulneraria*, *Antirrhinum majus*, *Aphanes arvensis*, *Apium graveolens*, *Arachis hypogaea*, *Aralia* spp., *Arbutus unedo*, *Arctium* spp., *Argania spinosa*, *Armoracia rusticana*, *Artemisia* spp., *Artocarpus altilis*, *Ascophyllum nodosum*, *Asimina triloba*, *Aspalathus linearis*, *Asparagus* spp., *Asplenium* spp., *Astracantha* spp., *Astragalus* spp., *Astrantia major*, *Athamanta macedonica*, *Atractylodes* spp., *Avena* spp., *Averrhoa carambola*, *Baccharis genistelloides*, *Bacopa monnieri*, *Bactris gasipaes*, *Balanites aegyptiaca*, *Ballota* spp., *Bambusa* spp., *Barbarea* spp., *Bellis perennis*, *Berberis* spp., *Bergenia crassifolia*, *Bertholletia excelsa*, *Beta vulgaris*, *Betula* spp., *Bixa orellana*, *Blainvillea acmella*, *Borago officinalis*, *Boronia megastigma*, *Boswellia* spp., *Brassica* spp., *Bupleurum* spp., *Bursera tomentosa*, *Caesalpinia bonduc*, *Cakile maritima*, *Calendula* spp., *Calluna vulgaris*, *Calophyllum inophyllum*, *Camelina* spp., *Camellia* spp. *Canarium acutifolium*, *Canavalia ensiformis*, *Cannabis sativa*, *Capparis spinosa*, *Capsella bursa-pastoris*, *Carex arenaria*, *Carica papaya*, *Carissa carandas*, *Carlina* spp., *Carpinus betulus*, *Carthamus* spp., *Carum carvi*, *Cassia* spp., *Castanea sativa*, *Catalpa bignonioides*, *Ceanothus americanus*, *Cecropia peltata*, *Cedrus libani*, *Ceiba pentandra*, *Centaurea* spp., *Centaurium erythraea*, *Centella asiatica*, *Centranthus ruber*, *Cerasus* spp., *Ceratonia siliqua*, *Cercis siliquastrum*, *Ceterach officinarum*, *Cetraria islandica*, *Chaenomeles speciosa*, *Chamaemelum nobile*, *Chamaecrista nomame*, *Chelone glabra*, *Chenopodium* spp., *Chimaphila umbellata*, *Chiococca alba*, *Chionanthus virginicus*, *Chlorella vulgaris*, *Chondrus crispus*, *Chrysanthellum* spp., *Chrysophyllum cainito*, *Chrysopogon zizanioides*, *Cichorium* spp., *Cinchona* spp., *Cinnamomum* spp., *Cistanche salsa*, *Cistus* spp., *Citrullus lanatus*, *Citrus* spp., *Cladonia rangiferina*, *Clematis* spp., *Clinopodium vulgare*, *Clitoria ternatea*, *Cnicus benedictus*, *Cochlearia officinalis*, *Cocos nucifera*, *Codonopsis pilosula*, *Coffea* spp., *Coix lacryma-jobi*, *Cola* spp., *Combretum* spp., *Comm iphora* spp., *Conyza canadensis*, *Copaifera langsdorffii*, *Coptis* spp., *Corallina officinalis*, *Cordia myxa*, *Coriandrum sativum*, *Cornus domestica*, *Cornus* spp., *Corrigiola telephiifolia*, *Corylus avellana*, *Corymbia citriodora*, *Coscinium fenestratum*, *Cotinus coggygria*, *Crambe maritima*, *Crataegus* spp., *Crithmum maritimum*, *Crocus sativus*, *Crossostephium chinense*, *Croton nitens*, *Cruciata laevipes*, *Cryptocarya agathophylla*, *Cucumis* spp., *Cucurbita maxima*, *Cuminum cyminum*, *Cupressus sempervirens*, *Curcuma* spp., *Cuscuta* spp., *Cyamopsis tetragonoloba*, *Cyathula officinalis*, *Cyclanthera pedata*, *Cydonia oblonga*, *Cymbopogon* spp., *Cynara* spp., *Cyperus rotundus*, *Cytinus hypocistis*, *Daemonorops draco*, *Dahlia pinnata*, *Daucus carota*, *Dendranthema grandiflorum*, *Descurainia sophia*, *Dianthus caryophyllus*, *Dimocarpus longan*, *Dioscorea* spp., *Diospyros* spp., *Diplotaxis tenuifolia*, *Dipsacus* spp., *Dorstenia contrajerva*, *Dracocephalum moldavica*, *Drimys winteri*, *Drosera* spp., *Dunaliella salina*, *Durio zibethinus*, *Durvillea antartica*, *Dysphania botrys*, *Echinacea* spp., *Echium plantagineum*, *Elaeis guineensis*, *Elettaria cardamomum*, *Eleutherococcus senticosus*, *Elymus repens*, *Epilobium* spp., *Equisetum* spp., *Erica* spp., *Eriobotrya japonica*, *Eriodictyon californicum*, *Erodium cicutarium*, *Eruca vesicaria*, *Eryngium campestre*, *Eschscholtzia*, *Eucalyptus* spp., *Eucheuma* spp., *Eucommia ulmoides*, *Eugenia* uniflora, Euphrasia spp., Euterpe oleracea, Evernia prunastri, Exostema caribaeum, Fabiana imbricata, Fagopyrum esculentum, Fagus sylvatica, Fallopia spp., Ferula assafoetida, Ficus spp., Filipendula spp., Foeniculum vulgare, Forsythia suspensa, Fragaria spp., Frangula spp., Fraxinus spp., Fucus spp., Fumaria officinalis, Galega officinalis, Galeopsis segetum, Galium spp., Garcinia spp., Gardenia jasminoides, Gastrodia elata, Gaultheria procumbens, Gelidium spp., Gentiana lutea, Geranium spp., Geum spp., Ginkgo biloba, Glycine max, Glycyrrhiza spp., Gossypium herbaceum, Gracilaria gracilis, Griffonia simplicifolia, Grindelia spp., Guaiacum spp., Guazuma ulmifolia, Gynostemma pentafillum, Gypsophila paniculata, Haematococcus pluvialis, Haematoxylum campechianum, Hamamelis virginiana, Handroanthus impetiginosus, Haplopappus baylahuen, Harpagophytum spp., Hebanthe eriantha, Hedeoma pulegioides, Hedera helix, Hedychium coronarium, Helianthus spp., Helichrysum spp., Heracleum sphondylium, Herniaria spp., Hesperis matronalis, Hibiscus sabdariffa, Hieracium pilosella, Hierochloe odorata, Himanthalia elongata, Hippophae rhamnoides, Hizikia fusiformis, Hordeum vulgare, Houttuynia cordata, Humulus lupulus, Hydrangea arborescens, Hygrophila auriculata, Hymenaea courbaril, Hypericum perforatum, Hyssopus officinalis, Ilex spp., Illicium verum, Impatiens balsamina, Indigofera tinctoria, Inula spp., Ipomoea batatas, Isatis tinctoria, Jasminum spp., Jateorhiza palmata, Juglans spp., Jumellea fragrans, Juniperus communis, Justicia spp., Kaempferia galanga, Kavalama urens, Kickxia spuria, Knautia arvensis, Krameria lappacea, Lactuca spp., Lagerstroemia speciosa, Laminaria spp., Lamium album, Larix spp., Laurus nobilis, Lavandula spp., Lawsonia inermis, Ledum palustre, Lens culinaris Medik, Leonurus cardiaca, Lepidium spp., Leptospermum spp., Lespedeza capitata, Leucanthemum vulgare, Levisticum officinale, Lilium brownii, Linaria vulgaris, Lindera aggregata, Linum usitatissimum, Liquidambar styraciflua, Litchi chinensis, Lithothamnion calcareum, Litsea cubeba, Lobaria pulmonaria, Lonicera japonica, Lotus spp., Luma chequen, Lycium spp., Lycopersicon esculentum, Lycopodium clavatum, Lycopus spp., Lysimachia vulgaris, Lythrum salicaria, Macadamia ternifolia, Macrocystis pyrifera, Magnolia spp., Malpighia glabra, Malus spp., Malva sylvestris, Mammea americana, Mangifera indica, Manihot esculenta, Manilkara zapota, Maranta arundinacea, Marchantia polymorpha, Marrubium vulgare, Marsdenia spp., Mastocarpus stellatus, Matricaria chamomilla, Medicago sativa, Melaleuca spp., Melilotus spp., Melissa officinalis, Melittis melissophyllum, Mentha spp., Mentzelia cordifolia, Menyanthes trifoliata, Mesembryanthemum crystallinum, Mespilus germanica, Mikania amara, Mitchella repens, Momordica spp., Monarda spp., Morinda spp., Moringa oleifera, Morus spp., Murraya koenigii, Musaxparadisiaca, Myrciaria dubia, Myrica gale, Myristica fragrans, Myroxylon spp., Myrtus communis, Nardostachys jatamansi, Nasturtium officinale, Nelumbo nucifera, Nepeta spp., Nephelium lappaceum, Nigella sativa, Ocimum spp., Oenanthe aquatica, Oenothera biennis, Olea spp., Ononis spp., Onopordon acanthium, Ophioglossum vulgatum, Ophiopogon japonicus, Opopanax chironius, Opuntia ficus-indica, Orchis mascula, Origanum spp., Orthosiphon spp., Oryza sativa, Oxalis acetosella, Pachira spp., Padus avium, Paeonia spp., Palmaria palmata, Panax spp., Panicum miliaceum, Panzerina lanata, Papaver rhoeas, Parietaria officinalis, Parmelia saxatilis, Parthenium hysterophorus, Parthenocissus tricuspidata, Passiflora incarnata, Pastinaca sativa, Paullinia cupana, Pedalium murex, Pelargonium spp., Perilla frutescens, Persea americana, Persicaria spp., Petiveria alliacea, Petroselinum crispum, Peucedanum ostruthium, Peumus boldus, Phaseolus vulgaris, Phellodendron amurense, Phillyrea latifolia, Phlebodium aureum, Phoenix dactylifera, Photinia melanocarpa, Phyla scaberrima, Phyllanthus spp., Phymatolithon calcaneum, Physalis spp., Picea abies, Picramnia antidesma, Pimenta spp., Pimpinella spp., Pinus spp., Piper spp., Pistacia spp., Pisum sativum, Plantago spp., Platycodon grandiflorus, Plectranthus barbatus, Pogostemon cablin, Polygala spp., Polygonatum odoratum, Polygonum aviculare, Populus spp., Porphyra umbilicalis, Portulaca oleracea, Potentilla spp., Prangos pabularia, Primula spp., Protium spp., Prunella vulgaris, Prunus spp., Psidium spp., Pterocarpus spp., Pueraria spp., Pulmonaria officinalis, Punica granatum, Pyrola rotundifolia, Pyropia tenera, Pyrus communis, Quercus spp., Quillaja saponaria, Raphanus spp., Raphia farinifera, Rehmannia glutinosa, Rhamnus spp., Rheum spp., Rhodiola crenulata, Rhus spp., Ribes spp., Robinia pseudoacacia, Roccella phycopsis, Rosa spp., Rosmarinus officinalis, Rubia cordifolia, Rubus spp., Rumex spp., Ruscus spp., Sabatia angularis, Saccharina latissima, Saccharum officinarum, Salix spp., Salvia spp., Sambucus spp., Sanguisorba spp., Sanicula elata, Santalum album, Santolina chamaecyparissus, Saponaria officinalis, Saposhnikovia divaricata, Sarcopoterium spinosum, Sargassum fusiforme, Sarracenia purpurea, Satureja spp., Saussurea costus, Schinus molle, Schisandra chinensis, Scorzonera hispanica, Scrophularia ningpoensis, Scutellaria spp., Secale cereale, Sedum spp., Selenicereus grandiflorus, Sempervivum tectorum, Senna spp., Sequoiadendron giganteum, Serenoa repens, Sesamum indicum, Seseli tortuosum, Sideritis syriaca, Sigesbeckia orientalis, Silaum silaus, Silybum marianum, Simarouba amara, Simmondsia chinensis, Siraitia grosvenorii, Sisymbrium officinale, Sium latifolium, Smilax spp., Solanum spp., Solidago virgaurea, Sorbus aucuparia, Sorghum bicolor, Spatholobus suberectus, Spergularia rubra, Spinacia oleracea, Spirulina spp., Stachys officinalis spp., Stellaria media, Stemmacantha carthamoides, Styphnolobium japonicum, Styrax spp., Symplocarpus foetidus, Syringa vulgaris, Syzygium spp., Tagetes spp., Tamarindus indica, Tamarix gallica, Tanacetum spp., Taraxacum officinale, Term inalia spp., Thalictrum flavum, Theobroma cacao, Thlaspi arvense, Thymus spp., Tilia spp., Trachyspermum ammi, Tragopogon porrifolius, Tribulus terrestris, Trichilia catigua, Trichosanthes kirilowii, Tridax procumbens, Trifolium spp., Trigonella spp., Trillium erectum, Triticum spp., Tropaeolum spp., Tsuga Canadensis, Turnera diffusa, Ulmus spp., Ulva lactuca, Uncaria spp., Undaria pinnatifida, Urtica spp., Usnea spp., Vaccinium spp., Valeriana spp., Valerianella locusta, Vanilla planifolia, Veratrum viride, Verbascum spp., Verbena officinalis, Veronica spp., Viburnum spp., Vicia spp., Vigna angularis, Viola spp., Viscum album, Vitex spp., Vitis vinifera, Withania somnifera, Xeranthemum annuum, Yucca spp., Zanthoxylum spp., Zea mays, Zingiber officinale, and Ziziphus jujube.

In some embodiments having plant/fungal/extract active ingredients, active ingredients may be synthetically derived, naturally derived or naturally extracted constituents (e.g., molecules and proteins) of plant matter harvested from Sceletium species including combinations thereof. Examples of such species from which constituents may be extracted or modelled are Sceletium albanense, Sceletium anatomicum, Sceletium archeri, Sceletium boreale, Sceletium compactum, Sceletium concavum, Sceletium crassicaule, Sceletium dejagerae, Sceletium emarcidum, Sceletium exalatum, Sceletium expansum, Sceletium framesii, Sceletium gracile, Sceletium joubertii, Sceletium namaquense, Sceletium ova-

*tum, Sceletium regium, Sceletium rigidum, Sceletium, strictum, Sceletium subvelutinum, Sceletium tortuosum, Sceletium tugwelliae,* and *Sceletium varians.*

In some embodiments having plant/fungal/extract active ingredients, active ingredients may be synthetically derived, naturally derived or naturally extracted constituents (e.g., molecules and proteins) of plant matter harvested from *Astragalus* species including combinations thereof. Examples of such species from which constituents may be extracted or modelled are *Astragalus amblolepis, Astragalus angustifolia, Astragalus armatus, Astragalus aspen, Astragalus aureus, Astragalus baibutensis, Astragalus bicuspis, Astragalus bombycinus, Astragalus campylosema, Astragalus caprinus, Astragalus caspicus, Astragalus caucasicus, Astragalus chivensis, Astragalus cicer, Astragalus corniculatus, Astragalus cruciatus, Astragalus dissectus, Astragalus eremophilus, Astragalus erinaceus, Astragalus ernestii, Astragalus flavescens, Astragalus galegiformis, Astragalus halicacabus, Astragalus hareftae, Astragalus hamosus, Astragalus icmadolphilus, Astragalus illyricus, Astragalus kahiricus, Astragalus lehmannianus, Astragalus macropus, Astragalus membranaceus, Astragalus microephalus, Astragalus mongholicus, Astragalus mucidus, Astragalus oldenbergii, Astragalus oleifolius, Astragalus orbiculatus, Astragalus peregrinus, Astragalus propinquus, Astragalus schottianus, Astragalus sieversianus, Astragalus stereocalyx, Astragalus taschkendicus, Astragalus tauricolus, Astragalus tomentosus, Astragalus unifoliolatus, Astragalus verrucosus,* and *Astragalus wiedemannianus.*

In some embodiments having plant/fungal/extract active ingredients, active ingredients may be herbal or mushroom extracts classified as nootropics function such as *Astragalus membranaceus* (astragalus), *Withania somnifera* (ashwagandha), *Bacopa monnieri, Inonotus obliquus* (chaga), *Cordyceps sinensis, Cordyceps militaris* (cordyceps), *Turnera diffusa* (damiana), *Eleutherococcus senticosus* (eleuthero), Ginger root, *Ginkgo biloba, Panax ginseng* (asian *ginseng*), *Panax quinquefolius* (american *ginseng*), *Centella asiatica* (gotu kola), *Huperzia serrata* (toothed clubmoss), *Ocimum tenuiflorum* (holy basil), *Sceletium tortuosum* (kanna), *Piper methysticum* (kava), *Pleurotus eryngii* (king oyster), *Hericium erinaceus* (lion's mane), *Lepedium meyenii* (maca), *Grifola fondosa* (maitake), *Pleurotus ostreatus* (oyster), *Poria cocos* (poria), *Ganoderma lingzhi* (reishi), *Rhodiola rosea, Crocus sativus* (saffron), *Schisandra chinensis* (schisandra), *Lentinula edodes* (shiitake), *Tremella fuciformis* (snow fungus), *Hypericum perforatum* (St. John's wort), *Curcuma longa* (turmeric), *Trametes versicolor* (turkey tail), *Valeriana officinalis* (valerian root), *Mucuna pruriens* (velvet bean), and combinations thereof.

In some embodiments having plant/fungal/extract active ingredients, active ingredients may include extracts and phytochemicals extracted from *Astragalus membranaceus* such as kumatakenin (logP~=2.5), astragalosides, calycosin, formononetin, astramembranoside A, astramembranoside B, astragaloside III, astragaloside VII, huangqiyenin E, huangqiyenin F, huangqiyegenin III, huangqiyegenin IV, trideacetylhuangqiyegenin III, eriodictiol-7-O-glucoside, liquiritigenin, calycosin-7-O-β-D-glucopyranoside, odoration, ononin, calycosin 7-O-β-D-{6''-[(E)-but-2-enoyl]}-glucoside, calycosin 7-O-β-D-(6''-acetyl)-glucoside, pratensein, pratensein 7-O-β-D-glucopyranoside, 6''-acetylononin, ammopiptanoside A, 7,5'-dihydroxy-3'-methoxy-isoflavone-7-O-β-D-glucopyranoside, (3R,4R)-3-(2-hydroxy-3,4-dimethoxy-phenyl)-chroman-4,7-diol-7-O-β-D-glucopyranoside, (3R)-8,2'-dihydroxy-7,4'-dimethoxyisoflavane, (R)-3-

(5-hydroxy-2,3,4-trimethoxyphenyl)-chroman-7-ol, isomucronulatol 7-O-β-glucoside, isomucronulatol, (–)-methylinissolin 3-O-β-D-(6'-acetyl)-glucoside, (–)-methylinissolin 3-O-β-D-{6'-[(E)-but-2-enoyl]}-glucoside, (–)-methylinissolin 3-O-β-D-glucoside, licoagroside D, vesticarpan, (–)-methylinissolin, isoliquiritigenin, pendulone, β-sitosterol, β-sitosterol β-D-glycopyranoside, gentisin, chlorogenic acid, caffeic acid, and combinations thereof.

In some embodiments having plant/fungal/extract active ingredients, active ingredients may include extracts and phytochemicals extracted from *Bacopa monnieri* such as bacoside A3 (logP~=2.1), bacopaside II (logP~=2), bacopaside X (logP~=2.2), bacopasaponin C (logP~=2), bacopaside B (logP~=2.8), jujobogenin, bacosine, bacoside A1, bacoside A2, bacopasaponin A, bacopasaponin B, bacopasaponin D, bacopasaponin E, bacopasaponin F, bacopasaponin G, bacopasaponin H, bacopaside I, bacopaside III, bacopaside IV, bacopaside V, bacopaside IX, bacopaside XI, bacopaside XII, bacopaside N1, bacopaside N2, and combinations thereof.

In some embodiments having plant/fungal/extract active ingredients, active ingredients may include extracts and phytochemicals extracted from *Coleus barbatus* such as forskolin, barbatusin, barbatusol, carlocal, coleon C, coleon E, coleon F, coleon O, coleon S, coleon T, cyclobutatusin, plectrin, and plectrinon B In some embodiments having plant/fungal/extract active ingredients, active ingredients may include extracts and phytochemicals extracted from *Crocus sativus* (saffron) such as alpha-crocin (logP~=–1.5), crocetin, safranal, zeaxanthan, picrocrocin, apigenin, quercetin, kaempferol, luteolin, crocetin diglucose ester, crocetin gentiobiose glucose ester, and combinations thereof.

In some embodiments having plant/fungal/extract active ingredients, active ingredients may include extracts and phytochemicals extracted from *Curcuma longa* (turmeric) such as curcumin, desmethoxycurcumin, bidesmethoxycurcumin, turmerone, and combinations thereof.

In some embodiments having plant/fungal/extract active ingredients, active ingredients may include extracts and phytochemicals extracted from *Echinacea purpurea* such as cinnamic acid derivatives, caffeic acid, chlorogenic acid, cichoric acid (chicory acid), quercetin, nicotinflorin (kaempferol 3-O-rutinoside), rutin (quercetin 3-O-rutinoside), nitidanin diisovalerianate, undeca-2E,4Z-dien-8,10-diynoic acid isobutylamide, dodeca-2E,4Z-dien-8,10-diynoic acid isobutylamide, dodeca-2E,4Z,10E-trien-8-ynoic acid isobutylamide, dodeca-2E,4Z-dien-8,10-diynoic acid 2-methylbutylamide, undeca-2E,4Z-dien-8,10-diynoic acid 2-methylbutylamide, kaempferol, ferulic acid, and 4-hydroxy benzoic acid In some embodiments having plant/fungal/extract active ingredients, active ingredients may include extracts and phytochemicals extracted from *Huperzia serrata* (toothed clubmoss) such as caffeic acid, ferulic acid, huperzine-A In some embodiments having plant/fungal/extract active ingredients, active ingredients may include extracts and phytochemicals extracted from *Lavandula Angustifolia* (lavender) such as β-pinene, myrcene, limonene, 1,8-cineole, (Z)-β-ocimene, (E)-β-ocimene, camphor, linalool, linalyl acetate, (E)-caryophyllene, terpinene-4, lavandulyl acetate, lavandulol, α-terpineol, borneol In some embodiments having plant/fungal/extract active ingredients, active ingredients may include extracts and phytochemicals extracted from *Melissa Officinalis* (lemon balm) such as camphene, α-pinene, β-caryophyllene, camphene, carane, cinerone, citronellal, caryophyllene oxide, cubenole, cis-p-meth-2 en-7-ol, 2-pinen-4-one, nerol acetate, nerol, patchoulene, 1R-a-pinene, geraniol, isogeraniol, geraniol acetate, verbenol, menthol, cis-Z-bisabolene oxide, verbenone, aromadendrene oxide, andropholide, cis-myrtanol, germanicol, longifolene, himachalane, himachala-2,4-diene, pimara-7,15-dien-3-one, cycloisolengifolene, cholest-5-en-7-ol, lupan-3-ol acetate In some embodiments having plant/fungal/extract active ingredients, active ingredients may include extracts and phytochemicals extracted from *Mentha piperita* (peppermint) such as menthol, menthone, menthofuran, cis-carane, limonene, 1,8-cineole, trans-caryophyllene, neomenthol, β-pinene, α-pinene, germacrene-D, trans-sabinene hydrate, and neoisomenthyl acetate In some embodiments having plant/fungal/extract active ingredients, active ingredients may include extracts and phytochemicals extracted from *Mentha spicata* (spearmint) such as α-pinene, β-pinene, myrcene, 3-octanol, p-mycene, limonene, (Z)-β-ocimene, 1,8-cineole, cis-sabinene hydrate, trans-limonene oxide, cis-limonene oxide, cis-p-menth-2-en-1-ol, linalool, borneol, δ-terpineol, 4-terpineol, α-terpineol, dihydrocarveol, cis-dihydrocarveol, trans-carveol, cis-carveol, pulegone, carvone, isobornyl acetate, iso-dihydrocarveol acetate, β-bourbonene, β-elemene, β-caryophyllene, germacrene D, germacrene A, spathulenol, and caryophyllene oxide In some embodiments having plant/fungal/extract active ingredients, active ingredients may include extracts and phytochemicals extracted from *Ocimum Tenuiflorum* (holy basil) such as rosmarinic acid (logP~=1.6), oleanolic acid, ursolic acid, eugenol, carvacrol, linalool, β-caryophyllene, β-elemene, germacrene, luteolin In some embodiments having plant/fungal/extract active ingredients, active ingredients may include phytochemicals extracted from *Origanum Vulgare* (oregano) such as 3-carene, carvacrol, caryophyllene, linoleic acid, linolenic acid, oleic acid, p-cymene, palmitic acid, thymol In some embodiments having plant/fungal/extract active ingredients, active ingredients may include extracts and phytochemicals extracted from *Passiflora incarnata* (passionflower) such as chrysin, isovitexin, vitexin, isovitexin-2"-O-β-glucoside, coumarin, orientin, isoorientin, isoorientin-2"-O-β-glucoside, apigenin, luteolin, saponarin, schaftoside, isoschaftoside, vicenin-2, lucenin-2, harman, harmol, harmine, harmalol, harmaline, 2-hydroxy benzoic acid methyl ester, 2-phenylethyl alcohol, benzyl alcohol, α-bergamatol, carvone, eugenol, isoeugenol, hexanol, trans-anethol, β-ionone, limonene, cumene, α-pinene, prezizaene, zizaene, zizanene, maltol, gynocardin and umbelliferone In some embodiments having plant/fungal/extract active ingredients, active ingredients may include extracts and phytochemicals extracted from *Piper methysticum* (kava) such as (E)-1-cinnamoylpyrrolidine (logP~=2.2), (R)-kawain (logP~=2.7), 11-hydroxyyangonin (logP~=2.2), 5,6-dehydrokawain (logP~=2.9), 5,6-dihydroyangonin (logP~=2.5), 7,8-dihydromethysticin (logP~=2.2), 7,8-dihydroyangonin (logP~=2.9), pipermethystine (logP~=1.8), yangonin (logP~=2.8), 10-methoxyyangonin, 11-hydroxy-12-methoxydihydrokawain, 11-methoxy-12-hydroxydehydrokawain, 11-methoxy-5,6-dihydroyangonin, 11-methoxyyangonin, 11,12-dimethoxy-5,6-dihydrokawain, 5,6-dehydromethysticin, 5,6,7,8-tetrahydroyangonin, 7,8-dihydro-5-hydroxykawain, 7,8-dihydrokawain, hydroxykawain, methysticin, flavokavin A, flavokavin B, flavokavin C, and combinations thereof.

In some embodiments having plant/fungal/extract active ingredients, active ingredients may include extracts and phytochemicals extracted from *Rhodiola rosea* such as rhodosin (salidroside) (logP~=−1), rhodiolin (logP~=2), rhodioniside, rosiridin, rosavin, rosin, rosarin, p-tryosol, geraniol, myrtenol, 1-octanol, phenethyl alcohol, cinnamyl alcohol, proanthocyanidins, quercetin, gallic acid, chlorogenic acid, kaempferol In some embodiments having plant/fungal/extract active ingredients, active ingredients may include phytochemicals extracted from *Rosmarinus officinalis* (rosemary) such as p-cymene, p-cymenene, thymol, α-pinene, β-pinene, α-thujene, camphene, myrcene, eucalyptol, γ-terpinene, linalool, β-caryophyllene, camphre, carvacrol, trans-verbenol, borneol, terpinene-t-ol, α-terpineol, and combinations thereof.

In some embodiments having plant/fungal/extract active ingredients, active ingredients may include extracts and phytochemicals extracted from *Satureja hortensis* (summer savory) such as α-phellandrene, α-pinene, α-terpinene, α-thujene, β-pinene, myrcene, carvacrol, thymol, camphene, p-cymene, limonene, γ-terpinene, ledene, α-bisabolene, β-bisabolene, and spathulenol.

In some embodiments having plant/fungal/extract active ingredients, active ingredients may include phytochemicals extracted from *Sceletium tortuosum* (kanna) such as mesembrine (logP~=1.5), mesembrenone (logP~=1.3), mesembrenol (logP~=2.4), tortuosomine (logP~=3), chennaine, D7-mesembrine, D7-mesembrenone, epimesembranol, epimesembrenol, and mesembrane In some embodiments having plant/fungal/extract active ingredients, active ingredients may include extracts and phytochemicals extracted from *Schisandra chinensis* (schisandra) such as (+)-schisandrin (logP~=5), (−)-schisandrin A (logP~=3.6), schisandrol A (logP~=3.4), (−)-schisandrin B (logP~=4), (−)-schisandrin C (logP~=3.5), schisandroside C (logP~=1.6), deoxyschizandrin, gomisins, pregomisin In some embodiments having plant/fungal/extract active ingredients, active ingredients may include extracts and phytochemicals extracted from *Thymus vulgaris* (thyme) such as carvacrol, caryophyllene, γ-terpinene, p-cymene, thymol In some embodiments having plant/fungal/extract active ingredients, active ingredients may include extracts and phytochemicals extracted from *Turnera diffusa* (damiana) such as tetraphyllin B (logP~=−2.5), gonzalitonsin I, arbutin, tricosan-2-one, acacetin, p-cymene, beta-sitosterol, 1,8-cineole, apigenin, β-carotene, β-pinene, tannins, thymol, hexacosanol In some embodiments having plant/fungal/extract active ingredients, active ingredients may include extracts and phytochemicals extracted from *Withania somnifera* (ashwagandha) such as 6a-chloro-5b-hydroxywithaferin A (logP~=3.2), 6a-chloro-5b,17a-dihydroxywithaferin A, withaferin A, (22R)-5b-formyl-6b,27-dihydroxy-1-oxo-4-norwith-24-enolide, 2,3-dihydrowithaferin A, 3-methoxy-2,3-dihydrowithaferin A, 2,3-didehydrosomnifericin, withanone, withanoside IV, withanoside X, tropine, cuscohygrine In some embodiments having plant/fungal/extract active ingredients, active ingredients may include extracts and phytochemicals extracted from *Panax ginseng* (asian *ginseng*) such as ginsenoside rb1 (logP~=−1), ginsenoside rg1 (logP~=0.8), ginsenoside rb2, ginsenoside rh2, ginsenoside rg3, ginsenoside rh1, ginsenoside re In some embodiments having plant/fungal/extract active ingredients, active ingredients may include extracts and phytochemicals extracted from *Zingiber officinale* (ginger) such as 2-gingerol, 4-gingerol, 6-gingerol, 8-gingerol, 10-gingerol, 12-gingerol, 6-shogaol, 10-shogaol, 6-paradol, quercetin, zingerone, gingerenone-A, gingerenone-B, gingerenone-C, 6-dehydrogingerdione, β-bisabolene, α-curcumene, zingiberene, α-farnesene, and β-sesquiphellandrene, zerumbone, β-phellandrene, (+)-camphene, 1,8-cineole, geraniol, citral A, citral B, linalool, α-terpineol, borneol, zingiberol, and zingibain In some embodiments having plant/fungal/extract active ingredients, active ingredients may be fungal matter such as fruiting bodies, spores, mycelium, and combinations thereof.

In some embodiments having plant/fungal/extract active ingredients, active ingredients may be fungal matter, extractions of fungal matter, or bioactive molecules and macromolecules contained in fungal matter from one or many species of fungus such as *Inonotus obliquus* (chaga), *Chlorella, Cordyceps sinensis, Cordyceps mihtaris, Pleurotus eryngii* (king oyster), *Hericium erinaceus* (lion's mane), *Grifola fondosa* (maitake), *Pleurotus ostreatus* (oyster), *Poria cocos* (poria), *Ganoderma lingzhi* (reishi), *Lentinula edodes* (shiitake), *Tremella fuciformis* (snow fungus), *Spirulina*, and *Trametes versicolor* (turkey tail), including their geographic and heirloom varieties.

In some embodiments having plant/fungal/extract active ingredients, active ingredients may include extracts and phytochemicals extracted from *Cordyceps* mihtaris such as cordycepin, cordymin, lovastatin, ergothioneine, D-mannitol, galactose, lutein, zeaxanthin, lycopene, beta-carotene, pentostatin, ophiocordin, cephalosporolide C, cephalosporolide E, cephalosporolide F, pyridine-2,6-dicarboxylic acid, myriocin, cicadapeptide I, cicadapeptide II, and 2-carboxymethyl-4-(3'-hydroxybutyl) furan In some embodiments having plant/fungal/extract active ingredients, active ingredients may include extracts and phytochemicals extracted from *Cordyceps sinensis* such as cordycepin, cordymin, cordycedipeptide A, cordysinocan, cordycepic acid, ergosteryl-3-O-β-D-glucopyranoside, 2,23-dihydroergosteryl-3-O-β-D-glucopyranoside, 5α,8α-epidioxy-24(R)-methylcholesta-6,22-dien-3β-D-gluco-pyranoside, 5α,6α-epoxy-24(R)-methylcholesta-7,22-dien-3β-ol, mannoglucan In some embodiments having plant/fungal/extract active ingredients, active ingredients may include extracts and phytochemicals extracted from *Grifola fondosa* (maitake) such as ergosterol, fungisterol, lanosterol, uronic acid, mannose, beta-glucan, In some embodiments having plant/fungal/extract active ingredients, active ingredients may include extracts and phytochemicals extracted from *Hericium erinaceus* (lion's mane) such as hericerin (logP~=6.4), herinacine A (logP~=2.5), isoericerin, isohericenone J, hericerin A, N-dephenylethyl isohericer, hericenone B, hericenone J, 4-(3',7'-dimethyl-2',6'-octadienyl)-2-ormyl-3-hydroxy-5-methoxy-benzylalcohol, erinacine A, erinacine E, erinacerin A, erinacerin B, erinacerin C, erinacerin M, erinacerin N, erinacerin O, erinacerin P, erinaceolactone A, erinaceolactone B, erinaceolactone C, and ergosterol In some embodiments having plant/fungal/extract active ingredients, active ingredients may include phytochemicals extracted from *Inonotus obliquus* (chaga) such as melanin, oxalate, inotodiol, betulin, betulinic acid, inonotusol A, inonotusol B, inonotusol C, inonotusol D, inonotusol E, inonotusol F, inonotusol G, inonotusic acid, trametenolic acid, 3β,22-dihydroxylanosta-8,24-dien-11-one, ergosta-7-en-3β-ol, ergosterol, vanillic acid, and protocatehuic acid In some embodiments having plant/fungal/extract active ingredients, active ingredients may include extracts and phytochemicals extracted from *Lentinula edodes* (shiitake) such as 1-octen-3-ol, 2-octanone, 1,2,4-trithiolane, 1,2,3,5, 6-pentathiepane, eritadenine, ergosterol, α-tocopherol, linoleic acid, oleic acid, butyric acid, gallic acid, caffeic acid, quercetin, chlorogenic acid, pentanal, linalool, and 1-octen-3-ol In some embodiments having plant/fungal/extract active ingredients, active ingredients may include extracts and phytochemicals extracted from *Pleurotus eryngii* (king oyster) such as gallic acid, epicatechingallate, epigallocatechigallate, ferulic acid, and β-glucan In some embodiments having plant/fungal/extract active ingredients, active ingredients may include extracts and phytochemicals extracted from *Poria Cocos* such as trametenolic acid, dehydrotrametenolic acid, 3-epi-dehydrotrametenolic acid, 16α-hydroxytrametenolic acid, 3-O-Acetyl-16α-hydroxytrametenolic acid, 3-O-Acetyl-16α-hydroxydehydrotrametenolic acid, 16α-27-dihydroxydehydrotrametenoic acid, dehydrotrametenonic acid, 3β,16α-dihydroxylanosta-7,9(11),24-trien-21-oic acid, eburicoic acid, dehydroeburicoic acid, 16α-25-dihydroxydehydroeburicoic acid, dehydroeburiconic acid, 16-α-hydroxyeburiconic acid, 16α-25-dihydroxydehydroeburiconic acid, pachymic acid, dehydropachymic acid, 16α-hydroxydehydropachymic acid, 25-hydroxypachymic acid, tumulosic acid, dehydrotumulosic acid, 3-epi-dehydrotumulosic acid, 15α-hydroxydehydrotumulosic acid, 25-hydroxy-3-epi-tumulosic acid, 25-hydroxy-3-epi-hydroxytumulosic acid, 3β-hydroxybenzoyldehydrotumulosic acid, 5α-8α-peroxydehydrotumulosic acid, polyporenic acid C, 6α-hydroxypolyporenic acid C, 29-hydroxypolyporenic acid C, poriacosone A, poriacosone B, poricoic acid B, 16-deoxyporicoic acid B, poricoic acid BM, poricoic acid E, poricoic acid G, poricoic acid GM, poricoic acid A, poricoic acid C, poricoic acid D, poricoic acid F, poricoic acid H, poricoic acid AM, poricoic acid CM, poricoic acid DM, poricoic acid HM, 6,7-dehydroporicoic acid H, 25-hydroxyporicoic acid C, 25-hydroxyporicoic acid H, 26-hydroxyporicoic acid DM, and 25-methoxyporicoic acid A In some embodiments having plant/fungal/extract active ingredients, active ingredients may include extracts and phytochemicals extracted from *Trametes versicolor* (Turkey Tail) such as p-hydroxybenzoic acid, homogentisic acid, vanillic acid, protocatehuic acid, linoleic acid, linolenic acid, oleic acid, palmitic acid, stearic acid, caffeic acid, p-coumaric acid, o-coumaric acid, ferulic acid, esculetin, scopoletin, umbelliferon, quinic acid, chlorogenic acid, gallic acid, syringic acid, daidzein, genistein, amentoflavone, catechin, epicatechin, naringenin, rutin, quercetin, quercitrin, quercetin-3-O-glucoside, kaempferol, kaempferol-3-O-glucoside, hyperoside, isorhamnetin, apigenin, apigenin-7-O-glucoside, baicalein, luteolin, luteolin-7-O-glucoside, chrysoeriol, vitexin, apiin, and baicalin In some embodiments having plant/fungal/extract active ingredients, active ingredients may include phytochemicals extracted from *Tremella fuciformis* (Snow Fungus) such as 4-hydroxybenzoic acid, coumaric acid, gentisic acid, and protocatehuic acid.

In some embodiments having plant/fungal/extract active ingredients, active ingredients may be heterogeneous natural active ingredients with either an unknown chemical composition, unknown bioactive components therein, biological activity that is not sufficiently understood to describe the active ingredient using chemical structure arguments, complex biological activity and complex compositions that can be described as providing entourage effects where incorporating the active ingredient does not allow for treating the components separately, and combinations thereof.

In some embodiments having plant/fungal/extract active ingredients, active ingredients may be a botanical or fungal matter, in part or in full, mixtures of such, or an extraction thereof.

In some embodiments having plant/fungal/extract active ingredients, active ingredients may be plant matter and fungal matter, or their extracts, where the plant matter and fungal matter is used without mechanical processing. In some embodiments having plant/fungal/extract active ingredients, active ingredients may be plant matter and fungal matter, or their extracts, where the plant matter and fungal matter may be mechanically processed before extraction or before addition as an ingredient with at least one mechanical process such as grinding, stomaching, shaking, centrifuging, In some embodiments having plant/fungal/extract active ingredients, active ingredients may be plant matter and fungal matter, or their extracts, where the plant matter and fungal matter may be chemically processed before extraction or before addition as an ingredient with at least one chemical process such as exposure to electromagnetic radiation, heating, exposure to gases such as $CO_2$, $O_2$, and $H_2$, exposure to liquids such as basic aqueous solutions and organic solvents like ethanol to alter macromolecule networks (e.g. chemically, structurally, organizationally) and disrupt cell walls, respectively, and combinations thereof.

In some embodiments having plant/fungal/extract active ingredients, active ingredients may be plant matter and fungal matter, or their extracts, where the plant matter and fungal matter may be chemically processed before extraction or addition as an ingredient In some embodiments having plant/fungal/extract active ingredients, active ingredients may be a member of the kingdom Plantae and called botanical matter, plant matter, plant, herb, herbal medicine, or any portion of the plant whether intact or originating from the plant such as bark, stem, roots, flowers, leaves, buds, branches, seeds, and combinations thereof.

In some embodiments having plant/fungal/extract active ingredients, active ingredients may be extracts of plant matter and fungal matter and bioactive molecules (regardless of purity) isolated from plants or fungi, including bioactive molecule content of plant and fungal matter extracts in part, where the bioactive molecules and extracts have their solvent used for extraction and any purification removed before addition of the bioactive molecules and extracts as an ingredient to a product.

In some embodiments having plant/fungal/extract active ingredients, active ingredients may be bioactive molecules and extracts of plant and fungal matter without drying the matter extracted beforehand such as harvesting fresh Reishi fruiting bodies and extracting bioactive terpenoids and of interest with ethanol to maximize the amount of volatile bioactive molecules retained in the extraction that would otherwise be lost during the fruiting body drying process.

In some embodiments having plant/fungal/extract active ingredients, active ingredients may be bioactive molecules and extracts of plant and fungal matter that is dehydrated before the extraction process, an example being products with desired bioactive components classified as hydrophobic extracted in the presence of water decreasing extraction efficiency and subsequent concentrations of bioactive components extracted in comparison to extractions performed with only trace amounts of water in the plant or fungal matter. An example of when dehydrating matter extracted to optimize extraction efficiency and final concentration of bioactive molecule in extract is the case of extracting berberine from Golden Seal dried plant matter with ethanol, where berberine solubility in ethanol decreases rapidly with water content.

In some embodiments having plant/fungal/extract active ingredients, active ingredients may be bioactive molecules and extracts of plant and fungal matter extracted and purified as necessary with carbon dioxide in various states of matter in isolation or in combination.

In some embodiments having plant/fungal/extract active ingredients, active ingredients may be bioactive molecules and extracts of plant and fungal matter extracted and purified as necessary with supercritical carbon dioxide.

In some embodiments having plant/fungal/extract active ingredients, active ingredients may be bioactive molecules and extracts of plant and fungal matter extracted and purified as necessary with subcritical carbon dioxide.

In some embodiments having plant/fungal/extract active ingredients, active ingredients may be extracts produced with a menstruum ratio of 1:N where for every 1 g of the plant matter or fungal matter extracted, N mL of the solvent is utilized for the extraction. An example of a menstruum ratio for an extraction is a coconut oil and ethanol miscible mixed solvent extraction of *Bacopa monnieri* (*bacopa*) plant matter at menstruum ratio of 1:5 where the coconut oil and ethanol are mixed in a 1:1 ratio such that for 1 kg of *bacopa* 5 L of 1:1 coconut oil and ethanol (2.5 L coconut oil and 2.5 L ethanol) is used for soaking with 10 minutes of ultrasound applied before filtration and storage.

In some embodiments having plant/fungal/extract active ingredients, active ingredients may be extracts produced with a menstruum ratio of 1:(N) with N mL of extraction solvent used during the extraction process but where before or after filtering extraction solvent is removed by evaporation such as with water or ethanol containing extracts, providing a final menstruum ratio of 1:(N−M) with M mL of solvent removed for every 1 g of plant or fungal matter extracted before use in production or packaging for distribution.

In some embodiments having plant/fungal/extract active ingredients, active ingredients may be extracts to which salts or other solutes are added to the extraction solvent before or after filtration of the plant and fungal matter extracted as a processing aid for increasing extraction efficiency, as a stabilizer for the extract or contents of the extract, and combinations thereof.

In some embodiments having plant/fungal/extract active ingredients, active ingredients may be extracts filtered with a sub-micron or micron filter to remove a plant or fungal matter from suspension.

In some embodiments having plant/fungal/extract active ingredients, active ingredients may be plant matter from a single or multiple species in the genus *Panax* such as *Panax ginseng, Panax notoginseng, Panax quinquefolius,*

In some embodiments having plant/fungal/extract active ingredients, an active ingredient may be a mineral tar, resin, humic substance, or other high viscosity materials with majority composition of humic acids, fulvic acids, humin, and other organic acids such as Shilajit (Mumijo) and isolated organic components from soil (soil organic matter).

1.6. Examples of Live Active Ingredients

In some embodiments having live active ingredients, active ingredients may be cells, organisms, life, alive, living, dormant life, conscious life, and combinations thereof.

1.6.1. Examples of Non-cellular Life as Live Active Ingredients

In some embodiments, active ingredients may be non-cellular life such as Acytota and Aphanobionta. In some embodiments having non-cellular life as active ingredients, an active ingredient may be non-cellular life categorized into the domain of Virusobiota such as viruses and viroids. In some embodiments having non-cellular life as active ingredients, an active ingredient may be non-cellular life categorized into the domain of Prionobiota such as prions and intrinsically disordered proteins.

In some embodiments having non-cellular life as active ingredients, active ingredients may be Virusobiota classified as a Virus serve as an Active Ingredient with a Formulation from one or multiple of the six recognized virus realms, estabilisted by the International Committee on Taxonomy of Viruses, including Adnariria (containing archaeal filamentous viruses with A-form double-stranded DNA, dsDNA, genomes encoding a unique alpha-helical major capsid protein), Duplodnaviria (containing all dsDNA viruses that encode the HK-97-fold major capsid protein), Monodnaviria (containing all single-stranded DNA, ssDNA, viruses that encode a HUH superfamily endonuclease and their descendants), Riboviria (containing all RNA viruses that encode RNA-dependent RNA polymerase and all viruses that encode reverse transcriptase), Ribozyviria (containing hepatitis delta-like viruses with circular, negative-sense ssRNA genomes), and Varidnaviria (containing all dsDNA viruses that encode a vertical jelly roll major capsid protein).

In some embodiments having non-cellular life as active ingredients, active ingredients may be Virusobiota classified as viruses, and modified such that their protein coating is stripped, or viroids (small single-stranded, circular RNAs with no protein coating, and known to primarily, if not exclusively, inhabit flowering plants) serve as an Active Ingredient within a Formulation. In some embodiments having non-cellular life as active ingredients, viroids from the family of Pospiviroidae or Avsunviroidae.

In some embodiments having non-cellular life as active ingredients, active ingredients may be Prions, or Prionobiota, (e.g., misfolded proteins, intrinsically disordered proteins), whether classified as Life or otherwise.

1.6.2. Examples of Cellular Life as Live Active Ingredients

In some embodiments having cellular life as active ingredients, active ingredients may be cellular life such as Cytota. In some embodiments having cellular life as active ingredients, an active ingredient may be cellular life categorized into the domain of Bacteria. In some embodiments having cellular life as active ingredients, an active ingredient may be cellular life categorized into the domain of Archaea.

In some embodiments having cellular life as active ingredients, active ingredients may be probiotics, prebiotics, and other microbiota or microbiome supporting ingredients.

In some embodiments having cellular life as active ingredients, active ingredients may be a strain (species) or mixtures of bacteria for their probiotic properties. In some embodiments having cellular life as active ingredients, active ingredients may be a strain (species) or mixtures of bacterial strains such as *Bifidobacterium adolescentis, Bifidobacterium animalis, Bifidobacterium bifidum, Bifidobacterium breve, Bifidobacterium infantis, Bifidobacterium lactis, Bifidobacterium longum, Enterococcus faecium, Escherichia coli, Lactobacillus acidophilus, Lactobacillus bulgaricus, Lactobacillus casei, Lactobacillus delbrueckii (bulgaricus), Lactobacillus fermentum, Lactobacillus gasseri, Lactobacillus helveticus, Lactobacillus paracasei, Lactobacillus paraplantarum, Lactobacillus plantarum, Lacto-*

*bacillus reuteri, Lactobacillus rhamnosu, Lactobacillus salivarius, Lactococcus lactis, Saccharomyces boulardi, Saccharomyces cervisiae, Streptococcus thermophilus,* and cultures or colonies containing combinations thereof.

In some embodiments having cellular life as active ingredients, active ingredients may be a species or mixture of species of anaerobic bacteria and other organisms such as common microbes in the human gut microbiome, primarily the colon or large intestine.

In some embodiments having cellular life as active ingredients, active ingredients may be cellular life categorized within the domain of Eukaryota.

1.6.3. Examples of Protists as Live Active Ingredients

In some embodiments having live protists as active ingredients, active ingredients may be cellular life categorized within the domain of Eukaryota and the kingdom of Protista, referred to as protists.

1.6.4. Examples of Plants as Live Active Ingredients

In some embodiments having live plants as active ingredients, active ingredients may be cellular life categorized within the domain of Eukaryota and the kingdom of Plantae, referred to as plants.

1.6.5. Examples of Fungi as Live Active Ingredients

In some embodiments having fungi as active ingredients, active ingredients may be cellular life categorized within the domain of Eukaryota and the kingdom of Fungi, referred to as fungi.

1.6.6. Examples of Animals as Live Active Ingredients

In some embodiments having animals as active ingredients, active ingredients may be cellular life categorized into the domain of Eukaryota within the kingdom of Animalia. In some embodiments having animals as active ingredients, active ingredients may be cellular life in whole, or one or more cells harvested or modified from multicellular life, in the biological kingdom of Animalia and referred to as animals (metazoa) or animal cells.

In some embodiments having animals as active ingredients, active ingredients may be forms of cellular life, in whole or part and regardless of classifications as single-cellular or multicellular life, may function as an active ingredient, encapsulated or otherwise.

2. Inactive Ingredients 2.1. Phase Media as Inactive Ingredients 2.1.1. Hydrophobic Phase Media as Inactive Ingredients In some embodiments having hydrophobic phase media as inactive ingredients, a hydrophobic medium may be defined as any substance that is not an active ingredient and makes up the bulk (at least 50.1% by weight) of the hydrophobic phase. In some embodiments having hydrophobic phase media as inactive ingredients, a hydrophobic medium may be in liquid state in room temperature. In some embodiments having hydrophobic phase media as inactive ingredients, a hydrophobic medium may be in solid state in room temperature and in liquid state in elevated temperatures (e.g., 60, 80, 95, 97, 100, 120, 150, or 180° C.). In some embodiments having hydrophobic phase media as inactive ingredients, particles may be formed in a temperature in which the carrier oil is in the liquid state. In some embodiments having hydrophobic phase media as inactive ingredients, a hydrophobic medium may be in a liquid state in room temperature and irreversibly form a solid at elevated temperatures such that the particles may be formed at a temperature in which the carrier oil (hydrophobic dispersed phase medium) is in the liquid state.

In some embodiments having hydrophobic phase media as inactive ingredients, a hydrophobic medium may be chosen because it is entirely insoluble or very nearly insoluble (e.g., solubility of less than 100 mg in 100 grams, or solubility of less than 1 gram in 100 grams, or solubility of less than 10 grams in 100 grams) in water under the range of environmental conditions the system would be exposed to during its lifetime.

In some embodiments having hydrophobic phase media as inactive ingredients, a hydrophobic medium may be chosen because all the hydrophobic components, both active and inactive, in the system have a sufficient solubility in the medium to form a homogenous phase. In some embodiments having hydrophobic phase media as inactive ingredients, a sufficient solubility for an active ingredient would be one that would allow a sufficiently high mass of the active to be encapsulated in a desired volume of the final particle solution. In some embodiments having hydrophobic phase media as inactive ingredients, a sufficient solubility for a stabilizer may be one that would allow for a sufficiently high concentration of the stabilizer to deliver the desired stabilizing effects on the particle system. In some embodiments having hydrophobic phase media as inactive ingredients, a hydrophobic medium may be chosen because some or all the hydrophilic components in the system may be insoluble or nearly insoluble in the hydrophobic medium.

In some embodiments having hydrophobic phase media as inactive ingredients, a hydrophobic medium may be chosen for the effect it has on the bioavailability of the active ingredients. In some embodiments having hydrophobic phase media as inactive ingredients, a hydrophobic medium may increase the bioavailability of the active ingredient by shielding it from decomposition in the mouth, esophagus, stomach, small and large intestine, and blood stream. In some embodiments having hydrophobic phase media as inactive ingredients, a hydrophobic medium may be chosen because of the effect it has on the absorption pathway of the particles and encapsulated active ingredients. In some embodiments having hydrophobic phase media as inactive ingredients, particles may be absorbed into the portal vein, and enter the bloodstream with minimal uptake time. In some embodiments having hydrophobic phase media as inactive ingredients, the particles may be absorbed into the lymphatic system, bypass first pass metabolism, and may further prevent enzymatic decomposition of the active ingredient by liver enzymes.

In some embodiments having hydrophobic phase media as inactive ingredients, the hydrophobic medium may be chosen because of its stability. In some embodiments having hydrophobic phase media as inactive ingredients, the hydrophobic medium may be chosen because it is inert and nonreactive with all the components, both hydrophilic and hydrophobic, of the encapsulation system as well as any chemical species present from the systems environment, both at ambient conditions as well as any environmental conditions present during manufacturing, storage, or consumption. In some embodiments having hydrophobic phase media as inactive ingredients, a hydrophobic medium must be chosen that does not decompose when exposed to cavitation from ultrasonic waves. In some embodiments having hydrophobic phase media as inactive ingredients, a hydrophobic medium must be chosen that does not react with the active ingredients added to the particle system. In some embodiments having hydrophobic phase media as inactive ingredients, a hydrophobic medium must be chosen that does not react with the stabilizers added to the particle system. In some embodiments having hydrophobic phase media as inactive ingredients, a hydrophobic medium must be chosen that does not react with the hydrophilic medium. In some embodiments having hydrophobic phase media as inactive ingredients, a hydrophobic medium must be chosen that does not react with any components added postproduction (e.g., packaging, flavorants, flavorings, preservatives).

In some embodiments having hydrophobic phase media as inactive ingredients, the hydrophobic medium may be chosen because of its rheological properties. In some embodiments having hydrophobic phase media as inactive ingredients, the hydrophobic medium may be chosen because its viscosity is sufficiently low at the temperature of production that it may be easily mixed via magnetic stirring or shear mixing. In some embodiments having hydrophobic phase media as inactive ingredients, the hydrophobic medium may be chosen because its viscosity is sufficiently high at ambient conditions that it stabilizes the particles by decreasing the frequency of collisions particles in the phase. In some embodiments having hydrophobic phase media as inactive ingredients, the hydrophobic medium may be chosen because its viscosity is sufficiently high at ambient conditions that it forms a physical barrier preventing diffusion of encapsulated components into the continuous phase.

In some embodiments having hydrophobic phase media as inactive ingredients, a carrier oil may be medium chain triglycerides (MCT) oil. MCTs may be defined as esters of glycerol and 3 fatty acids, where at least 2 fatty acids must each have an aliphatic tail of at least 6 but no more than 12 carbon atoms. In some embodiments having hydrophobic phase media as inactive ingredients, coconut oil, palm kernel oil, another similar natural oil, or refined or otherwise purified forms of natural oils may be used as a source of MCT. Alternatively, the MCT oil may be of a synthetic origin, such as Abitec Captex 300, Abitec Captex 355, Abitec Captex 1000, Abitec Captex 8000, Labrafac lipofile WL1349, Labrafac PG. MCT oil may be chosen as a carrier oil as it may increase absorption and bioavailability of some active ingredients (e.g., cannabinoids). MCT oil may increase bioavailability of cannabinoids due to its ability to easily solubilize cannabinoids and shuttle them through the stomach lining into the hepatic portal system. MCT may further increase bioavailability of cannabinoids by shielding them from first pass metabolism in the liver. In addition to increasing bioavailability of cannabinoids, MCT oil may also reduce the onset times by efficiently shuttling them into the blood stream. In some embodiments having hydrophobic phase media as inactive ingredients, MCT oil may be choses due to the high solubility (>20% by weight) of oleo-gelling agents such as ethylcellulose in MCT. When copious amounts of oleo-gelling agents are present in MCT, its solidification temperature may be increased to elevated temperatures (e.g., 60, 70, 80, 85, 90, 96° C.).

In some embodiments having hydrophobic phase media as inactive ingredients, the carrier oil used may be long chain triglyceride (LCT) oil. LCTs may be defined as esters of glycerol and 3 fatty acids, where the fatty acids must each have an aliphatic tail of at least 12 but no more than 21 carbon atoms. In some embodiments having hydrophobic phase media as inactive ingredients, the LCT oil may be derived from a natural plant source such as almond oil, apricot kernel oil, avocado oil, basil oil, Brazil nut oil, cashew oil, cocoa butter, corn oil, cottonseed oil, grapeseed oil, hazelnut oil, hemp oil, macadamia nut oil, palm oil, peanut oil, rice bran oil, soybean oil, olive oil, sunflower oil, canola (rapeseed) oil, safflower oil, sesame oil, walnut oil, or any refined or otherwise purified forms of natural plant oils. Additionally, the oil may come from a natural animal source such as butter, clarified butter, ghee, shortening, beef tallow, mutton tallow, fish oil, lard, or any refined or otherwise purified form of natural animal fats. In some embodiments having hydrophobic phase media as inactive ingredients, the LCT oil may come from processed or synthetic sources such as hydrogenated vegetable shortening, modified or functionalized natural and synthetic LCT oils, and pure LCT or mixed LCT synthetic products including those from Abitec such as Captex GTO, Sterotex NF, or Sterotex P. In some embodiments having hydrophobic phase media as inactive ingredients, LCT oil may be used as the carrier oil as it may increase bioavailability by allowing some active ingredients (e.g., cannabinoids) to bypass first pass digestion in the liver and otherwise shielding cannabinoids from enzymatic decomposition. Use of LCT as a carrier oil may lead to increased bioavailability for cannabinoids if it is able to shuttle cannabinoids from the epithelial cells into the lymphatic system rather than the hepatic portal vein, thereby bypassing first pass digestion. Use of LCT oil as a carrier oil may lead to increase bioavailability for cannabinoids if it is sufficiently hydrophobic enough to prevent the transport of aqueous digestive enzymes to the encapsulated cannabinoids or vice versa. In some embodiments having hydrophobic phase media as inactive ingredients, LCT may be chosen as a hydrophobic medium because of its increased hydrophobicity compared to MCT or SCT. In some embodiments having hydrophobic phase media as inactive ingredients, certain hydrophilic or amphiphilic active ingredients in an internal hydrophilic phase may be unable to diffuse though a hydrophobic phase made up of LCT due to their low solubilities in LCT.

In some embodiments having hydrophobic phase media as inactive ingredients, the carrier oil used may be SCT (short chain triglyceride) oil. SCTs may be defined as esters of glycerol and 3 fatty acids, where the fatty acids must each have an aliphatic tail of more than 0 but less than 6 carbon atoms. Examples of short chain triglycerides are those triglycerides with three bound fatty acids such as formic acid, acetic acid, propionic acid, butyric acid, isobutyric acid, valeric acid, isovaleric acid, 2-methylbutyric acid, including mixtures thereof.

In some embodiments having hydrophobic phase media as inactive ingredients, the carrier oil used may be VLCT (very long chain triglyceride) oil. VLCTs may be defined as esters of glycerol and 3 fatty acids, where the fatty acids must each have an aliphatic tail of more than 21. An example of VLCT's is glyceryl tribehenate.

In some embodiments having hydrophobic phase media as inactive ingredients, the carrier oil may be a non-triglyceride oil. In some embodiments having hydrophobic phase media as inactive ingredients the oil might be naturally occurring, such as bees wax, terpenes, spermaceti, lanolin, carnauba wax, jojoba oil, candelilla wax, ouricury wax, shellac, Japan wax, and rice bran wax.

In some embodiments having hydrophobic phase media as inactive ingredients, the hydrophobic media may be an organic solvent. In some embodiments having hydrophobic phase media as inactive ingredients, the hydrophobic media may be benzene, butanol, butyl acetate, carbon tetrachloride, chloroform, cyclohexane, dichloromethane, dichloroethane, diethyl ether, ethyl acetate, heptane, hexane, isooctane, methyl ethyl ketone, methyl tertbutyl ether, pentane, petroleum ether, toluene, tetrachloroethylene, or trichloroethylene. In some embodiments having hydrophobic phase media as inactive ingredients, these solvents may be completely or partially removed during or after manufacturing such that the system is safe for human or animal consumption.

In some embodiments having hydrophobic phase media as inactive ingredients, a blend of MCT, LCT, and other hydrophobic media, known as a mixed hydrophobic media, may be used to impart some of the benefits of each type of hydrophobic media into the desired formulation. In some embodiments having hydrophobic phase media as inactive ingredients, MCT may be present as the carrier oil of an active ingredient contained within dispersed O/W particles in the range of 1-99%, e.g. making up 5, 10, 15, 20, 25, 30, 35, 40, 45, 50, 55, 60, 65, 70, 75, 80, 85, 90, 95, or 99% of the particle carrier oil by weight. In some embodiments having hydrophobic phase media as inactive ingredients, LCT might be present as the carrier oil in between 1-99%, e.g., making up 5, 10, 15, 20, 25, 30, 35, 40, 45, 50, 55, 60, 65, 70, 75, 80, 85, 90, 95, or 99% of the carrier oil by weight. In some embodiments having hydrophobic phase media as inactive ingredients, portions of a mixed hydrophobic media may be partially soluble in the hydrophilic phase in addition to being miscible in the hydrophobic phase.

2.1.2. Examples of Hydrophilic Phase Media as Inactive Ingredients

In some embodiments having hydrophilic phase media as inactive ingredients, the hydrophilic medium may be defined as any substance that is not an active ingredient and makes up the bulk (at least 50.1% by weight) of the hydrophilic phase. In some embodiments having hydrophilic phase media as inactive ingredients, the hydrophilic medium may be in liquid state in room temperature. In some embodiments having hydrophilic phase media as inactive ingredients, the hydrophobic medium may be in solid state in room temperature and in liquid state in elevated temperatures (e.g., 60, 80, 95, 97, 99° C.) such that particles may be formed in a temperature in which the hydrophilic medium is in the liquid state. In some embodiments having hydrophilic phase media as inactive ingredients, the hydrophilic medium may be in a liquid state in room temperature and irreversibly form a solid at elevated temperatures such that particles may be formed at a temperature in which the hydrophilic medium is in the liquid state.

In some embodiments having hydrophilic phase media as inactive ingredients, the hydrophilic medium may be chosen because it is entirely insoluble or very nearly insoluble (e.g., solubility of less than 100 mg in 100 grams, or solubility of less than 1 gram in 100 grams, or solubility of less than 10 grams in 100 grams) in the hydrophobic phase under the range of environmental conditions the system would be exposed to during its lifetime.

In some embodiments having hydrophilic phase media as inactive ingredients, the hydrophilic medium may be chosen because all the hydrophilic components, both active and inactive, in the system have a high enough solubility in the medium to form a homogenous phase. In some embodiments having hydrophilic phase media as inactive ingredients, the hydrophilic medium may be chosen for some or all the hydrophobic components in the system that are insoluble or nearly insoluble in the hydrophobic medium.

In some embodiments having hydrophilic phase media as inactive ingredients, the hydrophilic medium may be a pure compound. In some embodiments having hydrophilic phase media as inactive ingredients the hydrophilic medium may be generally regarded as safe by the FDA, such as water, glycerol, or ethanol. In some embodiments having hydrophilic phase media as inactive ingredients, the hydrophilic medium may be a mixture of several pure compounds, known as a mixed hydrophilic media. In some embodiments having hydrophilic phase media as inactive ingredients, portions of a mixed hydrophilic media may be partially soluble in the hydrophobic phase in addition to being miscible in the hydrophilic phase.

2.2. Examples of Stabilizing Agents

A stabilizing agent may be any component added to the system that increases the stability of the particle system either by reducing the surface energy of the phases present at the interfaces of the system (surface stabilizing agents) or by reducing the probability of processes that degrade the particle system such as coalescence, flocculation, creaming, or sedimentation (media stabilizing agent). A surface stabilizing agent reduces the surface energy (the difference in energy between a molecule at the interface versus in the bulk of a given phase) at an internal (existing between any combination of a hydrophobic and hydrophilic phases in the system) interface and has the effect of allowing smaller particles to be formed with the same input of energy. A media stabilizing agent increases the viscosity of a phase. In some embodiments, adding a media stabilizing agent increases stability of a particle system by increasing the viscosity of a phase which decreases the rate of collisions between dispersed particles in that phase and therefore the likelihood of cohesion, creaming, flocculation, and sedimentation occurring between those dispersed particles. In some embodiments, adding a media stabilizing agent may increase the stability of a particle system by increasing the viscosity of a phase such that its mechanical properties may be improved, making it more resilient towards degradation or deformation, either under stress or ambient conditions. In some embodiments, adding a media stabilizing agent increases stability of a particle system by increasing the viscosity of a phase such that it forms a gel or rigid network, making it more resilient towards degradation or deformation, either under stress or ambient conditions. In some embodiments, adding a media stabilizing agent increases stability of a particle system by decreasing the solubility of immiscible phases or components in the phase it was added.

2.2.1. Examples of Phase Stabilizing Agents

In some embodiments, phase stabilizing agents may be added to a phase to increase the stability of the phase, and thereby the entire particle system, by altering its rheological properties. In some embodiments, the increase in stability may be due to an increased viscosity of the phase which occurs when the phase stabilizing agent is added to the phase. The observed increase in viscosity, or thickening, may be due to interactions between molecules of the stabilizing agent, either as individual molecules, colloids, or networks, interacting with the media. Thickening caused by phase stabilizing agents interacting with the media occur above some critical concentration of the phase stabilizing agent, dependent on a several factors including temperature, the properties of the phase stabilizing agent, the identity of the medium, and any other components present in the phase. Above this critical concentration, viscosity of the phase continues to increase with increasing phase stabilizing agent concentration, with the rate being dependent on temperature, the identity of the medium, any other components present in the phase, and the properties of the phase stabilizing agent such as molecular weight or propensity for intermolecular interaction. In some embodiments, adding a media stabilizing agent increases stability of a particle system by increasing the viscosity of a phase which decreases the rate of collisions between dispersed particles in that phase and therefore the likelihood of cohesion, creaming, flocculation, and sedimentation occurring between those dispersed particles. In some embodiments, adding a media stabilizing agent may increase stability of a particle system by increasing the viscosity of a phase such that its mechanical properties may be improved, making it more resilient towards degradation or deformation, either under stress or ambient conditions. In some embodiments, increasing the concentration of phase stabilizing agent in a phase may lead to the formation of colloids, regions of crystallization in the phase, or formation of networks or gels. Formation of these solid or semi-solid regions may be dependent on the temperature, the identity of the medium, any other components present in the phase, and the properties of the phase stabilizing agent such as molecular weight or propensity for intermolecular interaction. In some embodiments, formation of these solid or semi solid regions leads to an increase in viscosity of the phase. In some embodiments, formation of these solid or semi solid regions leads to a change in the state of matter of the entire phase, such as a transition from liquid to gel, solid, or semi-solid. In some embodiments, a phase change to a gel, solid, or semisolid stabilizes a particle system by making it more resilient towards degradation or deformation, either under stress or ambient conditions. In some embodiments, adding a media stabilizing agent increases stability of a particle system by decreasing the solubility of immiscible phases or components in the phase it was added.

2.2.1.1. Examples of Hydrophobic Medium Stabilizing Agents

In some embodiments having hydrophobic medium stabilizing agents, a phase stabilizing agent or combination thereof may be added to the hydrophobic phase to increase the viscosity of a medium, sometimes to the point of gel formation.

In some embodiments having hydrophobic medium stabilizing agents, hydrophobic macromolecules may be chosen as a hydrophobic phase stabilizing agent. In some embodiments having hydrophobic medium stabilizing agents, the hydrophobic macromolecules added may be modified natural polymers that are generally regarded as safe by the FDA, such as ethyl cellulose. In some embodiments having hydrophobic medium stabilizing agents, the ethylcellulose chosen may be Ashland Aqualon Ec-N100, Ashland Aqualon Ec-N300, EC Ethocel Standard 20 Premium, EC Ethocel Standard 7 Premium, Ethocel standard 10 Premium, or Spectrum ethylcellulose. In some embodiments having hydrophobic medium stabilizing agents, the modified natural polymers may be GRAS and are modified starches, such as starch sodium octenyl succinate. In some embodiments having hydrophobic medium stabilizing agents, the hydrophobic macromolecules added may be synthetic polymers such as polylactides, polyglycolides, polycaprolactones, polyacrylates, polystyrenes, polyesters, or copolymers thereof. In some embodiments having hydrophobic medium stabilizing agents, the hydrophobic phase stabilizer may be a natural resin such as shellac.

In some embodiments having hydrophobic medium stabilizing agents, hydrophobic small molecules may be chosen as a hydrophobic phase stabilizing agent. In some embodiments having hydrophobic medium stabilizing agents, the small molecules may be generally regarded as safe by the FDA, such as mono- or di-glycerides of palmitate, palminate, laurate, linoleate, myristate, oleate, or stearate, or fatty acid esters of sugars (e.g., sorbitan monostearate, sorbitan monopalminate, sucrose stearate). In some embodiments having hydrophobic medium stabilizing agents, the small molecules chosen might be biocompatible such as polyicosanol or 12-hydroxystearic acid. In some embodiments having hydrophobic medium stabilizing agents, the small molecules choses as hydrophobic phase stabilizing agents may also serve as surface stabilizing agents. In some embodiments having hydrophobic medium stabilizing agents, the hydrophobic small molecules chosen to be hydrophobic phase stabilizing agents may be waxes that are generally regarded as safe by the FDA, such as rice bran wax, carnauba wax, or candelilla wax.

2.2.1.2. Examples of Hydrophilic Medium Stabilizing Agents

In some embodiments having hydrophilic medium stabilizing agents, a phase stabilizing agent may be added to the hydrophilic phase to increase the viscosity of a medium, sometimes to the point of gel formation. In some embodiments having hydrophilic medium stabilizing agents, hydrophilic macromolecules may be chosen as a hydrophilic phase stabilizing agent. In some embodiments having hydrophilic medium stabilizing agents, polysaccharides such as starches, pectins, or natural gums may be chosen as a hydrophilic phase stabilizing agent that is generally regarded as safe (GRAS) by the FDA. In some embodiments having hydrophilic medium stabilizing agents, the starch may be a flour or starch derived from wheat, corn, potato, rice, arrowroot, tapioca, or other edible plant. In some embodiments having hydrophilic medium stabilizing agents, the starch may be chemically modified, such as dextrin. In some embodiments having hydrophilic medium stabilizing agents, the pectin may be derived from a plant-based source such as apple, citrus peel, apricot, blackberry, cherry, peach, or pineapple. In some embodiments having hydrophilic medium stabilizing agents, the natural gum chosen as a hydrophilic phase stabilizing agent may be generally regarded as safe by the FDA such as agar, alginic acid, sodium alginate, carob gum, carrageenan, gum Arabic, gum tragacanth, karaya gum, guar gum, locust bean gum, glucomannan, tara gum, gellan gum, or xanthan gum. In some embodiments having hydrophilic medium stabilizing agents, cellulose may be chosen as a hydrophilic phase stabilizing agent, either in its natural or modified form, such as methyl cellulose. In some embodiments having hydrophilic medium stabilizing agents, other GRAS polysaccharides may be used such as maltodextrin, alginic acid, alginate, or agar. In some embodiments having hydrophilic medium stabilizing agents, a protein source such as collagen, gelatin, casein, or one derived from eggs or other high protein sources may be used as a hydrophilic phase stabilizing agent that is generally regarded as safe by the FDA. In some embodiments having hydrophilic medium stabilizing agents, the hydrophilic stabilizing agent may be a natural resin such as shellac. In some embodiments having hydrophilic medium stabilizing agents, synthetic macromolecules may be used as hydrophilic phase stabilizing agents such as polyethylene glycol, carbomer, carboxymethyl cellulose, hyaluronic acid, polyurethanes, acrylic polymers, latex, polystyrenes, or polyolefins such as polybutadiene or polyvinyl alcohol, either as pure polymers or copolymers. In some embodiments having hydrophilic medium stabilizing agents, minerals may be used as hydrophilic phase stabilizing agents such as silica, bentonite, and magnesium silicate.

In some embodiments having hydrophilic medium stabilizing agents, the hydrophilic phase stabilizing agent increases the stability of the phase though interactions with other components in the particles system. In some embodiments having hydrophilic medium stabilizing agents, an interaction occurs between the phase stabilizing agent and a surface stabilizing agent, such as the interaction between NaCl and anionic surfactants. In some embodiments having hydrophilic medium stabilizing agents, an interaction occurs between the phase stabilizing agent and another phase stabilizing agent, such as the interaction between divalent cations such as calcium and sodium alginate. In some embodiments having hydrophilic medium stabilizing agents, an inorganic calcium source such as calcium carbonate or calcium chloride may be added to the system to induce ionic crosslinking and increase the viscosity of the phase, sometimes to the point of gelling. In some embodiments having hydrophilic medium stabilizing agents, an organic calcium source such as calcium stearoyl lactylate, calcium stearate, or calcium lactylate may be added to the system to induce ionic crosslinking and increase the viscosity of the phase, sometimes to the point of gelling. In some embodiments having hydrophilic medium stabilizing agents, other phase stabilizing agents, such as proteins, may be crosslinked through interactions with divalent cations. In some embodiments having hydrophilic medium stabilizing agents, the phase stabilizing protein may be crosslinked may be a dairy-derived protein such as casein or whey, an egg-derived protein, or a vegetable derived protein such as gluten, pea protein, or rice protein. In some embodiments having hydrophilic medium stabilizing agents, cross linking may be induced by addition and dissolution of a divalent cation salt to the solution containing the cross-linking species (cross-linked species). In some embodiments having hydrophilic medium stabilizing agents, cross linking may be induced by addition and dissolution of a crosslinking species to a solution containing a divalent cation salt. In some embodiments having hydrophilic medium stabilizing agents, both crosslinking species and divalent salt may be present in solution together but retarded by some other property of the solution, when this property is appropriately modified, crosslinking may be then able to occur. For example, both sodium alginate and calcium chloride may be present in a solution in concentrations sufficient to crosslink and form a gel under some conditions, but a low pH (high concentration of free $H^+$) may be present such that the carboxylic acid groups on the alginate are fully protonated. Upon raising the pH sufficiently to deprotonate the carboxylic acids into carboxylate groups, calcium ions may form cross-linking bridges between the carboxylate groups and the phase stabilizing agents such that a gel may be formed. In some embodiments having hydrophilic medium stabilizing agents, crosslinking and gelation of a phase stabilizing agent may be induced by changes in temperature during processing such as the crosslinking of a protein (e.g., whey) via temperature induced denaturing which leads to the formation of disulfide bonds between individual protein strands.

2.2.2. Examples of Interface Stabilizing Agents

In some embodiments, an interface stabilizing agent reduces the surface energy (e.g. surface energy, defined as the difference in energy between a molecule or collection thereof at the interface versus in the bulk of a given phase) at an internal (existing between any combination of a hydrophobic and hydrophilic phases in the system) interface and has the effect of allowing smaller particles to be formed with the same input of energy.

2.2.2.1. Examples of Hydrophobic Interface Stabilizing Agents

In some embodiments having hydrophobic interface stabilizing agents, interface stabilizing agents added to the hydrophobic phase may include lecithin varieties such as canola, rapeseed, milk, egg, egg yolk, soybean, sunflower, and cottonseed as well as their de-oiled, purified subsets of phospholipids and other chemically modified varieties thereof.

In some embodiments having hydrophobic interface stabilizing agents, an interface stabilizing agent added to the hydrophobic phase may be composed of the former and saturated or unsaturated fatty acids either linear or branched in form including those containing common functional groups that are naturally occurring or referenced herein.

In some embodiments having hydrophobic interface stabilizing agents, an interface stabilizing agent added to the hydrophobic phase may be composed of fatty acid esters of sugars such as Span 20, Span 40, Span 60, Span 65, Span 80, or Span 85.

In some embodiments having hydrophobic interface stabilizing agents, an interface stabilizing agent added to the hydrophobic phase may include a combination of those previously mentioned emulsifiers (or solely) with polyglycerol polyricinoleate (PGPR), other glycerol and polyglycerol-based emulsifiers.

In some embodiments having hydrophobic interface stabilizing agents, no emulsifier may be added to the oil phase.

In some embodiments having hydrophobic interface stabilizing agents, interface stabilizing agents may include combinations of pure and mixed phospholipids of natural or synthetic origin such as lecithin, chemically modified lecithin, purified components of lecithin, phosphatidylcholine, phosphatidylglycerol, phosphatidic acid, phosphatidylethanolamine, phosphatidylserine, phosphatidylinositol, sphingomyelin, and cardiolipin, or hydrogenated products thereof (for example, hydrogenated soybean phosphatidylcholine (HSPC)).

In some embodiments having hydrophobic interface stabilizing agents, interface stabilizing agents may include hydrogenated phospholipids such as hydrogenated soybean phosphatidylcholine, sphingomyelin, hydrogenated soybean phosphatidylcholine, and other phospholipid derivatives in which the phospholipid moiety may be modified. In some embodiments having hydrophobic interface stabilizing agents, modified phospholipid derivates are encompassed in the term 'phospholipid' unless specified otherwise.

In some embodiments having hydrophobic interface stabilizing agents, interface stabilizing agents may be lipids containing no phosphoric acid or phosphate in their molecular structure including examples (not intended as limiting) such as glycerolipids and sphingolipids that do not contain a phosphoric acid or phosphate moiety in the molecule. In some embodiments having hydrophobic interface stabilizing agents, interface stabilizing agents may be lipids other than phospholipids. In some embodiments having hydrophobic interface stabilizing agents, the term "lipids other than phospholipids" may also encompass derivatives of lipids other than phospholipid in which modifications have been made to lipids other than phospholipids.

2.2.2.2. Examples of Hydrophilic Interface Stabilizing Agents

In some embodiments having hydrophilic interface stabilizing agents, an interface stabilizing agent may be added to a hydrophilic phase may be polysorbates such as Tween 20, Tween 40, Tween 60, Tween 65, Tween 80, or other polymeric or small molecule emulsifiers such as Polyglycery-6 laurate, Oleth-20, vitamin E TPGS. In some embodiments having hydrophilic interface stabilizing agents, an interface stabilizing agent may be added to the hydrophilic phase may be polymeric, such a poloxamers. In some embodiments having hydrophilic interface stabilizing agents, an interface stabilizing agent may be added to a hydrophilic phase may be mono- or di-glycerides such as E471. In some embodiments having hydrophilic interface stabilizing agents, an interface stabilizing agent may be added to the hydrophilic phase may be acid esters of mono or di glycerides such as ACETEM, LACTEM, CITREM, or DATEM. In some embodiments having hydrophilic interface stabilizing agents, an interface stabilizing agent may be added to the hydrophilic phase may be a salt such as sodium stearoyl lactylate. In some embodiments having hydrophilic interface stabilizing agents a combination of any of the previously mentioned hydrophilic interface stabilizing agents may be added to the hydrophilic phase. In some embodiments having hydrophilic interface stabilizing agents, no emulsifier may be added to the water phase.

In some embodiments having hydrophilic interface stabilizing agents, an interface stabilizing agent may be added to a hydrophilic phase classified as GRAS may be poloxamers. Examples of poloxamers include poloxamer 407 and poloxamer 188.

In some embodiments having hydrophilic interface stabilizing agents, an interface stabilizing agent added to a hydrophilic phase may be saponins. In some embodiments having hydrophilic interface stabilizing agents, saponins may be certified as natural or organic. In some embodiments having hydrophilic interface stabilizing agents, these saponin sources may be derived from *Quillaja* species. In some embodiments having hydrophilic interface stabilizing agents, other natural plant extracts, plant matter (dry or fresh), and combinations thereof may be utilized as interface stabilizing agents. Target species that may be used include other species high in saponin content, examples being such as the Quillajaceae family (e.g., *Quillaja* saponin, *Quillaja brasiliensis*), Rosaceae family, Caryophyllaceae.

In some embodiments having hydrophilic interface stabilizing agents, saponin sources may be from the paraphyletic group of the Dicotyledones (dicotyledonous plants) including *Hippocastani* (seeds, etc.), *Primulae* (roots, flowers, etc.), Hedrae (leaves, etc.), *Ginseng* (roots, etc.), *Quillaja* (bark, etc.), Glycyrrbizae (roots, etc.), Senegae (roots, etc.), Polygalae *Amarae* (leaves, etc.), Saponariae (roots, etc.), *Glycine max* (seeds, etc.), Herniariae (leaves, etc.), and others including combinations thereof. In some embodiments having hydrophilic interface stabilizing agents, saponin sources may include members of the legume family including soybeans, beans, peas, and combinations thereof. In some embodiments having hydrophilic interface stabilizing agents, the above saponin sources may be chosen for their triterpene saponin content.

In some embodiments having hydrophilic interface stabilizing agents, saponin sources may be from genetic families including Agavaceae, Alliaceae, Asparagaceae, Dioscoreaceae, Liliaceae, Amaryllidaceae, Bromeliaceae, Palmae, Scrophulariaceae, the like and combinations thereof. Additionally, crop plants may function as a saponin source, an example being yams (e.g., *Dioscorea villosa*, *Dioscorea pseudojaponica*), alliums, *asparagus*, fenugreek, *yucca*, *ginseng*, others, and combinations thereof. In some embodiments having hydrophilic interface stabilizing agents, extracts of members of the Solanaceae family (e.g., potatoes, tomatoes, aubergines, *capsicum*) may be used as a saponin source. In some embodiments having hydrophilic interface stabilizing agents, the above saponin sources may be chosen for their steroidal saponin content.

More examples of species that may be used as a saponin or other interface stabilizing agent source (isolated or within an extract) includes *Phytolacca dodecandra* (gopo berry), *Allium* (e.g., onion, garlic), *asparagus*, oats (*Avena sativa*), spinach, sugar beet (*Beta vulgaris*, leaves), *Camellia sinensis* var. *sinensis* (white tea, yellow tea, green tea, oolong, dark tea, pu-erh tea, black tea, kukicha, etc.), *Camellia sinensis* var. *assamica*, *Camellia sinensis* var. *pubilimba*, *Camellia sinensis* var. *dehungensis*, *Camellia sinensis* var. *lasiocaly*, *Coffea* canephor, *Coffee robusta*, *Coffea arabica*, *Coffea liberica*, *Coffea stenophylla*, *Coffea mauritiana*, *Coffea racemosa*, yam, soap bark tree (*Quillaja saponaria*), *Mojave yucca* (*Yucca schidigera*), ginseng (*Panax* species), fenugreek (Trigonellafoenum-graceum), alfalfa (*Medicago sativa*), horse chestnut (*Aesculus hippocastanum*), soapwort (*Saponaria* officinaux), *Gypsophila* genus (*Gypsophila paniculata*), sarsaparilla (*Smilax officinalis*), quinoa (*Chenopodium quinoa*), chickpea (*Cicer arietinum*), saffron *crocus* (*Crocus* savitus), soybean (*Glycine max*), licorice (*Glycyrrhiza* species), licorice root (*Glycyrrhiza* glabbra root), ivy (*Hedera helix*), alfalfa (*Medicago sativa*), Chinese *ginseng* (*Panax ginseng*), American *ginseng* (*Panax quinquefolius*), *Panax notoginseng*, green pea (*Pisum sativum*), milkwort (*Polygala* spp.), primula (*Primula* spp.), *Solanum* species, *Calendula officinalis* (Asteraceae, oleananesaponin containing), *Salvia* species, *Digitalis* species, *Verbascum* species, mediterranean thyme (*Thymus capitatus*), balm (*Melissa officinalis*), wild marjoram (*Origanum vulgare*), hop marjoram (*Origanum Dictamnus*), hyssop (*Hyssopus officinalis*), wild yam (*Dioscorea villosa*), wild violet (*Viola tricolor*), sage (*Salvia officinalis*), Tribulus (*Tribulus terrestris*), members of the genus *Ruscus, Mussaenda pubescens* (Rubiaceae), *Bupleurum chinense, Clinopodium chinense* var. *parviflorum, Clematic chinensis Osbeck* (Ranunculaceae), *Yucca elephantipes, Calamus leptospadix, Stauntonia brachyanthera, Camellia oleifera, Tribulus terrestris, Sapindus mukorossi*, and combinations thereof.

In some embodiments having hydrophilic interface stabilizing agents, extracts from the members of the Leguminosae family may be used as saponin sources. An exemplar of the above is the *Glycyrrhiza* genus including *Glycyrrhiza uralensis, Glycyrrhiza glabra*, and *Glycyrrhiza inflata*.

In some embodiments having hydrophilic interface stabilizing agents, active ingredients may be extracts from oat species (e.g., *Avena sativa*) may be used as a source of both triterpenoid and steroidal saponins.

In some embodiments having hydrophilic interface stabilizing agents, inactive ingredients may be interface stabilizing agents, added to the hydrophilic phase, composed of proteins such as milk proteins, casein, pea proteins, whey proteins, collagen, or other natural proteins. In some embodiments having hydrophilic interface stabilizing agents, inactive ingredients may be interface stabilizing agents, added to the hydrophilic phase, composed of polysaccharides such as cellulose, carboxymethyl cellulose, gum Arabic, or other gums. In some embodiments having hydrophilic interface stabilizing agents, an interface stabilizing agent added to the hydrophilic phase may be composed of nanoparticles or other colloids dispersed in the hydrophilic phase.

In some embodiments having hydrophilic interface stabilizing agents, encapsulation of an amphiphilic or water soluble molecule of interest, such as caffeine or other methylated-xanthine derivatives (e.g., methylliberine, paraxanthine, theacrine), may be further stabilized against degradation or diffusion out of the particle by crosslinking linear polysaccharides, branched polysaccharides, gums, molecules containing multiple hydroxyl groups, the former molecules modified by replacing a subset of the hydroxyl groups, or elsewhere, with functional groups (e.g., where x may be 0-100, $-O(CH_2)_xCH_3$, $-O(CH_2O)_{x+1}CH_3$, $-CO_2^-$, $-SO_3^{2-}$, $-OSO_3^{2-}$, $-NH_3^+$, $-S^-$, $-N_3$, $-CN$, or combinations thereof) rationally chosen to impart solubility in other solvent combinations or to tune other physiochemical parameters discussed herein to change the behavior of subsets or the entire ensemble of dispersed particles. In some embodiments having hydrophilic interface stabilizing agents, covalent crosslinking may be achieved by irradiating the dispersed particles with ultraviolet light (such as 400 nm, 355 nm, 266 nm, 192 nm, and other wavelengths available from pulsed or continuous laser sources or noble gas lamps, filtered or unfiltered) sufficient to generate reactive radical species generated by photoinitiated electron ejection or molecular rearrangement, or nuclear dissociation of molecules. In some embodiments having hydrophilic interface stabilizing agents, radical species may be generated by persistent radical species of excipients doped into the Wi phase, containing molecules of interest, to initiate or catalyze crosslinking, whether the excipients are integrated into the covalent network or not. In some embodiments having hydrophilic interface stabilizing agents, covalent crosslinking may be achieved with heating to a temperature such as 95 C in the case of locust bean gum. In some embodiments having hydrophilic interface stabilizing agents, NaOH, or other strongly alkaline salts, may be added to the Wi phase at concentrations between 0.1 M to 5 M and a poly-carboxylic acid or combination of such (e.g., dicarboxylic, tri-carboxylic, tetra-carboxylic, ad infinitum) is added to both facilitate and participate in the covalent crosslinking reaction via esterification under basic conditions.

In some embodiments having hydrophilic interface stabilizing agents, interface stabilizing agents and phase stabilizing agents may be an amphiphilic or hydrophilic cellulose-based polymers such as ethylcellulose, methylcellulose, hydroxypropylcellulose, cellulose acetate, hydroxypropylmethylcellulose, hydroxyethylcellulose, carboxymethyl cellulose, cellulose acetate sodium carboxymethyl cellulose, cellulose diacetate, cellulose triacetate, cellulose alkanylate, cellulose trivalerate, cellulose trioctanoate, cellulose tripionate, cellulose diesters, cellulose di succinate, cellulose acetate valerate, cellulose acetaldehyde, dimethylcellulose acetate, cellulose dimethylaminoacetate, hydroxyalkylcelluloses, carboxyalkylcelluloses, cellulose ethers, and mixtures thereof. In some embodiments having hydrophilic interface stabilizing agents, interface stabilizing agents and phase stabilizing agents may be an amphiphilic or hydrophilic cellulose-based polymers, cellulose metabolites and derivatives thereof such as glucose, fructose, mannitol, mannose, galactose, sorbitol, pullulan, dextran, water-soluble hydrophilic polymers hydroxyethyl propylene glycol alginate, sodium alginate, methyl carbamate, methylcarbamate, polydiethylaminomethylstyrene, sulfonated polystyrenes, styrenes, cellulose acetophthalate, polyvinyl alcohol, polyacrylates, polymethacrylates, and their combinations including covalent networks and mixed aggregates.

In some embodiments having hydrophilic interface stabilizing agents, an interface stabilizing agent or interface stabilizing ingredient, within a continuous or dispersed phase, may also function as a phase stabilizing agent, phase medium, or combination thereof.

In some embodiments having hydrophilic interface stabilizing agents, particles may be formed by or include self-emulsifying systems such as hydrophobic, isotropic mixtures of oils, surfactants, and cosurfactants—that spontaneously form O/W particle dispersions in aqueous conditions. Such systems may be within the range of 20 nm to 200 nm in diameter and therefore, in addition to several other favorable characteristics, may function as effective vehicles for the delivery of small molecules. Lipids, by their nature, have many intrinsic advantages applied to small-molecule delivery, including poor solubility of both carriers and actives and problems associated with metabolism and therapeutic efficacy. In addition, most self-emulsifying systems may be GRAS, highlighting their biocompatibility and degradation into nontoxic byproducts. These fine emulsions may be reported to form in the gastrointestinal tract after oral delivery, thereby bypassing the liver and leading to considerable improvement in bioavailability and absorption profile. Vitamin E TPGS is one commonly used example in this class and studies have demonstrated effective delivery of chemotherapeutics targeted to different regions of the body, both alone and in tandem with multiple emulsifiers and cosurfactants by a range of preparative formulations, from liquids to spray-dried powders.

In some embodiments having hydrophilic interface stabilizing agents, non-GRAS products, including those containing non-GRAS ingredients may include non-GRAS surfactants.

In some embodiments having hydrophilic interface stabilizing agents, hydrophilic interface stabilizing agents may be one or more non-GRAS ingredients and non-GRAS surfactants such as sodium octyl sulfate, sodium dodecyl sulfate, sodium tetradecyl sulfate, decyltrimethylammonium bromide, dodexyltrimethylammonium bromide, hexadecyltrimethylammonium bromide, penta(ethyleneglycol)monooctyl ether, penta(ethyleneglycol)monodecyl ether, and penta(ethyleneglycol)monododecyl ether.

In some embodiments having hydrophilic interface stabilizing agents, hydrophilic interface stabilizing agents may be composed of neutral interface stabilizing agents such as penta(ethyleneglycol)monooctyl ether, penta(ethyleneglycol)monodecyl ether, and penta(ethyleneglycol)monododecyl ether.

In some embodiments having hydrophilic interface stabilizing agents, hydrophilic interface stabilizing agents may be composed of anionic interface stabilizing agents such as sodium octyl sulfate, sodium dodecyl sulfate, and sodium tetradecyl sulfate.

In some embodiments having hydrophilic interface stabilizing agents, hydrophilic interface stabilizing agents may be composed of cationic interface stabilizing agents such as decyltrimethylammonium bromide, dodexyltrimethylammonium bromide, and hexadecyltrimethylammonium bromide.

In some embodiments having hydrophilic interface stabilizing agents, hydrophilic interface stabilizing agents may be composed of zwitterionic interface stabilizing agents such as phospholipids.

4. Product Certifications

In some embodiments, product or ingredient composition, manufacture, handling, or combinations thereof may be certified by organizations including examples such as FDA, USP, USDA, ISO, or multiple organizations.

1. Organic

In some embodiments, products, ingredients, or processing aids may be certified "organic." In the United States, the USDA certifies the "organic" status of products. Guidelines for USDA organic certification address soil quality, animal husbandry practices, pest control, weed control, and the use of additives, among other factors. Organic producers rely on natural ingredients and physical, biological, and mechanical farming techniques. In some embodiments, products, ingredients, or processing aids may be certified "organic" if all of its components are organic certified and no "non-organic" processing techniques are utilized.

In some embodiments, products, ingredients, or processing aids may be derived from organic produce grown in soil where no prohibited substances have been applied in the past three years, prior to organic farming. Determining what substances are prohibited and which substances are expressly allowed, the USDA maintains a 'National List of Allowed and Prohibited Substances.' The USDA also maintains a 'List of Petitioned Substances.' An agent may petition for a new substance to be added to the allowed or prohibited lists by filing a petition with the National Organic Standards Board (NOSB). In some instances, synthetic substances may be approved if detailed evidence exists for its safety and efficacy. An example of this is the use of pheromones to confuse insects as a form of pest control. Likewise, in some instances a natural substance may be deemed a prohibited substance due to its deleterious impacts on human health and the environment including arsenic which has been prohibited for organic labeling. Organic meats require that animals be raised accommodating natural behaviors (e.g., roaming and grazing), fed 100% organic feed, and not administered antibiotics or hormones.

Processed and multi-ingredient foods have additional considerations under USDA guidelines. USDA organic standards prohibit artificial colors, fillers, preservatives, and flavors. Products may contain some approved non-agricultural ingredients. The label "made with organic ingredients" on a packaged product indicates 70% of the ingredients must be organic. The remainder must still refrain from prohibited practices (e.g., genetic engineering) but need not have been produced organically. The label "organic" implies at least 95% of the ingredients used are organic, whereas the label "100% organic" implies ingredients are 100% organic.

For example, an organic product may be an O/W particle system containing an herbal organic extract and using all organic ingredients such as an organic O/W particle system containing organic kanna extract may be formed by dissolving 0.7 mL of a 3:1 kanna:organic cane ethanol extract and 3 g of organic sunflower lecithin in 5 mL of organic MCT to form the 0 phase. The 0 phase is subsequently heated to 95° C. until all ethanol is removed by evaporation and then cooled to 80° C. The W phase, composed of 15 mL of RO water being mixed by magnetic stirring is then exposed to ultrasonication, which is provided by a 10 mm horn run at 60% amplitude being driven by a 1.8 kW generator in a continuous fashion, is continued for 10 s before the 0 phase is slowly added over the course of 15 seconds. Ultrasonication is continued for 10 minutes to yield an organic product containing kanna with an average particle size of 350±150 nm.

2. FDA Approved

In some embodiments, entire products, ingredients, or processing aids may be labelled as FDA approved. FDA approved products refer to active ingredients that have FDA approval to claim certain intended physiological effects backed by testing to confirm safety and efficacy. Much of the FDA approval process is governed by the FDA's Center for Drug Evaluation and Research (CDER). After testing and documenting an intended claim for an active ingredient or product containing several active ingredients as well as safety testing, experimental evidence and data is sent to CDER for evaluation. The process initiates with animal studies, for ascertaining initial safety and efficacy claims, then transitions into human studies to determine the parameters of usage and exact effects for humans.

The FDA also maintains a separate approval process for all food additives. Any additive that is intentionally added for consumption must obtain FDA safety approval, unless it is already on the GRAS (generally recognized as safe) list. Other substances on the BAN list are expressly banned due to toxicity. Food additive tolerances were set by the Federal Food, Drug, and Cosmetic Act.

3. EU Pharmacopeia

In some embodiments, entire products, ingredients, or processing aids may be labelled as EU pharmacopeia. The EU pharmacopeia is a text which contains individual monographs outlining specifications in quality and dosage forms for specific medicines and pharmaceutical ingredients. An ingredient or product may be labelled EU pharmacopeia grade if it adheres to all of the specifications outlined in the EU Pharmacopeia monograph for that specific ingredient or product.

4. USP

In some embodiments, entire products, ingredients, or processing aids may be labelled as United States Pharmacopeia (USP). The US pharmacopeia is a text which contains individual monographs outlining specifications in quality and dosage forms for specific medicines and pharmaceutical ingredients. An ingredient or product may be labelled US pharmacopeia grade if it adheres to all of the specifications outlined in the US Pharmacopeia monograph for that specific ingredient or product.

5. Food Grade

In some embodiments, entire products, ingredients, or processing aids may be labelled as food grade (FG). Food grade means the material is either fit for human consumption, or the material is regarded as safe for contact with food. Food grade materials must be nontoxic to humans. Equipment must be designed to be safe and not leach toxins into food and beverage under the intended usage parameters (e.g., under acidic or high heat conditions). Food grade does not encompass other qualities like cleanability. Any substances that is FDA approved as a food additive is considered food grade. Food grade is generally a more stringent term than food safe, implying that food material is safe for contact with under intended conditions (e.g., acidic environment, elevated temperatures).

In some embodiments, entire products, ingredients, or processing aids may be considered food grade if entire composition is food grade and any processing tools used in its manufacturing are food safe. For example, a food grade W/O emulsion containing caffeine maybe be prepared. A W phase is first prepared by dissolving 200 mg of food grade caffeine in 15 mL of water at 80° C. An 0 phase is prepared by dissolving 3 mL of food grade Palsgaard PGPR in 40 mL of food grade MCT at 70° C. The 0 phase, which is mixed by magnetic stirring, is then exposed to ultrasonication, which is provided by a 10 mm horn run at 60% amplitude being driven by a 1.8 kW generator in a continuous fashion for 10 s before the W phase is slowly added over the course of 15 seconds. Ultrasonication is continued for 10 minutes to yield a food grade product containing caffeine with an average particle size of 1000±250 nm.

6. Gluten-Free

In some embodiments, entire products, ingredients, or processing aids may be labelled as gluten-free. A gluten free designation means products are produced without gluten. The FDA regulates the definition of the term gluten free. A gluten free product must contain fewer than 20 parts per million of gluten. Gluten free designation requires testing and validation, even if no gluten-containing ingredients are used, as there is always risk of cross contamination. Despite these requirements, gluten free claims are largely self-policed, and the FDA does not provide any official certification.

In some embodiments, a product may be designated gluten free if the product meets the FDA standards for gluten free such as a O/W particle system containing CBD which contains fewer than 20 parts per million of gluten.

7. GRAS

In some embodiments, entire products, ingredients, or processing aids may be labelled as generally regarded as safe (GRAS). GRAS stands for generally recognized as safe. A substance or material can garner GRAS status either through scientific testing procedures or by being widely used and recognized as safe in food from before 1958. The burden of evidence required for granting GRAS status to any product is the same as the required for FDA approval for food additives. These requirements are guided by the code of federal regulations (CFR) title 21 170.30(b). When a non-GRAS ingredient is used without obtaining prior approval, the FDA will send a warning letter demanding compliance with regulations.

In some embodiments, a product may be labelled GRAS such as a W/O particle system containing turmeric extract where all the components have been certified GRAS.

8. Halal

In some embodiments, entire products, ingredients, or processing aids may be labelled as halal. Halal is an Arabic word meaning 'permissible' and is used to denote anything permitted under Islamic laws. In the context of food and beverage, halal refers to any food or beverage that is permissible under Islamic guidelines. These rules generally prohibit pork (including pork-derived products like gelatin), alcohol, carnivorous animals, and scavengers. Some communities prohibit shrimp while others permit it but prohibit fish without scales. Carrion and blood are also forbidden. Livestock must be fed vegetarian diet and should be butchered according to Islamic rules. Additives and machinery and surfaces in contact with the food must also be halal.

In some embodiments, a product may be labelled Halal such as a W/O particle system containing turmeric extract where all the components, machinery, processes, and surfaces used are halal.

9. Kosher

In some embodiments, entire products, ingredients, or processing aids may be labelled as kosher. The word kosher is a Hebrew word signifying proper or acceptable and refers to a series of Jewish traditions, largely deriving from the Torah, governing what is acceptable for consumption and how it is to be prepared. In general, pork, reptiles, frogs, and shellfish are prohibited. So are blood and carrion. Furthermore, dairy may not be mixed with meat. Livestock animals must be butchered in strict observance of Jewish religious law to be kosher. Surfaces and utensils that come into contact with kosher food or beverage must also be kosher. There are several agencies that perform kosher certification, and the certification of one agency may not be accepted by other rabbinical circles.

In some embodiments, a product may be labelled kosher such as a W/O particle system containing turmeric extract where all the components, machinery, processes, and surfaces used are kosher.

10. Natural

In some embodiments, entire products, ingredients, or processing aids may be labelled as natural. A natural product is any compound, substance, or material that ultimately derives from some life form in nature. There is no formal FDA definition or regulation of the term natural. However, the FDA does require that labeling information be "truth and not misleading." The USDA defines a natural product as being minimally processed with no artificial ingredients, and it requires an explanation of the term if used as a label. While detailed definitions from the USDA and FDA are lacking, court case precedents show that products containing artificial, synthetic, or GMO ingredients cannot be labeled as natural.

In some embodiments, a product may be labelled natural such as a W/O particle system containing kana where all the components utilized in the product are labelled natural.

11. Non-GMO

In some embodiments, entire products, ingredients, or processing aids may be labelled as non-GMO or absent of genetically modified organisms (GMOs), GMO byproducts or GMO constituents. A genetically modified organism (GMO) is a life form whose DNA has been altered in a laboratory setting (i.e., not through traditional modification techniques such as crossbreeding). The use of GMO ingredients is prohibited in organic labeling, so organic products are automatically non-GMO. The Non-GMO Project is a nonprofit, third party verification and certification organization certifying non-GMO compliance of products. They verify that each ingredient used in a product bearing their "non-GMO verified" contains no GMOs (within a 0.9% threshold due to testing limitations) and perform annual audits.

In some embodiments, a product may be labelled natural such as a W/O particle system containing kanna where all the components utilized in the product are labelled non-GMO.

12. Synthetic

In some embodiments, entire products, ingredients, or processing aids may be labelled as synthetic. A synthetic product is any compound, substance, or material that is chemically synthesized and does not come from a natural life form. Substances may be completely synthesized or semi-synthesized. Simpler molecules may be simple enough to feasibly synthesize from starting components. With more complex molecules, it is often advantageous to begin with a naturally obtained precursor molecule.

In some embodiments, a product may be considered synthetic if any component is synthetic such as a W/O particle system containing CBD which utilizing a synthetic surface stabilizer such as tween-80 may be labeled synthetic.

13. Raw

In some embodiments, entire products, ingredients, or processing aids may be labelled as raw. Raw is a relatively recent food designation that is not subject to oversight or regulation by the FDA or USDA. However, claims made must still be "truthful and not misleading." As such, high heat (in excess of 115 F) and pasteurization cannot be used on products designated raw. A few private organizations have begun issuing raw certifications for products that meet a stringent definition of raw.

In some embodiments, a product may be considered raw if all components are raw and manufacturing does not require temperatures in excess of 115 F such as a W/O particle system containing all raw ingredients that is manufactured at or below 114 F.

14. Vegan

In some embodiments, entire products, ingredients, or processing aids may be labelled as vegan. The vegan label refers to food and beverage that was not produced from or contain any animal products. In some cases, for ingredients hard to come by in plants, bacteria and fungi may be engineered to produce these ingredients for vegan purposes. An example is yeast that has been modified to produce vegan collagen. For the purposes of labeling there is no official certification or definition from the FDA, USDA, or other government agencies. There are various private agencies that provide vegan certifications. Often these certifications require that not only is a product free of animal-based products, but also that no product testing or production involving animals has been done.

In some embodiments a product may be labelled as vegan such as a O/W particle system containing CBD that only utilizes components that are labelled vegan.

5. Stability

In some embodiments, the particles may have an expected shelf life of about 1 year. In some other embodiments, the particles may have an expected shelf life of about 6 months, about 2 months, about 1 month, about 1 week, or about 1 day. Such particles may tolerate a wide range of temperatures without affecting quality. The permeability of the particles is another factor in determining the shelf life of the particles. In some embodiments, the particles are stable in the temperature range of 0-95, 5-90, 5-65, or 5-50 degrees of Celsius over these durations of time.

In some embodiments, a product or particles may include a preservative. Examples of suitable preservatives include sodium benzoate, sodium metabisulfite, or potassium sorbate. In some embodiments, preservatives may be incorporated to inhibit growth of bacteria, molds, or yeasts and extend shelf life of a product without imparting any undesired changes in taste, odor, viscosity, or color thereto, partially, or entirely. In some embodiments, preservatives may also function as an anti-bitterness agent (e.g., sodium benzoate or potassium sorbate).

In some embodiments, products and particles may be designed for a particular container or a container may be chosen to enhance the stability of the products and particles. In some embodiments, a container structure, and materials from which the container is composed may include chemicals and electrostatic interactions components of the contained product and particles that require special consideration in their design to optimize their lifetime and functionalities. In some embodiments, particles and products may be made stable against metal containers that may be susceptible to corrosion owing to electrostatic activity on the material surface. In some embodiments, particles and products may be made stable against surface charges of metal cans are generally approximately neutral, with small mixtures of positive and negative charges. In some embodiments, particles and products may be made stable against container corrosion that typically occurs through interactions with aggressive, catalytic ions. In some embodiments, particles and products may be made stable against metal surfaces that are typically hydrophilic surfaces, hence at risk for interaction with aqueous solutions. In some embodiments, particles and products may be made stable against plastic polymers that are employed in most food and beverage metal containers, providing a hydrophobic, nonpolar surface over the metal container that is in contact with the food or beverage ingredients. In some embodiments, particles and products may be made stable against surface charges from polymers used to coat a container that are minimal as they are insulator materials, with lesser amounts of positive and negative charges. In some embodiments, particles and products may be made stable against the presence of an electric field that induce may surface charges on interfaces of polymer coatings. In some embodiments, particles and products may be made stable against charges that may appear in the presence of DC and AC voltage, with greater surface charges occurring under DC voltage. In some embodiments, particles and products may be made stable against normal electric fields (relative to the tangent plane of the inner interface of a container) that may induce positive charges or tangential electric fields that may induce electrostatic distributions of primarily negative surface charges. In some embodiments, particles and products may be made stable against the accumulation and dissipation of interfacial charge by modifying the nanoscale interfacial structure interior to a container such as surface fluorination of the container lining. In some embodiments, particles and products may be made stable against polymer coatings that may have interactions with the components leading to adsorption of nonpolar ingredients on the material surface. In some embodiments, particles and products may be made stable against interaction and adsorption to nonpolar surfaces by avoiding the use of nonionic surfactants, such as the polysorbate and sorbitan systems. In some embodiments, particles and products may be made stable against container interactions that may adversely affect taste, texture, and functionality of the food and beverage products and any contained particles. In some embodiments, particles and products may be made stable against container interactions by precoating polymer coatings with nonionic surfactants that may act to reduce contained protein adsorption on nonionic surfaces.

6. Sensory Experience

1. Visual Appearance (Optical Properties)

In some embodiments, particles and products may be formed to achieve ranges of opacity, transparency, light scattering behavior, absorption cross-sections for wavelengths and energies of light, color, and combinations thereof.

In some embodiments, particles and products may include one or more additives, such as natural or artificial flavoring agents, or natural or artificial coloring agents. Examples of flavoring agents include flavor extracts (e.g., peach extract, orange extract, strawberry extract, oakwood extract). Examples of artificial coloring agents include FD&C, Blue No. 1, Blue No. 2, Green No. 3, Red No. 40, Red No. 3, Yellow No. 5, and Yellow No. 6. Examples of natural coloring agents include caramel E150, annatto E160b, chlorophyll E140, cochineal E120, betanin, turmeric E100, saffron E160a, paprika E160c, elderberry juice, pandan, and butterfly pea.

2. Mouth Feel

In some embodiments, the particles are so small in diameter that the consumer does not feel the particles in his/her mouth. In some other embodiments, the particles are big enough in diameter that the consumer may bite down, squeezes, or otherwise causes one or more such particles to break open in his/her mouth. In some other embodiments, the particles are big enough that the consumer may feel them in his/her mouth but not too big that he/she may bite them. In some embodiments, different type of particles with different encapsulated materials are mixed.

3. Taste Control

In some embodiments, particles may be designed to control the taste of their dispersions to impart properties to a product such as taste control, taste carrying, taste masking, or combinations thereof. In some embodiments, particles may alter the sense of taste or gustatory system, the sensory system partially responsible for the perception of taste. In some embodiments, particles may alter composite ingredients interaction with taste receptors (TRs) and other chemoreceptors expressed in the cell membranes in the oral cavity and elsewhere may. In some embodiments, particles and their components may have altered interactions with type I TRs such that sweet taste sensation or sweetness of the product is affected. In some embodiments, particles and their components may have altered interactions with type II TRs such that bitter taste sensation or bitterness of the product is affected. In some embodiments, particles and their components may have altered interactions with both type I and type II TRs. In some embodiments, particles and their composite ingredients may change the sensation of taste categorized as savory, umami, sweetness taste, bitterness taste, sourness taste, saltiness taste, carbonation and fat taste, and their combinations.

In some embodiments, particles and their surrounding phase media may further include a sweetener such as sugars, fructose, corn syrup, and inverted sugars. In some embodiments, a sweetener added as an ingredient may additionally improve spherification (particle formation) as the mass of that sweetener prevents a sphere from floating at the surface of the composition thereby negatively impacting mechanical strength or sphere integrity. In some embodiments, a sweetener may also function as a thickening agent such as fructose or other inverted sugars.

In some embodiments, particles may possess a phase or interface around phases and ingredients further in the particle interior to mask flavors induced by the interior phases and ingredients such as a particle with outer-most phase composed of guar gum at 5% by mass.

In some embodiments, particles or phases surrounding particles may contain cyclodextrins, including their chemically modified varieties, to alter the taste of other ingredients. Examples of cyclodextrins and chemically modified cyclodextrins include alpha-cyclodextrin, beta-cyclodextrin, gamma-cyclodextrin, randomly methylated beta-cyclodextrin, sulfoxide beta-cyclodextrin, and hydroxypropyl beta-cyclodextrin.

4. Smell Control

In some embodiments, particles may be designed to control the smell of their dispersions to impart properties to a product such as smell control, smell carrying, smell masking, or combinations thereof. In some embodiments, particles may be designed to control the taste and smell of their dispersions to impart properties to a product such as taste and smell control, carrying, masking, or combinations thereof. In some embodiments, particles may alter the sense of taste or olfactory system, the sensory system partially responsible for the perception of smell. In some embodiments, particles may alter composite ingredients interaction with olfactory receptors (ORs) and other chemoreceptors expressed in the cell membranes of olfactory receptor neurons. In some embodiments, particles and their components may have altered interactions with ORs such that particle contained odorants that possess an odor have variable detection to the same odorants when not a particle component. In some embodiments, particle may alter the interaction of encapsulated odorants with ORs and other members of the class A rhodopsin-like family of G protein-coupled receptors (GPCRs).

In some embodiments, particles and their components may have altered interactions with ORs such that demonstrate affinities for binding many different odorants with similar physiochemical properties and conversely a single odorant may bind many different ORs with varied affinity and tuned by the particle composition. Once an odorant binds to an OR, the receptor undergoes structural changes that activate olfactory-type G-proteins in the OR neuron interior. The activate G-proteins in turn activate the lyase (adenylate cyclase), converting ATP into cAMP (cyclic AMP). cAMP interacts with cyclic nucleotide-gated ion channels, allowing calcium and sodium ions to into the OR neuron, depolarizing the neuron, and creating an action potential to communicate with the brain.

In some embodiments, particles and their components may have altered interactions with receptors of the olfactory epithelium bind odorants (ORs) and pheromones (vomeronasal receptors).

In some embodiments, particles and their components may have altered interactions with class I ORs and fish-like receptors that detect primarily hydrophilic odorants. In some embodiments, particles and their components may have altered interactions with class II ORs and tetrapod specific receptors that detect primarily hydrophobic odorants.

7. Bioavailability & Bioenhancers

In some embodiments, particles may enhance or decrease the bioavailability of contained particle ingredients such that the fraction of active ingredients administered that enter circulation unaltered is increased or decreased, respectively. In some embodiments, particle may enhance or decrease oral bioavailability such that the bioavailability of an orally administered compound is increased or decreased, respectively. In some embodiments, particles may enhance or decrease variability by altering how active compounds are degraded in the intestinal tract by mechanisms such as microbial and enzymatic metabolism. In some embodiments, particles may enhance or decrease variability by altering how active compounds are altered through hepatic metabolism is increased or decreased, respectively. In some embodiments, particles may enhance or decrease variability by altering how active compounds are eliminated through the feces, urine, or otherwise leaving the organism unchanged or as a metabolite (reversible or irreversible metabolite) of contrasting character is increased or decreased, respectively.

In some embodiments, particles and particle dispersions may contain active ingredients with poor bioavailability generally hampered in commercial development, including examples such as berberine, an alkaloid with a range of purported health benefits, has bioavailability below 1%. One study estimated that 56% is not absorbed and eliminated via feces while 43% is affected by first-pass digestion with a minimal amount of bioavailability is lost to hepatic metabolism.

In some embodiments, the bioavailability of hydrophobic active ingredients within a particle may be increased with the use of hydrophobic dispersed phase media (carrier oils, liquids immiscible with water), In some embodiments, the bioavailability of hydrophobic active ingredients within a particle may be increased with the use of the use of bioenhancers. In some embodiments, the bioavailability of hydrophobic active ingredients within a particle may be increased by nano-structuring particles in a product including their surface roughness and stability in vivo. In some embodiments, the bioavailability of hydrophobic active ingredients within a particle may be increased with the use of a combination of these strategies.

In some embodiments, the bioavailability of hydrophobic active ingredients may be enhanced by increasing their water solubility (hydrophilicity) and dissolution rates. In some embodiments, the bioavailability of hydrophobic active ingredients may be enhanced by micelle formation or other lipid nanostructures.

In some embodiments, particles may be formed with a particular choice of dispersed phase media from which the particles are composed to affect the primary pathway of absorption. In some embodiments, particles may be formed with longer chain fatty acids such that absorb occurs via the lymphatic system. In some embodiments, particles may be formed with shorter chain fatty acids such that absorb into the portal vein is increased and particles and composite ingredients may then be transported to the liver. Fatty acids are typically present in oils in foods in the form of triglycerides. Upon consumption, a series of enzymes, like lipases, act on these triglycerides, breaking them into monoglycerides and free fatty acids. These free fatty acids complex with bile salts to form micelle structures that facilitate intestinal absorption. Micelles formed from medium chain fatty acids tend to absorb directly into the portal vein, whereas long chain fatty acids tend to form chylomicrons that are subsequently absorbed in the lymphatic fluids. One of the longest chain fatty acids, oleic acid, has been found to absorb 85% via the lymphatic system and 15% via the portal vein.

In some embodiments, particles may contain bioenhancers, or biopotentiators, which are compounds, devoid of significant pharmacological activity (bioactivity) of their own but instead are incorporated to promote and increase biological activity, bioavailability, or absorption of pharmacologically active ingredients, when administered in combination. An example of a bioenhancer is piperine, an alkaloid isolated from *Piper nigrum*, black pepper. In some embodiments, piperine may be an ingredient to inhibit enzymes that otherwise prevent intestinal absorption of active compounds such as UGT, P-glycoprotein, CYP2EI, and CYP3A4.

In some embodiments, particles may contain bioenhancers such as allicin, capsaicinoids, caryophyllene, curcumin, deoxycholic acid, genistein, gingerol, naringin, piperine, quercetin, or mixtures thereof.

In some embodiments, particles may contain bioenhancers that are surfactants simulating or enhancing the effect of bile salts and other steroidal anionic surfactants that complex with fatty acids and monoglycerides from digested triglycerides to form micelles such that lipids and other contents of the micelles formed during particle degradation or the particles themselves more efficiently cross the intestinal mucosa.

In some embodiments, particles may contain bioenhancers that are bile acids and bile salts such as cholic acid (CA), deoxycholic acid (DCA), chenodeoxycholic acid (CDCA), ursodeoxycholic acid (UDCA), taurocholic acid (TCA), glycocholic acid (GCA), taurochenodeoxycholic acid (TCDCA), glycochenodeoxycholic acid (GCDCA), taurodeoxycholic acid (TDCA), glycodeoxycholic acid (GDCA), tauroursodeoxycholic acid (TUDCA), glycoursodeoxycholic (GUDCA), lithocholic acid (LCA), their combinations and associated salts.

In some embodiments, particles may contain bioenhancers organized into conventional dosing forms, mixed micellar systems, bilosomes (liposome of bile acids and bile salts), bile acid-polymer nanocarriers, bile acid-containing microcapsules, bile acid-drug conjugates, and their combinations.

In some embodiments, the primary strategy for increasing absorption and bioavailability of particles or hydrophobic ingredients may be via enhancement of micelle formation in the gastrointestinal tract. In some embodiments, hydrophobic compounds are well-solubilized in bile salt-phospholipid mixed micelles. In some embodiments, triglycerides may be broken down during digestion by a series of lipase enzymes into free fatty acids and monoglycerides. In some embodiments, triglycerides, and their metabolites (e.g., free fatty acids, monoglycerides, diglycerides) may complex with bile salts, phospholipids, cholesterol, and other compounds to form micelles which may then diffuse across the intestinal mucosa, facilitating absorption. The exact absorption parameters of the resultant micelles depend on several factors, including temperature, pH, and additional compounds present. In some embodiments, bile salts and acids may be present at concentrations more than the critical micelle concentration (CMC) and self-assemble into micelle aggregates. Naturally occurring bile acids have CMC values in the range of 2-20 mM. In some embodiments, bile acids may form smaller micelles with high CMC values compared to conventional surfactants and may enhance stability and formation of micelles in low-pH conditions of the gastrointestinal tract. The presence of different surfactants may influence the development and solubility of the resulting mixed micelles. In some embodiments, surfactants may be chosen on the basis of resultant mixed micelle behavior such as examples including complexation with ionic surfactants for low solubility, combination with alcohol ethoxylate surfactants for intermediate solubility, and the presence of nonionic polysorbate surfactants for high solubility mixed micelles. In some embodiments, phospholipids, and cholesterols may have a negligible or no effect on solubility. In some embodiments, particles include ingredients such as lecithin and polar lipids that may increase solution surface tension and subsequently accelerate the process of micelle formation. Among ionic surfactants, cationic surfactants inhibit micellar solubility the most. In some embodiments, particles in the containing or presence of high bile salt concentrations may impede micelle formation in the presence of ionic surfactants but promote micelle formation in the presence of nonionic surfactants. Mixed micelles may often be of larger size than pure bile salt micelles and of smaller size than micelles of conventional surfactants. Polysorbate 20 forms micelles of diameter 8-10 nm, sodium taurodeoxycholate (NaTDC) forms ~5 nm diameter micelles, and a mixture of polysorbate 20 and NaTDC forms ~7 nm diameter micelles. The presence of long chain surfactants with hydrophilic heads provides the greatest boost to solubility. In some embodiments, sodium cholate and Tween 20 and Tween 60 may be used in combination to further induce micelle formation enhanced by strong interactions between sodium cholate, Tween 20, and Tween 60 during micelle formation compared to the same mixtures where sodium cholate is swapped for sodium deoxycholate, strengthened my sodium cholates more hydrophilic nature. Specifically, sodium cholate has more axial hydroxyl groups, hence there is more hydrogen bonding between the a-axial hydroxyl groups of sodium cholate and the proton acceptor ethoxy groups of the polar head of Tween 20 and Tween 60. In some embodiments, the reactivity of sodium cholate with surfactant classes may be used with variation in reactivity dependent on surfactant classes such as cationic surfactants, nonionic surfactants, and anionic surfactants, listed from most to least reactive. In some embodiments, glycerol and various monoglycerides may complex with bile salts in micelle formations, with the polar backbone pointing outside and the hydrocarbon to the interior of the micelle. In some embodiments, ingredients such as monoglycerides of C16 or below (monoglycerides containing bound acids with 16 carbon atoms or less) and monoglycerides of oleic acid may improve solubility of other fatty acids and ingredients. In some embodiments, oleic acid and associated glycerides may increase micellar solubility and absorption of stearic and palmitic acid. In some embodiments, particles may induce lipolysis to micelle formation by multiplicative factors of up to two or three over the digestion and absorption period. In some embodiments, particles may accelerate micelle formation and absorption.

In some embodiments, products and particle dispersions may contain triglycerides that are the main dietary source of lipids (96%) at dosages suitable for 80-120 grams per day and dietary phospholipids at dosages suitable for achieving 2-4 grams per day. In some embodiments, products and particle dispersions may contain triglycerides at dosages suitable for achieving 7-20 grams day induced by endogenous processes, such as bile, shed intestinal cells, and sterols. In some embodiments, products and particle dispersions may contain dietary fats, sterols, and phospholipids at dosages suitable for achieving 60-100 grams per day of these ingredients where 90% may be from triglycerides and 10% may be from cholesterols, sterols, and phospholipids. In some embodiments, products and particles may be designed such that their digestion begins in the stomach with lingual lipase hydrolyzing triglycerides in the acidic stomach environment. In some embodiments, products and particles may be designed such that initial or further hydrolysis of their components takes place with gastric lipase creating partial glycerides and free fatty acids in an emulsion. In some embodiments, particles may be designed such that their fatty acid content improves absorption, particularly for individuals with low salivary lipase activity. In some embodiments, products and particles may be initially or further hydrolyzed by pancreatic lipase where the enteroendocrine cells of the duodenum produce a peptide hormone, cholecystokinin (e.g., pancreozymin), subsequently releasing bile and digestive enzymes from the pancreas. In some embodiments, products and particles may pass through the duodenum where pancreatic bicarbonates increase the luminal pH optimizing pancreatic enzyme action and provide a function as dictated by the exterior interface of the particles and phases from which they are composed. In some embodiments, products and particles are designed to interact with lipase, a water-soluble enzyme that can only act on the surface of triglyceride droplets. In some embodiments, products and particles may have a functional response to the lumen entering the small intestines via the duodenum such that lipids are further hydrolyzed and subsequently mix with bile salts. In some embodiments, products and particles may supply lipids that once digested form an emulsified oil phase in equilibrium with a micellar phase to expedite absorption or perform other various functions by design. In some embodiments, products and particles containing fats may distribute throughout the gastrointestinal phases, with triglycerides, diglycerides, and sterols tending to the oil phase and monoglycerides tending to the micellar phase. In some embodiments, products and particles may control the phase partition preference of fatty acids by varying their chain length and controlling local or global gut pH such that longer chain fatty acids prefer hydrophobic phases and shorter chain acids progressively prefer micellar phase and start to appear in molecular, dispersed form in the hydrophilic phase. In some embodiments, products and particles may include components that are metabolized into fatty acids and monoglycerides such that the monoglycerides bind with bile salts to form the micelles along with any phospholipids, cholesterol, and vitamins present in vivo or as product and particle ingredients. In some embodiments, particles and micelles resulting from product digestion may enable transport across the enterocyte layer of the intestines. In some embodiments, products and particles may promotes the formation of long chain fatty acid complexes that interact with bile salts before diffusion and flow towards the lumen. In some embodiments, products, and particles function to control or utilize protein transporters taking the fatty acid and monoglyceride ingredients or metabolites to endoplasmic reticulum where they may again synthesize triglycerides (via acyltransferase) that may pass to the Golgi apparatus to be packaged into chylomicrons. Chylomicrons are vesicle structures with outer shells composed of phospholipids and apoproteins and inner chambers containing triglycerides. In some embodiments, chylomicrons resulting from product or particle administration may be ejected from cells into the surrounding tissue to diffuse into the lymphatic system to achieve a particular bioactivity and resulting physiological response. In some embodiments, products and particles may contain short chain and medium chain fatty acids to facilitate micelle formation and diffusion into capillary tributaries of the portal vein upon crossing the enterocyte layer where the fatty acids and any other associated ingredients or bioactive components may be taken to the liver for hepatic metabolism.

8. Controlled Release

In some embodiments, particles and their composite ingredients may undergo pharmacokinetic stages and processes following their administration to an organism including liberation (the disintegration, dispersion or dissolution of the active ingredient, media containing active ingredient, or a combination of both), absorption (the adsorption to an interface to initiate a process, absorption from volume of liberation to a volume of bioaction, or permeation through a target membrane of the active ingredient, media containing active ingredient, or a combination of both after liberation), distribution (the diffusion, transport, and distribution of the active ingredient throughout the organism, such as a human, after administration of the active ingredient), metabolism (the chemical conversion of active ingredient components inside the organism to which the active ingredient was administered), excretion (the elimination of the active ingredient and metabolites thereof via bile, urine, breath, skin, and other pathways of organism excretion), and combinations thereof in time sequence as listed or otherwise.

In some embodiments, particle, inactive ingredient, and active ingredient metabolism is may undergo phase I metabolism involving the metabolism of molecules with the introduction of reactive or polar groups by cytochrome P450 oxidases to increase hydrophilicity and reactivity for further stages of metabolism. Common subcategories of Phase I transformations include oxidation, reduction, hydrolysis, cyclization, decyclization, recyclization, and addition of oxygen or dehydrogenation. In the case of Phase I oxidations, the enzymes.

In some embodiments, particle, inactive ingredient, and active ingredient metabolism is may undergo phase II metabolism involving the metabolism of compounds modified in Phase I by further conjugation towards increasingly hydrophilic molecules, in many cases catalyzed by transferase enzymes such as glutathione S-transferases.

In some embodiments, particle, inactive ingredient, and active ingredient metabolism is may undergo phase III metabolism involving any further enzyme catalyzed chemical transformations before being recognized by efflux transporters and pumped into the extracellular space before excretion.

In some embodiments, particle, inactive ingredient, and active ingredient metabolism is may undergo combinations of phase I, phase II, and phase III metabolism, or experience no metabolism whatsoever.

In some embodiments, active ingredients may be delivered to target organs or parts of an organism, including portions of organs or interfaces within an organism, by enzyme or pH triggered degradation of particles. In some embodiments, active ingredients may be delivered across the blood brain barrier. In some embodiments, active ingredients may be delivered to the small intestine for absorption. In some embodiments, active ingredients may be delivered to the liver for absorption or metabolism.

In some embodiments, active ingredients may have different onset time for physiological effects when contained in a particle. In some embodiments, a product may be designed such that the kinetics of release for the active ingredient when consumed differ from the release kinetics of the active ingredient when consumed by itself. The change in release kinetics of an active is referred to as modified release, as opposed to the release kinetics of the active by itself, known as immediate release. In some embodiments, modified release may lead to the release of the active ingredient over a prolonged period, known as extended release. In some embodiments, extended release may lead to the release of the active ingredient at a programed rate by design, known as sustained release. In some embodiments, extended release may lead to the release of the active ingredient at a constant rate, known as controlled release.

In some embodiments, the kinetics of enhanced release are controlled by altering the solubility or bioavailability of an active ingredient. In some embodiments, a complexing agent which forms a complex with the active that is more soluble than the active itself can lead to enhanced release such as the addition of cyclodextrin to an aqueous product containing CBD to form a complex of CBD and cyclodextrin that is more soluble than CBD in water. In some embodiments, the bioavailability of an active ingredient may be increased through components added to a product in order to create an enhanced release such as the encapsulation of CBD in micelles of vitamin E TPGS to increase the rate at which CBD is absorbed by the stomach and intestines.

In some embodiments, the kinetics of extended release are controlled by diffusion of the active ingredient through a barrier, which is innately slower than the kinetics of dissolution of the active by itself. In some embodiments, the barrier is formed by phase stabilizing agents added to the product. In some embodiments, the barrier is insoluble or less soluble than the active under physiological conditions such that it remains intact during release of the active. In some embodiments, the barrier with which the active must diffuse through is present throughout the entire dispersed phase such as caffeine encapsulated in a W/W system consisting of covalently crosslinked polysaccharide will be released and absorbed more slowly from the particles than it would be without the particles. In some embodiments, the barrier may exist as a distinct layer outside the encapsulated active ingredient that the active must diffuse through to be released such as caffeine encapsulated in the inner hydrophilic phase of a W/O/W system will be released slower than caffeine by itself as it must diffuse through the hydrophobic phase in which it is less soluble in than the hydrophilic phase. In some embodiments, the barrier layer may be added using conventional coating mechanisms such as a conventional coating pan, an airless spray technique, a fluidized bed, a spray dryer, or the like.

In some embodiments, the kinetics of extended release are controlled by dissolution of a non-active component. In some embodiments, the non-active component which controls release may be a solid or gelled phase stabilizing agent, hydrophobic phase, or coating. In some embodiments, the non-active component must encapsulate or surround the portion of active to be released in an extended manner. In some embodiments, the active must be unable to readily diffuse through the encapsulating non-active on a time scale on the order of the dissolution time of the non-active barrier. In some embodiments, the barrier whose dissolution controls the release of the active is present throughout the dispersed phase such as CBD encapsulated in a O/W system where the oil phase contains a concentration of rice bran wax sufficient to solidify the phase. In this case, the wax must dissolve for the encapsulated CBD to be released. In some embodiments, the barrier whose dissolution controls the release of the active is present as a distinct layer outside of the encapsulated ingredient such as caffeine encapsulated in the inner hydrophilic phase of a W/O/W system where the secondary hydrophobic phase contains a concentration of rice bran wax sufficient to solidify the phase. In this case, the wax in the secondary phase must first dissolve for the caffeine to be released.

In some embodiments, a product may be designed such that the release kinetics of the active are dependent on a specific stimulus that the particles must be exposed to before release of the active begins. In some embodiments, this stimulus may be a specific temperature such as caffeine encapsulated in the inner hydrophilic phase of a W/O/W particles system where the secondary hydrophobic phase contains phase stabilizing agents or a phase media such that the phase is a solid and impermeable towards diffusion of the active below physiological temperature but becomes a liquid which is permeable to the active above at or above physiological temperature. In some embodiments, the stimuli may be exposure to a chemical species. In some embodiments, the chemical stimuli which begins release of the active ingredient may be the concentration of free hydrogen cations (W) or pH in the environment around the particle system; for example, glutathione can be encapsulated in the inner phase of a W/W/W particle system where the secondary hydrophobic phase contains a polymer which is impervious to the active and water at the low pH present in the stomach, but swells and allows diffusion of water and glutathione at higher pH, such as physiological pH or the pH present in the intestines. In some embodiments, the chemical stimuli which begins release of the active ingredient may be the presence of specific biomolecules by design such as particular enzymes.

10. Example Use Cases

1. Examples of Energy Stimulants

In some embodiments, ingredients may be energy stimulants. In some embodiments, ingredients may be energy stimulants such as adenosine and xanthine derivatives (e.g., caffeine and theobromine).

2. Examples of OTC Drugs

In some embodiments, ingredients may be over the counter (OTC) drugs. In some embodiments, ingredients may be over the counter (OTC) drugs to either increase the efficacy of the OTC drugs experientially, increase the bioavailability, control drug release and absorption, or any of the particle properties whether before or after administration, oral or otherwise.

In some embodiments, ingredients may be non-steroidal anti-inflammatory drugs (NSAIDs) including salicylate derivatives (e.g., aspirin, salicylic acid, diflunisal, salsalate), propionic acid derivatives (e.g., ibuprofen, dexibuprofen, naproxen, fenoprofen, ketoprofen, dexketoprofen, flurbiprofen, oxaprozin, loxoprofen, pelubiprofen, zaltoprofen), acetic acid derivatives (e.g., indomethacin, tolmetin, sulindac, etodolac, ketorolac, diclofenac, aceclofenac, bromfenac, nabumetone), enolic acid derivatives (e.g., piroxicam, meloxicam, tenoxicam, droxicam, lornoxicam, isoxicam, phenylbutazone), antranilic acid derivatives (e.g., mefenamic acid, meclofenamic acid, flufenamic acid, tolfenamic acid), selective COX-2 inhibitors (e.g., celecoxib, rofecoxib, valdecoxib, parecoxib, lumiracoxib, etoricoxib, firocoxib), sulfonanilides (e.g., nimesulide), and those not captured in the structural and functional classifications listed here (e.g., clonixin, licofelone, H-harpagide in figword, devil's claw).

In some embodiments, ingredients may include members of the racetam drug family such as racetam, oxiracetam, paracetamol, and piracetam.

3. Examples of Alkaloids

In some embodiments, ingredients may be alkaloids. In some embodiments, ingredients may be alkaloids, or other phytochemicals, such as the methylated xanthine family of molecules including caffeine, Dynamine™ (methylliberine), theacrine theophylline, and theobromine. In some embodiments, ingredients may be alkaloids and other related phytochemicals such as berberine and other quaternary salts. In some embodiments, ingredients may be alkaloids, and other related phytochemicals such as terpenoids (e.g., curcuminoids).

4. Examples of Essential Oils

In some embodiments, ingredients may be essential oils. In some embodiments, ingredients may be essential oils such as amyrin, carvacrol, caryophyllene, cinnamaldehyde, citral, cuminaldehyde, humulene, eugenol, limonene, menthol, myrcene, pinene, and thymol. In some embodiments, ingredients may be essential oils that are meant to illicit a pharmacological response such as mood alteration or clearing sinuses.

5. Examples of Antioxidants, Flavonoids, & Phenols

In some embodiments, ingredients may be antioxidants. In some embodiments, ingredients may be antioxidants such as apigenin, betulinic acid, chrysin, crocetin, crocin, CoQ10 (ubiquinol), fisetin, forskolin, glutathione (GSH), luteolin, oroxylin-A, pyrroloquinoline quinone (PQQ), quercetin, resveratrol, and ursolic acid. In some embodiments, ingredients may be flavonoids. In some embodiments, ingredients may be phenols.

6. Examples of Adaptogens & Herbs

In some embodiments, ingredients may be derived from herbs. In some embodiments, ingredients may be adaptogens. In some embodiments, ingredients may be plant matter or fungal matter extracts and isolated phytochemicals from species including *Abelmoschus moschatus, Astragalus Membranaceus, Bacopa monnieri, Celastrus paniculatus, Coleus barbatus, Crocus sativus, Echinacea angustifolia, Echinacea purpurea, Eleutherococcus senticosus, Epimedium brevicornum, Epimedium grandiflorum, Epimedium koreanum, Epimedium pubescens, Epimedium sagittatum, Eurycoma longifolia, Gingko biloba, Hibiscus rosa-sinensis, Hibiscus sabdariffa, Hibiscus syriacus, Huperzia serrata, Hypericum perforatum, Lepedium meyenii, Mangifera indica, Mucuna pruriens, Ocimum tenuiflorum, Oroxylum indicum, Panax ginseng, Panax quinquefolium, Passiflora incarnata, Piper methysticum, Psidium guajava, Rhodiola rosea, Sceletium tortuosum, Schisandra chinensis, Serenoa repens, Turnera diffusa, Tribulus terrestris, Withania somnifera,* closely related species, varieties (including those that have been genetically modified) and combinations thereof.

7. Examples of *Cannabis* Phytochemicals & Cannabinoids

In some embodiments, ingredients may be derived from *Cannabis*. In some embodiments, ingredients may be *Cannabis* phytochemicals and cannabinoids (e.g., cannabidiol and *Cannabis* terpenes).

8. Examples of Probiotics

In some embodiments, ingredients may be probiotics.

9. Examples of Minerals

In some embodiments, ingredients may be minerals. In some embodiments, ingredients may be elements and minerals containing nuclei of as boron, chlorine, iodine, phosphorous, silicon, sulfur, calcium, chromium, cobalt, copper, iron, magnesium, manganese, molybdenum, potassium, selenium, sodium, zinc, and combinations thereof.

10. Examples of Vitamins

In some embodiments, ingredients may be vitamins. In some embodiments, ingredients may be vitamins such as vitamin A, vitamin B, vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folate), vitamin B12 (cobalamin), vitamin C (ascorbic acid), vitamin D, vitamin D2, vitamin D3, vitamin E, vitamin K, and their combinations.

11. Examples of Nootropics

In some embodiments, ingredients may be nootropics.

12. Examples of Amino Acids & Collagen

In some embodiments, ingredients may be collagen. In some embodiments, ingredients may be collagen such as type I, type II, type III, other types of the more than 25 varieties identified in humans including fibral and non-fibral varieties.

In some embodiments, ingredients may be amino acids. In some embodiments, ingredients may be amino acids whether in the form of isolate amino acids or in peptides and proteins such as 5-HTP, acetyl-L-carnitine, alpha-GPC, citicoline, N-acetyl-L-cysteine, N-acetyl-L-tyrosine, phosphatidylcholine, phosphatidylserine, aspartic acid, cysteine, glutamic acid, L-alanine, L-arginine, L-asparagine, L-glutamine, L-histidine, L-isoleucine, L-leucine, L-lysine, L-phenylalanine, L-serine, L-theanine, L-threonine, L-tryptophan, L-tyrosine, L-valine, methionine, taurine, uridine, and their combinations and isomers.

13. Examples of Proteins

In some embodiments, ingredients may be proteins. In some embodiments, ingredients may be proteins such as caseins and their salts, egg proteins, pea proteins, plant proteins, rice proteins, soy proteins, and whey proteins.

14. Examples of Mushrooms (Fungi)

In some embodiments, ingredients may be derived from mushrooms. In some embodiments, ingredients may be mushrooms, including their extracts and isolated phytochemicals, such as *Cordyceps militaris, Cordyceps sinensis, Ganoderma lingzhi, Grifola fondosa, Hericium erinaceus, Inonotus obliquus, Lentinula edodes, Pleurotus eryngii, Pleurotus ostreatus, Poria cocos, Trametes versicolor*, and *Tremella fuciformis*.

15. Examples of Ketones

In some embodiments, ingredients may ketones. In some embodiments, ingredients may be members of the molecular class of ketones.

11. Example Use Case Categories

1. Relaxing, Anxiolytic, & Antistress

In some embodiments, a product may be administered to induce relaxation, anxiolytic qualities, and antistress responses. In some embodiments, active ingredients, particles, and products may be classified into the relaxation, anxiolytic, and antistress category referring to compounds, extractions, and microorganisms that mitigate measures of stress, relax the mind and body, and reduce levels of anxiety. These active ingredients may exert their effects through one or more mechanisms, including through reductions in stress-signaling molecules, inflammatory markers, modulating neurotransmitter and central nervous system activity, and physiological changes. As an example, various extracts of holy basil (*Ocimum tenuiflorum*) have been demonstrated to reduce cortisol, a primary stress hormone in the human body. Extracts of Ashwagandha (*Withania somnifera*), have been shown to increase serotonin and reduce inflammation in the body.

2. Focus & Memory Aids

In some embodiments, a product may be administered to induce improvements in memory and focus. In some embodiments, active ingredients, particles, and products may be classified into the focus and memory aids grouping referring to compounds, extracts, and microorganisms that increase measures of attention span, awareness, enhance memory, or boost some measure of cognitive performance. The adaptogen *Bacopa monnieri* serves as an example of a focus and memory aid. Administration of *Bacopa* extracts have been shown to boost measures of performance for working memory, verbal recall, and visual-spatial reasoning.

3. Sleep Aids

In some embodiments, a product may be administered to improve or change the quality of sleep. In some embodiments, active ingredients, particles, and products may be classified into the Sleep aids category referring to any compound, extract, or microorganism that enhances some dimension of sleep quality. Some sleep aid ingredients work directly through sedating the central nervous system, while other sleep aid active ingredients may modulate physiological activity in the body in a manner that improves some dimension of sleep quality. An example of the former is melatonin, a hormone secreted nocturnally in the body and thought to be intimately tied to the sleep-wake cycle. Melatonin is often taken as a dietary sleep aid supplement. An example of the latter is saffron (i.e., *Crocus sativus*) extract which has been shown in several human trials to improve various dimensions of sleep quality without direct sedative effects.

4. Energy & Endurance

In some embodiments, a product may be administered to increase energy and endurance. In some embodiments, active ingredients, particles, and products may be classified into the energy and endurance category referring to any compound, extract, or microorganism that increases energy levels, promote alertness and wakefulness, or have other ergogenic effects. A key example is caffeine, which reduces feelings of fatigue through its action on the adenosine receptors. Forskolin is an example of a compound that may boost energy levels at cellular level by upregulating expression of cAMP, a primary energy-signaling molecule.

5. Weight Loss

In some embodiments, a product may be administered to aid in weight loss or weight management. In some embodiments, active ingredients, particles, and products may be classified into the weight loss category referring to any compounds, extracts, and microorganisms that may be used for managing weight such as compounds and macromolecules like hydroxycitric acid, caffeine, other methylated-xanthine derivatives (e.g. Dynamine™ and methylliberine), raspberry ketones, endogenous ketones, glucomannan, catechins, conjugated linoleic acid, or synephrine and extracts from natural sources like *Garcinia cambogia* fruit, green coffee beans, green tea leaves, *guayusa*, guarana, kola nut, elephant yam, forskolin, orange and other citrus fruits, or cocoa bean.

6. Skin & Hair Care

In some embodiments, a product may be administered to improve the skin and hair health. In some embodiments, active ingredients, particles, and products may be classified as products and associated components in the skin care category, hair care category, or combination thereof referring to compounds, extracts, and microorganisms that increase or improve some measure of skin or hair quality. For instance, bioavailable forms of the mineral silicon have been shown to play a key role in the insertion matrix that deposits collagen and minerals into the skin and hair; hence, supplementation has been shown to improve the quality nails, skin, and hair with increased collagen deposition. Extracts of *Hibiscus syriacus* have been shown to facilitate skin elasticity and resilience via activation of genes connected with skin hydration and epithelium formation.

7. Cardiovascular Health & Blood Flow

In some embodiments, a product may be administered to control blood flow or improve cardiovascular health. In some embodiments, active ingredients, particles, and products may be classified into the cardiovascular health and blood flow category referring to compounds, extracts, and microorganisms that are cardioprotective, enhance cardiovascular vigor, and improve blood flow. One of the main mechanisms of action for the latter is through increased nitric oxide production. The amino acid L-arginine is primary component of the body's nitric oxide production system and common in supplements promoting vascular health. Forskolin is an example of a compound that promotes heart health through direct modulation of the activities of cardiac cells, increasing cAMP activity.

8. Gastrointestinal Health

In some embodiments, a product may be administered to improve gastrointestinal health, including in some cases gastrointestinal microbiota health. In some embodiments, active ingredients, particles, and products may be classified into the Gastrointestinal health category referring to any compound, extract or microorganism that promotes healthy activity in the gastrointestinal tract. Probiotics, such as various species of *Bifidobacterium*, can help promote healthy digestion, elimination, and reduce the prevalence of maladaptive species of bacteria in the gut microbiome. Certain strains of *Bifidobacterium* have been found to help with constipation and irritable bowel syndrome. Berberine is an example of a non-probiotic, alkaloid compound that can improve gastrointestinal health through indirect modulation of the gut microbiome.

9. Mood Boosting & Euphoric

In some embodiments, a product may be administered to improve mood (emotional state) or provide a sensation of euphoria. In some embodiments, active ingredients, particles, and products may be classified into the mood boosting and euphoric category referring to compounds, extractions, and microorganisms that improve some measure of emotional state or promote a general feeling of euphoria. The mechanisms of action may vary but generally entail direct or indirect modulation of central nervous system activity and of neurotransmitter levels. A prominent example is kanna, i.e., *Sceletium tortuosum*, which has shown both serotonin reuptake inhibitor and monoamine oxidase inhibitor activity leading to antidepressant effects and the promotion of euphoric feelings.

10. Aphrodisia

In some embodiments, a product may be administered to influence sexual health, performance, desire, experience, or a combination thereof. In some embodiments, active ingredients, particles, and products may be classified as an aphrodisiac referring to any compound, extraction, or microorganism that boosts sexual appetite, sexual performance, sexual sensation, or sexual behavior. An example of an aphrodisiac agent is yohimbine, a main active ingredient isolated from the bark of *Corynanthe johimbe*. Its primary activities are the blocking of certain adrenergic receptors and the dilation of blood vessels resulting in increased blood flow to the genitalia.

11. Immune System Booster

In some embodiments, a product may be administered to control or increase immune system performance. In some embodiments, active ingredients, particles, and products may be classified into the immune booster category referring to any compounds, extractions, and microorganisms that modulate immune system activity in manner that promotes immune system function or reduces dysfunction. *Echinacea purpurea* extracts are an example of immune boosters and are frequently included in commercial immune boosting products. The active elements in *Echinacea* stimulate immune system activity, while mitigating excessive amounts of dysfunctional inflammatory immune system cytokines.

12. Antimicrobial & Preservation

In some embodiments, a product may be administered with antimicrobial or preservative properties to increase freshness or imbue the target organism for administration with antimicrobial and antifungal care. In some embodiments, active ingredients, particles, and products may be classified into the category of antimicrobials and preservatives referring to compounds and extracts that demonstrate antibacterial, antifungal, antiviral, or antimicrobial activities, either directly or through the inhibition of some mechanism of microbial propagation and proliferation. An example of such agents are essential oils and their individual constituents, which tend to have antimicrobial properties. A specific example may be seen in cinnamaldehyde, a major component of cinnamon essential oil that gives it its distinctive flavor. Cinnamaldehyde has been noted to exhibit strong inhibitory activity against many strains of fungi.

12. Example Formats

1. Liquids

In some embodiments, a product may be in a liquid format such that the continuous phase defining the product is in a liquid state of matter.

1.1. Extraction

In some embodiments, a product may be an extract format formed by extraction which is the process of removing solid and liquid compounds from a substrate using a solvent substance. The process of extraction is used to separate and isolate active compounds from undesired materials (fibers and excipients). The solvent may be a polar (e.g., aqueous solvents) or nonpolar (e.g., acetone, methanol, and ethanol).

1.2. Liquid Concentrate

In some embodiments, a product may be a liquid concentrate such as substance that has been concentrated in a solvent or liquid vehicle by removing or eliminating much of the solvent or vehicle. Liquid concentrate formats are often easier to incorporate into beverage products than dried formats and are often more bioavailable. However, liquid concentrate formats can be more challenging to store long term.

1.3. Aerosol Spray

In some embodiments, a product may be an aerosol spray as a delivery system for liquid format products. Active ingredients in a liquid vehicle are delivered via an aerosol mist of liquid particles. Modern aerosol spray systems generally consist of the container, the spray valve, and the trigger or button to release the aerosols. Typically, an appropriate compressed fluid propellant is required for the spray device to function correctly. Spray formats are commonly used for nasal sprays and for skin and hair sprays.

2. Solid

In some embodiments, a product may be in a solid format such that the continuous phase defining the product is in a solid state of matter such as powder and tablets (e.g., chewable tablets, orally disintegrating tablets, sublingual tablets, effervescent tablets).

2.1. Powder

In some embodiments, a product may be in a dried extract powder format. In some embodiments, small amounts of anti-caking agents and other additives are incorporated to ensure the powder is free flowing. The process of drying and powdering creates some risk of contamination, hence powder formats tend to be less safe than liquid concentrates. Powder formats tend to be more convenient and portable than liquid formats.

2.2. Tablets

In some embodiments, a product may be in a tablet format containing active compounds bound with a binder powder, the molded and pressed into form. Tablets may have additional coatings for easy swallowing, protection, and targeted delivery.

2.2.1. Chewable Tablets

In some embodiments, a product may be in a chewable tablets format designed for mastication and subsequent release and absorption of active compounds. Chewable tablets offer rapid release, and the process mastication and the exposure to saliva can aid in the digestion of certain active ingredients. Chewable tablets may come in different flavors.

2.2.2. Orally Disintegrating and Sublingual Tablets

In some embodiments, a product may be in a Sublingual and orally disintegrating tablet format such that tablets designed to dissolve either in the oral cavity in general, or under the tongue in particular. This format generally offers the fastest delivery, with active ingredients absorbing directly into the bloodstream via the oral cavity, bypassing digestion entirely. Ingredients must be of an appropriate size and in an appropriate format to accommodate orally disintegrating tablets.

2.2.3. Effervescent Tablets

In some embodiments, a product may be in an effervescent tablet format designed to be disintegrated into an appropriate beverage, then drunk.

3. Gels/Semi-solids/Hybrid Formats

In some embodiments, a product may be in a format that does not strictly fall under the categories of liquid and solid formats such as gels, gelatins, semi-solids, capsules, soft gels, lotions, gummies, gums, or combinations thereof.

3.1. Capsules

In some embodiments, a product may be in a format such that solid active ingredients (e.g., in powder format) are encapsulated in a hard or soft shell (often made from gelatin). The shell of the capsule breaks down after contact with gastrointestinal environment. Capsules may be coated for targeted, delayed, and sustained delivery.

3.2. Soft Gels

In some embodiments, a product may be in a soft gel format such that the active ingredients are in liquid format, typically suspended in gelatin or some similar substance. Liquid format active ingredients can have greater bioavailability than their solid counterparts.

3.3. Gels

In some embodiments, a product may be in a gel format such that a sol with solid active components is incorporated into it. The mixture meshes into a rigid or semi-rigid form. The crosslinking of polymers in a gel makes the mixture more viscous. However, a gel is still relatively fluid compared to most solids, a convenience for making gel flow with relatively little force. This makes gels highly appropriate for formats where a relatively free flowing substance for surface application is desired.

3.4. Lotion

In some embodiments, a product may be in a lotion format where it is a semi-rigid matrix for delivering active ingredients in topical applications. Unlike gels, lotions have lower viscosity due to increased water content and are generally oil-in-water emulsions or extensions thereof. In some embodiments, a product may be a lotion format with additives may include preservatives, stabilizers, fragrances, and thickening agents.

In some embodiments, a product may be in a lotion format intended for application to the skin for the absorption of ultraviolet light and other wavelengths of light from the sun to protect against photodamage to an organism. In some embodiments, a product may be a sunscreen lotion that protects from specific varieties of ultraviolet light such as UVA and UVB, like UVA and UVB protecting colloids of silicon dioxide or titanium dioxide particles dispersed in a lotion.

3.5. Gummy

In some embodiments, a product may be in a gummy format that is a chewable, gelatin-based format. A chewable matrix is constructed from gelatin, starch, water, sugar, and other additives (including colors, flavors, and fragrances). Sometimes pectin is substituted for gelatin. Gummy formats can be used to contain active ingredients, particularly foul-tasting active ingredients. A major risk with the gummy format is moisture migration. Moisture can attract and accumulate inside of the gummy, causing undesirable effects such as stickiness, loss of flavor, and microbial growth. Gummies are also a popular format for children's candy. As such, another major concern with the gummy format, particularly for actives intended for children, is the possibility of inadvertent child consumption of the gummies thinking it is candy.

13. Example Delivery Routes

In some embodiments, a route of administration (delivery route) for a particular product, dispersion of particles, or any substance interacting with biological tissue, human or otherwise, may be the path by which the substance or components of the substance are absorbed, adsorbed, or otherwise into the organism or biological tissue.

In some embodiments, routes of administration may be broadly classified based on where the uptake or application event occurs such as topical (local), oral (administered via consumption, absorbed via the gastrointestinal tract), enteral (delivered through the gastrointestinal tract), buccal (through the mucosa of the cheek), nasal (via nasal mucosa), and sublingual (underneath the tongue). In some embodiments, the inventors' recommended route of administration of a dispersion of particles is oral administration, particularly in the case of a dispersion of particles.

In some embodiments, a product or particles may be topically administered transdermal products with several advantages over oral intravenous methods. In some embodiments, products may be recommended for topical transdermal administration to bypass the hepatic metabolism and first pass effects associated with oral and enteral administration. In some embodiments, products may be designed for administration to skin to transverse one or all layers of skin including the epidermis, the dermis, and the hypodermis. In some embodiments, products or particles may traverse through or absorb into the epidermis and stratum corneum, primarily composed of insoluble keratins (70%) and lipids (20%) and 15-20 μm (microns, micrometers) thick. In some embodiments, products or particles may traverse through or absorb into the layers below the stratum corneum such as the viable epidermis (typically, 130-180 μm thick, consisting of layers of epithelial cells). In some embodiments, products or particles may traverse through or absorb into keratinocytes, melanocytes, Langerhans cells, Merkel cells, or combinations thereof. In some embodiments, products or particles may traverse through or absorb into the dermis layer through 2-3 mm of mainly collagenous fibers (70%) and elastin. In some embodiments, products or particles may traverse through or absorb into nerves, macrophages, lymphatic vessels, and blood vessels within the dermis. In some embodiments, products or particles may traverse through or absorb into the hypodermis, a layer of majority fat cells (also, fibroblasts and macrophages) functioning to protect against physical shock, insulate temperatures, and provide support and conductance of the vascular and neural signals of the skin. In some embodiments, products or particles may be administered trans-epidermal such that active ingredients diffuse through the stratum corneum layer, through the other layers of skin, and into the blood or lymphatic system. Trans-epidermal transport may itself be divided into two pathways: intercellular and intracellular. The intracellular route involves diffusion through corneocytes, terminally differentiated keratinocytes, and is most suited for hydrophilic ingredients. The intercellular pathway involves the diffusion of hydrophobic ingredients via lipid matrix of the skin layers. One of the challenges of transdermal administration is that the intended active must breach the lipophilic stratum corneum and dermal layers and then absorb into the aqueous circulation system. The stratum corneum functions as an effective barrier and prevents permeation of many compounds. In some embodiments, products or particles may be administered trans-appendageal such that the active ingredients diffusion through the sweat glands and across hair follicles. In some embodiments, products or particles may be administered via trans-epidermal and trans-appendageal routes, sequentially or simultaneously. In some embodiments, skin permeability of active ingredients across the skin may be enhanced by particles or other delivery vehicles (e.g., vesicles, liposomes), chemical enhancers, electrical methods, and thermal methods. In some embodiments, ingredients may be penetration enhancers such as alcohols, azone, essential oils, fatty acids, pyrrolidones, sulphoxides, terpenes, terpenoids, and urea.

In some embodiments, a product or particles may be sublingual administration referring to any administration of active ingredients through the mucosal lining underneath the tongue. In some embodiments, a product or particles may be used for sublingual administration to avoid first pass metabolism, hepatic metabolism, the acidic gastric environment, microbiome metabolism, complexation with foods, or combinations thereof. In some embodiments, a product or particles may be used for sublingual administration to facilitate rapid onset time for active effects. In some embodiments, a product or particles may be used for sublingual administration to dissolve active ingredients rapidly and use smaller concentrations of active ingredients. In some embodiments, a product or particles may be used for sublingual administration to interact with the oral cavity environment containing saliva and some enzymes, particularly salivary lipase, and amylase. In some embodiments, a product or particles may be used for sublingual administration to keep the product and particles at pH closer to neutral and minimize enzymatic pressures compared to administrations that pass through the gut and nasal cavity.

In some embodiments, a product or particles may be used by nasal administration, the direct administration and absorption of active ingredients via the nasal mucosa with several distinct advantages. In some embodiments, a product or particles may be used by nasally administering in a sprayable format to be dispersed into and coat the nasal mucosa with particles containing active ingredients. In some embodiments, a product or particles may be used by nasal administration to circumvent the first pass, hepatic, pancreatic, and microbial metabolism associated with oral administration. In some embodiments, a product or particles may be used by nasal administration for rapid onset times or when intended effects or bioactivity is in the nasal cavity. In some embodiments, a product or particles may be used by nasal administration when the presence of saliva and salivary lipases is undesirable for achieving the intended physiological effects. In some embodiments, a product or particles may be used by nasal administration designed for transcellular transport involving a lipoidal route such that passive diffusion across the epithelium occurs when concentrations are sufficient and is well-suited for delivery of hydrophobic ingredients that may diffuse into the lipid bilayer of the cell membrane then traverse the cell in the cytoplasm. In some embodiments, a product or particles may be used by nasal administration designed for paracellular transport with slow, passive aqueous transport diffusion of through cellular junctions.

In some embodiments, a product or particles may be orally administered to deliver active ingredients requiring more complexity in design than buccal, nasal, sublingual, or topical administration routes. In some embodiments, a product or particles may be administered via one or multiple administration routes such as buccal, sublingual, and oral administration that may involve interactions with tastebuds with or without control for the flavor of the product or particles. In some embodiments, products and particles within the oral cavity may respond to saliva, the physical forces and motion of the tongue and teeth, and by several enzymes including salivary amylase and lipase to induce active ingredient release or remain stabilized leaving the interior of the particles intact. In some embodiments, products and particles may be swallowed and actives ingredients may be subjected to pH ranging from 1.5-3.5 and gastric enzymes, where either a function is performed by design, or the particles remain stable with the interior of particles intact. In some embodiments, products and particles may enter the small intestines where active ingredients are acted on by a host of pancreatic, hepatic, and gut wall enzymes, again, providing a function in response or remaining stable to the environment. In the intestines, active ingredients or intact particles may encounter the microflora and are acted on by a host of microbial enzymes. In some embodiments, particles and products may be decided to provide a particular function or remain stable against first pass metabolism, which plays a primary role in the degradation or chemical alteration of consumed active ingredients by oral administration. In some embodiments, products and particles may be designed administration to a mucosal membrane for a more direct and efficacious application. In some embodiments, hydrophobic ingredients, particularly hydrophobic media, may be chosen to drastically increase the absorption of hydrophobic active ingredients. In some embodiments, longer fatty acid chains may be incorporated to preferentially transport hydrophobic ingredients via diffusion into the lymphatic system. In some embodiments, shorter fatty acid chains may be incorporated to preferentially transport hydrophobic ingredients via the portal vein. In some embodiments, ingredients may include oleic acid and similar ingredients known to be preferential to lymphatic uptake (85%), whereas short chain fatty acids almost entirely (>95%) absorb via the portal vein. In some embodiments, products and particles control or inhibit P-glycoprotein (at the boundary of the intestinal mucosa, particularly in the intestinal epithelium) and other secondary mechanisms of metabolism whereby the dose of active ingredient delivered is reduced. In some embodiments, ingredients may be included that are P-glycoprotein inhibitors to help with the passage and absorption of active ingredients. Examples of P-glycoprotein inhibitors include glycosides, alkaloids, flavonoids, phenolics, terpenoids, taxols, and epipodophyllotoxins.

In some embodiments, a product or particles may be administered by routes such as auricular (otic), buccal, conjunctival, cutaneous, dental, electro-osmosis, endocervical, endosinusial, endotracheal, enteral, epidural, extra amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, vaginal, and combinations thereof.

14. Example Particle Formation Techniques

In some embodiments, processing tools may be used during production of a product to aid in formation of dispersed particles in a continuous phase. In some embodiments, these processing tools use mechanical energy to mix a solution of two or more phases together to form a homogenous solution. In some embodiments, a high energy processing tool such as an ultrasonicator may be used to input the highest power (defined here as energy per unit time, for example Watts [W] or Joules per second [J/s]) available for a particular combination of ultrasonic generator, transducer, and probe to reduce the average particle size of a system to a desired value in the minimum amount of time. In some embodiments, a low energy processing tool such as a shear mixer, rotor-stator homogenizer, or microfluidic device may be used to prevent degradation of components in the system, such as active live ingredients. In some embodiments, a low energy processing tool may be used to prevent degradation of particle systems already present in the system, for example, a rotor stator homogenizer may be chosen for dispersal of a W/O immiscible single-particle system into a hydrophilic phase to form a W/O/W double-particle system in order to prevent disruption of the hydrophilic dispersed phase encapsulated by the hydrophobic secondary phase. In some embodiments, spray drying, spray chilling, and combinations thereof may be utilized to both form a particle system and solidify the particles in one step (and in some instances, multiple steps) when solid products are desired.

In some embodiments, any number of processing tools may be used in the production of a product. In some embodiments, different processing tools are used for different dispersal steps; for example, using a ultrasonicator to form a W/O immiscible single-particle system and a rotor stator homogenizer to form a W/O/W double-particle system by dispersing the W/O immiscible single-particle system in a continuous hydrophilic phase. In some embodiments, multiple processing tools may be used in a single dispersal step, for example, using a conventional or rotor-stator shear mixer to initially disperse the hydrophobic and hydrophilic phases of a W/O immiscible single-particle system before using ultrasonication to reduce the average particle size to a desired value. In some embodiments, use of a low energy method followed by a high energy method may be used to reduce the time in which a system is subjected to high intensity acoustic waves, which may reduce the degradation of components of the system.

1. Ultrasonication

In some embodiments, ultrasonication may be used to process the ingredients of a product into a particle dispersion. In some embodiments, ultrasonication may be used to process the ingredients of a product into a final particle dispersion. In some embodiments, the sonicator frequency, sonicator horn size, sonicator power, sonication intensity, sonication time, or pulse pattern may be changed to vary the properties of the final particle dispersion. In some embodiments, the size of the sonicator horn may be chosen to be small to direct acoustic waves parallel to the bottom of the particle dispersion synthesis vessel (e.g., 1 mm, 2 mm, 5 mm, 10 mm, and intermediate sizes within the diameter range listed). In some embodiments, the size of the sonicator horn with relatively large diameters (e.g., 15 mm, 20 mm, 25 mm, 30 mm, 50 mm, 100 mm, and intermediate sizes within the diameter range listed) may be selected to direct more acoustic power perpendicular to the synthesis vessel bottom.

In some embodiments, the sonicator frequency may be changed to vary the properties of the final solution of particles, such as final average particle size. In some embodiments, a sonication frequency range of 20-30 kHz (or, in the following additional frequency ranges, 100-1000 Hz, 1-10 kHz, 10-100 kHz, 100-1000 kHz, 1-10 MHz, 10-100 MHz, 100-1000 MHz, 1-10 GHz) may be applied to produce particles of a desired size, form factor, or distribution. In some embodiments, higher frequencies may be used, which lead to higher cavitation rates, though may decrease the overall extent of cavitation and overall efficiency due to shorter cavitation lifetimes. In some embodiments, lower frequencies may be used to produce higher power waves.

In some embodiments, the sonicator horn size may be varied to scale with the desired batch size. In some embodiments, a smaller tip size of 10 (3, or 5) mm may be used to realistically fit the form factor of the desired reactor vessel while still providing sufficient acoustic energy to the whole volume of solution to give a final product with acceptable properties (e.g., particle diameters and polydispersity index, PDI). In some embodiments, larger batches of particle solution may be required and a bigger probe tip (e.g., 15, 20, 30, 50, or 80 mm) may be used as larger volumes of solution can be successfully cavitated per unit time at a higher power, leading to lower processing times to achieve acceptable particle properties (e.g., particle diameters and PDI).

In some embodiments, the sonicator may be chosen or adjusted to generate acoustic waves with varied amplitude, or intensity, to control the properties of the final particle dispersion. In some embodiments, the acoustic amplitude may be set to 60% (or 5, 10, 15, 20, 25, 30, 35, 40, 45, 50, 55, 65, 70, 75, 80, 85, 90, 95, 100%) of the maximum acoustic transducer power to produce a solution of particles with acceptable properties. In some embodiments, the maximum acoustic transducer power may be 1.8 kW. In some embodiments, the maximum acoustic transducer power may be strategically chosen to be lower than 1.8 kW (e.g., 1 W, 10 W, 100 W, 500 W, 1000 W, 1500 W, and powers intermediate to those aforementioned) to maintain better control and repeatability in particle formation. In some embodiments, the acoustic transducer or sonicator may be chosen to have powers higher than 1.8 kW (2 kW, 5 kW, 10 kW) to more efficiently achieve optimal particle uniformity on short timescales, as necessary. In some embodiments, increasing the sonicator intensity may increase the amplitude of the probe's vibrations, effectively increasing the power delivered to the system via acoustic waves, ceteris paribus. In some embodiments, the increased power delivered to the solution from increasing the intensity of the sonicator may lead to shorter sonication times to achieve acceptable particles properties (e.g., particle diameters and PDI). In some embodiments, certain properties of the solution (e.g., viscosity and boiling point) or the tip (e.g., composition, length, diameter) may not be suitable for sonication at higher intensities and may cause damage to the sonication equipment or adverse effects in the particles solution if higher intensities are used.

In some embodiments, optimal particle properties may be achieved by combining the application of one or more of the aforementioned acoustic frequencies with independently chosen power amplitudes, to generate acoustic waveforms of arbitrary complexity.

In some embodiments, the time the particle solution is exposed to sonication may be changed to vary the properties of the final solution of particles. In some embodiments, the particles solution may be sonicated for 10 (or 0.5, 1, 2, 5, 15, 20, 30, 45, 60) minutes to achieve to achieve acceptable particles properties (e.g., particle diameters and PDI). In some embodiments, the length of sonication time may be determined by experimentally determining the amount of time it takes a specific system for a particle solution to reach a minimum particle size and PDI for a given set of sonicator parameters. In some embodiments, the minimum amount of sonication time to achieve a minimum time may be used as additional sonication can lead to loss of components through evaporation or aerosolization or unnecessary heating.

In some embodiments, the vibrations of the sonicator may be pulsed in a regular manner. In some embodiments, the sonication pulse pattern may consist of periods of the sonicator being on and off in a ratio of 1:1 (or 2:1, 3:1, 5:1, 7.5:1, 10:1, 1:2, 1:3, 1:5, 1:7.5, or 1:10, or rational number multiples thereof). In some embodiments, the amount time the sonicator is on during the pulse pattern may be 1 (1-60) s. In some embodiments, pulsing of the sonicator may lead to reduced heating as the solution has time to cool down for some amount of time between periods of being heated by the sonication. In some embodiments, this reduced heating may lead to particle solutions with more desirable particle properties (e.g., particle diameters and PDI).

2. Shear Mixer

In some embodiments, shear mixing may be used to process the ingredients of a product into a particle dispersion. In some embodiments, shear mixing may be used to process the ingredients of a product into a final particle dispersion. In some embodiments, shear mixing may be used to ensure a system is being well mixed during processing; for example, using a magnetic stir bar or impeller during a batch processing using ultrasonication to ensure all portions of the solution are exposed to equal acoustic energy. A shear mixer is a device consisting of a rotor or impeller driven by some motor, either directly or through a coupled force (e.g., magnetism), which imparts shearing forces throughout a system. In some embodiments, the shear forces imparted on a system consisting of multiple phases may induce mixing of the phases. In some embodiments, this mixing may be sufficient to generate stable particles dispersed in a continuous phase. In some embodiments, a shear mixer may be a magnetically driven stir bar and appropriate magnetic stirring plate, a lab or industrial mixer with attached impeller, or a food processor or blender. In some embodiments, the speed of the rotor or impeller, its geometry, and the time a system is exposed to the shear mixing may be controlled to tune the average particle size of a system.

3. Homogenization

In some embodiments, homogenization may be used to process the ingredients of a product into a particle dispersion. In some embodiment, a homogenizer or high shear mixer may be used to process the ingredients of a product into a final particle dispersion. A homogenizer is a device specifically designed to generate high shearing forces in a liquid. In some embodiments, a high shear mixer may consist of a rotating rotor located inside a stator. The arms of the rotor may have a small clearance with the teeth of the stator, and when they rotate, may generate strong shearing forces along around the edges of the teeth, inducing mixing. In some embodiments, the geometry of the homogenizer, the speed at which it is operated, and the time a system is exposed to the high shear mixing may be tuned to control the average particle size of a system.

4. Spray Dryer

In some embodiments, spray drying may be used to process the ingredients of a product into a particle dispersion. In some embodiment, a spray dryer may be used to process the ingredients of a product into a final particle dispersion. In some embodiments, a spray dryer may be used to form a dry powder of bioactive molecules for use in products.

In some embodiments, a phase or phase mixture containing the bioactive molecules may be dispersed as it is released from a spray nozzle, which contacts a hot-air stream that vaporizes the surrounding liquid, creating dry, micron-scale particles.

In some embodiments, an ultrasonic nozzle may be used to assist in the formation more uniform particles of a smaller, more narrow size range. In some embodiments, active ingredients may be incorporated into particles if the precursor slurry contains amphiphilic molecules, such as starches and surfactants (interface stabilizers). As the solvent is evaporated, surface tension may cause these molecules to form micelles around the molecules of interest, thereby internalizing the load within a carrier structure.

In some embodiments, particles may be formed by spray drying with a three-fluid nozzle. In some embodiments, particles may be formed by spray drying with a three-fluid nozzle such that the outer nozzle contains a phase or phase mixture containing phase stabilizing agents, interface stabilizing agents, active ingredients, or combinations thereof. In some embodiments, particles may be formed by spray drying with a three-fluid nozzle such that the inner nozzle contains a phase or phase mixture containing phase stabilizing agents, interface stabilizing agents, active ingredients, or combinations thereof. In some embodiments, particles may be formed by spray drying with a three-fluid nozzle such that the inner and outer nozzles contain distinct phases or phase mixtures with phase stabilizing agents, interface stabilizing agents, active ingredients, or combinations thereof, with the two nozzles atomizing simultaneously, associating the outer phase or phase mixture around the inner nozzle phase or phase mixture to form stable, layered particles.

In some embodiments, particles may be formed by spray drying with a three-fluid nozzle to improve internalization and controlled release of multiple active ingredients in a multilayered, multifunctional structure.

In some embodiments, particles may be formed with the use of a hot-melt system to facilitate the use of waxes as phase and interface stabilizing agents where melted waxes are released from either a two- or three-fluid nozzle along with active ingredients and sprays the mixture with cool air, leading to solidification.

5. Microfluidics

In some embodiments, microfluidics may be used to process the ingredients of a product into a particle dispersion. In some embodiment, a microfluidic device may be used to process the ingredients of a product into a final particle dispersion. In some embodiments, particles may be formed with a microfluidic device made from a polymer such as polydimethylsiloxane (PDMS). In some embodiments, particles may be formed with a microfluidic device that deforms less than PDMS at higher flow rates and does not swell in the presence of some organic solvents such as silicon, glass, engraved metals, or combinations thereof with or without including PDMS. In some embodiments, particles may be formed with the use of microfluidic devices and ultrasound, directly or indirectly applied to the microfluidic device channels.

In some embodiments, particles may be formed with the use of microfluidic devices by passive droplet generation by utilizing at least one geometry such as cross-flowing (continuous and dispersed phases flow at an angle towards each other before mixing and dispersion), T-junction channels for cross flow, flow focusing (dispersed phase flows to meet continuous phase at an angle before undergoing a constraint for particle formation such as channel narrowing), and co-flowing the continuous and dispersed phase, including combinations thereof.

In some embodiments, particles may be formed with the use of microfluidic devices by active droplet generation such as active flow focusing.

In some embodiments, particles may be produced by microfluidic devices using picoinjection, controlled electrocoalesence with nanoelectrodes, chaotic advection, magnetic field control, droplet fusion, and combinations thereof.

6. Processing Techniques

Figure 11:
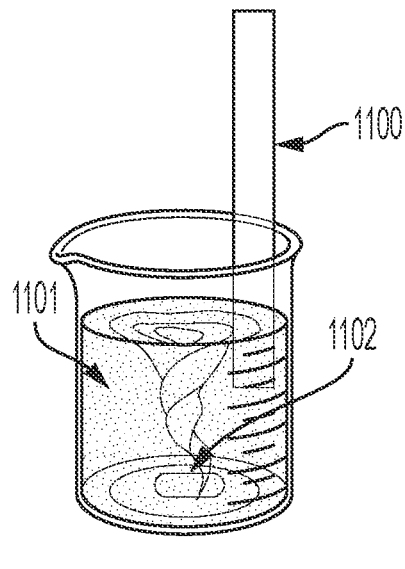
FIG. 11 is a schematic diagram that illustrates an example of a batch production process of a particle dispersion, in accordance with some embodiments.
Figure 12:
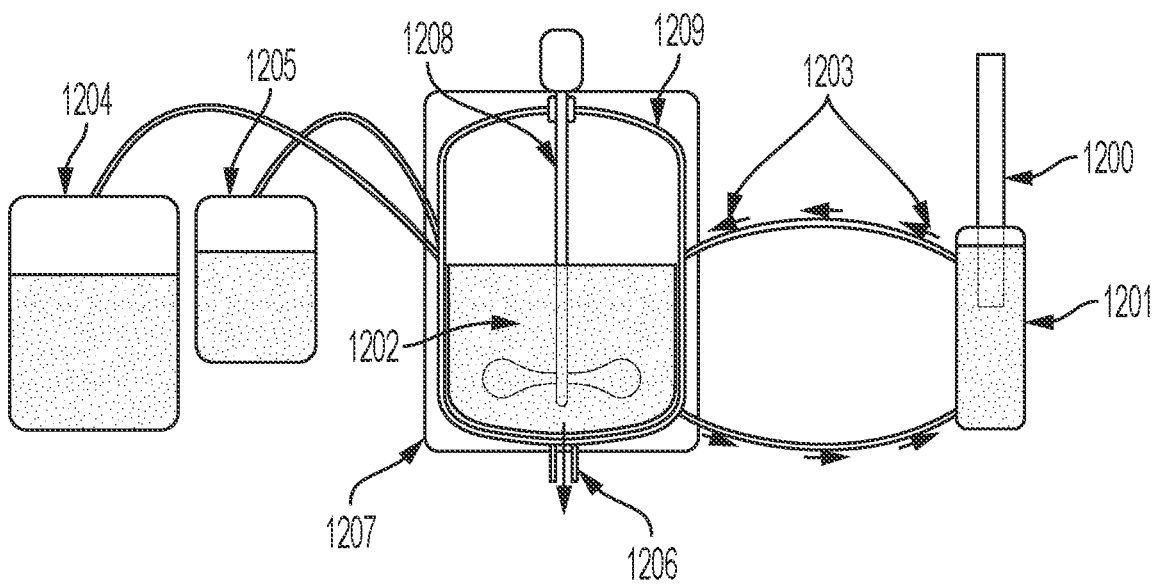
FIG. 12 is a schematic diagram that illustrates an example of a semi-continuous production process of a particle dispersion, in accordance with some embodiments.

In some embodiments, the processing tool 1100 may be immersed directly into the bulk of the components 1101 during processing, known as batch processing and depicted in FIG. 11. In some embodiments, an additional processing tool 1102 may be present to aid in mixing or processing. An example of a batch process would be the formation of a O/W particle system containing CBD, MCT, lecithin, and water (1101) using a benchtop sonicator 1100 immersed in the solution and magnetic stirring 1102. In some embodiments, processing occurs in a semi-continuous process, as seen in FIG. 12. In some embodiments, the processing tool 1200 may be situated in a separate vessel, known as a flow cell 1201, when a semi-continuous process is used. In some embodiments, a flow cell is utilized in semi-continuous processing by continuously cycling the components of a system from a separate vessel 1209 containing the bulk of the components 1202, through the flow cell 1201 where they are processed using a processing tool 1200, and back into the vessel containing the bulk of the components 1209, as depicted by the arrows 1203 which show the flow of components in the system. In some embodiments, multiple flow cells may be arranged in series such that the components experience a larger input of energy every unit of time. In some embodiments, processing is continued in batch or semi-continuous processing until the desired product properties (e.g., particle diameters and PDI) are achieved. In some embodiments, tanks or containers may have other fittings or connections; for example, connections to storage tanks for a hydrophilic phase 1204 and hydrophobic phase 1205 or an outlet to drain the tank after processing 1206.

In some embodiments, any of the processing components such as tanks, tubing, or flow cells may be heated either directly or via recirculating fluid run through jackets 1207. In some embodiments, any of the processing components such as tanks, tubing, or flow cells may be cooled either directly or via recirculating fluid run through jackets 1207. In some embodiments, tanks may be mixed using overhead mixers 1208 in order to ensure components are homogenized before being flowed through the flow cells.

An example of a semi-continuous process would be the formation of a O/W immiscible single-particle system containing CBD, MCT, lecithin, Tween-80, and water. The hydrophilic phase containing water and Tween 80 may be flowed 1203 from the hydrophilic phase tank 1204 to the mixing tank 1209, heated using recirculating fluid passed through the jacket 1207, and mixed using an overhead mixer 1208. The hydrophobic phase containing CBD, MCT, and lecithin may be flowed from the hydrophobic phase tank 1205 to the mixing tank to form a mixture of both phases 1202. The mixture may then be flowed through a flow cell 1201 outfitted with a sonicator 1200, where it is exposed to acoustical waves, and back into the tank it was stored in until desired particle properties are achieved. Once the desired particle system is achieved, the tank may be drained through 1206.

Figure 13:
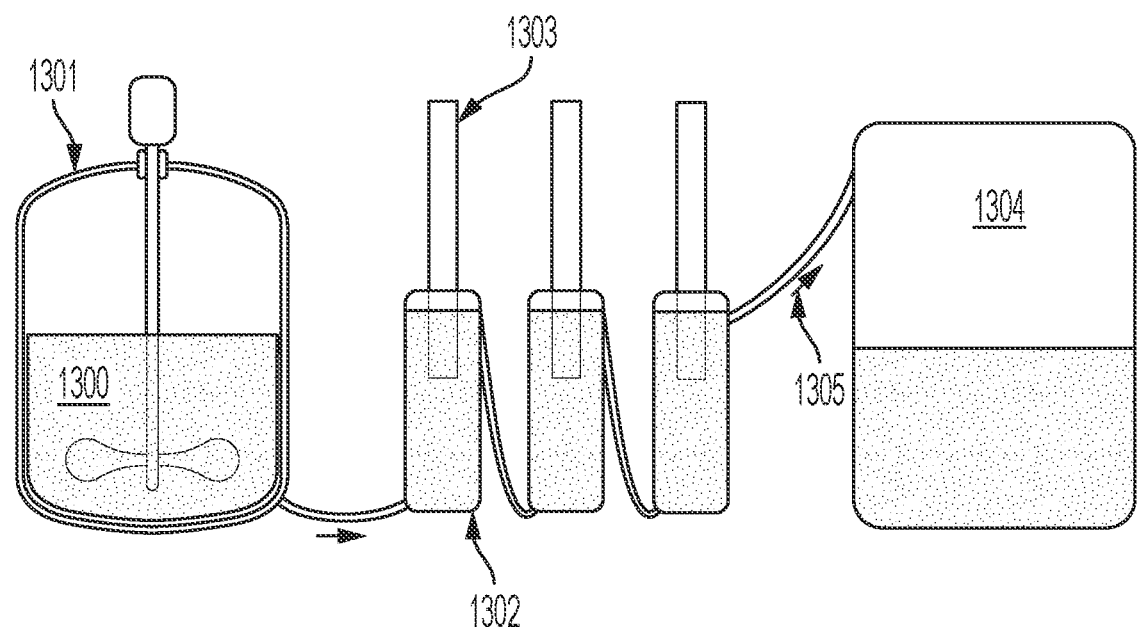
FIG. 13 is a schematic diagram that illustrates an example of a continuous production process of a particle dispersion, in accordance with some embodiments.

In some embodiments, the amount of energy required to produce a product with specific properties (e.g., particle diameters and PDI) may be measured, and by considering the total volume of the system, a volume independent requirement of energy per unit volume (Watts [W] or Joules per second [J/s]) may be determined for that specific system. In some embodiments, a continuous process, depicted in FIG. 13, may be used where the mixture of raw ingredients 1300 is transferred from an initial raw ingredients vessel 1301, through the flow cell 1302 or series of flow cells equipped with processing tools 1303, where they are subjected to the desired amount of energy to produce a finished product, and directly into a vessel for storage of a finished product 1304. Arrows 1305 in FIG. 13 depict the movement of components in the system. An example of a continuous process would be the formation of a O/W immiscible single-particle system containing CBD, MCT, MPGO, vitamin E TPGS, and water 1300 by flowing it through a flow cell 1302 outfitted with a sonicator 1303, where it is exposed to sufficient acoustical waves to achieve the desired particle properties, and into a finishing tank 1304.

In some embodiments, the flow rate and pressure in the flow cell may be altered to tune the amount of energy each aliquot of solution receives during its residency time in the flow cell. In some embodiments, the pressure in the flow cell may be increased to increase the net power output of the processing tool and the amount of energy imparted into the system. In some embodiments, the pressure in the flow cell may be increased by restricting flow at the outlet of the flow cell; for example, by using a smaller aperture for the flow cell outlet than its inlet. In some embodiments, the pressure in the flow cell may be increased by using a pump to pump the components into the flow cell that generates pressure during its operation, such as a reciprocating pump.

Figure 14:
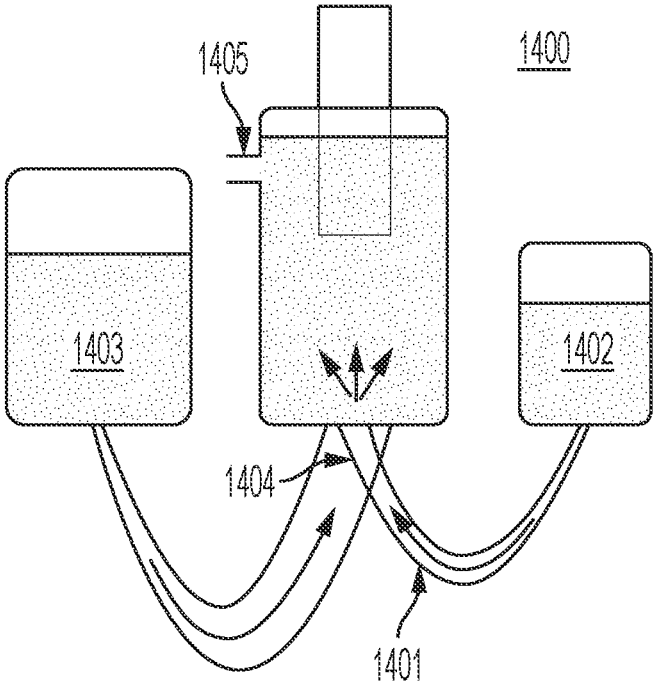
FIG. 14 is a schematic diagram that illustrates an example of a production process of a particle dispersion utilizing flow cell mixing, in accordance with some embodiments.

In some embodiments, the two phases being mixed in a processing step may be mixed directly in or immediately before entering a flow cell 1400 fitted with a processing tool, as is illustrated in FIG. 14. In some embodiments, mixing of phases directly before or in a flow cell may be accomplished by flowing (arrows 1401 denote the flow path of phases) the phase to be dispersed 1402 into the flow cell concurrently with a separate solution 1403 which contains the continuous phase. In some embodiments, the mixing may be achieved by using a nested pipe 1404 which carries the dispersed phase 1402 and expels it directly into the center of the flow of the separate solution 1403 and into the flow cell. In some embodiments, the dispersed phase 1402 may enter the flow cell directly adjacent to the inlet for the other solution 1403. In some embodiments, inlets for the dispersed phase 1402 and 1403 may be placed as close to one another as possible, if not on top of one another, to maximize mixing and create as homogenous of a solution as possible before the mixture of 1402 and 1403 reaches the processing tool. Once the mixture of 1402 and 1403 has passed through the flow cell and been subjected to an input of energy to drive particle formation, it may flow out of an outlet 1405. In some embodiments, the process may be fully continuous and the outlet 1405 may flow to a separate tank containing the processed particle system. In some embodiments, when a continuous process is used utilizing the system depicted in FIG. 14, 1403 may consist of solely continuous phase. In some embodiments, the process may be semi-continuous and the outlet 1405 may flow back to the tank containing 1403. In some embodiments, when a semi-continuous process is used utilizing the system depicted in FIG. 14, 1403 may consist of either solely a continuous phase, such as at startup of the system, or a partially formed particle system, such as during cycling of the system.

Figure 15:
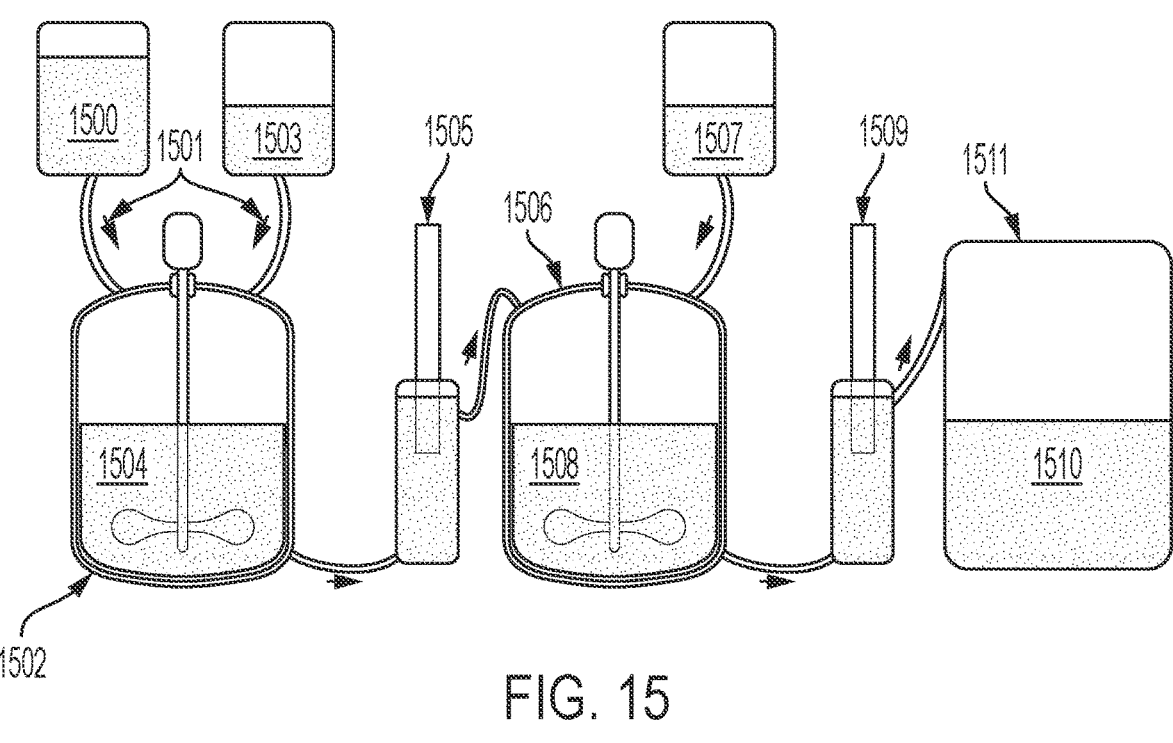
FIG. 15 is a schematic diagram that illustrates an example of a continuous production process of a double-phase particle dispersion, multi-phase particle dispersion, or particle aggregate dispersion, in accordance with some embodiments.

In some embodiments, a product may be more complex and require multiple processing steps in order to form the final particle system. In some embodiments, individual processing steps previously mentioned may be chained together to produce more complex products in a single production line. For example, a W/O/W double-particle system may be formed in a single production line, pictured in FIG. 15, as follows. A hydrophobic phase 1500 containing PGPR and LCT is flowed (denoted by arrows 1501) into a tank 1502 mixed by an overhead mixer. A hydrophilic phase 1503 containing hydrolyzed bovine collagen and water is flowed to the tank and mixed to form a W/O single-particle system 1504. The W/O single-particle system 1504 is subsequently passed through a flow cell outfitted with a sonicator 1505 and enough acoustical energy is passed into it to form hydrophilic particles with desired properties dispersed in the hydrophobic phase. The finished W/O single-particle system is then flowed into a second tank 1506 outfitted with an overhead mixer which has previously been filled with a second hydrophilic phase 1507 containing vitamin E TPGS and water and mixed to form the W/O/W single-particle system 1508. The W/O/W single-particle system is then flowed through a second flow cell outfitted with a sonicator 1509 and enough acoustical energy is passed into it to form hydrophobic particles with desired properties dispersed in the second hydrophilic phase. The finished W/O/W double-particle system 1510 is then flowed into a final tank 1511. In some embodiments, the different steps may be accomplished using different processing techniques (e.g., batch, semi-continuous, continuous). In some embodiments, one type of processing tool may be used to achieve the formation of each particle system. In some embodiments, multiple types of processing tools may be used, and in fact may be preferred, to achieve the formation of each particles system. For example, in the previous example, refinement of the W/O/W double-particle system may be achieved using a rotor-stator homogenizer after the initial W/O immiscible single-particle system is formed though ultrasonication.

Figure 16:
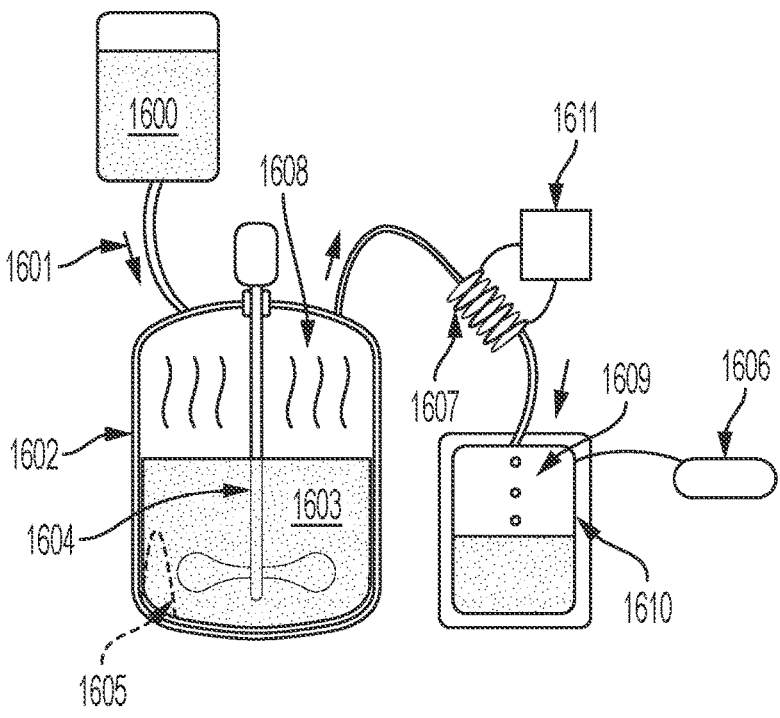
FIG. 16 is a schematic diagram that illustrates an example of a production process of a particle dispersion or extract utilizing evaporative removal of a processing aid or ingredient, in accordance with some embodiments.

In some embodiments, active ingredients which are added in the form of solutions using processing aids as a solvent; for example, the addition of actives which have been extracted into ethanol, may be used in the processing of a product. In some embodiments, when processing aid extracts are added to a phase, an additional step may be added to remove said processing aid before processing of the particle system begins, as illustrated in FIG. 16. In some embodiments, the processing aid extract 1600 may be flowed 1601 into the container 1602 which contains the other components of the phase 1603. In some embodiments, a shear mixer 1604 may be used to agitate the mixture. In some embodiments, the phase may be heated by, for example, a resistive heater 1605. In some embodiments, reduced pressure may be created in the container using a vacuum pump 1606. In some embodiments, the temperature and pressure of the contents of the tank may be adjusted such that the processing aid begins to evaporate. In some embodiments, an elbowed condenser 1607 may be affixed to the top of the tank such that the vapor of processing aid 1608 may pass through the elbow and condense in the condenser. In some embodiments, the now liquid processing aid 1609 may flow out of the condenser and into a collection tank 1610. In some embodiments, the condenser 1607 and collection tank 1610 may be actively cooled, for example, by a recirculating chiller 1611. This process may be continued until the desired amount of processing aid has been removed (e.g., 100, 99.9, 99, 95%). In some embodiments, when a reduced pressure is desired, the tank may be sealed except for the path consisting of the elbowed condenser, collection tank, and vacuum pump.

In some embodiments, a particle system processed using the aforementioned processing steps may be further processed into an aggregate. In some embodiments, the particle system may be formed into an aggregate with no further ingredient additions. In some embodiments, the particle system may be formed into an aggregate through the addition of phase stabilizing agents to the continuous phase. In some embodiments, the particle system may be formed into an aggregate through other processing methods such as a conventional coating method, spray drying, or spray chilling, as is illustrated in FIG. 17. For example, a particle system 1700 may be flowed (arrows 1701 denote the flow of ingredients) into a spray chilling device 1702 at a temperature above its melting or gelling point. Once in the spray chiller, the particle system 1700 may be aerosolized by a nozzle 1703 heated above the melting point of the particle system. Once aerosolized, the droplets of the particle system 1700 encounter air flow 1704 which may cool the droplets below their freezing or gelling point leading to the formation of a particle aggregate 1705 which may be collected as a solid or gel particle.

15. Examples of Particle Characterization Techniques

1. Dynamic Light Scattering (DLS)

In some embodiments, particle and particle dispersion properties may be determined and characterized with the use of dynamic light scattering (DLS), also known as photon correlation spectroscopy. in some embodiments, particle dispersion diameters and aspect ratio distributions may be measured with DLS. In some embodiments, particle dispersion diameters may be determined with varied timescales and timesteps before transforming to the correlation function for fitting for particle size distributions.

2. Laser Doppler Electrophoresis

In some embodiments, particle and particle dispersion properties may be determined and characterized with the use of laser doppler electrophoresis. In some embodiments, laser doppler electrophoresis may be used to determine the velocity of nanoparticles dispersed in solution resulting from an applied electric field, which, combined with the viscosity and dielectric constant of the dispersion medium, allows for an indirect determination of the stability, and evidences a tendency to flocculate and potential creaming through coalescence.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Similarly, reference to "a computer system" performing step A and "the computer system" performing step B can include the same computing device within the computer system performing both steps or different computing devices within the computer system performing steps A and B. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. To the extent bespoke noun phrases (and other coined terms) are used in the claims and lack a self-evident construction, the definition of such phrases may be recited in the claim itself, in which case, the use of such bespoke noun phrases should not be taken as invitation to impart additional limitations by looking to the specification or extrinsic evidence.

Various additional examples are described in pages 161 to the end of U.S. Provisional patent application 63/321,596, titled ALIMENTARY-RELATED PARTICLES, PRODUCTION METHODS, AND PRODUCTION APPARATUS, which is hereby incorporated by reference.

In this patent filing, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

I claim:

1. A composition for oral consumption, comprising:
an aqueous suspension, comprising:
a first plurality of active ingredients, wherein:
the first plurality of active ingredients are soluble in the aqueous suspension; and
one or more nanoparticles, wherein:
the one or more nanoparticles encapsulate a second plurality of active ingredients;
the second plurality of active ingredients are insoluble in the aqueous suspension;
the one or more nanoparticles solubilize the second plurality of active ingredients in the aqueous suspension;

the one or more nanoparticles have a Z-average diameter between 50 to 950 nanometers;
the Z-average diameter of the one or more nanoparticles changes less than 20% when the aqueous suspension is incubated at 40° C. for four weeks;
the one or more nanoparticles has a charge that is larger than 15 mV;
the one or more nanoparticles comprise a crosslinked hydrophilic polymer network at an interface of the one or more nanoparticles; and
the Z-average diameter of the one or more nanoparticles changes less than 20% when the aqueous suspension is incubated at 90° C. for 30 minutes.

2. The composition of claim 1, wherein:
the second plurality of active ingredients is selected from the group consisting of *Echinacea purpurea, Echinacea angustifolia, Echinacea pallida, Acmella oleracea, Helichrysum umbraculigerum, Radula marginata, kava, kanna*, black truffle, *Syzygium aromaticum, Rosmarinus oficinalis, Sceletium tortuosum*, Holy basil, Oregano, Lavender, Cinnamon, Malabathrum, *Cananga odorata, Ginkgo biloba, Bacopa*, and *Rhodiola rosea*, Ashwagandha, *Astragalus, Chaga, Cordyceps, Corydalis*, Curcumin, Damiana, Eleuthero, Ginger root, *Ginseng*, Gotu Kola, Lion's Mane, Maca, Passionflower, Saffron, Schisandra, St. John's Wort, Turmeric, Turkey Tail, Valerian root, Yohimbe, or combinations thereof.

3. The composition of claim 1, wherein:
the second plurality of active ingredients is selected from the group consisting of cannabidiol, cannabichromene, cannabigerol, cannabicyclol, cannabinol, cannabigerolic acid, cannabigerolic acid monomethylether, cannabigerol monomethyl ether, cannabichromanon, cannabichromenic acid, cannabichromevarin, cannabichromevarinic acid, tetrahydrocannabinol, iso-tetrahydrocannabinol, cannabinol methylether, cannabinol-C4, cannabinol-C2, cannabiorcol, cannabinodiol, cannabielsoin, cannabielsoic acid A, cannabielsoic acid B, cannabicyclol, cannabicyclolic acid, cannabicyclovarin, cannabicitran, cannabitriol, cannabitriolvarin, ethoxy-cannabitiolvarin, cannabivarin, cannabinodivarin, tetrahydrocannabivarin, cannabidivarin, cannabigerovarin, cannabigerovarinic acid, cannabifuran, dehydrocannabifuran, cannabiripsol cannabinoids, or combinations thereof.

4. The composition of claim 1, wherein the composition is a beverage, a gum, or a food snack.

5. The composition of claim 1, wherein the one or more nanoparticles further comprising:
a plurality of emulsifying agents selected from the group consisting of an extract of Quillaja, extract of Licorice, polysorbate 20, polysorbate 40, polysorbate 45, polysorbate 60, polysorbate 65, polysorbate 80, polysorbate 81 and polysorbate 85, polyglyceryl, gum acacia, Polyglycerol polyricinoleate, sorbitan 85, sorbitan 65, sorbitan 83, sorbitan 80, sorbitan 60, sorbitan 40, Xanthan gum, sorbitol, mannitol, glycerol, sodium alginate, lecithin, chemically modified lecithin, purified components of lecithin, phosphatidylcholine, phosphatidylglycerol, phosphatidic acid, phosphatidylethanolamine, phosphatidylserine, phosphatidylinositol, sphingomyelin, and cardiolipin, hydrogenated soybean phosphatidylcholine, hydrogenated soybean phosphatidylcholine, tocopherol polyethylene glycol succinate, fatty acid mono-and di-glycerides, acetic acid esters of mono-and di-glycerides, lactic acid esters of mono-and di-glycerides, citric acid esters of mono-and di-glycerides, diacetyl tartaric acid ester of mono-and di-glycerides, triglycerol monooleate, hexaglycerol octasterate, polyglycerol esters of oleic acid, decaglycerol mono-and di-oleate, glyceryl caprylate, glyceryl caprate, glyceryl caprate/caprylate, glyceryl monooleate, glycerly monostearate, poloxamers, milk proteins, casein, pea proteins, whey proteins, collagen, sodium stearoyl lactylate, extract of bacopa, withaferin A, withaferin B, withanolide A, withanolide B, withanolide C, withanolide D, withanolide E, withanolide F, withanolide G, withanoside I, withanoside II, withanoside III, withanoside IV, withanoside V, withanoside VI, withanoside VII, bacopaside I, bacopaside II, bacopaside III, bacopaside IV, bacopaside V, bacopaside VI, bacopaside VII, bacopaside VIII, bacopaside IX, bacopaside X, bacopaside XI, bacopaside XII, bacopaside N1, bacopaside N2, bacosaponin A, bacosaponin B, bacosaponin C, bacosaponin D, bacosaponin E, bacosaponin F, bacosaponin G, bacosaponin H, bacoside A3, bacosine, or combinations thereof.

6. The composition of claim 1, wherein the aqueous suspension further comprising:

a first polymer selected from the group consisting of alginic acid, gum Arabic, locust bean gum, sodium alginate, potassium alginate, calcium alginate, agar, guar gum, and xanthan gum.

7. The composition of claim 1, wherein the one or more nanoparticles further comprising:

a dispersed phase comprising:

a third plurality of active ingredients; and a second polymer.

8. The composition of claim 7, wherein:

the third plurality of active ingredients is selected from the group consisting of methylphenidate, dextroamphetamine, amphetamine, Caffeine, nicotine, Methamphetamine, 3,4-Methylenedioxymethamphetamine, Methylenedioxypyrovalerone, Mephedrone, Phenylpropanolamine, Propylhexedrine, Pseudoephedrine, *Catha edulis*, Modafinil, xanthines, theophylline, and theobromine, or combinations thereof.

9. The composition of claim 7, wherein:

the second polymer is selected from the group consisting of alginic acid, gum Arabic, locust bean gum, sodium alginate, potassium alginate, calcium alginate, agar, guar gum, and xanthan gum.

10. The composition of claim 1, wherein the one or more nanoparticles further comprising:

a first polymer selected from the group consisting of methyl cellulose, hydroxypropyl cellulose, hydroxypropyl methylcellulose, shellac, ethyl methyl cellulose, carboxymethyl cellulose, ethyl cellulose, microcrystalline cellulose, cellulose, 12-hydroxystearic acid, and a combination thereof.

11. The composition of claim 10, wherein the first polymer retards the release of the second plurality of active ingredients after consumption.

12. The composition of claim 1, wherein the one or more nanoparticles has a net negative charge that is −15 mV or lower.

13. The composition of claim 12, wherein the net negative charge of the one or more nanoparticles causes the one or more nanoparticles to repel each other with a force of repulsion that leads to stable dispersion of the one or more nanoparticles when the first composition is diluted at least up to 10 fold with an aqueous fluid.

14. The composition of claim 1, wherein the one or more nanoparticles has a net positive charge that is +15 mV or higher.

15. The composition of claim 14, wherein the net positive charge is mainly generated by a plurality of emulsifying agents, associated with the one or more nanoparticles, selected from the group consisting of Ethyl lauroyl arginate, dialkyl ammonium chloride, monoalkyl ammonium chloride, chitosan, n-dodecyl dimethyl benzyl ammonium chloride, n-dodecyl dimethyl ethylbenzyl ammonium chloride, n-hexadecyl dimethyl benzyl ammonium chloride, n-octadecyl dimethyl benzyl ammonium chloride, n-tetradecyl dimethyl benzyl ammonium chloride, n-tetradecyl dimethyl ethylbenzyl ammonium chloride, and a combination thereof.

16. The composition of claim 1, wherein size, polydispersity, and force of repulsion of the one or more nanoparticles produce a bloom effect, wherein the bloom effect of the one or more nanoparticles prevents sublimation of ice crystals from a surface of a substrate, thereby preventing freezer burn of the composition.

17. The composition of claim 1, wherein the one or more nanoparticles are 0.01 wt % to 70 wt % of the composition.

18. The composition of claim 1, wherein the one or more nanoparticles further comprises a bioenhancer ingredient selected from the group consisting of aloin A, aloin B, emodin, 2-gingerol, 4-gingerol, 6-gingerol, 8-gingerol, 10-gingerol, 12-gingerol, 6-shogaol, 10-shogaol, 6-paradol, Niazirin, niaziridin, bergamottin, genistein, isoquercetin, isorhamnetin, kaempferol, naringin, naringinin, nobiletin, quercetin, quercitrin, tangeritin, rutin, tamarixetin 6',7'-dihydroxybergamottin, resveratrol, trans-resveratro, cis-resveratrol, luteolin, luteolin-7-O-glucoside, stevioside, steviol, rebaudioside A, rebaudioside B, rebaudioside C, rebaudioside D, rebaudioside E, rebaudioside F, stigmasterol, stigmasterol-3-O-beta-d-glucoside, beta-sitosterol, caffeic acid, chicoric acid, cinnamic acid, chlorogenic acid, gallic acid, green tea, catechin, catechin gallate, epicatechin, epicatechin gallate, epigallocatechin, and epigallocatechin gallate, sodium and potassium salts of cholic acid, deoxycholic acid, chenodeoxycholic acid, ursodeoxycholic acid, taurocholic acid, glycocholic acid, taurochenodeoxycholic acid, glycochenodeoxycholic acid, taurodeoxycholic acid, glycodeoxycholic acid, tauroursodeoxycholic acid, glycoursodeoxycholic acid, lithocholic acid, or combinations thereof.

19. The composition of claim 1, wherein the composition further comprises a bioenhancer ingredient selected from the group consisting of Allicin, Capsaicinoids, Homocapsaicin, dihydrocapsaicin, homodihydrocapsaicin, noredihydrocapsaicin, nonivamide, capsaicin, alkaloids, berberine, bidesmethoxycurcumin, curcumin, desmethoxycurcumin, lysergol, piperine, piperidine, sinomenine, terpenes, terpenoids, 1-8 cineole, bergamotene, carvacrol, carvone, caryophyllene, elemene, eugenol, farnesene, geraniol, glycyrrhizin, humulene, kaurene, limonene, pinene, sterebin A, sterebin B, sterebin C, sterebin D, sterebin E, sterebin F, sterebin G, sterebin H, terpinen-4-ol, gamma-terpinene, alpha-terpineol, terpinolene, kavalactones, methysticin, dihydromethysticin, yangonin, desmethoxyyangonin, kavain, and dihydrokavain, alpha-boswellic acid, beta-boswellic acid, bile acid acids, cholic acid, deoxycholic acid, chenodeoxycholic acid, ursodeoxycholic acid, taurocholic acid, glycocholic acid, taurochenodeoxycholic acid, glycochenodeoxycholic acid, taurodeoxycholic acid, glycodeoxycholic acid, tauroursodeoxycholic acid, glycoursodeoxycholic, lithocholic acid, GRAS triglycerides, diglycerides, and monoglycerides, or combinations thereof.

20. A composition for oral consumption, comprising:

an aqueous suspension, comprising:

a first plurality of active ingredients selected from the group consisting of methylphenidate, dextroamphetamine, amphetamine, dextroamphetamine, Caffeine, nicotine, Methamphetamine, 3,4-Methylenedioxymethamphetamine, Methylenedioxypyrovalerone, Mephedrone, Phenylpropanolamine, Propylhexedrine, Pseudoephedrine, *Catha edulis*, Modafinil, xanthine derivatives, theophylline, and theobromine, wherein:

the first plurality of active ingredients are soluble in the aqueous suspension; and one or more nanoparticles, wherein:

the one or more nanoparticles encapsulate a second plurality of active ingredient selected from the group consisting of *Echinacea purpurea, Echinacea angustifolia, Echinacea pallida, Acmella oleracea, Helichrysum umbraculigerum, Radula marginata, kava, kanna*, black truffle, *Syzygium aromaticum, Rosmarinus oficinalis, Sceletium tortuosum*, Holy basil, Oregano, Lavender, Cinnamon, Malabathrum, *Cananga odorata, Ginkgo Biloba, Bacopa*, and *Rhodiola rosea*, Ashwagandha, *Astragalus, Chaga, Cordyceps*, Corydalis, Curcumin, Damiana, Eleuthero, Ginger root, *Ginseng*, Gotu Kola, Lion's Mane, Maca, Passionflower, Saffron, Schisandra, St. John's Wort, Turmeric, Turkey Tail, Valerian root, and Yohimbe;

the one or more nanoparticles further comprises:

a plurality of emulsifying agents selected from the group consisting of an extract of Quillaja, extract of Licorice, polysorbate 20, polysorbate 40, polysorbate 45, polysorbate 60, polysorbate 65, polysorbate 80, polysorbate 81 and polysorbate 85, polyglyceryl, gum acacia, Polyglycerol polyricinoleate, sorbitan 85, sorbitan 65, sorbitan 83, sorbitan 80, sorbitan 60, sorbitan 40, Xanthan gum, sorbitol, mannitol, glycerol, sodium alginate, lecithin, chemically modified lecithin, purified components of lecithin, phosphatidylcholine, phosphatidylglycerol, phosphatidic acid, phosphatidylethanolamine, phosphatidylserine, phosphatidylinositol, sphingomyelin, and cardiolipin, hydrogenated soybean phosphatidylcholine, hydrogenated soybean phosphatidylcholine, tocopherol polyethylene glycol succinate, fatty acid mono-and di-glycerides, acetic acid esters of mono-and di-glycerides, lactic acid esters of mono-and di-glycerides, citric acid esters of mono-and di-glycerides, diacetyl tartaric acid ester of mono-and di-glycerides, triglycerol monooleate, hexaglycerol octasterate, polyglycerol esters of oleic acid, decaglycerol mono-and di-oleate, glyceryl caprylate, glyceryl caprate, glyceryl caprate/caprylate, glyceryl monooleate, glycerly monostearate, poloxamers, milk proteins, casein, pea proteins, whey proteins, collagen, sodium stearoyl lactylate, extract of bacopa, withaferin A, withaferin B, withanolide A, withanolide B, withanolide C, withanolide D, withanolide E, withanolide F, withanolide G, withanoside I, withanoside II, withanoside III, withanoside IV, withanoside V, withanoside VI, withanoside VII, bacopaside I, bacopaside II, bacopaside III, bacopaside IV, bacopaside V, bacopaside VI, bacopaside VII, bacopaside VIII, bacopaside IX, bacopaside X, bacopaside XI, bacopaside XII, bacopaside N1, bacopaside N2, bacosaponin A, bacosaponin B, bacosaponin C, bacosaponin D, bacosaponin E, bacosaponin F, bacosaponin G, bacosaponin H, bacoside A3, bacosine, or combinations thereof;

the one or more nanoparticles solubilize the second plurality of active ingredients in the aqueous suspension;

the one or more nanoparticles have a Z-average diameter between 50 to 950 nanometers;

the one or more nanoparticles has a net negative charge that is-15 mV or lower;

the one or more nanoparticles comprise a crosslinked hydrophilic polymer network at an interface of the one or more nanoparticles;

the Z-average diameter of the one or more nanoparticles changes less than 20% when the aqueous suspension is incubated at 40° C. for four weeks; and the Z-average diameter of the one or more nanoparticles changes less than 20% when the aqueous suspension is incubated at 90° C. for 30 minutes.

* * * * *